US011254654B2

(12) United States Patent
Hathaway et al.

(10) Patent No.: US 11,254,654 B2
(45) Date of Patent: Feb. 22, 2022

(54) HETEROCHROMATIN GENE REPRESSION INHIBITORS

(71) Applicant: The University of North Carolina at Chapel Hill, Chapel Hill, NC (US)

(72) Inventors: Nate Hathaway, Chapel Hill, NC (US); Jian Jin, New York, NY (US); Ian MacDonald, Durham, NC (US); Kyle Butler, Salt Lake City, UT (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/622,073

(22) PCT Filed: Jun. 29, 2018

(86) PCT No.: PCT/US2018/040326
§ 371 (c)(1),
(2) Date: Dec. 12, 2019

(87) PCT Pub. No.: WO2019/006322
PCT Pub. Date: Jan. 3, 2019

(65) Prior Publication Data
US 2020/0181116 A1 Jun. 11, 2020

Related U.S. Application Data
(60) Provisional application No. 62/527,560, filed on Jun. 30, 2017.

(51) Int. Cl.
| *C07D 401/14* | (2006.01) |
| *C07D 401/12* | (2006.01) |
| *C07D 495/04* | (2006.01) |
| *G01N 33/574* | (2006.01) |
| *G01N 33/68* | (2006.01) |

(52) U.S. Cl.
CPC ......... *C07D 401/14* (2013.01); *C07D 401/12* (2013.01); *C07D 495/04* (2013.01); *G01N 33/57496* (2013.01); *G01N 33/6875* (2013.01); *G01N 2500/00* (2013.01)

(58) Field of Classification Search
CPC .. C07D 239/72; C07D 239/95; C07D 401/14; A61K 31/517; A61K 31/55; A61K 31/551
See application file for complete search history.

(56) References Cited

U.S. PATENT DOCUMENTS

| 6,156,758 A | 12/2000 | Kung et al. |
| 8,193,203 B2 | 6/2012 | Beard et al. |
| 2009/0312305 A1 | 12/2009 | Beard et al. |
| 2015/0057263 A1 | 2/2015 | Brown et al. |

FOREIGN PATENT DOCUMENTS

| AU | 2018291161 | 6/2018 |
| CA | 3068146 | 6/2018 |
| CN | 201880053161.3 | 6/2018 |
| EP | 18825397.45 | 6/2018 |
| JP | 2019-572097 | 6/2018 |
| KR | 10-2020-7002672 | 6/2018 |
| WO | PCT/US2018/040326 | 6/2018 |
| WO | WO-2019/006322 A1 | 1/2019 |

OTHER PUBLICATIONS

Acute Leukemia, Merck Manual (Online Edition) 6 pages, pp. 1-6 (2013).*
Simone, Oncology: Introduction, Cecil Textbook of Medicine, 20th Edition, vol. 1, pp. 1004-1010, 1996.*
Pearce et al., Failure modes in anticancer drug discovery and development, Cancer Drug Design and Discovery Edited by Stephen Neidle, Chapter 18, pp. 424-435 (2008).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Sandeep Sundriyal, et al. (2017) "Histone lysine methyltransferase structure activity relationships that allow for segregation of G9a inhibition and anti-Plasmodium activity," MedChemComm 8(5): 1069-1092.
Extended European Search Report dated Nov. 17, 2020 by the European Search Authority for EP Application No. 18825397.5, filed on Jun. 29, 2019 and published as EP 3645006 on May 6, 2020 (Applicant—The University of North Carolina at Chapel Hill) (9 pages).
U.S. Appl. No. 62/527,560, filed Jun. 30, 2017, Nate Hathaway.
International Search Report and Written Opinion dated Sep. 12, 2018 by the International Searching Authority for International Application No. PCT/US2018/040326, filed on Jun. 29, 2018 and published as WO 2019/006322 on Jan. 3, 2019 (Applicant—The University of North Carolina At Chapel Hill) (12 Pages).
International Preliminary Report on Patentability dated Dec. 31, 2019 by the International Searching Authority for International Application No. PCT/US2018/040326, filed on Jun. 29, 2018 and published as WO 2019/006322 on Jan. 3, 2019 (Applicant—The University of North Carolina At Chapel Hill) (5 Pages).

* cited by examiner

*Primary Examiner* — Deepak R Rao
(74) *Attorney, Agent, or Firm* — Ballard Spahr LLP

(57) ABSTRACT

The present disclosure relates to chemical compounds that inhibit HP1-mediated heterochromatin formation, pharmaceutical compositions containing such compounds, methods of identifying such compounds, and their use in the treatment of disorders related to heterochromatin formation such as, for example, a disorder of cellular proliferation (e.g., cancer). This abstract is intended as a scanning tool for purposes of searching in the particular art and is not intended to be limiting of the present invention.

14 Claims, 44 Drawing Sheets
Specification includes a Sequence Listing.

Screening Strategy

Day 0 — Plate 96 well adapted *CiA:Oct4* ES cells w/ CIP csHP1α system

Day 1 — Add media +/− rapamycin and compound

Day 2 — Add media +/− rapamycin and compound

Day 3 — High-throughput GFP screening by flow cytometry

FIG. 4A

HETEROCHROMATIN GENE REPRESSION INHIBITORS

CROSS-REFERENCE TO RELATED APPLICATIONS

This application is a national stage filing under 35 U.S.C. § 371 of International Application No. PCT/US2018/040326, filed on Jun. 29, 2018, which claims the benefit of U.S. Provisional Application No. 62/527,560, filed on Jun. 30, 2017, the contents of which are incorporated herein by reference in their entireties.

STATEMENT REGARDING FEDERALLY SPONSORED RESEARCH

This invention was made with government support under grant numbers R01GM122749, R01CA218600, and R01HD088626, awarded by the National Institutes of Health, and grant number R01GM100919, awarded by the National Institute of General Medical Sciences, U.S. National Institutes of Health (NIH). The government has certain rights in the invention.

REFERENCE TO SEQUENCE LISTING

The Sequence Listing submitted on Sep. 28, 2021 as a text file named "37571 0009U2 ST25.txt," created on Sep. 27, 2021, and having a size of 15,416 bytes is hereby incorporated by reference pursuant to 37 C.F.R. § 1.52(e)(5).

BACKGROUND

Histone methylation represents a critical post-translational modification that regulates gene expression and is critical for proper tissue specialization during mammalian development (Black, Van Rechem, & Whetstine, 2012; Greer & Shi, 2012). Disruptions to the careful balance of epigenetic pathways, such as histone methylation, have recently been identified as drivers of human cancer (Arrowsmith, Bountra, Fish, Lee, & Schapira, 2012; Dawson & Kouzarides, 2012; MacDonald & Hathaway, 2015). Histone methylation can correlate with either activating or repressive gene functions depending on the specific histone residue modified and the landscape of the chromatin where the histone methylation is placed. For example, Histone H3 Lysine 4 tri-methylation (H3K4me3) is typically representative of an active euchromatin state while H3K9me3 correlates with repressive heterochromatin. H3K9me3 was shown to be deposited by two primary mechanisms.

Classically, heterochromatin protein 1 (HP1) has been shown to mediate heterochromatin and stimulate gene repression. The chromodomain of HP1 allows for binding of H3K9me3, while the chromoshadow domain recruits in the histone methyltransferase enzymes Suv39H1/2 and SETDB1 to deposit subsequent H3K9me3 marks (Fritsch et al., 2010; Wallrath, Vitalini, & Elgin, 2014). HP1's function as a histone methyl-reader and scaffolding protein allows for the propagation of H3K9me3 to neighboring nucleosomes further spreading the heterochromatin domain leading to gene silencing. Recently, heterochromatin domains have been demonstrated to be mediated by the HUSH complex composed of TASOR, Mpp8, and Periphilin. This complex interacts with SETDB1 to deposit H3K9me3 (Tchasovnikarova et al., 2015). The heterochromatin pathway is perturbed in a diverse set of human cancers, making it an exciting new epigenetic target class to consider for future therapeutics (Ceol et al., 2011; Chiba et al., 2015; De Koning et al., 2009).

Despite HP1's importance in epigenetic regulation of genes and involvement in cancers, there are currently few small molecules which target any components in this pathway. Thus, there remains a need for compounds and compositions that inhibit HP1-mediated heterochromatin formation. These needs and others are met by the following disclosure.

SUMMARY

In accordance with the purpose(s) of the invention, as embodied and broadly described herein, the invention, in one aspect, relates to compounds, compositions, and methods for use in the prevention and treatment of disorders associated with heterochromatin formation such as, for example, a disorder of cellular proliferation (e.g, cancer).

Disclosed are compounds having a structure represented by a formula:

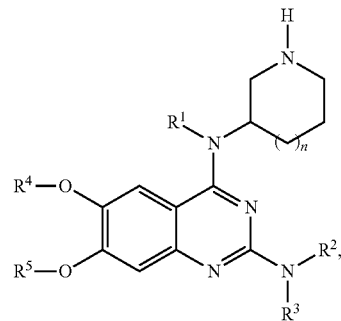

wherein n is selected from 0 and 1; wherein $R^1$ is H or C1-C4 alkyl; wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

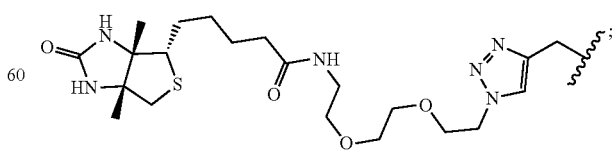

or
wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; or a pharmaceutically acceptable salt thereof.

Also disclosed are methods of treating a disorder related to heterochromatin formation, the method comprising administering to a mammal an effective amount of a compound having a structure represented by a formula:

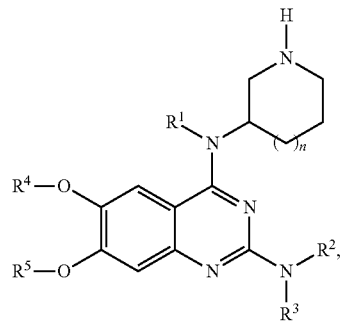

wherein n is selected from 0 and 1; wherein $R^1$ is H or C1-C4 alkyl; wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

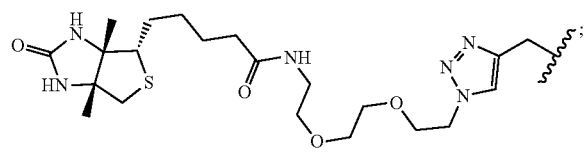 [SMILES: *Cc1cn(CCOCCOCCNC(=O)CCCC[C@@H]2SC[C@]3(C)NC(=O)N[C@]23C)nn1]

or
wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; or a pharmaceutically acceptable salt thereof.

Also disclosed are methods of inhibiting HP1-mediated heterochromatin formation, the method comprising administration of a compound having a structure represented by a formula:

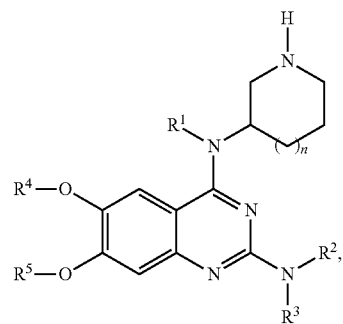

wherein n is selected from 0 and 1; wherein $R^1$ is H or C1-C4 alkyl; wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

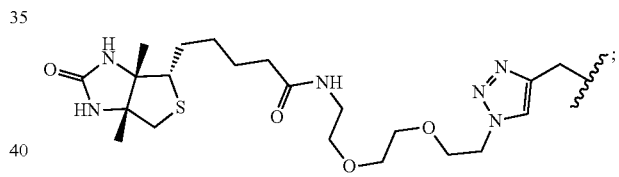

or
wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; or a pharmaceutically acceptable salt thereof.

Also disclosed are methods of identifying an inhibitor of HP1-mediated heterochromatin formation, the method comprising screening a candidate compound for binding with, or activity against, Kmt2B and/or Hdgfrp2.

Also disclosed are compounds identified by a disclosed method.

Also disclosed are methods of treating a disorder related to heterochromatin formation, the method comprising administering to a mammal an effective amount of a compound identified by a disclosed method.

Also disclosed are methods of treating a disorder related to heterochromatin formation, the method comprising administering to a mammal an effective amount of a disclosed compound.

Also disclosed are methods of making a disclosed compound.

Also disclosed are methods of using a disclosed compound.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 4A-D shows a representative high-throughput flow cytometry screen for modulators of HP1-mediated heterochromatin formation.

Figure 1:
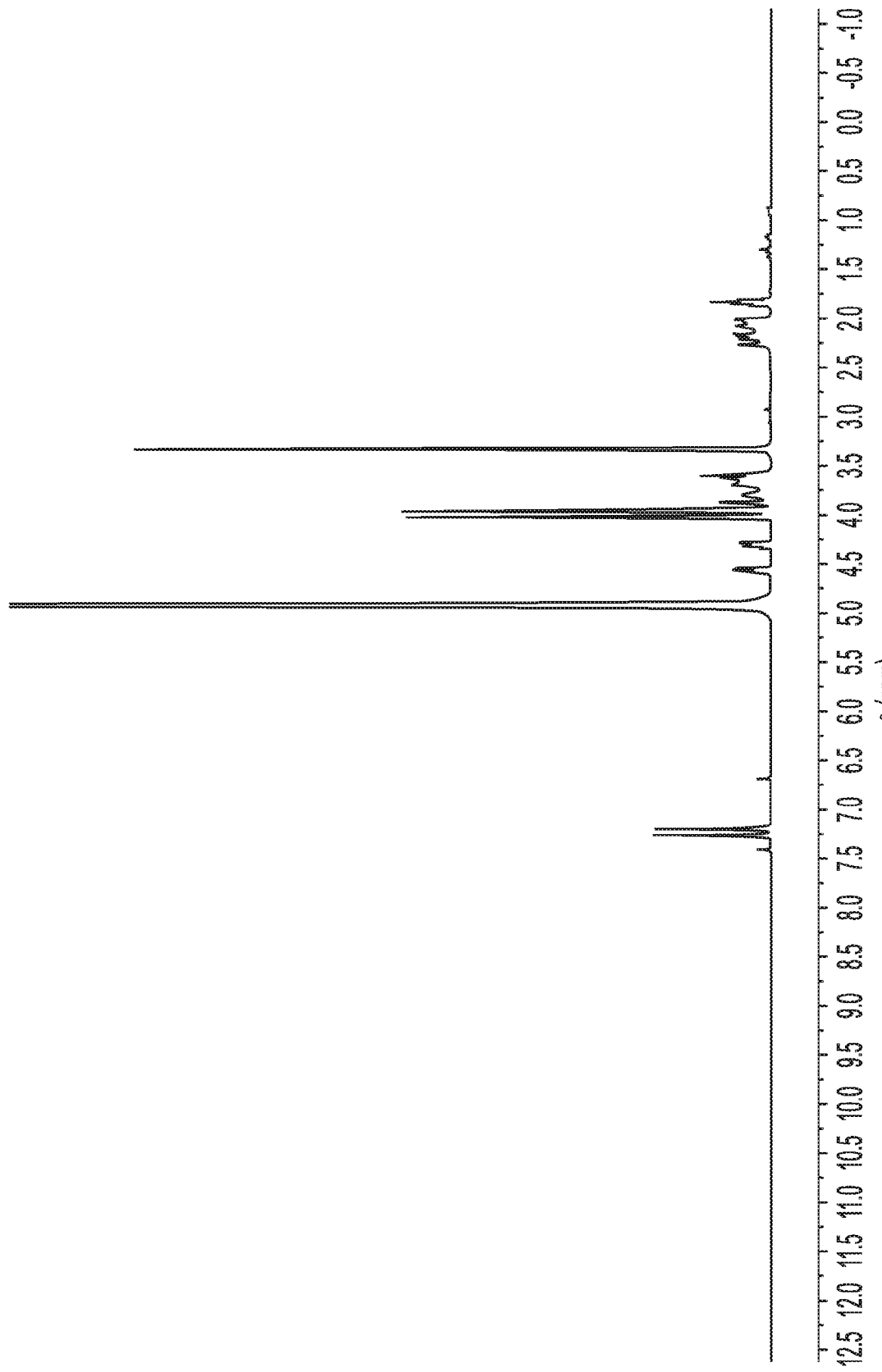
FIG. 1 shows a representative $^1$H NMR spectrum of compound 1.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a mammal (e.g., a human), and includes: (i) preventing the disease from occurring in a mammal that can be predisposed to the disease but has not yet been diagnosed as having it; (ii) inhibiting the disease, i.e., arresting its development; or (iii) relieving the disease, i.e., causing regression of the disease. In one aspect, the mammal is a human. The term "mammal" also includes domesticated animals (e.g., cats, dogs, etc.), livestock (e.g., cattle, horses, pigs, sheep, goats, etc.), and laboratory animals (e.g., mouse, rabbit, rat, guinea pig, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been mammaled to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a mammal. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount," that is, an amount effective for prevention of a disease or condition.

As used herein, "dosage form" means a pharmacologically active material in a medium, carrier, vehicle, or device suitable for administration to a mammal. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and singlestranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-O5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkynyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity,"

pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" or "CO" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1O A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN or —C≡N.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when mammaled to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —$O$—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —C(S)$R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-}$ $_4$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R●, -(haloR●), —(CH$_2$)$_{0-2}$OH, —(CH$_2$)$_{0-2}$OR●, —(CH$_2$)$_{0-2}$CH(OR●)$_2$; —O(haloR●), —CN, —N$_3$, —(CH$_2$)$_{0-2}$C(O)R●, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●, —(C$_{1-4}$ straight or branched alkylene)C(O)OR●, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

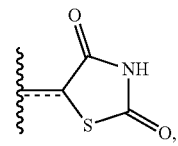

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, monosubstituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

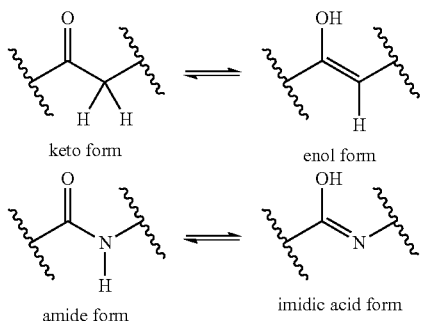

Likewise, amides with an N-hydrogen can exist in an equilibrium of the amide form and the imidic acid form. As another example, pyrazoles can exist in two tautomeric forms, $N^1$-unsubstituted, $3\text{-}A^3$ and $N^1$-unsubstituted, $5\text{-}A^3$ as shown below.

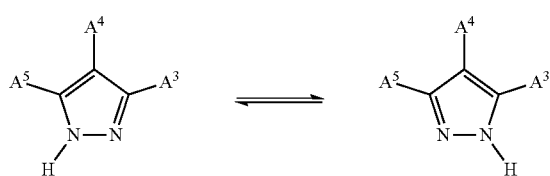

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

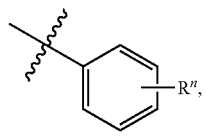

which is understood to be equivalent to a formula:

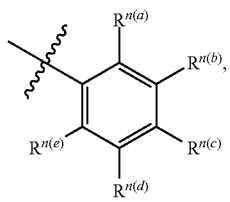

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, disclosed are compounds useful in treating or preventing a disorder associated with heterochromatin formation such as, for example, a disorder of cellular proliferation (e.g., cancer). In a further aspect, the disclosed compounds exhibit modulation of HP-1 mediated heterochromatin formation. In a still further aspect, the disclosed compounds exhibit inhibition of HP-1 mediated heterochromatin formation.

In one aspect, the compounds of the invention are useful in the treatment or prevention of disorders associated with heterochromatin formation and other diseases in which heterochromatin gene repression is involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

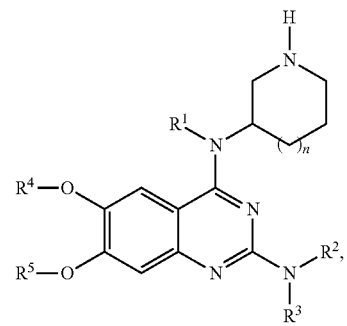

wherein n is selected from 0 and 1; wherein $R^1$ is H or C1-C4 alkyl; wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

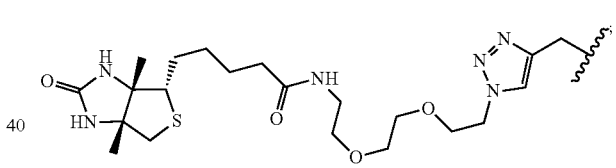

or wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; or a pharmaceutically acceptable salt thereof.

In a further aspect, the compound has a structure selected from:

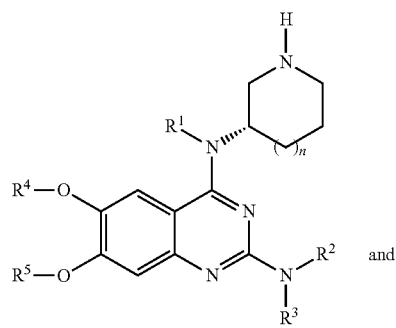

and

-continued
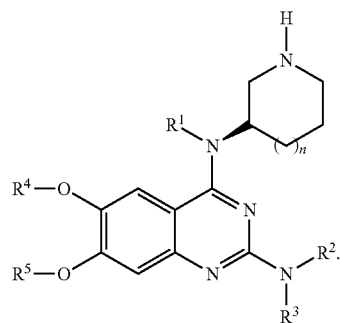
In a further aspect, the compound has the structure:
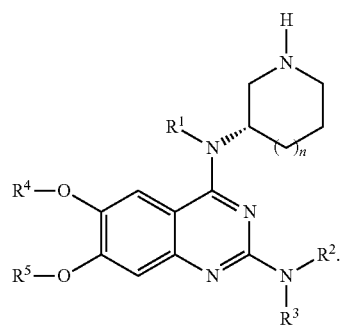
In a further aspect, the compound has the structure:
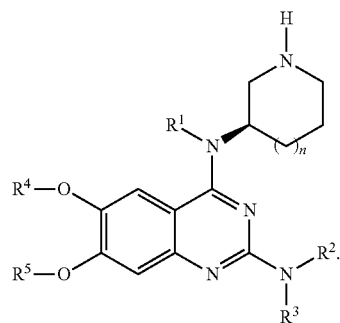
In a further aspect, the compound has a structure selected from:
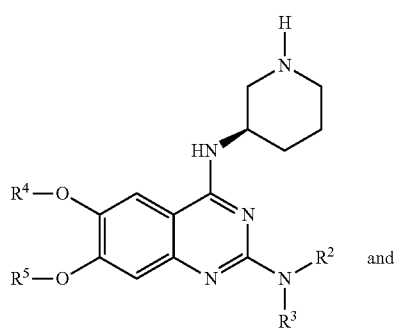
and
-continued
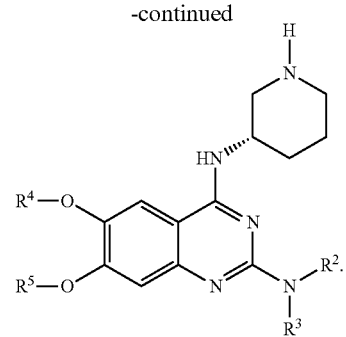
In a further aspect, the compound has the structure:
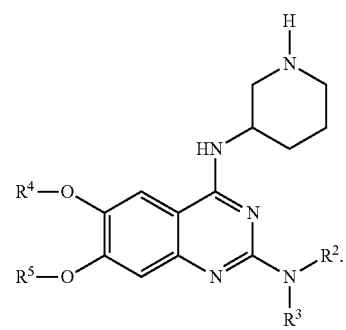
In a further aspect, the compound has a structure selected from:
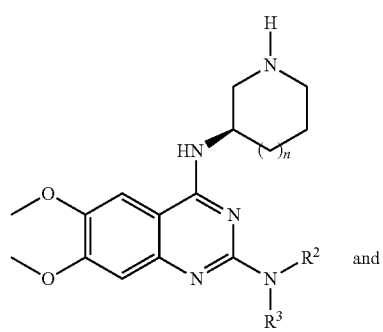
and
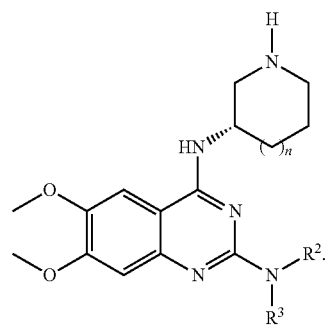

In a further aspect, the compound has the structure:
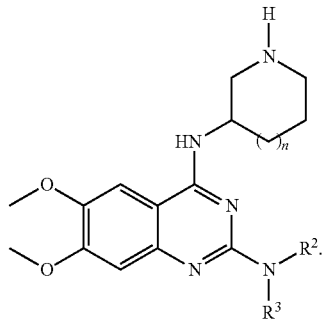
In a further aspect, the compound has a structure selected from:
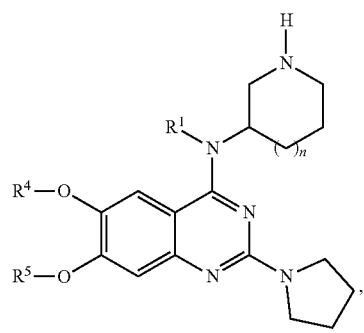
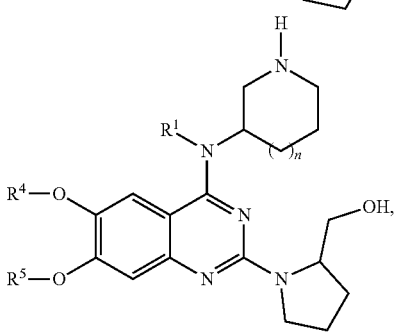
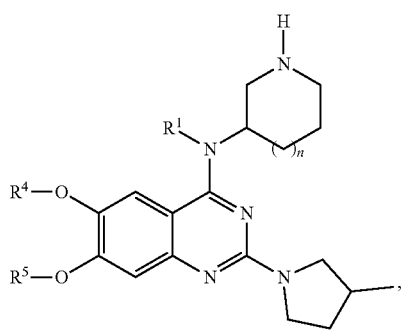
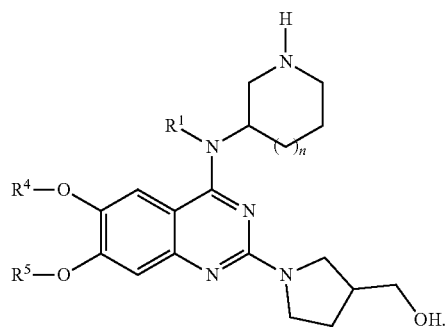
In a further aspect, the compound has the structure:
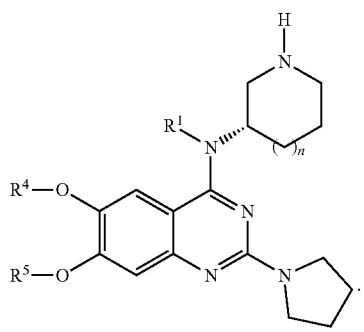
In a further aspect, the compound has the structure:
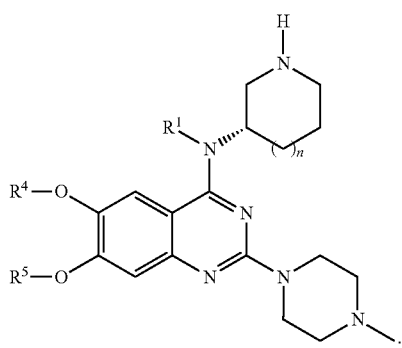
In a further aspect, the compound has a structure selected from:
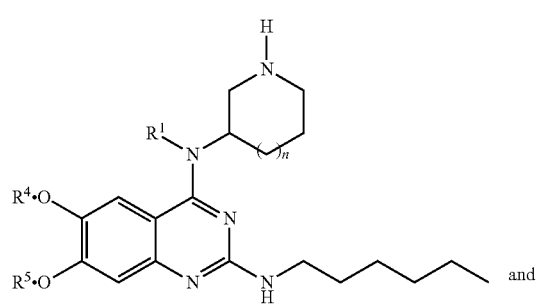

-continued

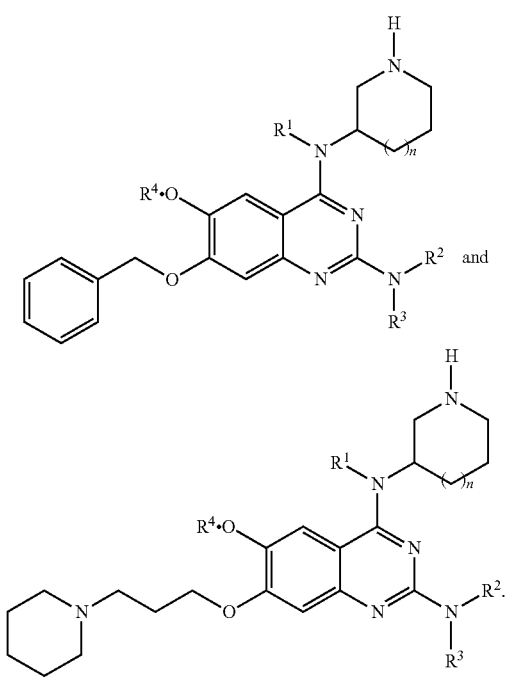

In a further aspect, the compound has a structure selected from:

In a further aspect, the compound has the structure:

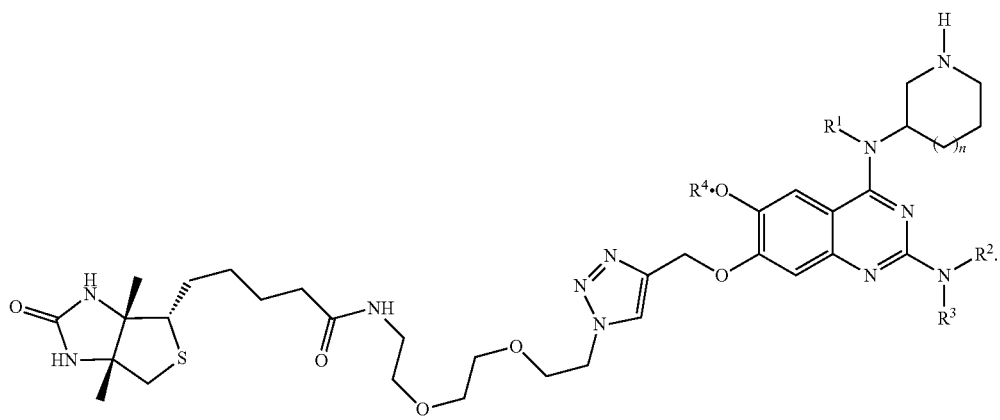

In one aspect, n is selected from 0 and 1. In a further aspect, n is 0. In a still further aspect, n is 1.

In one aspect, m is selected from 1, 2, 3, and 4. In a further aspect, m is selected from 1, 2, and 3. In a still further aspect, m is selected from 1 and 2. In yet a further aspect, m is 4. In an even further aspect, m is 3. In a still further aspect, m is 2. In yet a further aspect, m is 1.

In one aspect, p is selected from 0, 1, 2, 3, and 4. In a further aspect, p is selected from 0, 1, 2, and 3. In a still further aspect, p is selected from 0, 1, and 2. In yet a further aspect, p is selected from 0 and 1. In an even further aspect, p is selected from 1, 2, 3, and 4. In a still further aspect, p is selected from 1, 2, and 3. In yet a further aspect, p is selected from 1 and 2. In an even further aspect, p is 4. In a still further aspect, p is 3. In yet a further aspect, p is 2. In an even further aspect, p is 1. In a still further aspect, p is 0.

a. $R^1$ Groups

In one aspect, $R^1$ is H or C1-C4 alkyl. In a further aspect, $R^1$ is H.

In a further aspect, $R^1$ is selected from H, methyl, ethyl, n-propyl, i-propyl, n-butyl, i-butyl, s-butyl, and t-butyl. In a still further aspect, $R^1$ is selected from H, methyl, ethyl, n-propyl, and i-propyl. In yet a further aspect, $R^1$ is selected from H, methyl, and ethyl. In an even further aspect, $R^1$ is selected from H and ethyl. In a still further aspect, $R^1$ is selected from H and methyl.

In a further aspect, $R^1$ is selected from methyl, ethyl, n-propyl, i-propyl, n-butyl, i-butyl, s-butyl, and t-butyl. In a still further aspect, $R^1$ is selected from methyl, ethyl, n-propyl, and i-propyl. In yet a further aspect, $R^1$ is selected from methyl and ethyl. In an even further aspect, $R^1$ is ethyl. In a still further aspect, $R^1$ is methyl.

b. $R^2$ and $R^3$ Groups

In one aspect, each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a further aspect, each of $R^2$ and $R^3$ is H. In a still further aspect, one of $R^2$ and $R^3$ is H and one of $R^2$ and $R^3$ is selected from C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4.

In a further aspect, each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$. In a still further aspect, each of $R^2$ and $R^3$ is independently selected from H, C1-C4 alkyl, —$CH_2CH_2NH_2$, —$CH_2CH_2OH$, —$CH_2CH_2OCH_2CH_2OH$, —$CH_2CH_2$ $OCH_2CH_2$ $OCH_2CH_2OH$, —$CH_2CH_2OCH_2CH_2NH_2$, —$CH_2CH_2OCH_2CH_2OCH_2CH_2NH_2$, and —$CH_2CH_2$ $OCH_2$ $CH_2$ $OCH_2CH_2OCH_2CH_2NH_2$. In yet a further aspect, each of $R^2$ and $R^3$ is independently selected from H, methyl, ethyl, n-propyl, i-propyl, —$CH_2CH_2NH_2$, —$CH_2CH_2OH$, —$CH_2CH_2OCH_2CH_2OH$, —$CH_2CH_2OCH_2CH_2NH_2$, and —$CH_2CH_2OCH_2CH_2OCH_2CH_2NH_2$. In an even further aspect, each of $R^2$ and $R^3$ is independently selected from H, methyl, ethyl, —$CH_2CH_2NH_2$, —$CH_2CH_2OH$, and —$CH_2CH_2OCH_2CH_2NH_2$. In a still further aspect, each of $R^2$ and $R^3$ is independently selected from H, methyl, —$CH_2CH_2NH_2$, —$CH_2CH_2OH$, and —$CH_2CH_2OCH_2CH_2NH_2$.

In a further aspect, each of $R^2$ and $R^3$ is independently selected from H, —$CH_2CH_2NH_2$, —$(CH_2CH_2O)_m$—H, and —$(CH_2CH_2O)_m$—$CH_2CH_2NH_2$. In a still further aspect, each of $R^2$ and $R^3$ is independently selected from H, —$CH_2CH_2NH_2$, —$CH_2CH_2OH$, —$CH_2CH_2OCH_2CH_2OH$, —$CH_2CH_2OCH_2CH_2OCH_2CH_2OH$, —$CH_2CH_2OCH_2CH_2NH_2$, —$CH_2CH_2OCH_2CH_2OCH_2CH_2NH_2$, and —$CH_2CH_2OCH_2CH_2OCH_2CH_2OCH_2CH_2NH_2$. In yet a further aspect, each of $R^2$ and $R^3$ is independently selected from H, —$CH_2CH_2NH_2$, —$CH_2CH_2OH$, —$CH_2CH_2OCH_2CH_2OH$, —$CH_2CH_2OCH_2CH_2NH_2$, and —$CH_2CH_2OCH_2CH_2OCH_2CH_2NH_2$. In an even further aspect, each of $R^2$ and $R^3$ is independently selected from H, —$CH_2CH_2NH_2$, —$CH_2CH_2OH$, and —$CH_2CH_2OCH_2CH_2NH_2$.

In a further aspect, each of $R^2$ and $R^3$ is independently selected from H and C1-C8 alkyl. In a still further aspect, each of $R^2$ and $R^3$ is independently selected from H and C1-C4 alkyl. In yet a further aspect, each of $R^2$ and $R^3$ is independently selected from H, methyl, ethyl, n-propyl, and i-propyl. In an even further aspect, each of $R^2$ and $R^3$ is independently selected from H, methyl, and ethyl. In a still further aspect, each of $R^2$ and $R^3$ is independently selected from H and ethyl. In yet a further aspect, each of $R^2$ and $R^3$ is independently selected from H and methyl.

In a further aspect, each of $R^2$ and $R^3$ is independently selected from H and —$(CH_2CH_2O)_m$—$CH_2CH_2NH_2$. In a still further aspect, each of $R^2$ and $R^3$ is independently selected from H, —$CH_2CH_2OCH_2CH_2NH_2$, —$CH_2CH_2$ $OCH_2$ $CH_2OCH_2CH_2NH_2$, and —$CH_2CH_2OCH_2$ $CH_2OCH_2CH_2OCH_2CH_2NH_2$. In yet a further aspect, each of $R^2$ and $R^3$ is independently selected from H, —$CH_2CH_2OCH_2CH_2NH_2$, and —$CH_2CH_2OCH_2CH_2OCH_2CH_2NH_2$. In an even further aspect, each of $R^2$ and $R^3$ is independently selected from H and —$CH_2CH_2OCH_2CH_2NH_2$. In a still further aspect, each of $R^2$ and $R^3$ is independently selected from H and —$CH_2CH_2OCH_2CH_2NH_2$.

In a further aspect, $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, or 2 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In yet a further aspect, $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0 or 1 group selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In an even further aspect, $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is monosubstituted with a group selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is unsubstituted.

In a further aspect, $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0 or 1 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 1 further heteroatom selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In yet a further aspect, $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$.

In a further aspect, $R^2$ and $R^3$, together with the intervening N, form a five-membered non-aromatic heterocycle or a six-membered non-aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle or a six-membered non-aromatic heterocycle, wherein the heterocycle contains 0, 1, or 2 further heteroatoms selected from O, N, and S, and wherein the heterocycle is substituted with 0, 1, or 2 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In yet a further aspect, $R^2$ and $R^3$, together with the intervening N, form a five-membered non-aromatic heterocycle or a six-membered non-aromatic heterocycle, wherein the heterocycle contains 0, 1, or 2 further heteroatoms selected from O, N, and S, and wherein the heterocycle is substituted with 0 or 1 group selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In an even further aspect, $R^2$ and $R^3$, together with the intervening N, form a five-membered non-aromatic heterocycle or a six-membered non-aromatic heterocycle, wherein the heterocycle contains 0, 1, or 2 further heteroatoms selected from O, N, and S, and wherein the heterocycle is monosubstituted with a group selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle or a six-membered non-aromatic heterocycle, wherein the heterocycle contains 0, 1, or 2 further heteroatoms selected from O, N, and S, and wherein the heterocycle is unsubstituted.

In a further aspect, $R^2$ and $R^3$, together with the intervening N, form a five-membered non-aromatic heterocycle or a six-membered non-aromatic heterocycle, wherein the heterocycle contains 0 or 1 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle or a six-membered non-aromatic heterocycle, wherein the heterocycle contains 1 further heteroatom selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In yet a further aspect, $R^2$ and $R^3$, together with the intervening N, form a five-membered non-aromatic heterocycle or a six-membered non-aromatic heterocycle, wherein the heterocycle contains 0 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$.

In a further aspect, $R^2$ and $R^3$, together with the intervening N, form a five-membered non-aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle, wherein the heterocycle contains 0, 1, or 2 further heteroatoms selected from O, N, and S, and wherein the heterocycle is substituted with 0, 1, or 2 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In yet a further aspect, $R^2$ and $R^3$, together with the intervening N, form a five-membered non-aromatic heterocycle, wherein the heterocycle contains 0, 1, or 2 further heteroatoms selected from O, N, and S, and wherein the heterocycle is substituted with 0 or 1 group selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In an even further aspect, $R^2$ and $R^3$, together with the intervening N, form a five-membered non-aromatic heterocycle, wherein the heterocycle contains 0, 1, or 2 further heteroatoms selected from O, N, and S, and wherein the heterocycle is monosubstituted with a group selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle, wherein the heterocycle contains 0, 1, or 2 further heteroatoms selected from O, N, and S, and wherein the heterocycle is unsubstituted.

In a further aspect, $R^2$ and $R^3$, together with the intervening N, form a five-membered non-aromatic heterocycle, wherein the heterocycle contains 0 or 1 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$, together with the intervening N, form a five-membered non-aromatic heterocycle, wherein the heterocycle contains 1 further heteroatom selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In yet a further aspect, $R^2$ and $R^3$, together with the intervening N, form a five-membered non-aromatic heterocycle, wherein the heterocycle contains 0 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$.

In a further aspect, $R^2$ and $R^3$ and N together form a five-membered non-aromatic heterocycle substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^2$ and $R^3$ and N together form a five-membered non-aromatic heterocycle substituted with 0, 1, or 2 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In yet a further aspect, $R^2$ and $R^3$ and N together form a five-membered non-aromatic heterocycle substituted with 0 or 1 group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In an even further aspect, R$^2$ and R$^3$ and N together form a five-membered non-aromatic heterocycle monosubstituted with a group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$ and N together form a five-membered non-aromatic heterocycle monosubstituted with a group selected from methyl and —CH$_2$OH. In yet a further aspect, R$^2$ and R$^3$ and N together form an unsubstituted five-membered non-aromatic heterocycle.

In a further aspect, R$^2$ and R$^3$, together with the intervening N, form a six-membered non-aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$, together with the intervening N, form a six-membered non-aromatic heterocycle, wherein the heterocycle contains 0, 1, or 2 further heteroatoms selected from O, N, and S, and wherein the heterocycle is substituted with 0, 1, or 2 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, R$^2$ and R$^3$, together with the intervening N, form a six-membered non-aromatic heterocycle, wherein the heterocycle contains 0, 1, or 2 further heteroatoms selected from O, N, and S, and wherein the heterocycle is substituted with 0 or 1 group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In an even further aspect, R$^2$ and R$^3$, together with the intervening N, form a six-membered non-aromatic heterocycle, wherein the heterocycle contains 0, 1, or 2 further heteroatoms selected from O, N, and S, and wherein the heterocycle is monosubstituted with a group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$, together with the intervening N, form a six-membered non-aromatic heterocycle, wherein the heterocycle contains 0, 1, or 2 further heteroatoms selected from O, N, and S, and wherein the heterocycle is unsubstituted.

In a further aspect, R$^2$ and R$^3$, together with the intervening N, form a six-membered non-aromatic heterocycle, wherein the heterocycle contains 0 or 1 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$, together with the intervening N, form a six-membered non-aromatic heterocycle, wherein the heterocycle contains 1 further heteroatom selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, R$^2$ and R$^3$, together with the intervening N, form a six-membered non-aromatic heterocycle, wherein the heterocycle contains 0 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH.

In a further aspect, R$^2$ and R$^3$ and N together form a six-membered non-aromatic heterocycle substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$ and N together form a six-membered non-aromatic heterocycle substituted with 0, 1, or 2 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, R$^2$ and R$^3$ and N together form a six-membered non-aromatic heterocycle substituted with 0 or 1 group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In an even further aspect, R$^2$ and R$^3$ and N together form a six-membered non-aromatic heterocycle monosubstituted with a group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$ and N together form a six-membered non-aromatic heterocycle monosubstituted with a group selected from methyl and —CH$_2$OH. In yet a further aspect, R$^2$ and R$^3$ and N together form an unsubstituted six-membered non-aromatic heterocycle.

In a further aspect, R$^2$ and R$^3$, together with the intervening N, form a five-membered aromatic heterocycle or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$, together with the intervening N, form a five-membered aromatic heterocycle or a six-membered aromatic heterocycle, wherein the heterocycle contains 0, 1, or 2 further heteroatoms selected from O, N, and S, and wherein the heterocycle is substituted with 0, 1, or 2 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, R$^2$ and R$^3$, together with the intervening N, form a five-membered aromatic heterocycle or a six-membered aromatic heterocycle, wherein the heterocycle contains 0, 1, or 2 further heteroatoms selected from O, N, and S, and wherein the heterocycle is substituted with 0 or 1 group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In an even further aspect, R$^2$ and R$^3$, together with the intervening N, form a five-membered aromatic heterocycle or a six-membered aromatic heterocycle, wherein the heterocycle contains 0, 1, or 2 further heteroatoms selected from O, N, and S, and wherein the heterocycle is monosubstituted with a group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$, together with the intervening N, form a five-membered aromatic heterocycle or a six-membered aromatic heterocycle, wherein the heterocycle contains 0, 1, or 2 further heteroatoms selected from O, N, and S, and wherein the heterocycle is unsubstituted.

In a further aspect, $R^2$ and $R^3$, together with the intervening N, form a five-membered aromatic heterocycle or a six-membered aromatic heterocycle, wherein the heterocycle contains 0 or 1 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, $R^2$ and $R^3$, together with the intervening N, form a five-membered aromatic heterocycle or a six-membered aromatic heterocycle, wherein the heterocycle contains 1 further heteroatom selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, $R^2$ and $R^3$, together with the intervening N, form a five-membered aromatic heterocycle or a six-membered aromatic heterocycle, wherein the heterocycle contains 0 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH.

In a further aspect, $R^2$ and $R^3$, together with the intervening N, form a five-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, $R^2$ and $R^3$, together with the intervening N, form a five-membered aromatic heterocycle, wherein the heterocycle contains 0, 1, or 2 further heteroatoms selected from O, N, and S, and wherein the heterocycle is substituted with 0, 1, or 2 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, $R^2$ and $R^3$, together with the intervening N, form a five-membered aromatic heterocycle, wherein the heterocycle contains 0, 1, or 2 further heteroatoms selected from O, N, and S, and wherein the heterocycle is substituted with 0 or 1 group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In an even further aspect, $R^2$ and $R^3$, together with the intervening N, form a five-membered aromatic heterocycle, wherein the heterocycle contains 0, 1, or 2 further heteroatoms selected from O, N, and S, and wherein the heterocycle is monosubstituted with a group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, $R^2$ and $R^3$, together with the intervening N, form a five-membered aromatic heterocycle, wherein the heterocycle contains 0, 1, or 2 further heteroatoms selected from O, N, and S, and wherein the heterocycle is unsubstituted.

In a further aspect, $R^2$ and $R^3$, together with the intervening N, form a five-membered aromatic heterocycle, wherein the heterocycle contains 0 or 1 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, $R^2$ and $R^3$, together with the intervening N, form a five-membered aromatic heterocycle, wherein the heterocycle contains 1 further heteroatom selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, $R^2$ and $R^3$, together with the intervening N, form a five-membered aromatic heterocycle, wherein the heterocycle contains 0 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH.

In a further aspect, $R^2$ and $R^3$ and N together form a five-membered aromatic heterocycle substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, $R^2$ and $R^3$ and N together form a five-membered aromatic heterocycle substituted with 0, 1, or 2 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, $R^2$ and $R^3$ and N together form a five-membered aromatic heterocycle substituted with 0 or 1 group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In an even further aspect, $R^2$ and $R^3$ and N together form a five-membered aromatic heterocycle monosubstituted with a group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, $R^2$ and $R^3$ and N together form a five-membered aromatic heterocycle monosubstituted with a group selected from methyl and —CH$_2$OH. In yet a further aspect, $R^2$ and $R^3$ and N together form an unsubstituted five-membered aromatic heterocycle.

In a further aspect, $R^2$ and $R^3$, together with the intervening N, form a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, $R^2$ and $R^3$, together with the intervening N, form a six-membered aromatic heterocycle, wherein the heterocycle contains 0, 1, or 2 further heteroatoms selected from O, N, and S, and wherein the heterocycle is substituted with 0, 1, or 2 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, $R^2$ and $R^3$, together with the intervening N, form a six-membered aromatic heterocycle, wherein the heterocycle contains 0, 1, or 2 further heteroatoms selected from O, N, and S, and wherein the heterocycle is substituted with 0 or 1 group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In an even further aspect, $R^2$ and $R^3$, together with the intervening N, form a six-membered aromatic heterocycle, wherein the heterocycle contains 0, 1, or 2 further heteroatoms selected from O, N, and S, and wherein the heterocycle is monosubstituted with a group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$, together with the intervening N, form a six-membered aromatic heterocycle, wherein the heterocycle contains 0, 1, or 2 further heteroatoms selected from O, N, and S, and wherein the heterocycle is unsubstituted.

In a further aspect, R$^2$ and R$^3$, together with the intervening N, form a six-membered aromatic heterocycle, wherein the heterocycle contains 0 or 1 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$, together with the intervening N, form a six-membered aromatic heterocycle, wherein the heterocycle contains 1 further heteroatom selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, R$^2$ and R$^3$, together with the intervening N, form a six-membered aromatic heterocycle, wherein the heterocycle contains 0 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH.

In a further aspect, R$^2$ and R$^3$ and N together form a six-membered aromatic heterocycle substituted with 0, 1, 2, or 3 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$ and N together form a six-membered aromatic heterocycle substituted with 0, 1, or 2 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In yet a further aspect, R$^2$ and R$^3$ and N together form a six-membered aromatic heterocycle substituted with 0 or 1 group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In an even further aspect, R$^2$ and R$^3$ and N together form a six-membered aromatic heterocycle monosubstituted with a group selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH. In a still further aspect, R$^2$ and R$^3$ and N together form a six-membered aromatic heterocycle monosubstituted with a group selected from methyl and —CH$_2$OH. In yet a further aspect, R$^2$ and R$^3$ and N together form an unsubstituted six-membered aromatic heterocycle.

c. R$^4$ and R$^5$ Groups

In one aspect, each of R$^4$ and R$^5$ is independently selected from H, C1-C8 alkyl, benzyl, —(CH$_2$CH$_2$O)$_m$—H wherein m is 1, 2, 3, or 4, —(CH$_2$CH$_2$O)$_p$—CH$_2$CH$_2$NH$_2$ wherein p is 0, 1, 2, 3, or 4, —CH$_2$CCH, and a moiety having the structure:

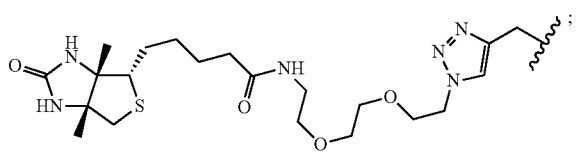 [SMILES: *Cc1cn(CCOCCOCCNC(=O)CCCC[C@@H]2SC[C@]3(C)NC(=O)N[C@]23C)nn1]

or wherein R$^4$ and R$^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —NH$_2$, —NHCH$_3$, —N(CH$_3$)$_2$, —CH$_2$OH, and —CH$_2$CH$_2$OH.

In a further aspect, each of R$^4$ and R$^5$ is independently selected from H, C1-C8 alkyl, benzyl, —(CH$_2$CH$_2$O)$_m$—H wherein m is 1, 2, 3, and 4, —(CH$_2$CH$_2$O)$_p$—CH$_2$CH$_2$NH$_2$ wherein p is 0, 1, 2, 3, and 4, —CH$_2$CCH, and a moiety having the structure:

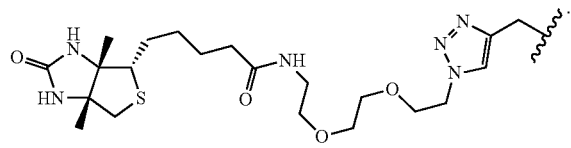

In a still further aspect, each of R$^4$ and R$^5$ is independently selected from H, C1-C4 alkyl, benzyl, —CH$_2$CH$_2$OH, —CH$_2$CH$_2$OCH$_2$CH$_2$OH, —CH$_2$CH$_2$OCH$_2$CH$_2$OCH$_2$CH$_2$OH, —CH$_2$CH$_2$NH$_2$, —CH$_2$CH$_2$OCH$_2$CH$_2$NH$_2$, —CH$_2$CH$_2$OCH$_2$CH$_2$OCH$_2$CH$_2$NH$_2$, —CH$_2$CH$_2$OCH$_2$CH$_2$OCH$_2$CH$_2$OCH$_2$CH$_2$NH$_2$, —CH$_2$CCH, and a moiety having the structure:

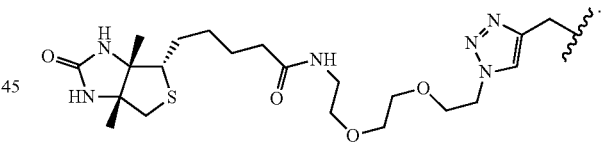

In yet a further aspect, each of R$^4$ and R$^5$ is independently selected from H, methyl, ethyl, n-propyl, i-propyl, benzyl, —CH$_2$CH$_2$OH, —CH$_2$CH$_2$OCH$_2$CH$_2$OH, —CH$_2$CH$_2$NH$_2$, —CH$_2$CH$_2$OCH$_2$CH$_2$NH$_2$, —CH$_2$CH$_2$OCH$_2$CH$_2$OCH$_2$CH$_2$NH$_2$, —CH$_2$CCH, and a moiety having the structure:

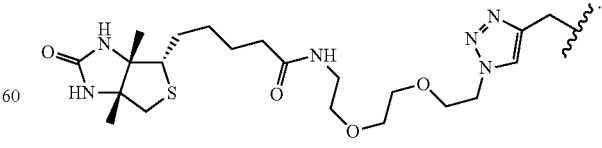

In an even further aspect, each of R$^4$ and R$^5$ is independently selected from H, methyl, ethyl, benzyl, —CH$_2$CH$_2$OH, —CH$_2$CH$_2$NH$_2$, —CH$_2$CH$_2$OCH$_2$CH$_2$NH$_2$, —CH$_2$CCH, and a moiety having the structure:

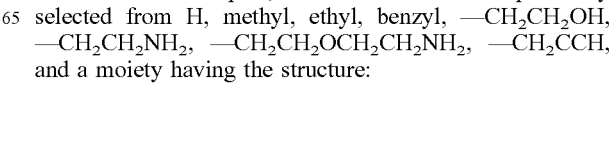

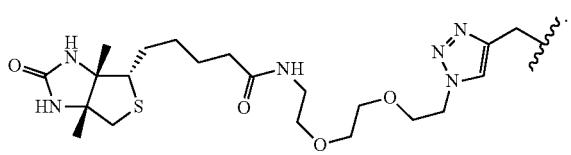 [SMILES: *Cc1cn(CCOCCOCCNC(=O)CCCC[C@@H]2SC[C@]3(C)NC(=O)N[C@]23C)nn1]

In a still further aspect, each of $R^4$ and $R^5$ is independently selected from H, methyl, benzyl, —$CH_2CH_2OH$, —$CH_2CH_2NH_2$, —$CH_2CCH$, and a moiety having the structure:

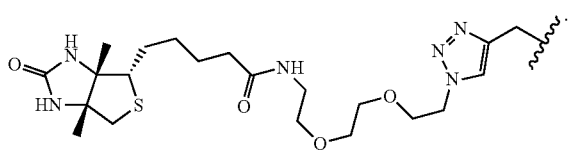

In a further aspect, each of $R^4$ and $R^5$ is independently selected from H, C1-C8 alkyl, benzyl, —$(CH_2CH_2O)_m$—H wherein m is 1, 2, 3, and 4, —$(CH_2CH_2O)_p$—$CH_2CH_2NH_2$ wherein p is 0, 1, 2, 3, and 4, and —$CH_2CCH$. In a still further aspect, each of $R^4$ and $R^5$ is independently selected from H, C1-C4 alkyl, benzyl, —$CH_2CH_2OH$, —$CH_2CH_2OCH_2CH_2OH$, —$CH_2CH_2OCH_2CH_2OCH_2CH_2OH$, —$CH_2CH_2NH_2$, —$CH_2CH_2OCH_2CH_2NH_2$, —$CH_2CH_2OCH_2CH_2OCH_2CH_2NH_2$, —$CH_2CH_2OCH_2CH_2$ $OCH_2CH_2OCH_2CH_2NH_2$, and —$CH_2CCH$. In yet a further aspect, each of $R^4$ and $R^5$ is independently selected from H, methyl, ethyl, n-propyl, i-propyl, benzyl, —$CH_2CH_2OH$, —$CH_2CH_2OCH_2CH_2OH$, —$CH_2CH_2NH_2$, —$CH_2CH_2OCH_2CH_2NH_2$, —$CH_2CH_2OCH_2CH_2OCH_2CH_2NH_2$, and —$CH_2CCH$. In an even further aspect, each of $R^4$ and $R^5$ is independently selected from H, methyl, ethyl, benzyl, —$CH_2CH_2OH$, —$CH_2CH_2NH_2$, —$CH_2CH_2OCH_2CH_2NH_2$, and —$CH_2CCH$. In a still further aspect, each of $R^4$ and $R^5$ is independently selected from H, methyl, benzyl, —$CH_2CH_2OH$, —$CH_2CH_2NH_2$, and —$CH_2CCH$.

In a further aspect, each of $R^4$ and $R^5$ is independently selected from H, C1-C8 alkyl, benzyl, and —$CH_2CCH$. In a still further aspect, each of $R^4$ and $R^5$ is independently selected from H, C1-C4 alkyl, benzyl, and —$CH_2CCH$. In yet a further aspect, each of $R^4$ and $R^5$ is independently selected from H, methyl, ethyl, n-propyl, i-propyl, benzyl, and —$CH_2CCH$. In an even further aspect, each of $R^4$ and $R^5$ is independently selected from H, methyl, ethyl, benzyl, and —$CH_2CCH$. In a still further aspect, each of $R^4$ and $R^5$ is independently selected from H, methyl, benzyl, and —$CH_2CCH$.

In a further aspect, each of $R^4$ and $R^5$ is independently selected from H and —$CH_2CCH$.

In a further aspect, each of $R^4$ and $R^5$ is independently selected from H, C1-C8 alkyl, and benzyl. In a still further aspect, each of $R^4$ and $R^5$ is independently selected from H, C1-C4 alkyl, and benzyl. In yet a further aspect, each of $R^4$ and $R^5$ is independently selected from H, methyl, ethyl, n-propyl, i-propyl, and benzyl. In an even further aspect, each of $R^4$ and $R^5$ is independently selected from H, methyl, ethyl, and benzyl. In a still further aspect, each of $R^4$ and $R^5$ is independently selected from H, methyl, and benzyl.

In a further aspect, each of $R^4$ and $R^5$ is independently selected from C1-C8 alkyl and benzyl. In a still further aspect, each of $R^4$ and $R^5$ is independently selected from methyl, ethyl, n-propyl, isopropyl, n-butyl, isobutyl, sec-butyl, tert-butyl, and benzyl. In yet a further aspect, each of $R^4$ and $R^5$ is independently selected from methyl, ethyl, n-propyl, isopropyl, n-butyl, isobutyl, and benzyl. In an even further aspect, each of $R^4$ and $R^5$ is independently selected from methyl, ethyl, n-propyl, isopropyl, and benzyl. In an even further aspect, each of $R^4$ and $R^5$ is independently selected from methyl, ethyl, and benzyl. In a still further aspect, each of $R^4$ and $R^5$ is independently selected from methyl and benzyl. In yet a further aspect, each of $R^4$ and $R^5$ is independently selected from ethyl and benzyl.

In a further aspect, each of $R^4$ and $R^5$ is C1-C8 alkyl. In a still further aspect, each of $R^4$ and $R^5$ is independently selected from methyl, ethyl, n-propyl, isopropyl, n-butyl, isobutyl, sec-butyl, and tert-butyl. In yet a further aspect, each of $R^4$ and $R^5$ is independently selected from methyl, ethyl, n-propyl, isopropyl, n-butyl, and isobutyl. In an even further aspect, each of $R^4$ and $R^5$ is independently selected from methyl, ethyl, n-propyl, and isopropyl. In an even further aspect, each of $R^4$ and $R^5$ is independently selected from methyl and ethyl. In a still further aspect, each of $R^4$ and $R^5$ is methyl. In yet a further aspect, each of $R^4$ and $R^5$ is ethyl.

In a further aspect, each of $R^4$ and $R^5$ is independently selected from H, —$(CH_2CH_2O)_m$—H wherein m is 1, 2, 3, and 4, and —$(CH_2CH_2O)_p$—$CH_2CH_2NH_2$ wherein p is 0, 1, 2, 3, and 4. In a still further aspect, each of $R^4$ and $R^5$ is independently selected from H, —$CH_2CH_2OH$, —$CH_2CH_2OCH_2CH_2OH$, —$CH_2CH_2OCH_2CH_2OCH_2CH_2OH$, —$CH_2CH_2NH_2$, —$CH_2CH_2OCH_2CH_2NH_2$, —$CH_2CH_2OCH_2CH_2OCH_2CH_2NH_2$, and —$CH_2CH_2OCH_2CH_2OCH_2CH_2OCH_2CH_2NH_2$. In yet a further aspect, each of $R^4$ and $R^5$ is independently selected from H, —$CH_2CH_2OH$, —$CH_2CH_2OCH_2CH_2OH$, —$CH_2CH_2NH_2$, —$CH_2CH_2OCH_2 CH_2NH_2$, and —$CH_2CH_2OCH_2CH_2OCH_2CH_2NH_2$. In an even further aspect, each of $R^4$ and $R^5$ is independently selected from H, —$CH_2CH_2OH$, —$CH_2CH_2NH_2$, and —$CH_2CH_2OCH_2CH_2NH_2$. In a still further aspect, each of $R^4$ and $R^5$ is independently selected from H, —$CH_2CH_2OH$, and —$CH_2CH_2NH_2$.

In a further aspect, each of $R^4$ and $R^5$ is a moiety having the structure:

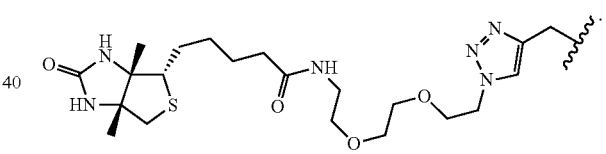

In a further aspect, $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In a still further aspect, $R^4$ and $R^5$, together with the intervening atoms, form a five-membered heterocycle or a six-membered heterocycle, wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In yet a further aspect, $R^4$ and $R^5$, together with the intervening atoms, form a five-membered heterocycle or a six-membered heterocycle, wherein the heterocycle is substituted with 0, 1, or 2 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$. In an even further aspect, $R^4$ and $R^5$, together with the intervening atoms, form a five-membered heterocycle or a six-membered heterocycle, wherein the heterocycle is substituted with 0 or 1 group selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —CH₂CH₂OH. In a still further aspect, R⁴ and R⁵, together with the intervening atoms, form a five-membered heterocycle or a six-membered heterocycle, wherein the heterocycle is monosubstituted with a group selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In yet a further aspect, R⁴ and R⁵, together with the intervening atoms, form a five-membered heterocycle or a six-membered heterocycle, wherein the heterocycle is unsubstituted.

In a further aspect, R⁴ and R⁵, together with the intervening atoms, form a five-membered heterocycle substituted with 0, 1, 2, 3, or 4 groups independently selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In a still further aspect, R⁴ and R⁵, together with the intervening atoms, form a five-membered heterocycle substituted with 0, 1, 2, or 3 groups independently selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In yet a further aspect, R⁴ and R⁵, together with the intervening atoms, form a five-membered heterocycle substituted with 0, 1, or 2 groups independently selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In an even further aspect, R⁴ and R⁵, together with the intervening atoms, form a five-membered heterocycle substituted with 0 or 1 group selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In a still further aspect, R⁴ and R⁵, together with the intervening atoms, form a five-membered heterocycle monosubstituted with a group selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In yet a further aspect, R⁴ and R⁵, together with the intervening atoms, form an unsubstituted five-membered heterocycle.

In a further aspect, R⁴ and R⁵, together with the intervening atoms, form a six-membered heterocycle substituted with 0, 1, 2, 3, or 4 groups independently selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In a still further aspect, R⁴ and R⁵, together with the intervening atoms, form a six-membered heterocycle substituted with 0, 1, 2, or 3 groups independently selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In yet a further aspect, R⁴ and R⁵, together with the intervening atoms, form a six-membered heterocycle substituted with 0, 1, or 2 groups independently selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In an even further aspect, R⁴ and R⁵, together with the intervening atoms, form a six-membered heterocycle substituted with 0 or 1 group selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In a still further aspect, R⁴ and R⁵, together with the intervening atoms, form a six-membered heterocycle monosubstituted with a group selected from methyl, ethyl, n-propyl, isopropyl, hydroxyl, fluoro, chloro, bromo, iodo, —NH₂, —NHCH₃, —N(CH₃)₂, —CH₂OH, and —CH₂CH₂OH. In yet a further aspect, R⁴ and R⁵, together with the intervening atoms, form an unsubstituted six-membered heterocycle.

In a further aspect, R⁴ and R⁵ are together isopropylidene.

2. Example Compounds

In one aspect, a compound can be present as one or more of the following structures:

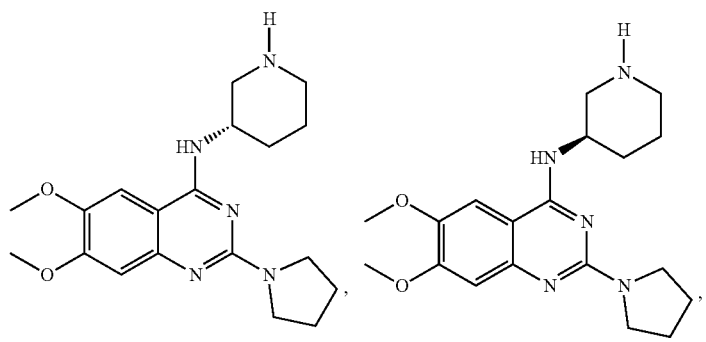

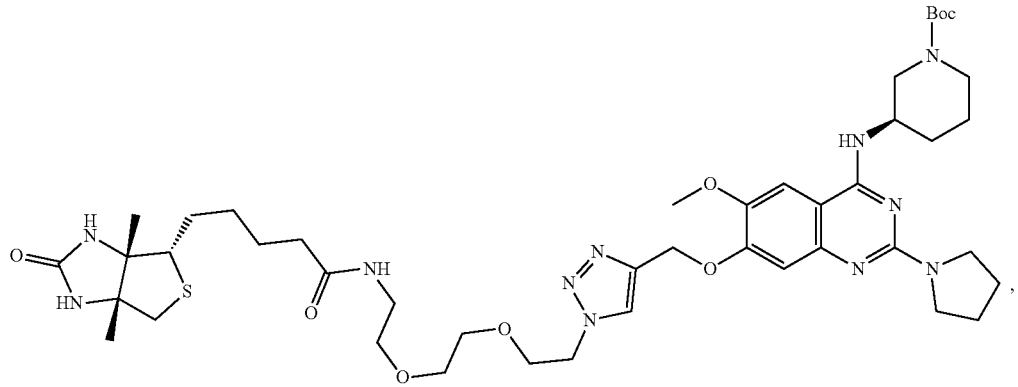

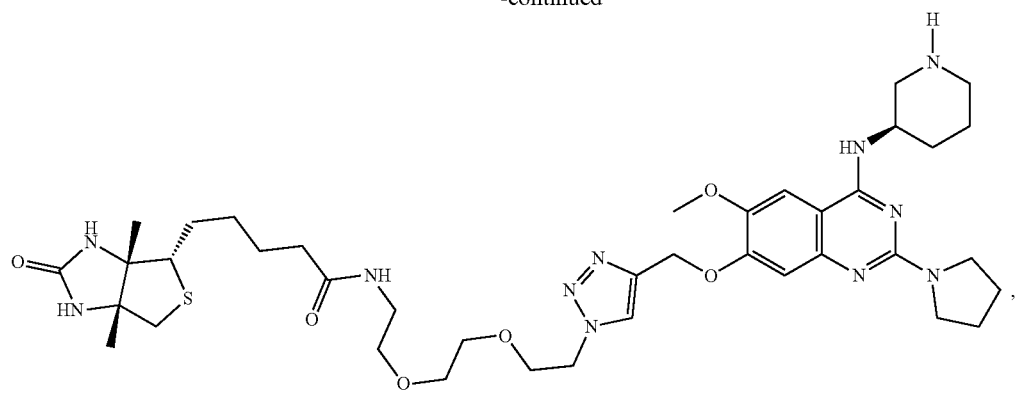
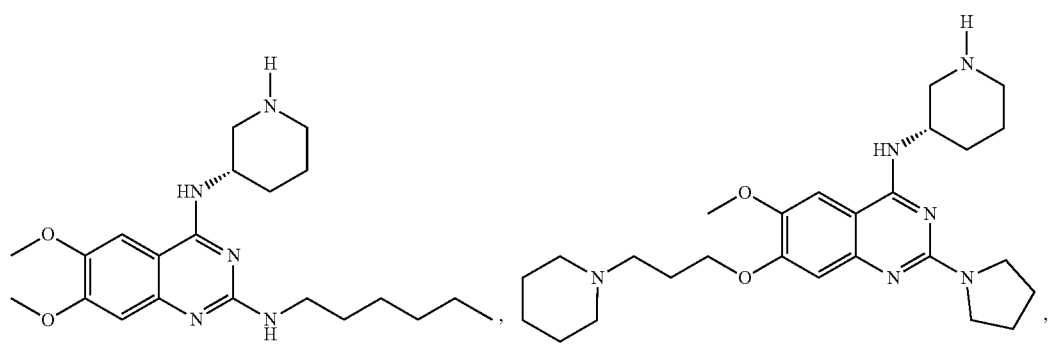
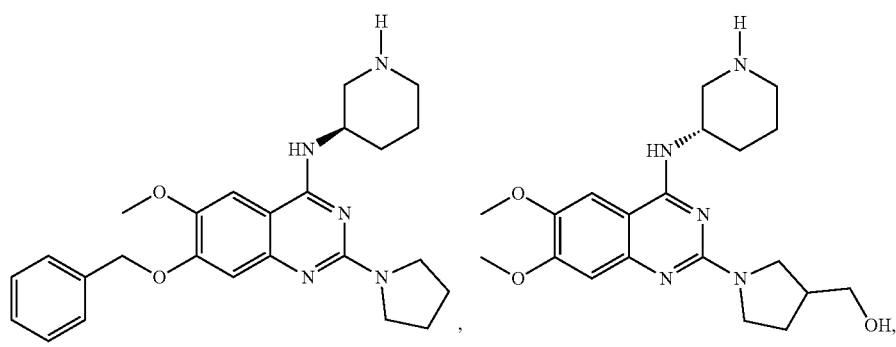
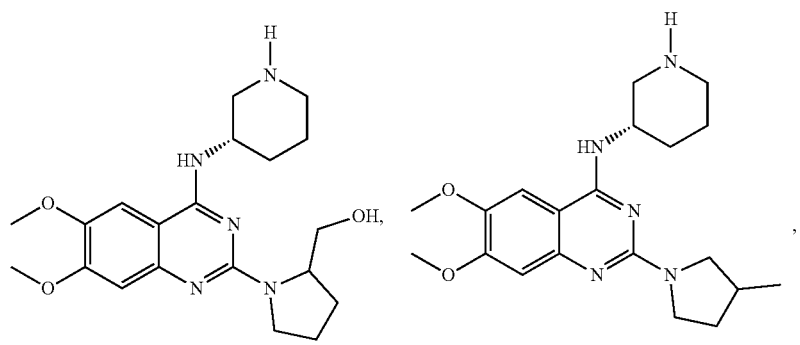

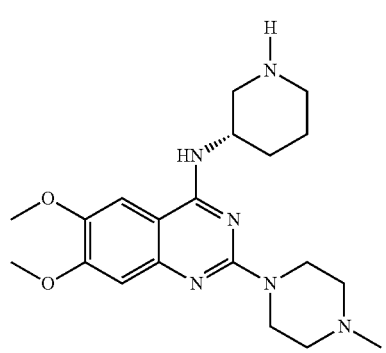 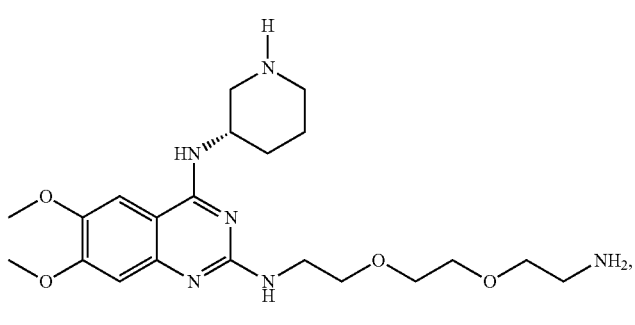
, and
or a pharmaceutically acceptable salt thereof.
In one aspect, a compound can be present as one or more of the following structures:
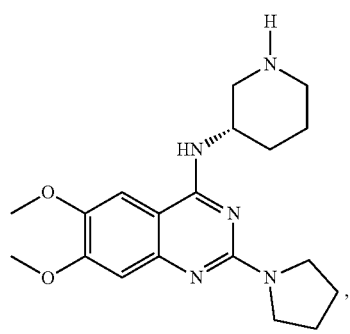 [SMILES: COc1cc2nc(N3CCCC3)nc(N[C@H]3CCCNC3)c2cc1OC] 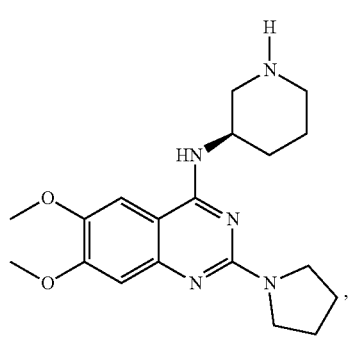
,
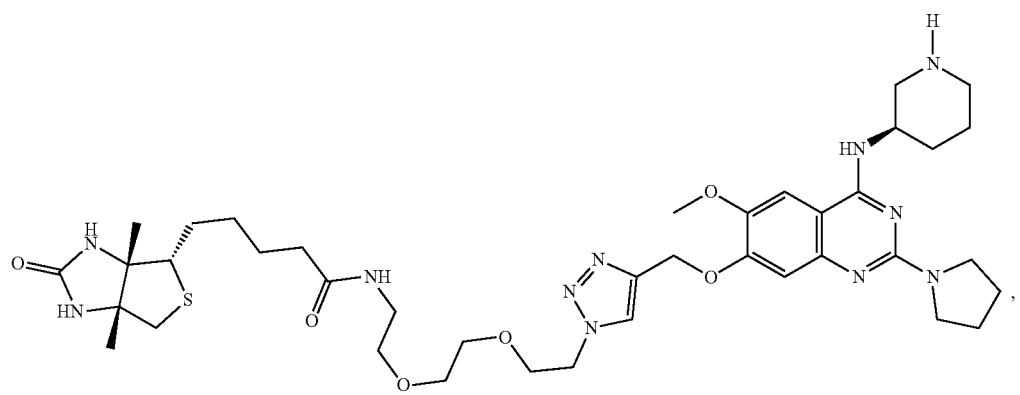
,
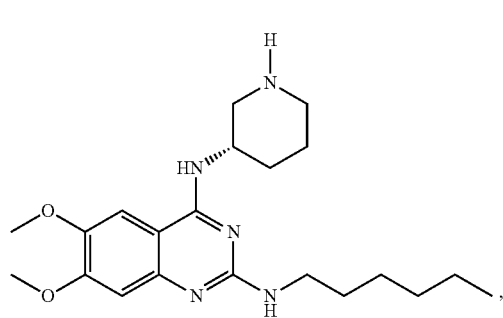 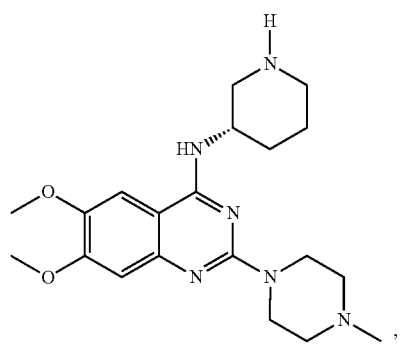
,

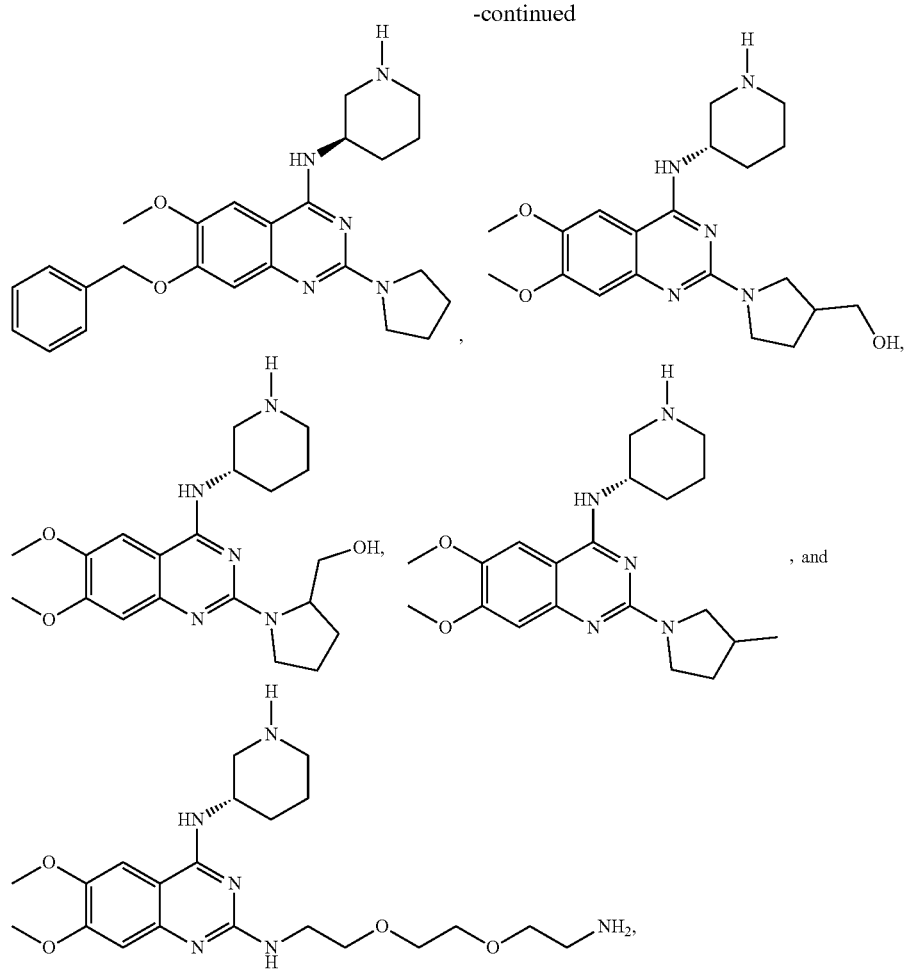

or a pharmaceutically acceptable salt thereof.

In one aspect, a compound can be present as the following structure:

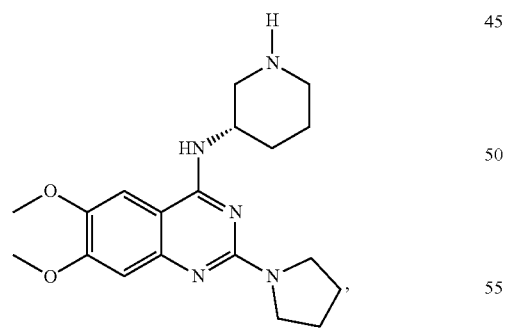

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of HP1-mediated heterochromatin formation, and such activity can be determined using the assay methods described herein.

In one aspect, a compound can be selected from:
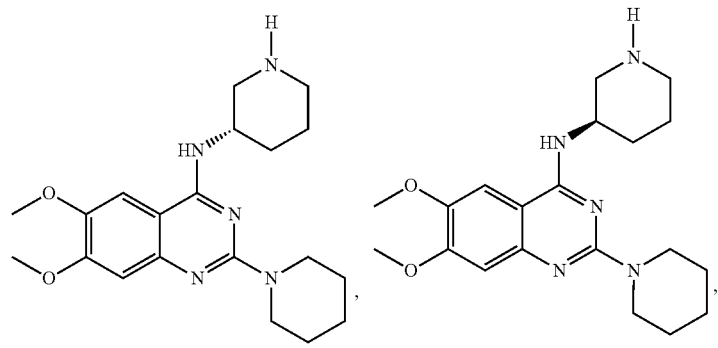
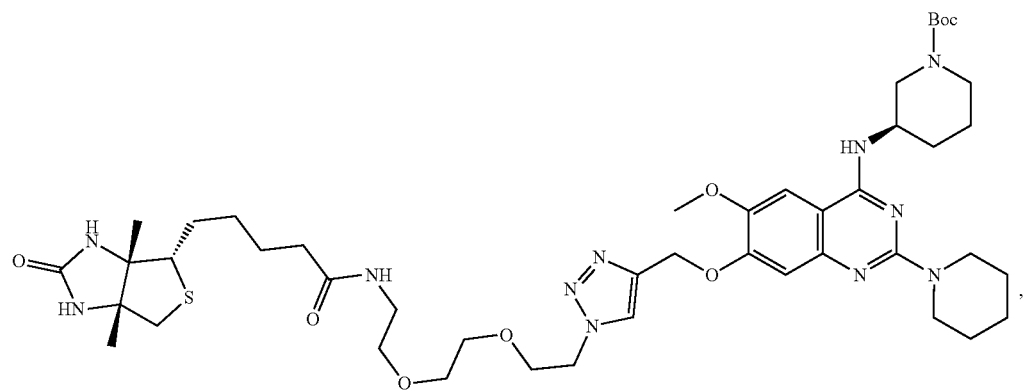
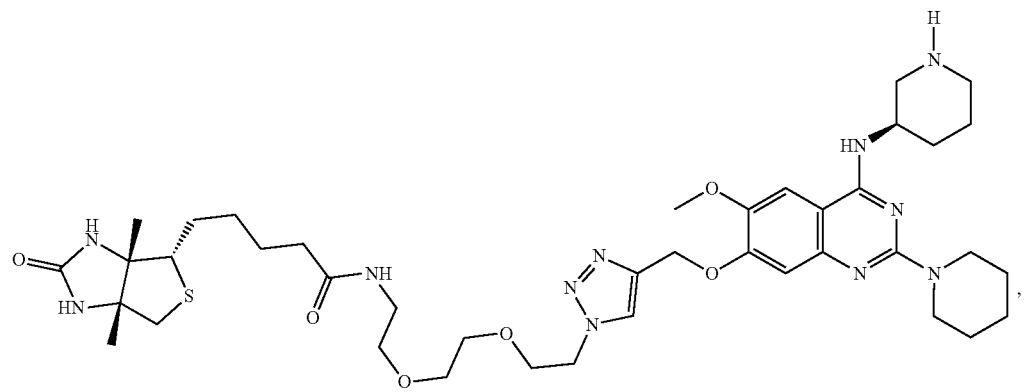
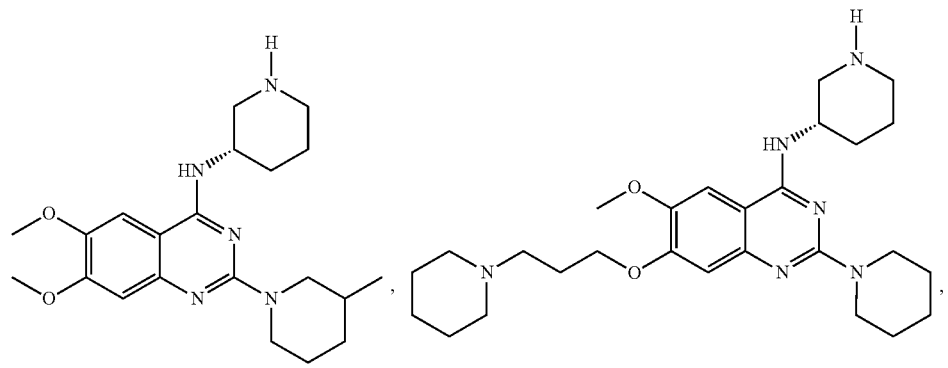

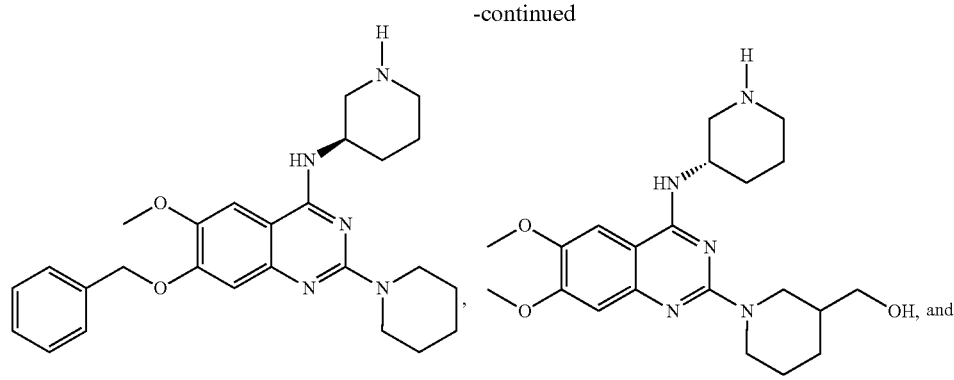
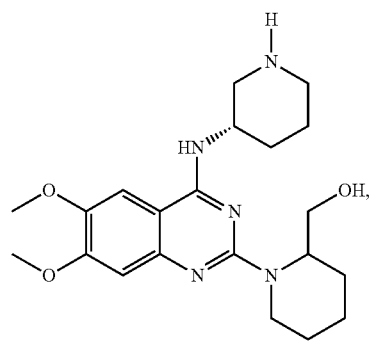
or a pharmaceutically acceptable derivative thereof.
In one aspect, a compound can be selected from:
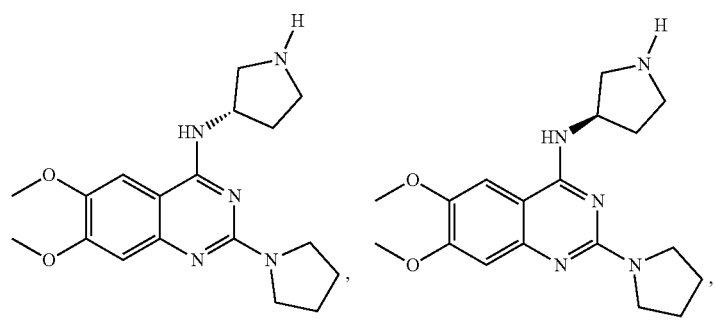
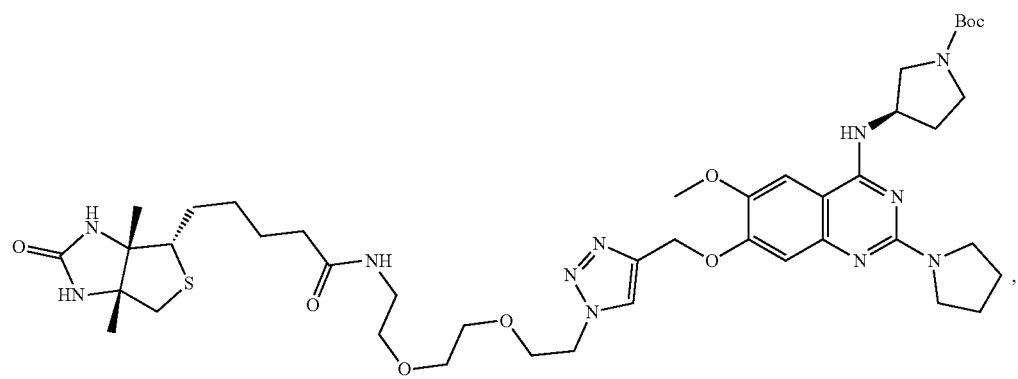

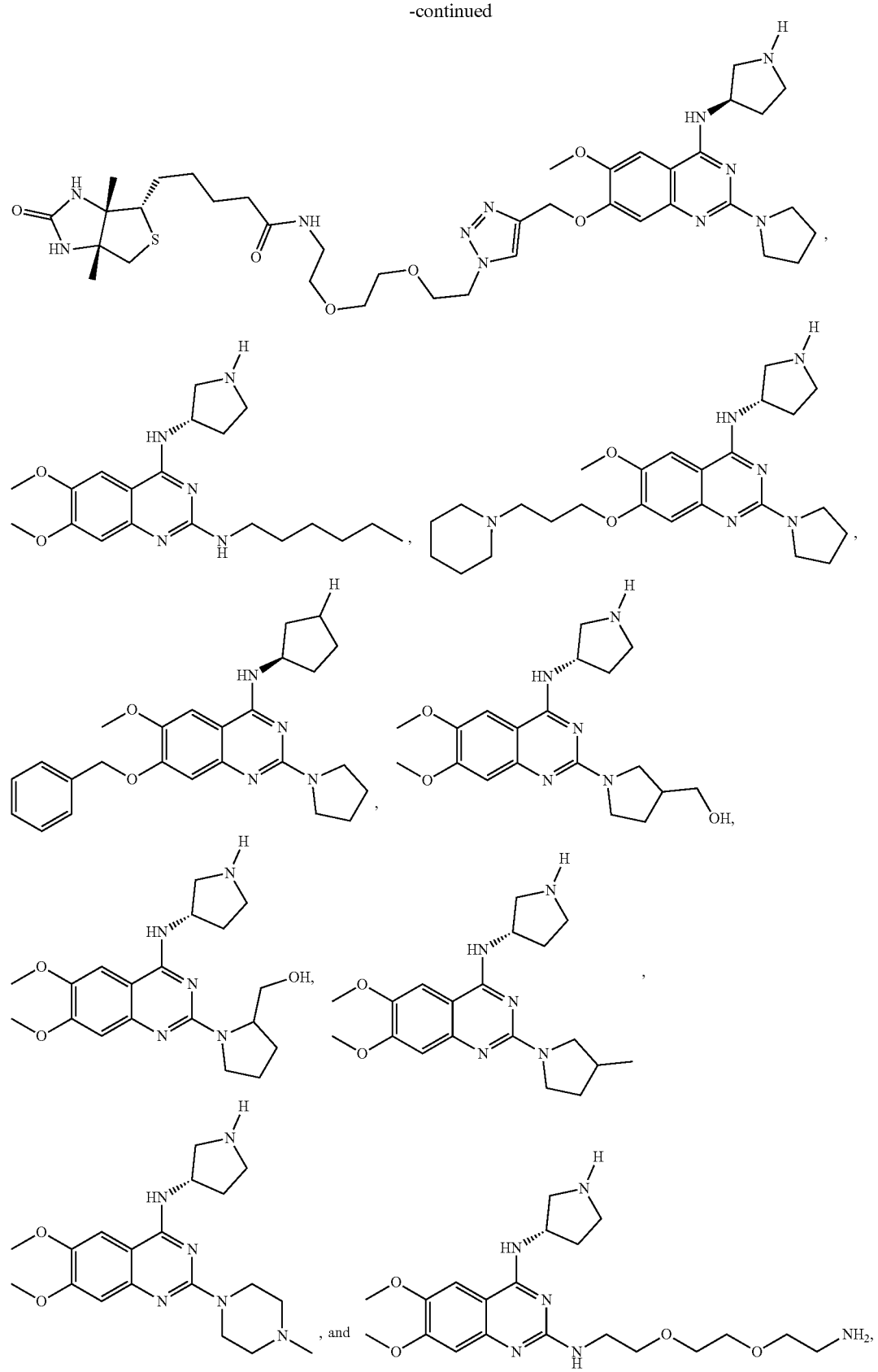
or a pharmaceutically acceptable derivative thereof.

C. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I and Route II, as described and exemplified below. The following examples are provided so that the invention can be more fully understood, are illustrative only, and should not be construed as limiting.

1. Route I

In one aspect, 6,7-disubstituted quinazolin-4-amine derivatives can be prepared as shown below.

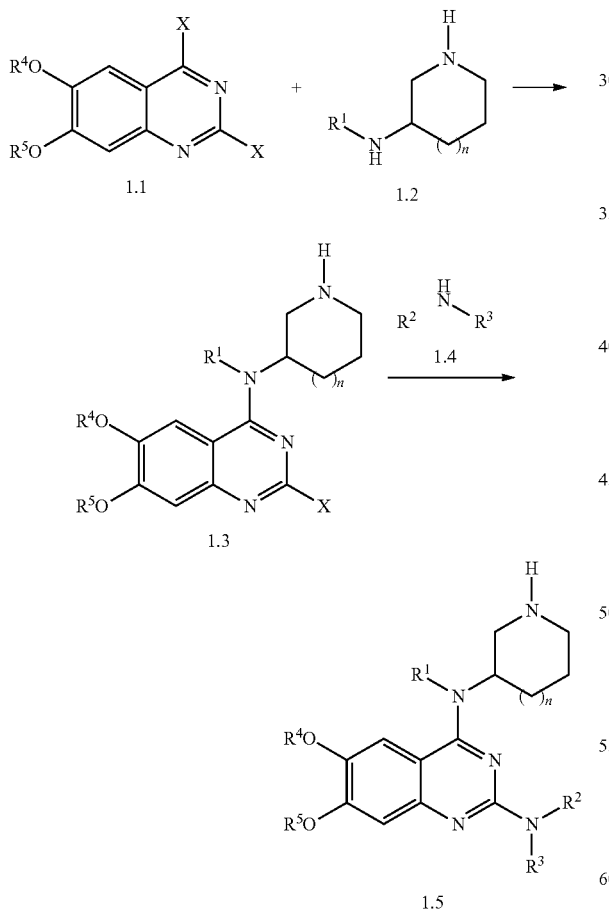

Compounds are represented in generic form, with substituents as noted in compound descriptions elsewhere herein; wherein X is halogen. A more specific example is set forth below.

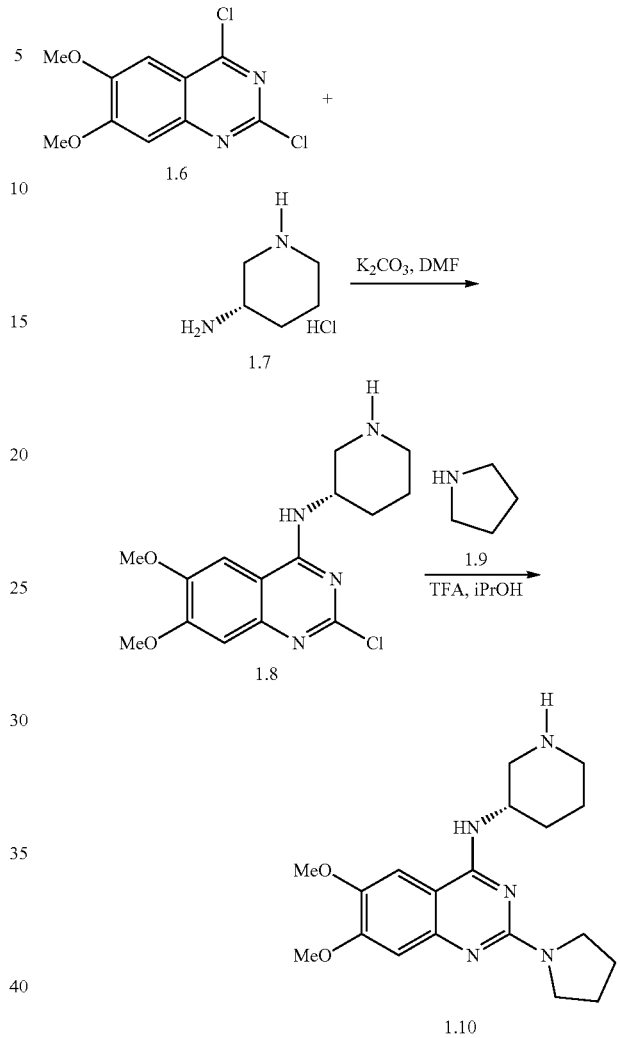

In one aspect, compounds of type 1.10, and similar compounds, can be prepared according to reaction Scheme 1B above. Thus, compounds of type 1.8 can be prepared by a substitution reaction of an appropriate aryl halide, e.g., 1.6 as shown above, and an appropriate amine, e.g., 1.7 as shown above. Appropriate aryl halides and appropriate amines are commercially available or prepared by methods known to one skilled in the art. The substitution reaction is carried out in the presence of an appropriate base, e.g., potassium carbonate, in an appropriate solvent, e.g., dimethylformamide. Compounds of type 1.10 can be prepared by a substitution reaction between an appropriate aryl halide, e.g., 1.8 as shown above, and an appropriate amine, e.g., 1.9 as shown above. Appropriate amines are commercially available or prepared by methods known to one skilled in the art. The substitution reaction is carried out in the presence of an appropriate acid, e.g., trifluoroacetic acid (TFA), in an appropriate solvent, e.g., isopropyl alcohol. As can be appreciated by one skilled in the art, the above reaction provides an example of a generalized approach wherein compounds similar in structure to the specific reactants above (compounds similar to compounds of type 1.1, 1.2, 1.3, and 1.4), can be substituted in the reaction to provide 6,7-disubstituted quinazolin-4-amine derivatives similar to Formula 1.5.

2. Route II

In one aspect, 6,7-disubstituted quinazolin-4-amine derivatives can be prepared as shown below.

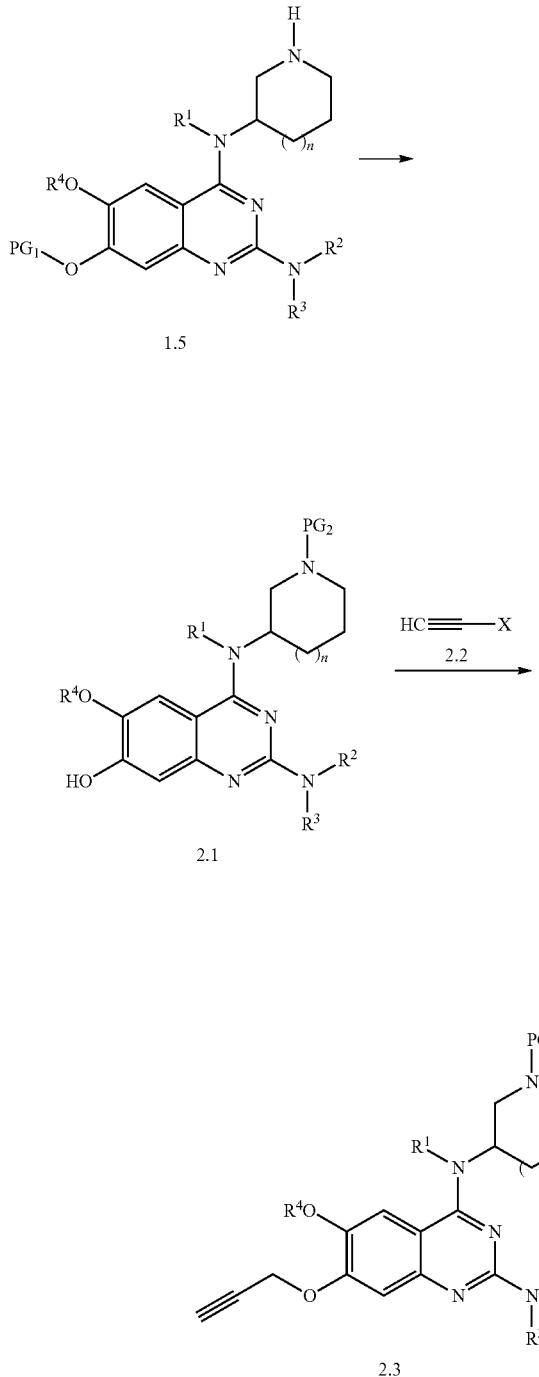

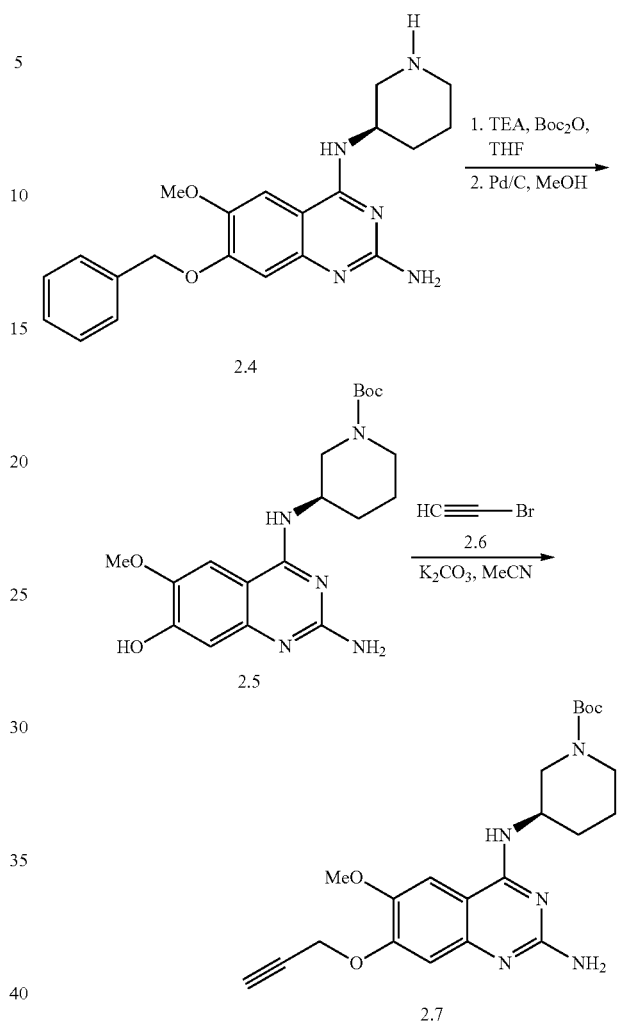

In one aspect, compounds of type 2.7, and similar compounds, can be prepared according to reaction Scheme 2B above. Thus, compounds of type 2.5 can be prepared by protection reaction, followed by a deprotection reaction of an appropriate quinazoline derivative, e.g., 2.4 as shown above. The protection reaction is carried out in the presence of an appropriate protecting group agent, e.g., di-tert-butyl dicarbonate, and an appropriate base, e.g., triethylamine (TEA), in an appropriate solvent, e.g., tetrahydrofuran (THF). The deprotection reaction is carried out in the presence of an appropriate catalyst, e.g., Pd/C, in an appropriate protic solvent, e.g., methanol. Compounds of type 2.7 can be prepared by an alkylation reaction between an appropriate alcohol, e.g., 2.5 as shown above, and an appropriate alkyl halide, e.g., 2.4 as shown above. Appropriate alkyl halides are commercially available or prepared by methods known to one skilled in the art. The alkylation reaction is carried out in the presence of an appropriate base, e.g., potassium carbonate, in an appropriate solvent, e.g., acetonitrile. As can be appreciated by one skilled in the art, the above reaction provides an example of a generalized approach wherein compounds similar in structure to the specific reactants above (compounds similar to compounds of type 1.5, 2.1, and 2.2), can be substituted in the reaction to provide 6,7-disubstituted quinazolin-4-amine derivatives similar to Formula 2.3.

Compounds are represented in generic form, with substituents as noted in compound descriptions elsewhere herein; wherein each of $PG_1$ is an alcohol protecting group, $PG_2$ is an amine protecting group, and X is halogen. Suitable alcohol and amine protecting groups are known to one skilled in the art. A more specific example is set forth below.

3. Route III

In one aspect, 6,7-disubstituted quinazolin-4-amine derivatives can be prepared as shown below.

SCHEME 3A.

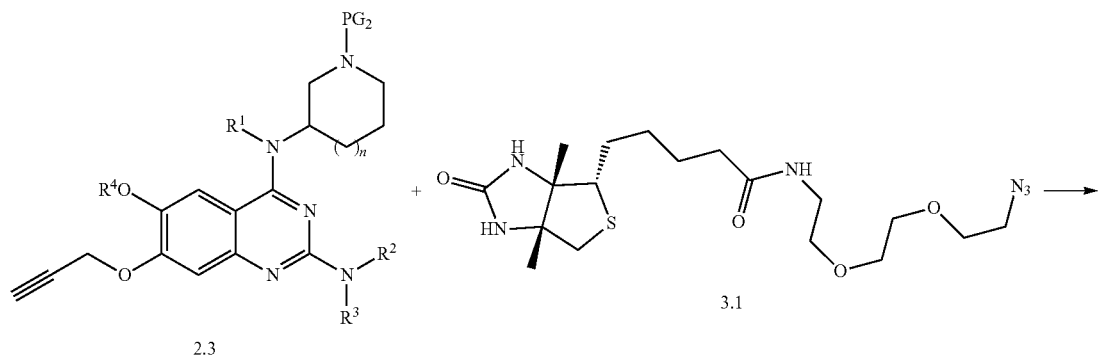

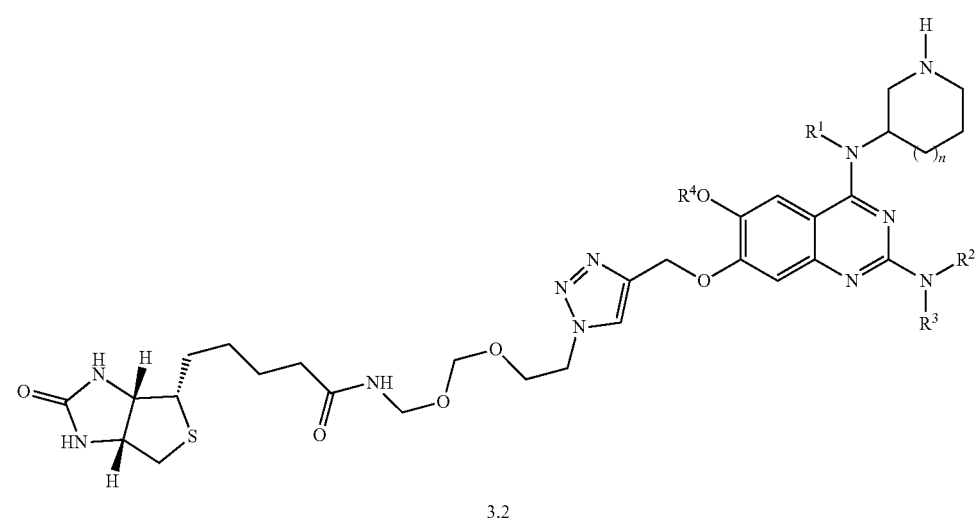

Compounds are represented in generic form, with substituents as noted in compound descriptions elsewhere herein; wherein PG$_2$ is an amine protecting group. Suitable amine protecting groups are known to one skilled in the art. A more specific example is set forth below.

SCHEME 3B.

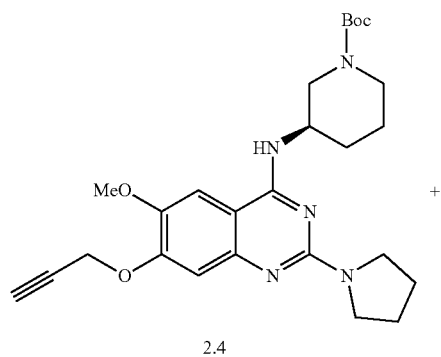

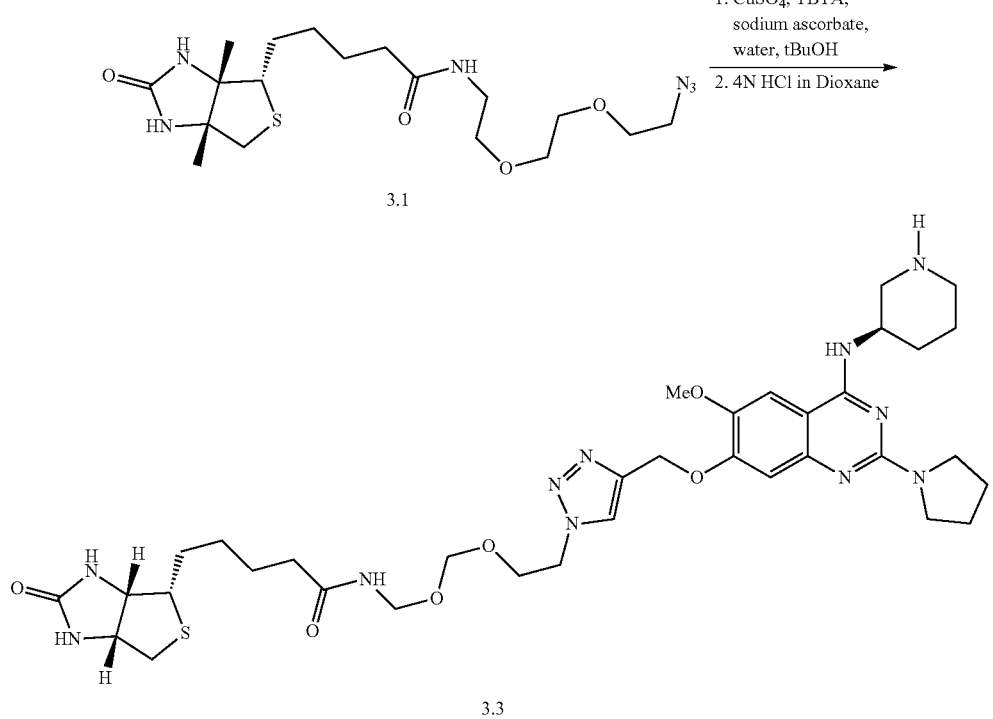

In one aspect, compounds of type 3.3, and similar compounds, can be prepared according to reaction Scheme 3B above. Thus, compounds of type 3.3 can be prepared by a "click" reaction between an appropriate alkyne, e.g., 2.4 as shown above, and an appropriate azide, e.g., 3.1 as shown above, followed by a deprotection reaction. The "click" reaction is carried out in the presence of an appropriate catalyst, e.g., copper (II) sulfate, an appropriate ligand, e.g., tris-[(1-benzyl-1H-1,2,3-triazol-4-yl) methyl]amine, and an appropriate reducing agent, e.g., sodium ascorbate, in an appropriate solvent system, e.g., water and tert-butanol. The deprotection reaction is carried out in the presence of an appropriate acid, e.g., 4N hydrochloric acid, in an appropriate solvent, e.g., dioxane. As can be appreciated by one skilled in the art, the above reaction provides an example of a generalized approach wherein compounds similar in structure to the specific reactants above (compounds similar to compounds of type 2.3 and 3.1), can be substituted in the reaction to provide 6,7-disubstituted quinazolin-4-amine derivatives similar to Formula 3.2.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

D. PHARMACEUTICAL COMPOSITIONS

In one aspect, disclosed are pharmaceutical compositions comprising a disclosed compound, or a pharmaceutically acceptable salt thereof and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with heterochromatin formation such as, for example, a disorder of cellular proliferation (e.g., cancer).

It is understood that the disclosed compositions can be prepared from the disclosed compounds. It is also understood that the disclosed compositions can be employed in the disclosed methods of using.

E. METHODS OF TREATING A DISORDER RELATED TO HETEROCHROMATIN FORMATION

In various aspects, the compounds and compositions disclosed herein are useful for treating, preventing, ameliorating, controlling or reducing the risk of a variety of disorders related to heterochromatin formation, including, for example, a disorder of cellular proliferation (e.g., cancer). Thus, in one aspect, disclosed are methods of treating a disorder related to heterochromatin formation in a mammal, the method comprising administering to the mammal an effective amount of at least one disclosed compound or a pharmaceutically acceptable salt thereof or at least one compound identified by a disclosed method.

In one aspect, disclosed are methods of treating a disorder related to heterochromatin formation, the method comprising administering to a mammal an effective amount of a compound having a structure represented by a formula:

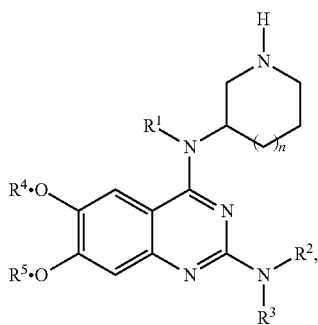

wherein n is selected from 0 and 1; wherein $R^1$ is H or C1-C4 alkyl; wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

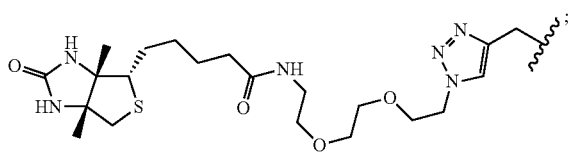 [SMILES: *Cc1cn(CCOCCOCCNC(=O)CCCC[C@@H]2SC[C@]3(C)NC(=O)N[C@]23C)nn1]

or wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; or a pharmaceutically acceptable salt thereof.

In various aspects, the disclosed compounds can be used in combination with one or more other drugs in the treatment, prevention, control, amelioration, or reduction of risk of disorders related to heterochromatin formation for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In a further aspect, the compound exhibits inhibition of HP1-mediated heterochromatin formation. In a still further aspect, the compound exhibits a decrease in HP1-mediated heterochromatin formation.

In a further aspect, the compound exhibits inhibition of HP1-mediated heterochromatin formation with an $IC_{50}$ of from about 0.001 µM to about 10 µM. In a still further aspect, the compound exhibits inhibition of HP1-mediated heterochromatin formation with an $IC_{50}$ of from about 0.01 µM to about 10 µM. In yet a further aspect, the compound exhibits inhibition of HP1-mediated heterochromatin formation with an $IC_{50}$ of from about 0.1 µM to about 10 µM. In an even further aspect, the compound exhibits inhibition of HP1-mediated heterochromatin formation with an $IC_{50}$ of from about 1 µM to about 10 µM. In a still further aspect, the compound exhibits inhibition of HP1-mediated heterochromatin formation with an $IC_{50}$ of from about 2 µM to about 10 µM. In yet a further aspect, the compound exhibits inhibition of HP1-mediated heterochromatin formation with an $IC_{50}$ of from about 3 µM to about 10 µM. In an even further aspect, the compound exhibits inhibition of HP1-mediated heterochromatin formation with an $IC_{50}$ of from about 5 µM to about 10 µM. In a still further aspect, the compound exhibits inhibition of HP1-mediated heterochromatin formation with an $IC_{50}$ of from about 0.001 µM to about 5 µM. In yet a further aspect, the compound exhibits inhibition of HP1-mediated heterochromatin formation with an $IC_{50}$ of from about 0.001 µM to about 3 µM. In an even further aspect, the compound exhibits inhibition of HP1-mediated heterochromatin formation with an $IC_{50}$ of from about 0.001 µM to about 2 µM. In a still further aspect, the compound exhibits inhibition of HP1-mediated heterochromatin formation with an $IC_{50}$ of from about 0.001 µM to about 1 µM. In yet a further aspect, the compound exhibits inhibition of HP1-mediated heterochromatin formation with an $IC_{50}$ of from about 0.001 µM to about 0.1 µM. In an even further aspect, the compound exhibits inhibition of HP1-mediated heterochromatin formation with an $IC_{50}$ of from about 0.01 µM to about 5 µM. In a still further aspect, the compound exhibits inhibition of HP1-mediated heterochromatin formation with an $IC_{50}$ of from about 0.1 µM to about 5 µM. In yet a further aspect, the compound exhibits inhibition of HP1-mediated heterochromatin formation with an $IC_{50}$ of from about 1 µM to about 5 µM. In an even further aspect, the compound exhibits inhibition of HP1-mediated heterochromatin formation with an $IC_{50}$ of from about 1 µM to about 3 µM.

In a further aspect, the mammal is a human.

In a further aspect, the mammal has been diagnosed with the disorder prior to administration.

In a further aspect, the mammal has been diagnosed with a need for treatment of the disorder prior to the administering step. In a still further aspect, the mammal is at risk for developing the disorder prior to the administering step.

In a further aspect, the method further comprises identifying a mammal at risk for developing the disorder prior to the administering step.

In a further aspect, the amount is a therapeutically effective amount. In a still further aspect, the amount is a prophylactically effective amount.

In a further aspect, the disorder is a disease of uncontrolled cellular proliferation. In a still further aspect, the disorder is cancer. In yet a further aspect, the cancer is a sarcoma. In an even further aspect, the cancer is a carcinoma. In a still further aspect, the cancer is a hematological cancer. In a yet further aspect, the cancer is a solid tumor.

It is understood that cancer refers to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer, bone cancer, brain and CNS cancer, choriocarcinoma, connective tissue cancer, esophageal cancer, eye cancer, cancer of the head and neck, gastric cancer, intra-epithelial neoplasm, larynx cancer, lymphoma including Hodgkin's and Non-Hodgkin's lymphoma, melanoma, myeloma, neuroblastoma, oral cavity cancer (e.g., lip, tongue, mouth, and pharynx), retinoblastoma, rhabdomyosarcoma, rectal cancer, cancer of the respiratory system, sarcoma, skin cancer, stomach cancer, testicular cancer, uterine cancer, cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, liver, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In a further aspect, the cancer is selected from a cancer of the breast, cervix, gastrointestinal tract, colorectal tract, brain, skin, prostate, ovary, thyroid, testes, genitourinary tract, pancreas, and endometrias. In a still further aspect, the cancer is a cancer of the breast. In yet a further aspect, the cancer of the breast is a hormone resistant cancer. In a still further aspect, the cancer is a cancer of the cervix. In yet a further aspect, the cancer is a cancer of the ovary. In an even further aspect, the cancer is a cancer of the endometrias. In a still further aspect, the cancer is a cancer of the genitourinary tract. In yet a further aspect, the cancer is a cancer of the colorectal tract. In an even further aspect, the cancer of the colorectal tract is a colorectal carcinoma. In a still further aspect, the cancer is a cancer of the gastrointestinal tract. In yet a further aspect, the cancer of the gastrointestinal tract is a gastrointestinal stromal tumor. In an even further aspect, the cancer is a cancer of the skin. In a still further aspect, the cancer of the skin is a melanoma. In yet a further aspect, the cancer is a cancer of the brain. In an even further aspect, the cancer of the brain is a glioma. In a still further aspect, the glioma is glioblastoma multiforme. In yet a further aspect, glioma is selected from is selected from an ependymoma, astrocytoma, oligodendroglioma, and oligoastrocytoma. In an even further aspect, the cancer of the brain is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, and hemangiopercytoma. In a still further aspect, the hematological cancer is selected from a leukemia, lymphoma, chronic myeloproliferative disorder, myelodysplastic syndrome, myeloproliferative neoplasm, and plasma cell neoplasm (myeloma). In yet a further aspect, the hematological cancer is leukemia. In an even further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia. In a still further aspect, the leukemia is acute lymphocytic leukemia. In yet a further aspect, the hematological cancer is lymphoma. In an even further aspect, the hematological cancer is myeloma. In a still further aspect, the myeloma is multiple myeloma.

In a further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

F. METHODS OF INHIBITING HP1-MEDIATED HETEROCHROMATIN FORMATION

In one aspect, disclosed are methods of inhibiting HP1-mediated heterochromatin formation, the method comprising administration of at least one disclosed compound, or a pharmaceutically acceptable salt thereof.

In one aspect, disclosed are methods of inhibiting HP1-mediated heterochromatin formation, the method comprising administration of a compound having a structure represented by a formula:

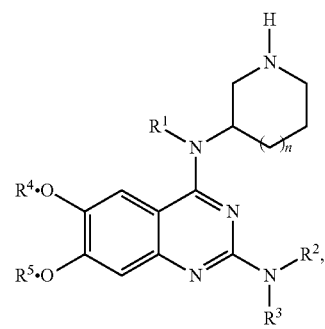

wherein n is selected from 0 and 1; wherein $R^1$ is H or C1-C4 alkyl; wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

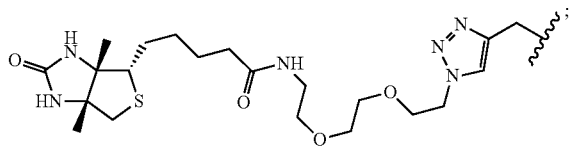 [SMILES: *Cc1cn(CCOCCOCCNC(=O)CCCC[C@@H]2SC[C@]3(C)NC(=O)N[C@]23C)nn1]

or wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; or a pharmaceutically acceptable salt thereof.

In a further aspect, administration is in vitro. In a still further aspect, administration is in vivo.

In a further aspect, administration is to a mammal. In a still further aspect, the mammal is a human.

G. METHODS OF IDENTIFYING AN INHIBITOR OF HP1-MEDIATED HETEROCHROMATIN FORMATION

In one aspect, disclosed are methods of identifying an inhibitor of HP1-mediated heterochromatin formation, the method comprising screening a candidate compound for binding with, or activity against, Kmt2B and/or Hdgfrp2. In a further aspect, the candidate compound has a structure represented by a formula:

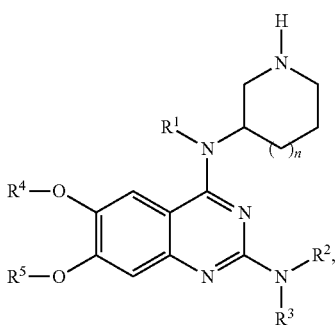

wherein n is selected from 0 and 1; wherein $R^1$ is H or C1-C4 alkyl; wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

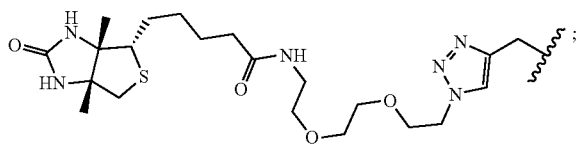 [SMILES: *Cc1cn(CCOCCOCCNC(=O)CCCC[C@@H]2SC[C@]3(C)NC(=O)N[C@]23C)nn1]

or
wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; or a pharmaceutically acceptable salt thereof.

In one aspect, disclosed are compounds identified by a disclosed method. In a further aspect, the compound has a structure represented by a formula:

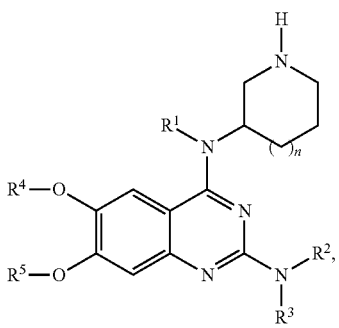

wherein n is selected from 0 and 1; wherein $R^1$ is H or C1-C4 alkyl; wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

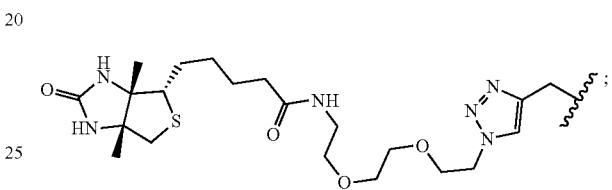

or
wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$; or a pharmaceutically acceptable salt thereof.

In one aspect, disclosed are methods of treating a disorder related to heterochromatin formation, the method comprising administering to a mammal an effective amount of a compound identified by a disclosed method.

H. METHODS OF USING THE COMPOSITIONS

Provided are methods of using of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, the invention relates to a method for the manufacture of a medicament for treating a disorder related to heterochromatin formation in a mammal, the method comprising combining a therapeutically effective amount of a disclosed compound or product of a disclosed method with a pharmaceutically acceptable carrier or diluent.

As regards these applications, the present method includes the administration to a mammal, particularly a human, of a therapeutically effective amount of the compound effective in the inhibition of heterochromatin formation and especially HP1-mediated heterochromatin formation. The dose administered to a mammal, particularly a human, in the context of the present invention should be sufficient to affect a therapeutic response in the animal over a reasonable time frame. One skilled in the art will recognize that dosage will depend upon a variety of factors including the condition of the mammal, the body weight of the mammal, as well as the severity and stage of the disorder.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

2. Use of Compounds and Compositions

Also provided are the uses of the disclosed compounds and compositions. Thus, in one aspect, the invention relates to the uses of inhibitors of heterochromatin formation, for example, HP1-mediated heterochromatin formation.

In a further aspect, the invention relates to the use of a disclosed compound or product of a disclosed method in the manufacture of a medicament for the treatment of a disorder related to heterochromatin formation such as, for example, a disorder of cellular proliferation (e.g., cancer).

In a further aspect, the use relates to a process for preparing a pharmaceutical composition comprising a therapeutically effective amount of a disclosed compound or a product of a disclosed method, and a pharmaceutically acceptable carrier, for use as a medicament.

In a further aspect, the use relates to a process for preparing a pharmaceutical composition comprising a therapeutically effective amount of a disclosed compound or a product of a disclosed method, wherein a pharmaceutically acceptable carrier is intimately mixed with a therapeutically effective amount of the disclosed compound or the product of a disclosed method.

In a further aspect, the use is the treatment of a disorder of cellular proliferation. In a still further aspect, the use is the treatment of cancer. In an even further aspect, cancer is leukemia. In a still further aspect, the cancer is a myeloma. In a yet further aspect, cancer is a solid tumor. In an even further aspect, the cancer is a lymphoma.

In a further aspect, the cancer is selected from the cancer is selected from cancers of the blood, brain, prostate, genitourinary tract, gastrointestinal tract, colon, rectum, breast, liver, kidney, lymphatic system, stomach, lung, pancreas, and skin. In an even further aspect, the cancer is selected from a cancer of the colon, rectum, breast, prostate, liver, skin and lung. In a still further aspect, the cancer is selected from a cancer of the breast, ovary, testes and prostate. In a yet further aspect, the cancer is a cancer of the breast. In various aspects, the cancer is a cancer of the liver. In a still further aspect, the cancer is a cancer of the prostate. In a yet further aspect, the cancer is a cancer of the colon or rectum.

It is understood that the disclosed uses can be employed in connection with the disclosed compounds, methods, compositions, and kits. In a further aspect, the invention relates to the use of a disclosed compound or composition of a medicament for the treatment of a disorder related to heterochromatin formation in a mammal.

In a further aspect, the invention relates to the use of a disclosed compound or composition in the manufacture of a medicament for the treatment of a disorder related to heterochromatin formation such as a disorder of cellular proliferation (e.g., cancer).

3. Kits

In one aspect, disclosed are kits comprising a disclosed compound and one or more of: (a) at least one chemotherapeutic agent; and (b) instructions for treating cancer.

In various aspects, the agents and pharmaceutical compositions described herein can be provided in a kit. The kit can also include combinations of the agents and pharmaceutical compositions described herein.

In various aspects, the chemotherapeutic agent is selected from one or more of the group consisting of an alkylating agent, an antimetabolite agent, an antineoplastic antibiotic agent, a mitotic inhibitor agent, an mTor inhibitor agent or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

In a further aspect, the mTor inhibitor agent is selected from one or more of the group consisting of everolimus, siroliumus, and temsirolimus, or a pharmaceutically acceptable salt, hydrate, solvate, or polymorph thereof.

In various aspects, the informational material can be descriptive, instructional, marketing or other material that relates to the methods described herein and/or to the use of the agents for the methods described herein. For example, the informational material may relate to the use of the agents herein to treat a mammal who has, or who is at risk for developing, a disorder related to heterochromatin formation. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable mammal, e.g., a human having, or at risk for developing, a disorder related to heterochromatin formation.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the compound and the chemotherapeutic agent are co-formulated. In a still further aspect, the compound and the chemotherapeutic agent are co-packaged.

In a further aspect, the kit further comprises a plurality of dosage forms, the plurality comprising one or more doses; wherein each dose comprises an effective amount of the compound and the chemotherapeutic agent. In a still further aspect, the effective amount is a therapeutically effective amount. In yet a further aspect, the effective amount is a prophylactically effective amount. In an even further aspect, each dose of the compound and the chemotherapeutic are co-packaged. In a still further aspect, each dose of the compound and the chemotherapeutic agent are co-formulated.

4. Mammals

In various aspects, the mammal of the herein disclosed methods is a vertebrate, e.g., a mammal. Thus, the mammal of the herein disclosed methods can be a human, non-human primate, horse, pig, rabbit, dog, sheep, goat, cow, cat, guinea pig or rodent. The term does not denote a particular age or sex. Thus, adult and newborn mammals, as well as fetuses, whether male or female, are intended to be covered. A patient refers to a mammal afflicted with a disease or disorder. The term "patient" includes human and veterinary mammals.

In some aspects of the disclosed methods, the mammal has been diagnosed with a need for treatment prior to the administering step. In some aspects of the disclosed method, the mammal has been diagnosed with a disorder related to heterochromatin formation prior to the administering step. In some aspects of the disclosed methods, the mammal has been identified with a need for treatment prior to the administering step. In one aspect, a mammal can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a mammal can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, Pa.). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, N.Y.).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

I. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Materials and Methods a. ES Cell Culturing and Cell Lines

Mouse embryonic stem cells were adapted to be grown on gelatin coated plates without feeder cells in DMEM supplemented with 4.5 g/L glucose, 15% FBS, L-glutamate, sodium pyruvate, HEPES buffer, NEAA, 2-mercaptoethanol, LIF, and penicillin/streptomycin (ES Media) at 37° C. supplemented with 5% $CO_2$. Media was aspirated and replaced daily.

The CiA:Oct4 recruitment system in mouse embryonic stem cells contains Gal4 and Zinc finger DNA binding arrays and a downstream nuclear eGFP gene in place of a single Oct4 allele as previously described (Hathaway et al., 2012). The CiA:Oct4 N118/N163 cell line containing viral integrations of N118 and N163 plasmids (N118-nLV EF-1α-Gal-FKBPx1-HA-PGK-Blast, N163-nLV EF-1α-HP1α (CS)-Frbx2(Frb+FrbWobb)-V5-PGK-Puro) was used for all experiments unless otherwise stated. The CiA:Oct4 N205 line containing the lentiviral construct N205 (N205-nLV EF-1α-ZFHD1-link-FKBP-HA <T2A> HP1αCS-Frbx2-V5-PGK-Blast) was used for shRNA experiments. CiA:Oct4 N118 was infected with the lentiviral construct N192 (N192-nLV Dual Promoter EF-1α-MCS-PGK-Puro HP1γ-(CS)-Frbx2(wobbmo)-V5) to yield the csHP1γ recruitment system CiA:Oct4 N118/N192. For orthogonal recruitment system, stable mESC cell line with blue fluorescent protein (BFP) reporter gene with tetracycline response elements (TRE) was generated by recombinase-mediated cassette exchange, by introducing the reporter cassette DNA in plasmid YR06 into a genetrap located on chromosome 15 at genome coordinates chr15:99941948 (Lienert et al. (2011) *Nature Genetics* 43(11): 1091-1097; Elling et al. (2017) *Nature* 550(7674): 114-118). Genetrap location is devoid of any kind epiegentic marks. Into this cell line, TetR-HP1-mCherry was introduced by lentiviral infection using nLV construct KS35(pEF1-TetR-HP1-P2A-mCherry). Reversal of TetR fusion protein binding was achieved by addition of 1 µg/ml doxycycline to ES cell culture medium. Plasmids N118, N163, and N205 are available through addgene. YR06 and KS35 are provided upon request.

b. Small Molecule High-Throughput Screen

Day 0, CiA:Oct4 N118/163 cells were grown in ES media and seeded at a density of 10,000 cells per well (100,000 cells/mL) into gelatin coated 96 well plates. Day 1, media was aspirated and replaced with 100 4 fresh ES media containing +/−6 nM rapamycin and 10 µM dilution of compounds from the EpiG compound set. Day 2, 100 µL fresh ES media containing +/−6 nM rapamycin and 10 µM dilution of compounds from the EpiG compound set was added as on Day 1. Day 3, the media was aspirated out of the wells and the cells were washed with PBS and trypsinized using 0.25% trypsin-EDTA. Trypsin was quenched with serum. Cells were resuspended by pipetting to prepare the plates for flow cytometry analysis.

C. Flow Cytometry and Cell Sorting

Flow cytometry was performed using an Intellicyt iQue Screener and analyzed with FlowJo software. Cell populations were gated based on forward and side scatter area. Single cell populations were isolated using forward scatter area by forward scatter height gating. Dead or dying cells that equally fluoresced in the GFP and APC channels upon excitation with 488 nm laser were omitted as autofluorescent, and the remaining cells were gated into GFP (−) and GFP (+) populations. Histograms demonstrate representative samples while bar graphs and charts contain all biological replicates. Statistics were performed using standard T-test analysis.

Cell sorting was performed on a BD FACSAria II cell sorter and used the above gating scheme to identify single cell populations. Upon doxycycline induction, turboRFP (+) cells were sorted to enrich for populations that were expressing the inducible pTRIPZ vector used for shRNA knockdown experiments.

d. Dose Response of Lead Screen Compounds

Day 0, CiA:Oct4 N118/163 cells were grown in ES media and seeded at a density of 10,000 cells per well (100,000 cells/mL) into gelatin coated 96 well plates. Day 1, media was aspirated and replaced with 100 µL fresh ES media containing +/−6 nM rapamycin and either 10, 5, 2.5, 1.25, or 0 µM dilution of compounds. Each dose was performed in triplicate. Day 2, culture media was aspirated away and 100 µL fresh ES media containing +/−6 nM rapamycin and either 10, 5, 2.5, 1.25 or 0 µM dilution of compounds were added as on Day 1. Day 3, the media was aspirated out of the wells and the cells were washed with PBS and trypsinized using 0.25% trypsin-EDTA. Trypsin was quenched with serum. Cells were resuspended by pipetting to prepare the plates for flow cytometry analysis as described above. Biological replicates were averaged and used to generate standard error bars.

e. Orthogonal TetR-HP1 Recruitment Assay

TetR-HP1 cell lines were continuously grown with 1 µg/ml doxycycline to maintain an open chromatin state. Day 0, TetR-HP1 cells were grown in ES media containing doxycycline and seeded at a density of 10,000 cells per well (100,000 cells/mL) into 96 well plates. Day 1, media was aspirated, and the wells were washed with 100 µL of PBS to remove residual doxycycline. PBS was removed and replaced with 100 µL fresh ES media containing +/−1 µg/mL doxycycline and 5 µM compounds. Each dose was performed in triplicate. Day 2, culture media was aspirated away and 100 µL fresh ES media containing +/−1 µg/mL doxycycline and 5 µM compounds were added as on Day 1. Day 3, the media was aspirated out of the wells and the cells were washed with PBS and trypsinized using 0.25% trypsin- EDTA. Trypsin was quenched with serum. Cells were resuspended by pipetting to prepare the plates for flow cytometry analysis as described above. Median BFP intensity was determined by FlowJo software analysis. Biological replicates were averaged and used to generate standard error bars.

f. csHP1r Inhibition Assay

Day 0, CiA:Oct4 N118/N192 cells were grown and cultured in 96 well plate format with 10,000 cells seeded per well. Day 1, media was aspirated and replaced with fresh ES media containing 5 µM of top screen compounds and +/−6 nM rapamycin. Day 2, media was aspirated and replaced with fresh ES media containing 5 µM of top screen compounds and +/−6 nM rapamycin. Day 3, wells were aspirated and washed with PBS prior to sample preparation and analysis by flow cytometry.

g. UNC2524 Structure-Activity Relationship Studies

Complete methods for the chemical compounds synthesized for structure-activity relationship studies are listed in the Supplemental Methods section. Briefly, chemical derivatives of UNC2524 (compound 1) were synthesized to determine if activity of UNC2524 could be increased, and to determine if the compound was amenable to biotin tagging for affinity purification.

Day 0, CiA:Oct4 N118/163 cells were grown in ES media and seeded at a density of 10,000 cells per well (100,000 cells/mL) into gelatin coated 96 well plates. Day 1, media was aspirated and replaced with 100 µL fresh ES media containing +/−6 nM rapamycin and 10 µM of each compound derived for SAR. Day 2, culture media was aspirated away and 100 µM fresh ES media containing +/−6 nM rapamycin and 10 µM of compounds were added as on Day 1. Day 3, the media was aspirated out of the wells and the cells were washed with PBS and trypsinized using 0.25% trypsin-EDTA. Trypsin was quenched with serum. Cells were resuspended by pipetting to prepare the plates for flow cytometry analysis as described above.

h. Compound 2 Activity and Fluorescence Microscopy

Day 0, CiA:Oct4 N118/N163 cells were plated into 96 well plate and 10 or 15 cm plate formats. Day 1, media was aspirated and replaced with fresh ES media +/−7.5 µM compound 2+/−6 nM rapamycin. Day 2, media was aspirated and replaced with fresh ES media +/−7.5 µM compound 2+/−6 nM rapamycin. Day 3, media was removed from 96 well plate and cells were washed with PBS prior to trypsinization and flow cytometry analysis as described above to confirm functional inhibition of compound 2.

Prior to imaging, ES media was removed from 10-15 cm plates and replaced with PBS to decrease background fluorescence. Cells were imaged using an Olympus IX71 microscope analyzed using Cellsens software. Representative images were taken in 2 random plate locations for each of the four conditions. Image levels were normalized using Adobe Photoshop.

i. Chromatin Immunoprecipitation (ChIP) Sample Prep and qPCR 10-15 cm plates of cells grown to confluence were washed with PBS and trypsinized 10 min with 0.25% trypsin-EDTA. ES media was added to quench the trypsin, and cells were resuspended prior to counting using a Countess II Automated Cell Counter (ThermoFisher). Cell suspension was centrifuged at 300×g for 5 min. Cell pellet was washed with PBS and pelleted at 300×g for 5 min. Cells were resuspended and crosslinked with 1% formaldehyde for 10 min. 2.5 M glycine (0.125 M final) was added and samples were put on ice to stop the crosslinking. Nuclei were isolated by incubating cells on ice for 10 min in CiA NP Rinse 1 (50 mM HEPES pH 8.0, 140 mM NaCl, 1 mM EDTA, 10% glycerol, 0.5% NP40, 0.25% Triton X100). Nuclei were pelleted at 1200×g for 5 min at 4° C. and resuspended in CiA NP Rinse 2 (10 mM Tris pH 8.0, 1 mM EDTA, 0.5 mM EGTA, 200 mM NaCl). Nuclei were pelleted at 1200×g for 5 min at 4° C. Nuclei were resuspended in shearing buffer (0.1% SDS, 1 mM EDTA pH 8, 10 mM Tris HCl, pH 8) and sonicated for 5 min using a Covaris sonicator (Hathaway et al., 2012). Input DNA and ChIP DNA was isolated according to Active Motif High Sensitivity ChIP-IT kit procedure. ChIP for H3K9me3 used Abcam (ab8898) primary antibody.

Enrichment of ChIP DNA was determined by qPCR. 384-well PCR plates contained 2 µL of template DNA and 8 µL of reaction mix of primers and FastStart Universal SYBR Green 2× master mix (Roche). Samples were run on a ViiA7 Real-Time PCR system (Applied Biosystems) (Pattenden et al., 2016). Plates were setup in technical duplicate or triplicate. Samples were analyzed using the comparative ΔΔCt method and normalized against an intergenic control region (Hathaway et al., 2012; Livak & Schmittgen, 2001). Experiment was performed in a minimum biological triplicate and data is representative of sample average. T-test were used to determine significant p-values.

j. Affinity Purification Sample Prep and iTRAQ LC-MS/MS Analysis

CiA:Oct4 N118/N163 cells were seeded and grown to confluency in a 15 cm tissue culture plate. Cells were trypsinized for 10 min and quenched in ES media. Cells were resuspended and pelleted at 300×g for 5 min. Cell pellet was washed with PBS and pelleted at 300×g for 5 min. Nuclei were harvested from the cell pellet as described above. Nuclei were resuspended in 2 ml of shearing buffer (0.1% SDS, 1 mM EDTA pH 8.0, 10 mM Tris HCl, pH 8.0) and sonicated using a probe sonicator resulting in a nuclear lysate. One sample of nuclear lysate was incubated with excess compound 2 to bind all available binding sites prior to pulldown. Compound 3 and 4 were incubated with magnetic streptavidin beads (Dynabeads M-280 Streptavidin, Invitrogen) and washed. Compound coated beads, beads alone, and compound 3+excess treated compound 2 were incubated overnight at 4° C. with nuclear lysate. Proteins bound to magnetic beads were washed with 50 mM HEPES, 150 mM NaCl and 1% NP-40 three times. Columns were eluted first with excess compound 2, and finished with an elution of 3 mM D-biotin. A portion of each sample was run on a gel electrophoresis to check bead washing and elution. Eluted fractions were combined and precipitated with cold acetone overnight at −20° C. and the pellet was used for isobaric tagging.

Sample Preparation: Each pull-down eluate was reduced with 5 mM DTT for 45 min at 37° C., alkylated with 15 mM iodoacetamide for 1 hr in the dark at room temperature, then digested with trypsin (Promega Gold) overnight at 37° C. The peptide samples were desalted using C18 spin columns (Pierce), then labeled with 4plex iTRAQ reagents according to manufacturer's protocol (Sciex). The iTRAQ labels 114, 115, 116 and 117 were used to label compound 3 active (sample), beads alone (control), compound 3+compound 2 (control), and compound 4 inactive (control), respectively. After labeling, the samples were combined then dried down via vacuum centrifugation.

LC/MS/MS Analysis: The combined iTRAQ sample was reconstituted in 0.1% formic acid, then analyzed by LC/MS/MS using an Easy nLC 1000 coupled to a QExactive HF (Thermo Scientific). Samples were injected onto an Easy Spray PepMap C18 column (75 µm id×25 cm, 2 µm particle size) (Thermo Scientific) and separated over a 120 min method. The gradient for separation consisted of 5-35% mobile phase B at a 250 nL/min flow rate, where mobile phase A was 0.1% formic acid in water and mobile phase B consisted of 0.1% formic acid in ACN. The QExactive HF was operated in data-dependent mode where the 20 most intense precursors were selected for subsequent HCD fragmentation. Resolution for the precursor scan (m/z 350-1600) was set to 120,000 (max IT: 50 ms; target AGC: 3e6), while MS/MS scans resolution was set to 15,000 (max IT: 100 ms; target AGC: 1e5). For MS/MS, the normalized collision energy for HCD was set to 30, with a fixed first mass of 110 m/z and an isolation window of 1.2 m/z. Precursors with unknown charge or a charge state of 1 and ≥8 were excluded.

Data Analysis: Raw data were searched against a Uniprot mouse database (containing 49,235 sequences, downloaded September 2015) using Sequest HT within Proteome Discoverer 2.1 (Thermo Scientific). The following parameters were used to identify tryptic peptides for protein identification: precursor mass tolerance of 10 ppm; product mass tolerance of 0.02 Da; up to two missed cleavages; carbamidomethylation (C) was set as a fixed modification; and oxidation (M), phosphorylation (S,T,Y), deamidation (N,Q) and iTRAQ 4plex (N-term, K) were set as variable modifications. The percolator node was used to calculate peptide false discovery rates (FDR) and a ≤5% FDR was used to filter all results. Proteins were reported only if ≥2 peptides were identified with a ≤50% co-isolation interference. The iTRAQ abundance ratio for each experimental comparison (sample versus controls) was calculated, and a ±1.4 fold change threshold was applied.

k. shRNA Construction

The doxycycline inducible lentiviral vector pTRIPZ containing the nonsense shRNA was used as the backbone for all subsequent shRNA cloning. Forward and reverse complement of shRNA containing oligos (Table 1) were synthesized and slowly annealed together in annealing buffer (10 mM Tris pH 7.5-8, 1 mM EDTA, 50 mM NaCl) to create dsDNA by raising the sample to 95° C. for 5 min and cooling the samples 1° C./min until room temperature is reached. pTRIPZ vector and insert were digested using XhoI and EcoRI-HF (NEB) and ligated using T4-ligase according to manufacturer instructions. Ligated constructs were transformed into One Shot Stab13 Chemically Competent  E. coli cells (ThermoFisher) and grown on LB ampicillin agarose plates. Ligation was confirmed by DNA sequencing.

TABLE 1

| Target | Infusion Primer shRNA Sequence (SEQ ID NO) |
|---|---|
| Kmt2b-<br>For<br>(IP014F) | CAACAGAAGGCTCGAGAAGGTATATTGCTGTTGACAGTG<br>AGCGGGAGAACTCTGATTGAGAAAGTAGTGAAGCCACAG<br>ATGTACTTTCTCAATCAGAGTTCTCCTGCCTACTGCCTC<br>GGAATTCAAGGGGCTAC (SEQ ID NO. 1) |
| Kmt2b-<br>Rev<br>(IP014R) | GTAGCCCCTTGAATTCCGAGGCAGTAGGCAGGAGAACTC<br>TGATTGAGAAAGTACATCTGTGGCTTCACTACTTTCTCA<br>ATCAGAGTTCTCCCGCTCACTGTCAACAGCAATATACCT<br>TCTCGAGCCTTCTGTTG (SEQ ID NO. 2) |
| Supt6H-<br>For<br>(IP016F) | CAACAGAAGGCTCGAGAAGGTATATTGCTGTTGACAGTG<br>AGCGCAGCACTGACTCATACATTGAAGTTCTTGTAGTGA<br>AGCCACAGATGTACAAGAACTTCAATGTATGAGTCAGTG<br>CTGTGCCTACTGCCTCGGAATTCAAGGGGCTAC<br>(SEQ ID NO. 3) |
| Supt6H-<br>Rev<br>(IP016R) | GTAGCCCCTTGAATTCCGAGGCAGTAGGCACAGCACTGA<br>CTCATACATTGAAGTTCTTGTACATCTGTGGCTTCACTA<br>CAAGAACTTCAATGTATGAGTCAGTGCTGCGCTCACTGT |

TABLE 1-continued

| | CAACAGCAATATACCTTCTCGAGCCTTCTGTTG<br>(SEQ ID NO.4) |
|---|---|
| Tmpo-<br>For<br>(IP017F) | CAACAGAAGGCTCGAGAAGGTATATTGCTGTTGACAGTG<br>AGCGCCTTCGGTCCTGACCAAAGACAAGTTGAATAGTGA<br>AGCCACAGATGTATTCAACTTGTCTTTGGTCAGGACCGA<br>AGGTGCCTACTGCCTCGGAATTCAAGGGGCTAC<br>(SEQ ID NO.5) |
| Tmpo-<br>Rev<br>(IP017R) | GTAGCCCCTTGAATTCCGAGGCAGTAGGCACCTTCGGTC<br>CTGACCAAAGACAAGTTGAATACATCTGTGGCTTCACTA<br>TTCAACTTGTCTTTGGTCAGGACCGAAGGCGCTCACTGT<br>CAACAGCAATATACCTTCTCGAGCCTTCTGTTG<br>(SEQ ID NO. 6) |
| Hdgfrp2-<br>For<br>(IP018F) | CAACAGAAGGCTCGAGAAGGTATATTGCTGTTGACAGTG<br>AGCGAAGTAGACCGCATCAGTGAATGGAAGAGATAGTGA<br>AGCCACAGATGTATCTCTTCCATTCACTGATGCGGTCTA<br>CTTTGCCTACTGCCTCGGAATTCAAGGGGCTAC<br>(SEQ ID NO. 7) |
| Hdgfrp2-<br>Rev<br>(IP018R) | GTAGCCCCTTGAATTCCGAGGCAGTAGGCAAAGTAGACC<br>GCATCAGTGAATGGAAGAGATACATCTGTGGCTTCACTA<br>TCTCTTCCATTCACTGATGCGGTCTACTTCGCTCACTGT<br>CAACAGCAATATACCTTCTCGAGCCTTCTGTTG<br>(SEQ ID NO. 8) |
| Target | qPCR Primers |
| β-actin-<br>For | CTCCTATGTGGGTGACGAG (SEQ ID NO. 9) |

| Target | Infusion Primer shRNA Sequence (SEQ ID NO) |
|---|---|
| β-actin-<br>Rev | TCTCAAACATGATCTGGGTC (SEQ ID NO. 10) |
| +484_4-<br>For | CAAGCTGGAGTACAACTACAAC (SEQ ID NO. 11) |
| +484_4-<br>Rev | AGTTCACCTTGATGCCGTTC (SEQ ID NO. 12) |
| IGR_1-<br>For | ATGCCCCTCAGCTATCACAC (SEQ ID NO. 13) |
| IGR_1-<br>Rev | TTGTCCATTCTCTCCTTTTCC (SEQ ID NO. 14) |
| Tmpo-<br>For | CCATTGTGGGAACAACCAG (SEQ ID NO. 15) |
| Tmpo-<br>Rev | TAGAGGATCTCGATTCAGTTCC (SEQ ID NO. 16) |
| Supt6H-<br>For | GGACCGAAAGAAATTAGAGGA (SEQ ID NO. 17) |
| Supt6H-<br>Rev | CAGGCACAGATGAAGTAAGG (SEQ ID NO. 18) |
| Kmt2B-<br>For | CCCAACTACTCACCGTCTC (SEQ ID NO. 19) |
| Kmt2B-<br>Rev | CAGGGAAGATGGACTTCCTG (SEQ ID NO. 20) |
| Hdgfrp2-<br>For | AGAGCGATTCTGACTCTGAC (SEQ ID NO. 21) |
| Hdgfrp2-<br>Rev | TAGAGACTGACACCTTCAAGAC (SEQ ID NO. 22) |

1. Lentiviral Production and Transfection

Second generation lentiviral packaging vectors psPAX2, pMD2.G, and plasmid DNA was transfected into 70-80% HEK Lenti-X 293T using PEI (1 μg/μL). Following overnight incubation at 37° C. in 5% CO2, the media was removed and replaced. 48 hrs post media replacement, the supernatant was removed and pelleted at 200×g for 5 min to remove cell debris. Supernatant was filtered through 0.45 µm filters. Supernatant was ultracentrifuged at 72,000×g for 2.5 hrs at 4° C. to pellet the virus. Supernatant was removed and the viral pellet was resuspended in PBS and resuspended with gentle shaking (Tiscornia, Singer, & Verma, 2006).

Mouse ES cells to be infected were grown and cultured as described above. Lentiviral suspensions were mixed with ES media containing polybrene (1000×) and added to the recipient cells. Culture plates were spinfected at 1000×g for 20 min to increase infection efficiency. Cells were selected with 2 µg/mL puromycin or 8 µg/mL blasticidin for a minimum of 5 days to ensure stable infection and integration of the lentiviral gene construct.

m. shRNA Knock-Down and qRT-PCR

Day 0, CiA:Oct4 N205 cells containing stably integrated doxycycline inducible shRNA constructs targeting compound 3 binding partners were seeded into 96 or 24 well tissue culture plates with 10,000 or 50,000 cells per well. Day 1, media was aspirated and replaced with fresh ES media +/−6 nM rapamycin and +/−1 µg/mL doxycycline to induce both csHP1α recruitment and shRNA induction as appropriate. Day 2, media was aspirated and replaced with fresh ES media +/−6 nM rapamycin and +/−1 µg/mL doxycycline. Day 3, media was aspirated and the cells were washed with PBS prior to cell trypsinization and sample preparation. 96 well plate was used for flow cytometry analysis as described above. Single cell populations were gated into GFP (+) positive and GFP (−) negative populations. Experiment was performed in biological triplicate.

Total RNA was isolated from CiA:Oct4 N205 cells grown in 24 well plates using Qiagen RNeasy Mini Kit according to manufacturer standard procedures. RNA was converted to cDNA using TaqMan® RNA-to-CT™ 1-Step Kit (ThermoFisher Scientific) and subsequently amplified using a ViiA7 Real-Time PCR system (Applied Biosystems). Samples were analyzed using the comparative ΔΔCt method and normalized against GAPDH or β-actin as a control. Experiment was performed in biological triplicate and data is representative of sample average.

n. Histone Acid Extraction

CiA:Oct4 N118/N163 cells were grown to confluency as described above in standard gelatin coated 6 well tissue culture plates. Media was aspirated and the cells were washed with 2 mL of PBS. The PBS was removed and the cells were trypsinized with 0.25% trypsin-EDTA until a single cell suspension was generated. Cells were transferred to a conical tube and pelleted at 300×g for 5 min. Supernatant was removed and the cells were washed with PBS and centrifuged at 300×g for 5 min. The PBS supernatant was removed. Nuclei were collected from the cells by resuspending the pellet in lysis buffer containing (50 mM HEPES pH 8.0, 140 mM NaCl, 1 mM EDTA, 10% glycerol, 0.5% NP40, 0.25% Triton X100). Cells were incubated in lysis buffer on ice for 10 min. Nuclei were pelleted at 1200×g for 5 min at 4° C. and the supernatant was removed. Pellet was resuspended and rinsed in a second buffer containing (10 mM Tris pH 8.0, 200 mM NaCl, 1 mM EDTA, 0.5 mM EGTA) and centrifuged at 1200×g for 5 min at 4° C. The supernatant was removed and the nuclei were resuspended in 500 µL of dH₂O. Acid extraction of histones was performed by HCl addition to a 0.2 N final concentration (Allfrey, Faulkner, & Mirsky, 1964). Samples remained at 4° C. overnight and then centrifuged at 6,500×g for 10 min at 4° C. Supernatant containing histones was removed and protein concentration was performed by standard Coomassie Bradford assay (Pierce) to be used for western blot analysis.

o. SDS-Page and Western Blot Analysis

Samples were mixed with 2× or 6× laemmli loading buffer and boiled for 5 min followed by centrifugation at 14,000×g for 2 min. Samples were run on 4-20% BioRad gradient gels according to manufacturer procedure. Gels were stained with Sypro Ruby (Thermo Fisher) according to manufacturer instructions.

SDS-PAGE sample gels were transferred to Millipore Immobilon-FL PVDF membranes either by semi-wet or wet transfer according to Bio-Rad procedure. Immobilon-FL PVDF membranes were blocked with Licor Odyssey Blocking Buffer (PBS) for at least one hour with shaking at room temperature. Primary antibodies (Active Motif anti-H3K9me3 39161, Active Motif anti-H3K9me2 39239, Active Motif anti-H4 61521) were incubated overnight at 4° C. with shaking. The membranes were washed in PBST (phosphate buffered saline and 0.1% Tween-20). Licor IRDye 680RD goat anti-mouse or Licor IRDye 800CW goat anti-rabbit at a concentration of 1:15,000 were used as secondary antibodies when appropriate. Secondary antibodies were incubated with the PVDF membranes for 30-60 minutes at room temperature. PVDF Membranes were washed in PBST (Phosphate buffered saline and 0.1% Tween-20). Western blot membranes were imaged using the Licor Odyssey scanner and data analyzed using Image Studio v5.2 software.

2. Chemical Synthesis for UNC2524 and Derivatives for SAR and Affinity Purification Studies a. Chemistry General Procedures HPLC spectra for all compounds were acquired using an Agilent 1200 Series system with DAD detector. Analytical HPLC chromatography was performed on a 2.1×150 mm Zorbax 300SB-C18 5 µm column with water containing 0.1% formic acid as solvent A and acetonitrile containing 0.1% formic acid as solvent B at a flow rate of 0.4 mL/min. The gradient program was as follows: 1% B (0-1 min), 1-99% B (1-4 min), and 99% B (4-8 min). High resolution mass spectra (HRMS) data were acquired in positive ion mode using an Agilent G1969A API-TOF with an electrospray ionization (ESI) source. Flash column chromatography was performed on a Teledyne ISCO CombiFlash Rf system equipped with a variable wavelength UV detector and a fraction collector using RediSep Rf normal phase silica columns. Microwave reactions were performed using a Discover SP CEM. Nuclear Magnetic Resonance (NMR) spectra were acquired on a Bruker DRX-600 spectrometer with 600 MHz for proton (1H NMR) and 150 MHz for carbon (13C NMR); chemical shifts are reported in ppm (δ). Preparative HPLC was performed on Agilent Prep 1200 series with UV detector set to 254 nm. Samples were injected onto a Phenomenex Luna 75×30 mm, 5 µm, C18 column at room temperature. The flow rate was 30 mL/min. A linear gradient was used with 10% (or 50%) of MeOH (A) in H2O (with 0.1% TFA) (B) to 100% of MeOH (A). HPLC was used to establish the purity of target compounds.

b. Synthesis of (S)-6,7-Dimethoxy-N-(Piperidin-3-yl)-2-(Pyrrolidin-1-yl)Quinazolin-4-Amine Trifluoroacetic Acid Salt (1)

c. Synthesis of (R)-6,7-Dimethoxy-N-(Piperidin-3-yl)-2-(Pyrrolidin-1-yl)Quinazolin-4-Amine Trifluoroacetic Acid Salt (2)

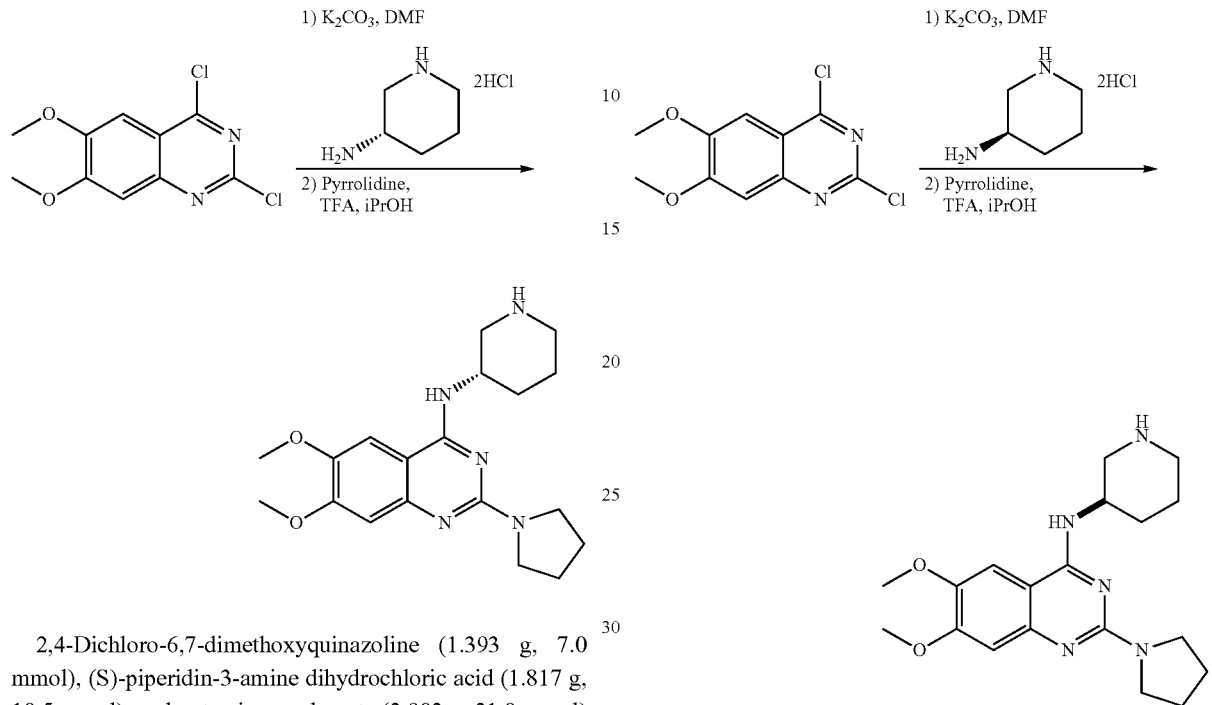

2,4-Dichloro-6,7-dimethoxyquinazoline (1.393 g, 7.0 mmol), (S)-piperidin-3-amine dihydrochloric acid (1.817 g, 10.5 mmol), and potassium carbonate (2.902 g, 21.0 mmol) were stirred at room temperature for 24 hours in 28 mL DMF. The solvent was removed by rotary evaporation, and the residue was partitioned between DCM and sat. aq. sodium bicarbonate. The organic layer was separated and the aqueous layer was extracted repeatedly with DCM. The combined DCM extracts were washed with brine and concentrated. The residue was purified by reverse phase C18 MPLC, giving (S)-2-chloro-6,7-dimethoxy-N-(piperidin-3-yl)quinazolin-4-amine TFA salt. Yield: 2.261 g, 5.18 mmol, 74%. MS (ESI) m/z: [M+H]+ Calcd for $C_{15}H_{19}ClN_4O_2$ 323.1; Found: 323.2.

The (S)-2-chloro-6,7-dimethoxy-N-(piperidin-3-yl)quinazolin-4-amine TFA salt (323 mg, 0.74 mmol) was placed in a microwave reactor vessel along with pyrrolidine (0.41 mL, 8 mmol), TFA (0.61 mL, 8 mmol), and isopropanol (4 mL). This was stirred under microwave irradiation for 30 minutes at 150° C. Purification by HPLC gave the product. Yield: 252 mg, 0.54 mmol, 54% yield over two steps. HRMS (ESI-TOF) m/z: [M+H]+ Calcd for $C_{19}H_{27}N_5O_2$ 358.2243; Found: 358.2243. $^1$H NMR (600 MHz, Methanol-d4) δ 7.26 (s, 1H), 7.20 (s, 1H), 4.57 (d, J=11.6 Hz, 1H), 4.31 (d, J=13.5 Hz, 1H), 4.01 (s, 3H), 3.96 (s, 3H), 3.81 (s, 2H), 3.74-3.53 (m, 5H), 2.31-1.99 (m, 6H), 1.85 (s, 2H). $^{13}$C NMR (151 MHz, MeOD) δ 163.57, 156.57, 149.16, 146.58, 138.70, 106.56, 102.53, 98.21, 55.49, 55.39, 50.34, 49.82, 48.20, 46.51, 46.25, 27.96, 25.32, 24.14, 22.68. HPLC Purity: >95%, $t_R$=3.03 min. See FIG. 1.

2,4-Dichloro-6,7-dimethoxyquinazoline (199 mg, 1.0 mmol), (R)-piperidin-3-amine dihydrochloric acid (260 mg, 1.5 mmol), and potassium carbonate (414 mg, 3.0 mmol) were stirred at room temperature for 24 hours in 4 mL DMF. The reaction mixture was purified by reverse phase C18 MPLC, giving (R)-2-chloro-6,7-dimethoxy-N-(piperidin-3-yl)quinazolin-4-amine TFA salt. Yield: 247 mg, 0.57 mmol. MS (ESI) m/z: [M+H]+ Calcd for $[C_{15}H_{19}ClN_4O_2+H]+$ 323.1; Found: 323.2.

Figure 2:
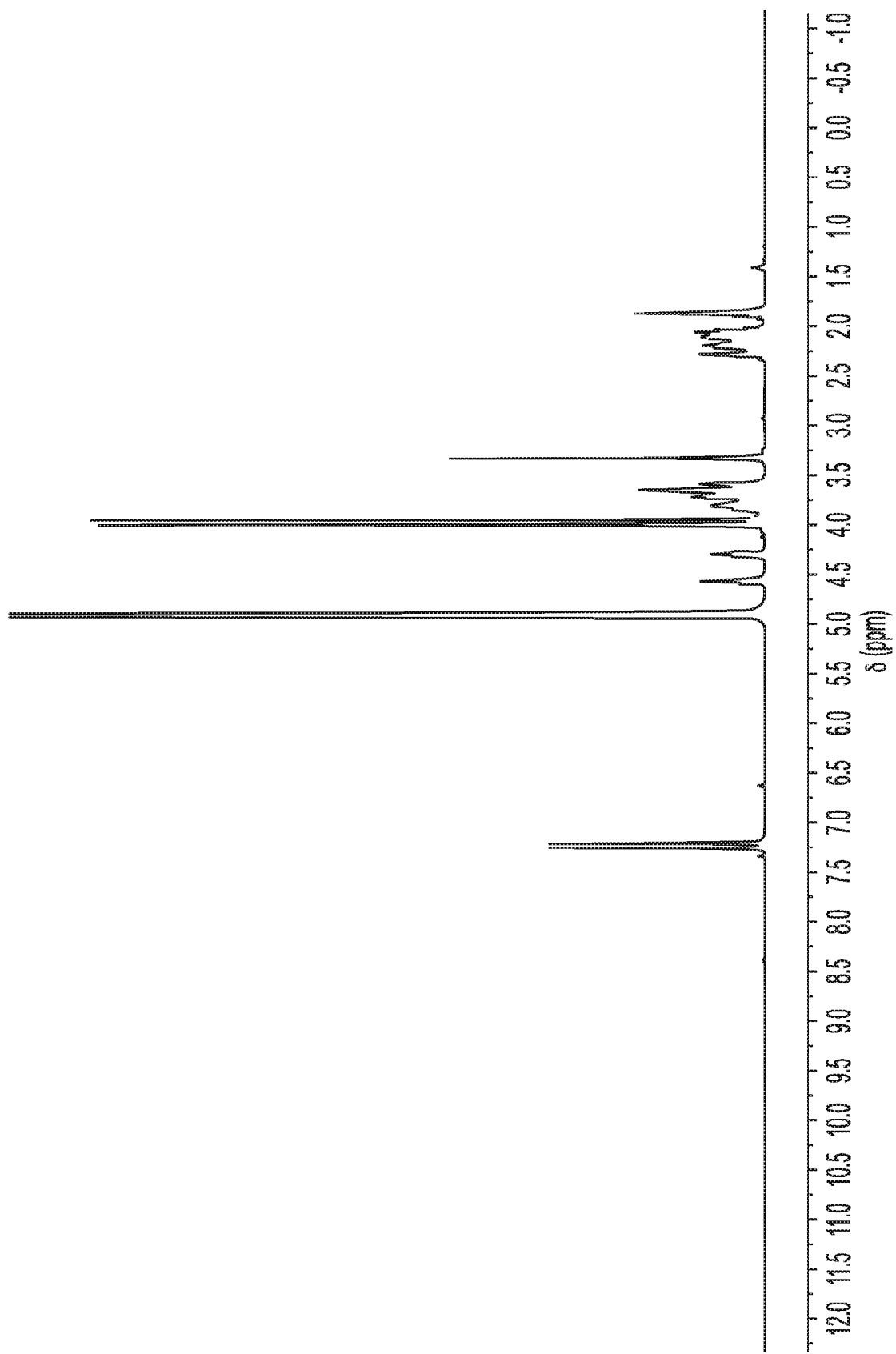
FIG. 2 shows a representative $^1$H NMR spectrum of compound 2.

The (R)-2-chloro-6,7-dimethoxy-N-(piperidin-3-yl)quinazolin-4-amine TFA salt (50 mg, 0.11 mmol) was placed in a microwave reactor vessel along with pyrrolidine (38 μL, 0.46 mmol), trifluoroacetic acid (TFA; 70 μL, 0.93 mmol), and isopropanol (1.2 mL). This was stirred under microwave irradiation for 30 minutes at 150° C. Purification by HPLC gave the product. Yield: 27 mg, 0.057 mmol, 30% yield over two steps. HRMS (ESI-TOF) m/z: [M+H]+ Calcd for $[C_{19}H_{27}N_5O_2+H]+$ 358.2243; Found: 358.2245. 1H NMR (600 MHz, Methanol-d4) δ 7.26 (s, 1H), 7.21 (s, 1H), 4.56 (d, J=12.7 Hz, $^1$H), 4.30 (d, J=13.6 Hz, 1H), 4.00 (s, 3H), 3.95 (s, 3H), 3.80 (s, 2H), 3.65 (t, J=10.9 Hz, 5H), 2.15 (dd, J=96.8, 38.5 Hz, 6H), 1.85 (t, J=9.0 Hz, 2H). $^{13}$C NMR (151 MHz, DMSO) δ 162.92, 155.69, 149.26, 145.87, 139.02, 107.34, 102.61, 99.58, 56.53, 56.22, 50.49, 50.16, 48.44, 47.01, 46.49, 28.29, 25.70, 24.55, 22.90. HPLC Purity: >95%, $t_R$=3.15 min. See FIG. 2.

d. Synthesis of (R)-7-(Benzyloxy)-6-Methoxy-N-(Piperidin-3-yl)-2-(Pyrrolidin-1-yl)Quinazolin-4-Amine Trifluoroacetic Acid Salt (10)

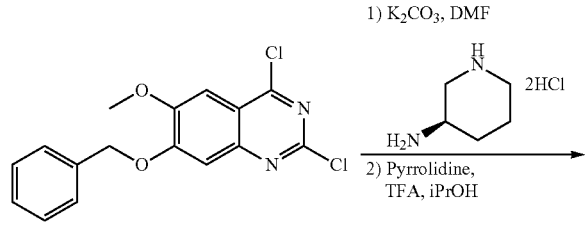

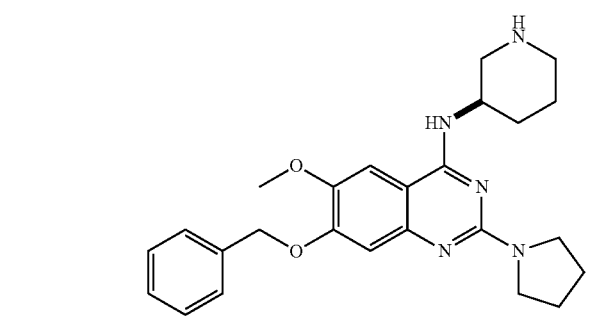

7-(Benzyloxy)-2,4-dichloro-6-methoxyquinazoline was prepared as previously described (J. Med. Chem., 2011, 54 (17), pp 6139-6150). (R)-7-(Benzyloxy)-6-methoxy-N-(piperidin-3-yl)-2-(pyrrolidin-1-yl)quinazolin-4-amine was prepared from 7-(Benzyloxy)-2,4-dichloro-6-methoxyquinazoline using the method described for the synthesis of compound 2. Yield: 41% over two steps. MS (ESI) m/z: [M+H]+ Calcd for $C_{25}H_{31}N_5O_2$ 434.3; Found: 434.4. 1H NMR (600 MHz, DMSO-d6) δ 11.85 (s, 1H), 8.10 (s, 3H), 7.49 (d, J=6.9 Hz, 2H), 7.45 (t, J=7.4 Hz, 2H), 7.39 (dd, J=13.3, 6.3 Hz, 2H), 7.25 (s, 1H), 5.26 (s, 2H), 4.47 (m, 1H), 4.24 (m, 1H), 3.89 (s, 3H), 3.75-3.46 (m, 7H), 2.18-1.86 (m, 6H), 1.70 (d, J=9.4 Hz, 2H).

e. Synthesis of Tert-Butyl (R)-3-((6-Methoxy-7-(Prop-2-yn-1-Yloxy)-2-(Pyrrolidin-1-yl)Quinazolin-4-yl)Amino) Piperidine-1-Carboxylate (11)

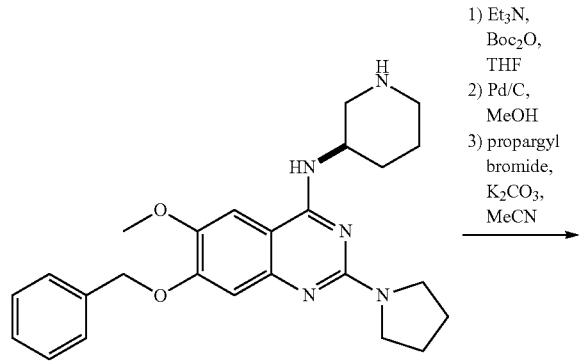

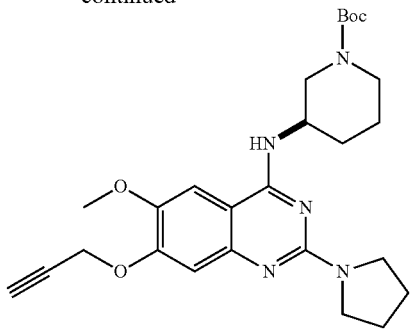

(R)-7-(Benzyloxy)-6-methoxy-N-(piperidin-3-yl)-2-(pyrrolidin-1-yl)quinazolin-4-amine trifluoroacetic acid salt (10) (400 mg, 0.72 mmol), triethylamine (0.372 mL, 2.88 mmol) and Boc anhydride (188 mg, 0.86 mmol) were stirred in 20 mL THF for 24 hours. The solvent was removed by rotary evaporation, and the residue was partitioned between DCM and sat. aq. sodium bicarbonate. The organic layer was separated and the aqueous layer was extracted repeatedly with DCM. The combined DCM extracts were washed with brine and concentrated. Silica gel chromatography (gradient of 0 to 10% MeOH in DCM as eluent) gave tert-butyl (R)-3-((7-(benzyloxy)-6-methoxy-2-(pyrrolidin-1-yl)quinazolin-4-yl)amino)piperidine-1-carboxylate. Yield: 308 mg, 0.58 mmol. MS (ESI) m/z: [M+H]+ Calcd for $C_{30}H_{39}N_5O_4$ 534.3; Found: 534.4.

5% palladium on carbon (50 mg) was added to the tert-Butyl (R)-3-((7-(benzyloxy)-6-methoxy-2-(pyrrolidin-1-yl)quinazolin-4-yl)amino)piperidine-1-carboxylate (275 mg, 0.52 mmol) in MeOH (10 mL) under argon. This was stirred for 24 hours under a balloon filled with hydrogen. The reaction mixture was filtered through celite and the celite was washed repeatedly with ethyl acetate. The collected solvents were evaporated, giving tert-butyl(R)-3-((7-hydroxy-6-methoxy-2-(pyrrolidin-1-yl)quinazolin-4-yl)amino)piperidine-1-carboxylate (214 mg, 0.48 mmol). MS (ESI) m/z: [M+H]+ Calcd for $C_{26}H_{35}N_5O_4$ 482.3; Found: 482.4.

tert-butyl (R)-3-((7-hydroxy-6-methoxy-2-(pyrrolidin-1-yl)quinazolin-4-yl)amino)piperidine-1-carboxylate (44 mg, 0.1 mmol), propargyl bromide (80% solution in toluene, 13 μL, 0.12 mmol), potassium carbonate (20 mg, 0.15 mmol) and acetonitrile (2 mL) were placed in a sealed tube for three hours. The product was purified by column chromatography (0 to 10% Methanol in DCM). Yield: 33 mg, 0.069 mmol, 51% over three steps. MS (ESI) m/z: [M+H]+ Calcd for [C21H27N5O2+H]+ 382.2; Found: 382.3. ¹H NMR (600 MHz, Methanol-d4) δ 7.35 (s, 1H), 7.30 (s, 1H), 4.90 (s, integration obscured by Methanol-d4 peak), 4.59 (d, J=10.2 Hz, 1H), 4.33 (d, J=14.1 Hz, 1H), 3.96 (d, J=11.5 Hz, 3H), 3.81 (s, 2H), 3.62 (d, J=37.5 Hz, 5H), 3.31 (m, integration obscured by Methanol-d4 peak), 2.30-1.97 (m, 6H), 1.85 (d, J=9.7 Hz, 2H).

f. Synthesis of Tert-Butyl (R)-3-((6-Methoxy-7-((1-(2-(2-(2-(5-((3aS,4S,6aR)-2-Oxohexahydro-1H-Thieno[3,4-D]Imidazol-4-yl)Pentanamido)Ethoxy)Ethoxy)Ethyl)-1H-1,2,3-Triazol-4-yl)Methoxy)-2-(Pyrrolidin-1-yl)Quinazolin-4-yl)Amino)Piperidine-1-Carboxylate (3)

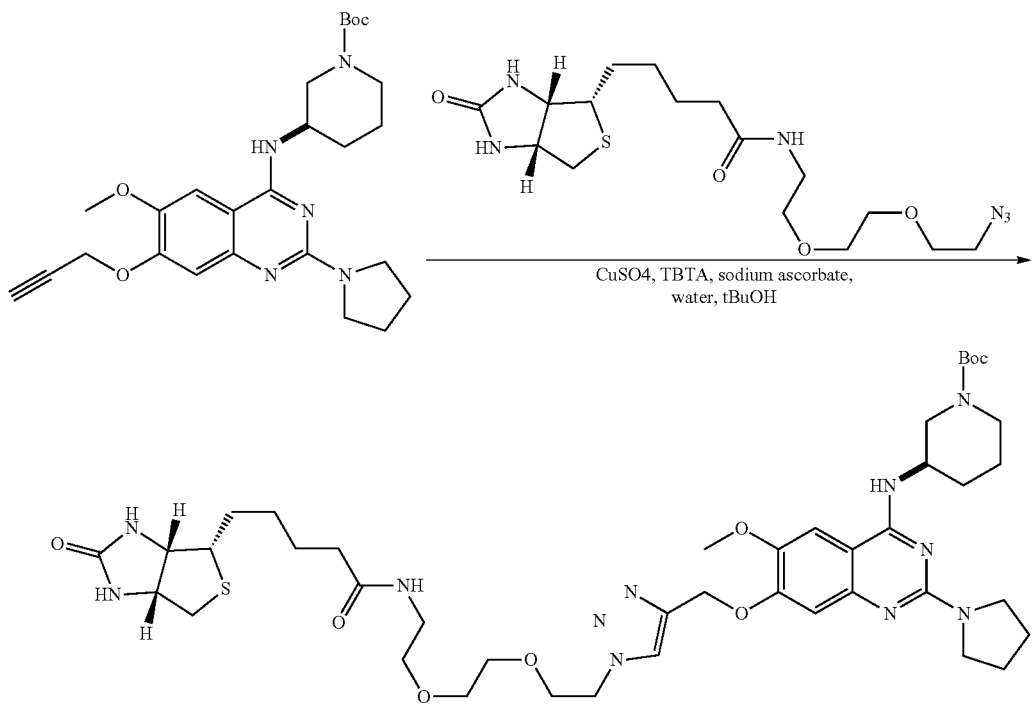

Figure 3:
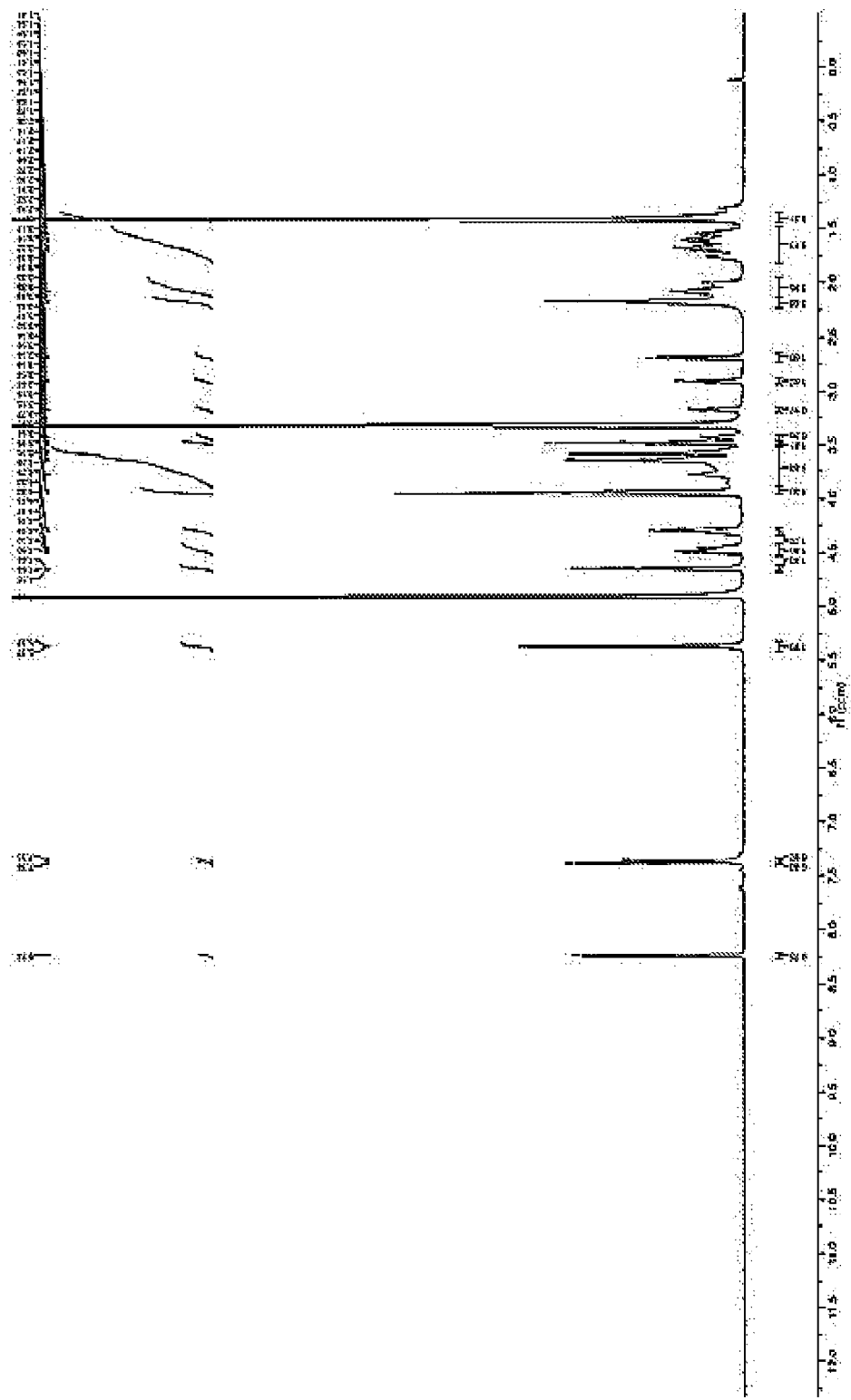
FIG. 3 shows a representative $^1$H NMR spectrum of compound 3.

Tert-butyl (R)-3-((6-methoxy-7-(prop-2-yn-1-yloxy)-2-(pyrrolidin-1-yl)quinazolin-4-yl)amino)piperidine-1-carboxylate (11) (16 mg, 0.034 mmol), N-(2-(2-(2-azidoethoxy)ethoxy)ethyl)-5-((3aS,4S,6aR)-2-oxohexahydro-1H-thieno[3,4-d]imidazol-4-yl)pentanamide (biotin-PEG2-azide; 14 mg, 0.034 mmol), tris[(1-benzyl-1H-1,2,3-triazol-4-yl)methyl]amine (TBTA; 1 mg) were dissolved in tBuOH (1 mL). A 0.1 M aqueous solution of copper sulfate (34 µL) was added and this was stirred for five minutes. A 0.1 M aqueous solution of sodium ascorbate (170 µL) was added and this was stirred for 24 hours. The product was purified by HPLC. Yield: 18 mg, 0.020 mmol, 60%. HRMS (ESI-TOF) m/z: [M+H]+ Calcd for $C_{42}H_{63}N_{11}O_8S$ 882.4660; Found: 883.4650. $^1$H NMR (600 MHz, Methanol-d4) δ 8.24 (s, 1H), 7.38 (s, 1H), 7.35 (s, 1H), 5.37 (d, J=2.3 Hz, 2H), 4.65 (t, J=4.9 Hz, 2H), 4.53-4.41 (m, 2H), 4.35-4.27 (m, 2H), 3.96-3.90 (m, 5H), 3.90-3.52 (m, 11H), 3.49 (t, J=5.5 Hz, 2H), 3.44 (d, J=10.6 Hz, 1H), 3.17 (dd, J=9.1, 4.7 Hz, 1H), 2.92 (dd, J=12.7, 5.0 Hz, 1H), 2.69 (d, J=12.8 Hz, 1H), 2.17 (t, J=7.4 Hz, 4H), 2.04 (d, J=46.6 Hz, 4H), 1.82-1.47 (m, 7H), 1.41 (s, 10H). HPLC Purity: >95%, $t_R$=4.40 min. See FIG. 3.

g. Synthesis of N-(2-(2-(2-(4-((((R)-Piperidin-3-yl)Amino)-2-(Pyrrolidin-1-yl)Quinazolin-7-yl)Oxy)Methyl)-1H-1,2,3-Triazol-1-yl)Ethoxy)Ethoxy)Ethyl)-5-((3aS,4S,6aR)-2-Oxohexahydro-1H-Thieno[3,4-d]Imidazol-4-yl)Pentanamide, Trifluoroacetic Acid Salt (4)

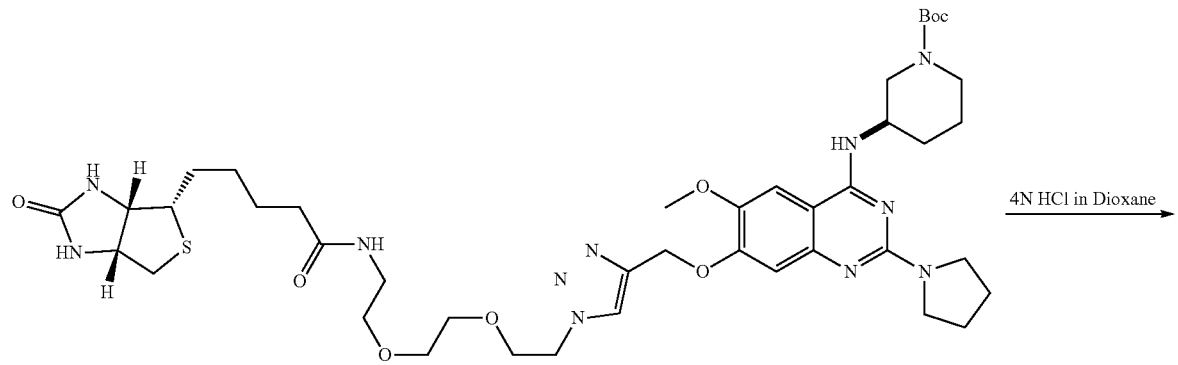

4N HCl in Dioxane

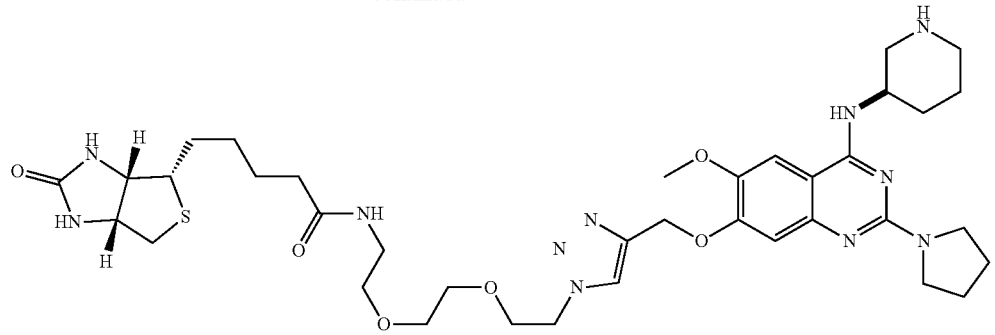

tert-Butyl (R)-3-(((6-methoxy-7-((1-(2-(2-(2-(5-((3aS,4S,6aR)-2-oxohexahydro-1H-thieno[3,4-d]imidazol-4-yl)pentanamido)ethoxy)ethoxy)ethyl)-1H-1,2,3-triazol-4-yl)methoxy)-2-(pyrrolidin-1-yl)quinazolin-4-yl)amino)piperidine-1-carboxylate (3) (15 mg, 0.017 mmol) was stirred in 1 mL of 4N HCl in dioxane for one hour. The mixture was purified by HPLC. Yield: 9 mg, 59%. HRMS (ESI-TOF) m/z: [M+H]+ Calcd for $C_{37}H_{55}N_{11}O_6S$ 782.4136; Found: 782.4140. 1H NMR (600 MHz, Methanol-d4) δ 8.24 (d, J=12.4 Hz, 1H), 7.42 (d, J=12.6 Hz, 1H), 7.27 (d, J=12.6 Hz, 1H), 5.38 (d, J=12.2 Hz, 2H), 4.68-4.55 (m, 3H), 4.50 (dd, J=7.8, 4.8 Hz, 1H), 4.37-4.24 (m, 2H), 3.93 (d, J=12.5 Hz, 5H), 3.87-3.61 (m, 7H), 3.61-3.53 (m, 4H), 3.48 (q, J=8.9, 7.2 Hz, 2H), 3.18 (dt, J=10.1, 5.0 Hz, 1H), 2.92 (dd, J=12.8, 5.0 Hz, 1H), 2.69 (d, J=12.7 Hz, 1H), 2.32-1.98 (m, 8H), 1.85 (d, J=10.1 Hz, 2H), 1.71-1.28 (m, 7H). HPLC Purity: >95%, tR=3.33 min.

h. Synthesis of (S)-6,7-Dimethoxy-N-(1-(Pent-4-en-1-yl)Piperidin-3-yl)-2-(Pyrrolidin-1-yl)Quinazolin-4-Amine, Trifluoroacetic Acid Salt (5)

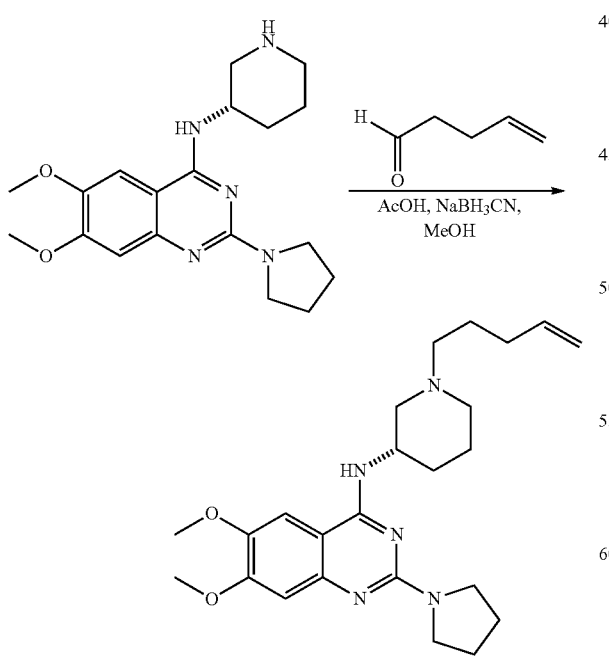

(S)-6,7-Dimethoxy-N-(piperidin-3-yl)-2-(pyrrolidin-1-yl)quinazolin-4-amine trifluoroacetic acid salt (1) (47 mg, 0.1 mmol), acetic acid (23 μL, 0.4 mmol), sodium cyanoborohydride (13 mg, 0.2 mmol), and 4-pentenal (20 μL, 0.2 mmol) were dissolved in methanol (1 mL) and stirred at room temperature for 18 hours. The mixture was purified by HPLC. Yield: 23 mg, 0.042 mmol, 42%. HRMS (ESI-TOF) m/z: [M+H]+ Calcd for $C_{24}H_{35}N_5O_2$ 426.2869; Found: 426.2859. 1H NMR (600 MHz, DMSO-d6) δ 12.03 (s, 1H), 9.04 (s, 1H), 8.93 (s, 1H), 7.32 (s, 1H), 7.21 (s, 1H), 5.12-4.98 (m, 2H), 4.64 (s, 1H), 4.30 (d, J=13.3 Hz, 1H), 3.95-3.90 (m, 3H), 3.90-3.86 (m, 3H), 3.63 (d, J=36.0 Hz, 11H, overlaps with water peak), 3.02 (d, J=7.5 Hz, 2H), 2.20 (d, J=12.1 Hz, 1H), 2.16-1.87 (m, 7H), 1.76-1.58 (m, 4H). HPLC Purity: >95%, $t_R$=3.50 min.

i. Tert-Butyl (R)-3-((6,7-Dimethoxy-2-(Pyrrolidin-1-yl)Quinazolin-4-yl)Amino)Piperidine-1-Carboxylate (6)

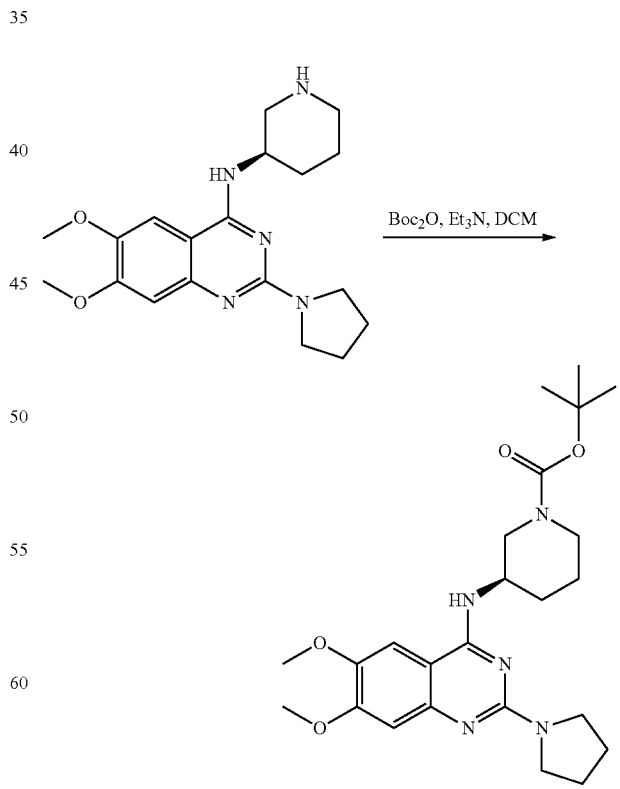

Compound 2 (42 mg, 0.09 mmol), boc anhydride (20 mg, 0.09 mmol) and triethylamine (46 uL, 0.36 mmol) were stirred in 1 mL DCM for 24 h. The mixture was purified by HPLC to give the title compound. Yield: 35 mg, 85%. 1H NMR (600 MHz, Methanol-d4) δ 7.32 (s, 1H), 7.19 (s, 1H), 4.43 (d, J=13.0 Hz, 1H), 4.28 (d, J=13.4 Hz, 1H), 4.03 (s, 3H), 3.90 (s, 3H), 3.84-3.51 (m, 6H), 3.45 (dd, J=13.0, 8.8 Hz, 1H), 2.27-1.95 (m, 6H), 1.83-1.60 (m, 2H), 1.41 (s, 9H). HRMS (ESI-TOF) m/z: [M+H]+ Calcd for $C_{24}H_{36}N_5O_4$: 458.2767; Found: 387.2514.

j. Synthesis of (S)—$N^2$-Hexyl-6,7-Dimethoxy-$N^4$-(Piperidin-3-yl)Quinazoline-2,4-Diamine (7)

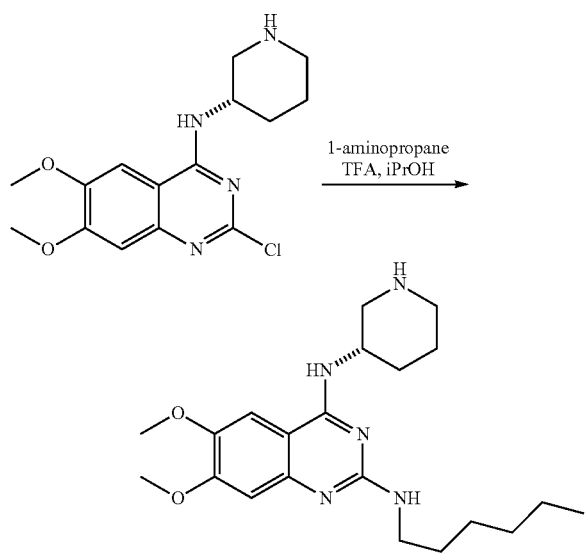

(S)-2-chloro-6,7-dimethoxy-N-(piperidin-3-yl)quinazolin-4-amine TFA salt (prepared as described in the synthesis of 1, 87 mg, 0.2 mmol) was placed in a microwave reactor vessel along with 1-aminopropane (0.11 mL, 0.8 mmol), TFA (0.11 mL, 1.4 mmol), and isopropanol (2 mL). This was stirred under microwave irradiation for 30 minutes at 150° C. Purification by HPLC gave the product. Yield: 23 mg, 23%. HRMS (ESI-TOF) m/z: [M+H]+ Calcd for $C_{21}H_{34}N_5O_2$: 388.2713; Found: 388.2714. 1H NMR (600 MHz, Methanol-d4) δ 7.24 (s, 1H), 7.02 (s, 1H), 4.58 (s, 1H), 4.30 (s, 1H), 4.01 (s, 3H), 3.95 (s, 3H), 3.62 (d, J=72.0 Hz, 5H), 2.27 (s, 1H), 2.05 (s, 1H), 1.94-1.80 (m, 2H), 1.71 (t, J=7.6 Hz, 2H), 1.53-1.28 (m, 6H), 1.00-0.88 (m, 2H).

k. Synthesis of (S)-6-Methoxy-7-(3-(Piperidin-1-yl)Propoxy)-N-(Piperidin-3-yl)-2-(Pyrrolidin-1-yl)Quinazolin-4-Amine Trifluoroacetic Acid Salt (8)

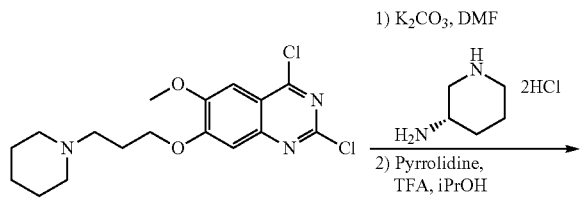

-continued

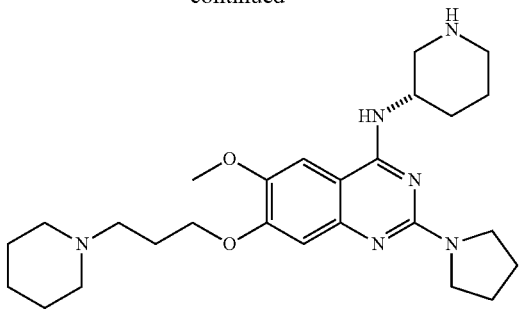

2,4-Dichloro-6-methoxy-7-(3-(piperidin-1-yl)propoxy)quinazoline was prepared as previously described (J. Med. Chem., 2011, 54 (17), pp 6139-6150). The product was prepared using the same methods and reagents as described for compound 1. Yield: 33% over 2 steps. HRMS (ESI-TOF) m/z: [M+H]+ Calcd for $C_{26}H_{40}N_6O_2$ 469.3291; Found: 469.3291. 1H NMR (600 MHz, Methanol-d4) δ 7.28 (s, 1H), 7.23 (d, J=1.3 Hz, 1H), 4.61-4.51 (m, 1H), 4.33-4.23 (m, 3H), 3.98-3.90 (m, 3H), 3.82-3.58 (m, 9H), 3.40-3.37 (m, 2H), 3.03-2.94 (m, 2H), 2.38 (dt, J=12.8, 7.2 Hz, 2H), 2.27-1.98 (m, 8H), 1.91-1.78 (m, 5H), 1.57 (tdd, J=12.6, 8.8, 5.2 Hz, 1H). 13C NMR (151 MHz, DMSO) δ 162.86, 154.54, 149.09, 145.83, 138.62, 107.48, 102.69, 100.02, 66.78, 56.28, 53.93, 52.75, 50.29, 50.19, 48.49, 46.98, 46.47, 28.15, 25.66, 24.48, 23.54, 23.02, 22.83, 21.55.

3. Small Molecule Primary Screen for Epigenetic Modulators of the HP1 Pathway

Heterochromatin protein 1 (HP1) is critical for the formation of heterochromatin domains leading to gene repression that enables cell differentiation and development (Moazed, 2001). HP1 is composed of two domains, a chromodomain (CD) which facilitates binding to H3K9me3 linked to a chromoshadow domain (CSD) which recruits H3K9 specific histone methyltransferases including Suv39H1/2 and SETDB1. These enzymes deposit H3K9me2/3 marks on neighboring histones. Subsequent binding of additional HP1 proteins facilitates the spreading of H3K9me3 induced heterochromatin resulting in DNA compaction and gene repression (Canzio et al., 2011). Dysregulation of HP1 expression has also been linked to certain cancer types including breast, uterine, prostate, and pancreatic carcinomas (De Koning et al., 2009). Despite HP1's importance in epigenetic regulation of genes and involvement in cancers, there are currently few small molecules which target any components in this pathway.

To identify modulators of the HP1 pathway, a small molecule chemical genetics-based screening approach was employed using a set of compounds and derivatives with demonstrated activity in epigenetic pathways. This EpiG compound set includes ~960 small molecules designed to target diverse epigenetic pathways, making it an ideal small molecule library to interrogate the HP1 pathway. A high-throughput flow cytometry-based screening platform was developed using the CiA:Oct4 system in a mouse embryonic stem (ES) cell line expressing enhanced nuclear GFP as a reporter for chromatin dynamics (Hathaway et al., 2012). This approach allowed for compounds to be screened in high-format and to determine specific effects on chromatin state with single cell resolution in a temporally controlled manner.

Figure 4B:
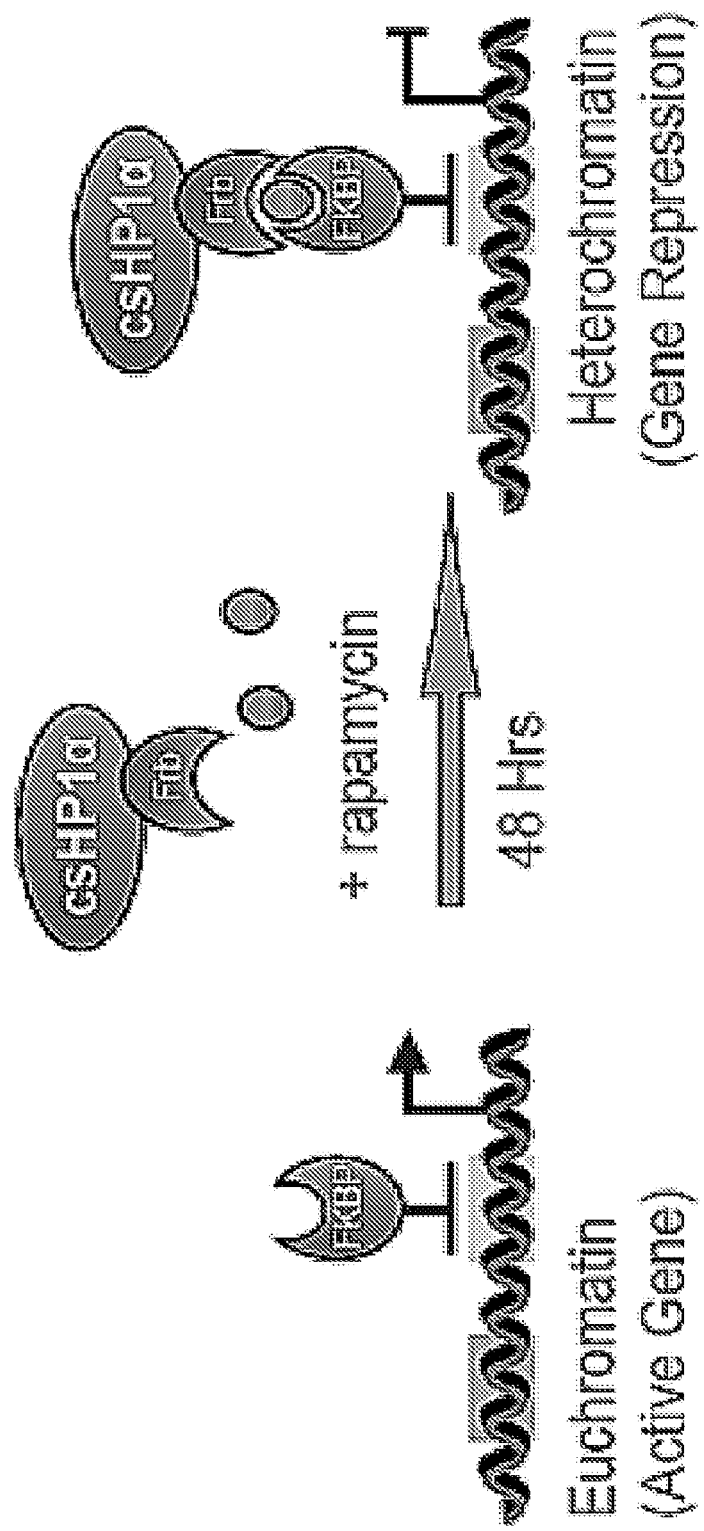

Here, the CiA:Oct4 system combined with CIP-mediated recruitment to the CiA promoter region was used to measure activity by GFP expression. Lentiviral infection into the CiA:Oct4 cell line yielded stable expression of the Gal4-FKBP (N118) and FRB-csHP1a (N163) fusion proteins. Rapamycin addition bridged the FKBP and FRB domains rapidly recruiting csHP1a to the Oct4 locus (FIG. 4B). Recruitment was followed by removal of active chromatin marks such as H3K4me3, deposition of repressive H3K9me3, and gene repression. This method mimics the physiologic chromatin transformation that occurs at the Oct4 locus upon cellular differentiation of embryonic stem cells.

Figure 4C:
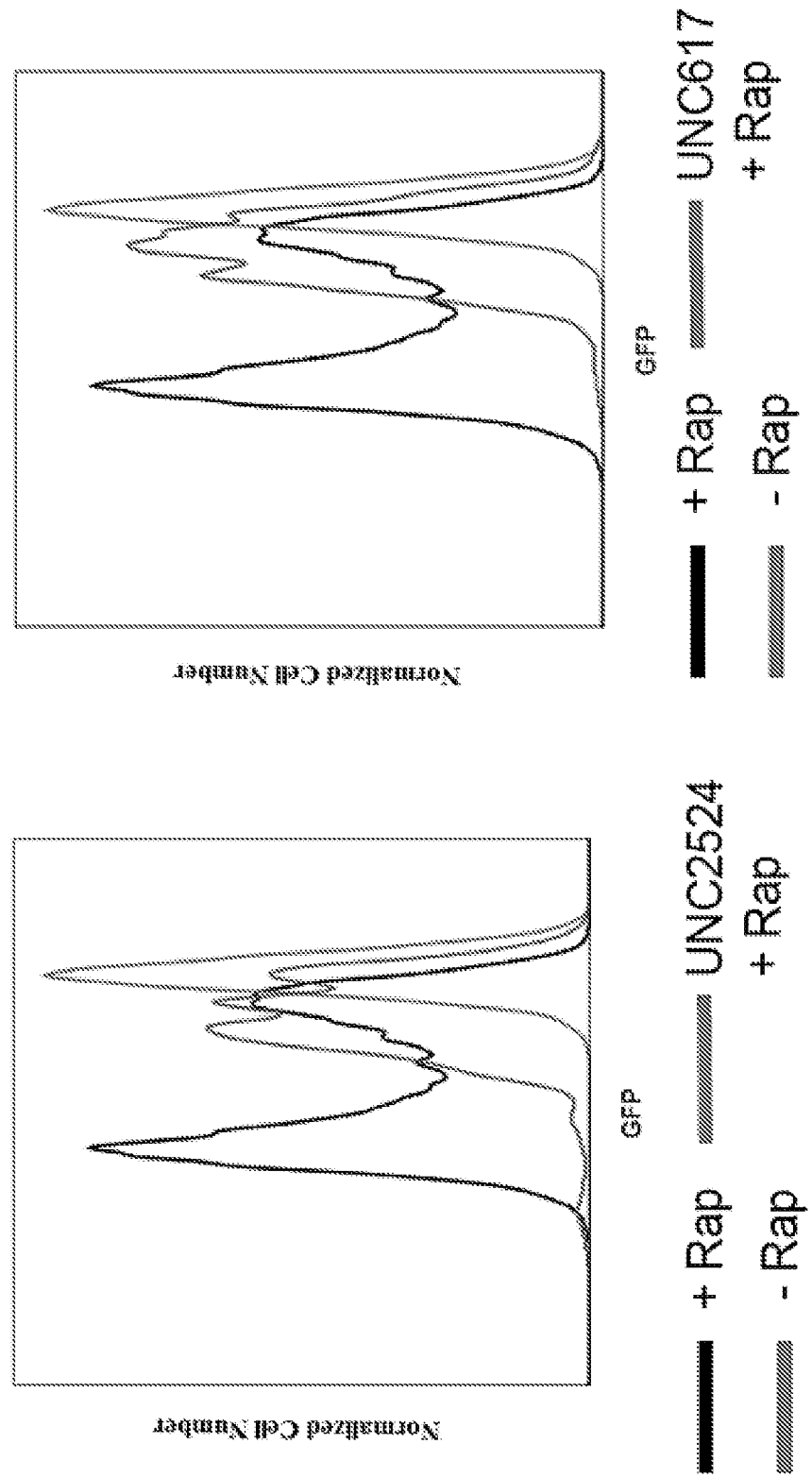
Figure 4D:
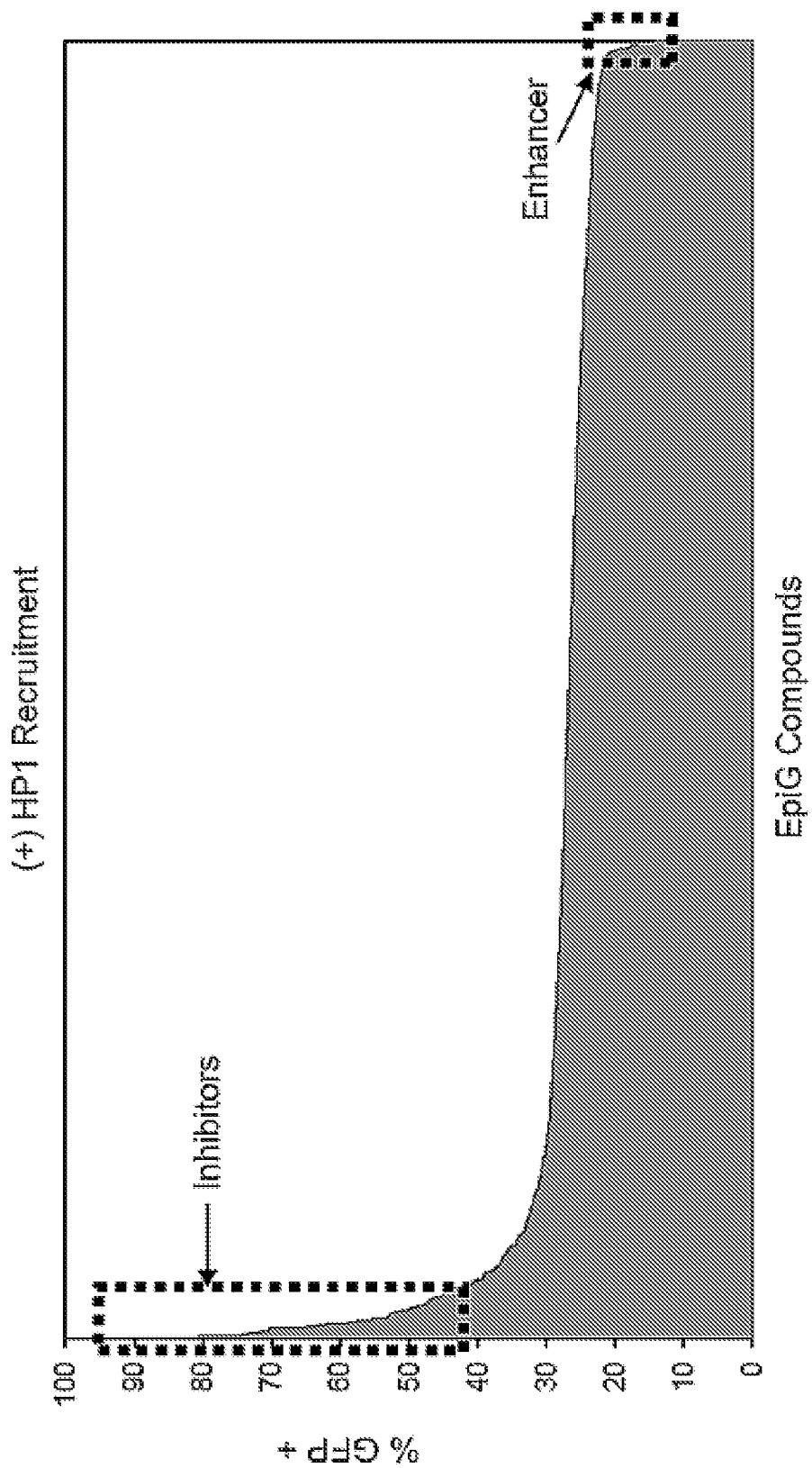
Figure 5A:
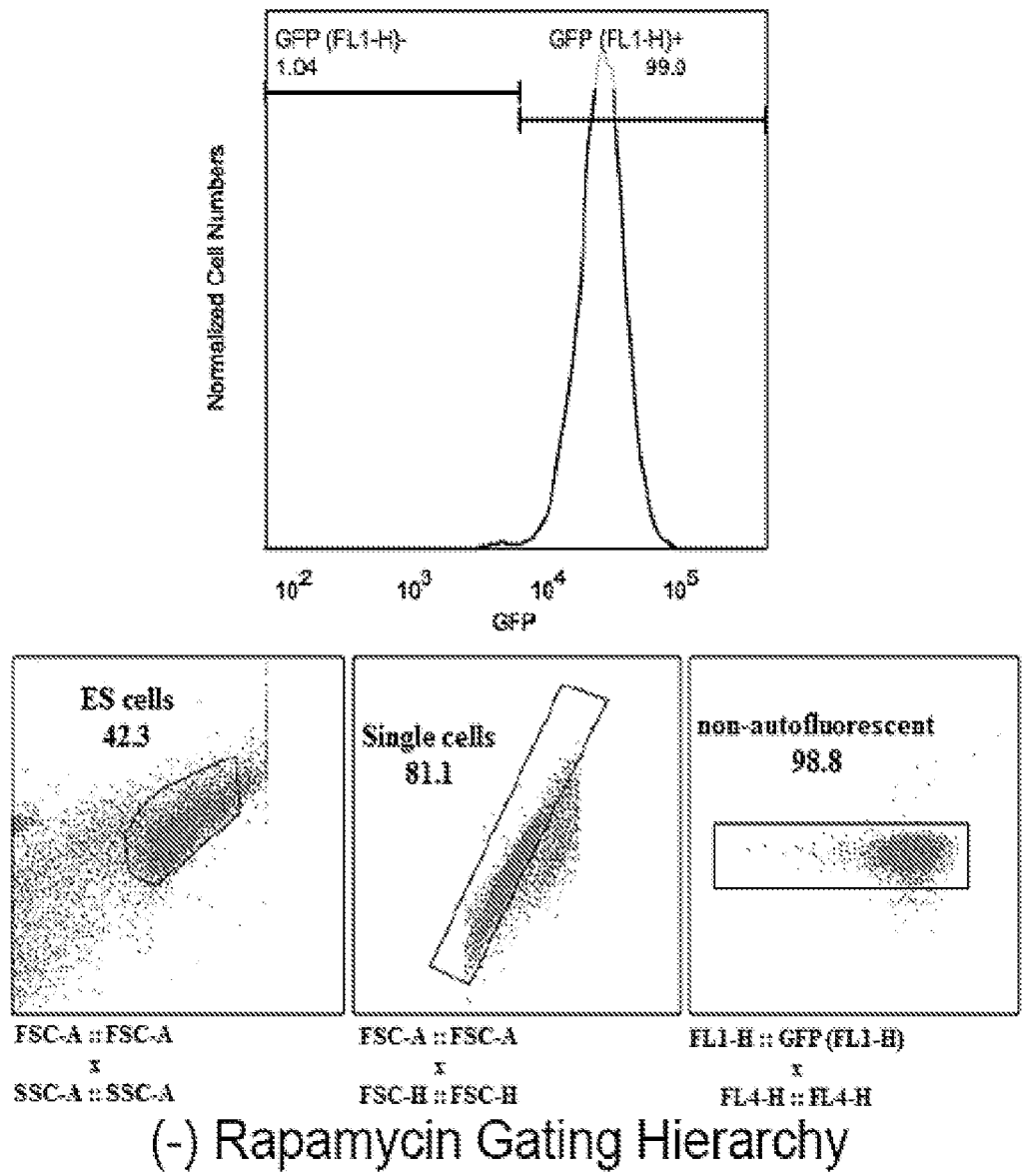
FIG. 5A-E shows a representative primary screen flow cytometry gating hierarchy and representative (−) Rapamycin counterscreen results.
Figure 5B:
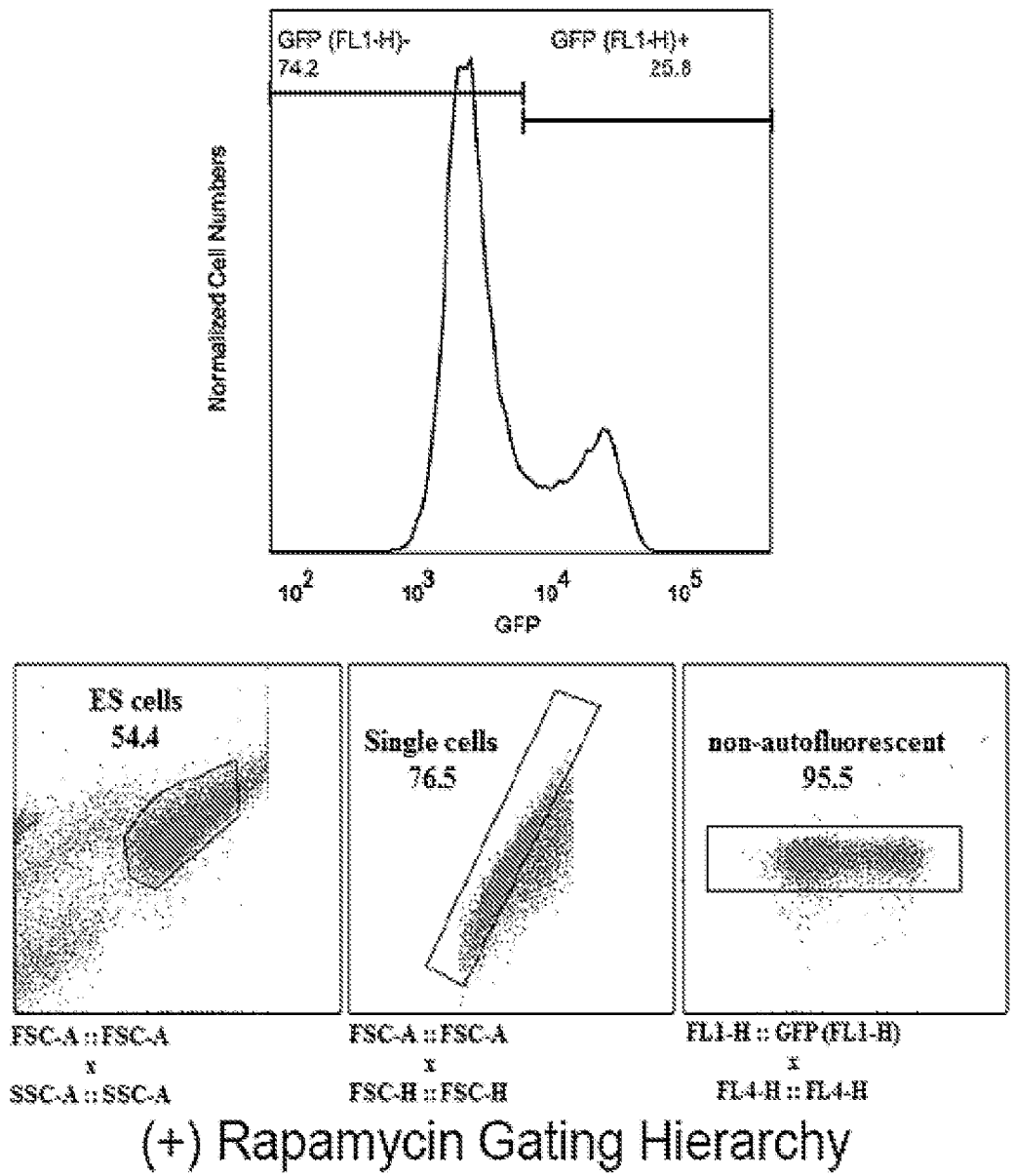

The EpiG compound set was screened at 10 µM with and without rapamycin for 48-hours prior to analysis by high-throughput flow cytometry using the CiA:Oct4 N118/163 cell line (FIG. 4A and FIG. 5A). % GFP (+) positive populations were determined by gating on the GFP (−) populations in control samples treated with rapamycin (FIG. 5B). In the primary screen recruiting csHP1α, 78 compounds had fewer than 200 cell events detected by flow cytometry so were removed due to lack of statistical confidence in the data. Without wishing to be bound by theory, this lack of cells was likely due to compound toxicity at the 10 µM screening dose. Remaining compounds were arranged from highest to lowest % GFP (+) population (FIG. 4D). Inhibitors were defined as being 2 standard deviations above the mean. 34 inhibitors were identified, with UNC617 and UNC2524 representing the top compound hits from the screen. Representative histograms of flow cytometry data show how csHP1α recruitment facilitated by rapamycin addition (black line) resulted in cell populations shifting to be GFP (−) negative. Cells treated without rapamycin (grey line) remain near 100% GFP (+) positive as no csHP1α is recruited to the locus in these samples. Inhibitors of the HP1-heterochromatin pathway, UNC2524 and UNC617 (red line), result in an increased expression of GFP despite csHP1α recruitment leading to a greater percentage of GFP (+) positive cells (FIG. 4C). Compound UNC00000202 demonstrated an ability to enhance HP1 pathway repression with nearly 10% less GFP expression than controls.

Figure 5C:
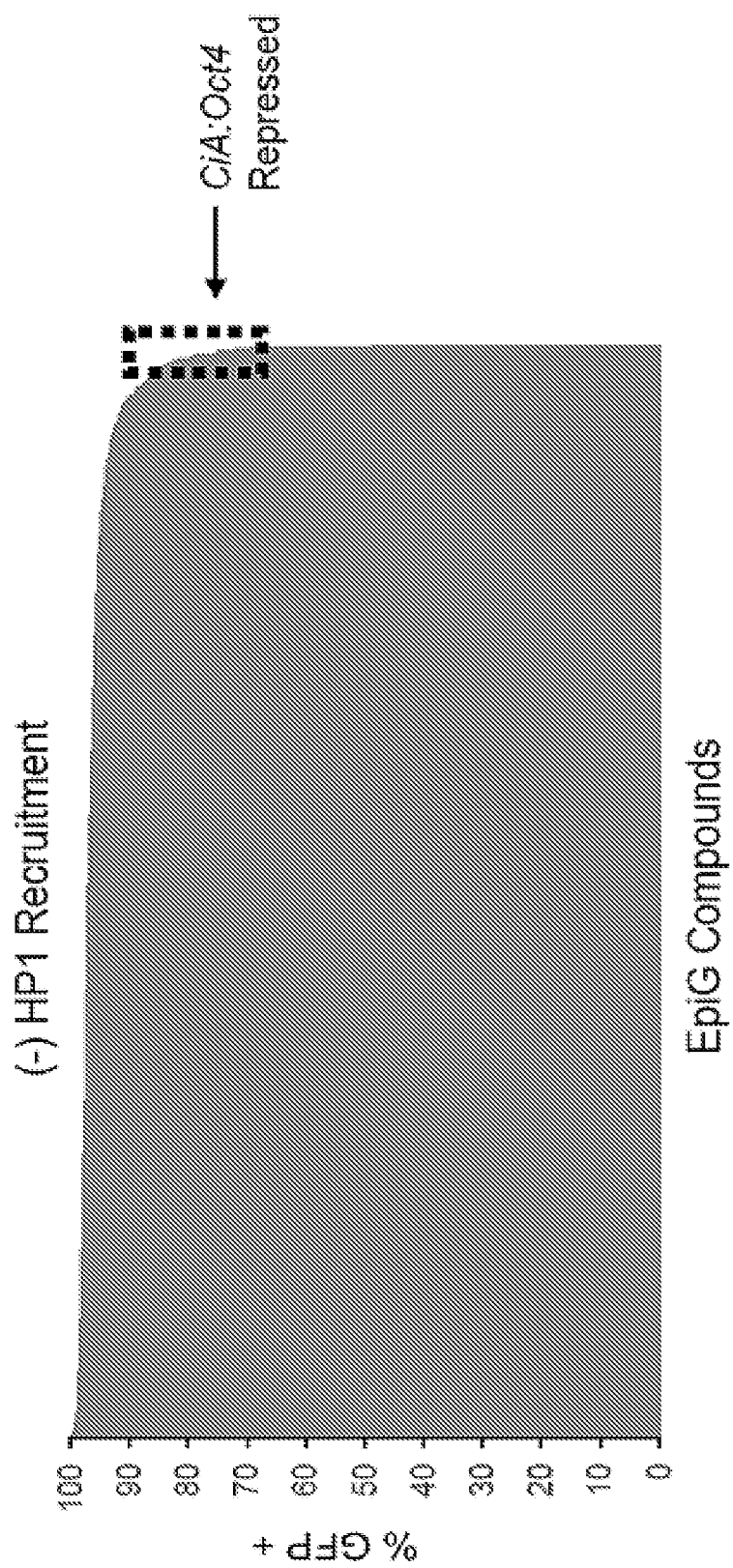

The CiA:Oct4 N118/N163 recruitment system also functions as an internal counter screen for toxicity and cell differentiation in the absence of rapamycin recruited csHP1α. ES cell differentiation causes the Oct4 locus to be silenced resulting in a decreased GFP expression. The EpiG compound set was screened at 10 µM without rapamycin induced csHP1α recruitment for 48 hrs prior to analysis by high-throughput flow cytometry. Lack of csHP1α recruitment results in near 100% GFP positive cells (FIG. 5A). 72 compounds were identified below the 200-event cutoff in the minus rapamycin counter screen and could not be interpreted (FIG. 5C).

Figure 5D:
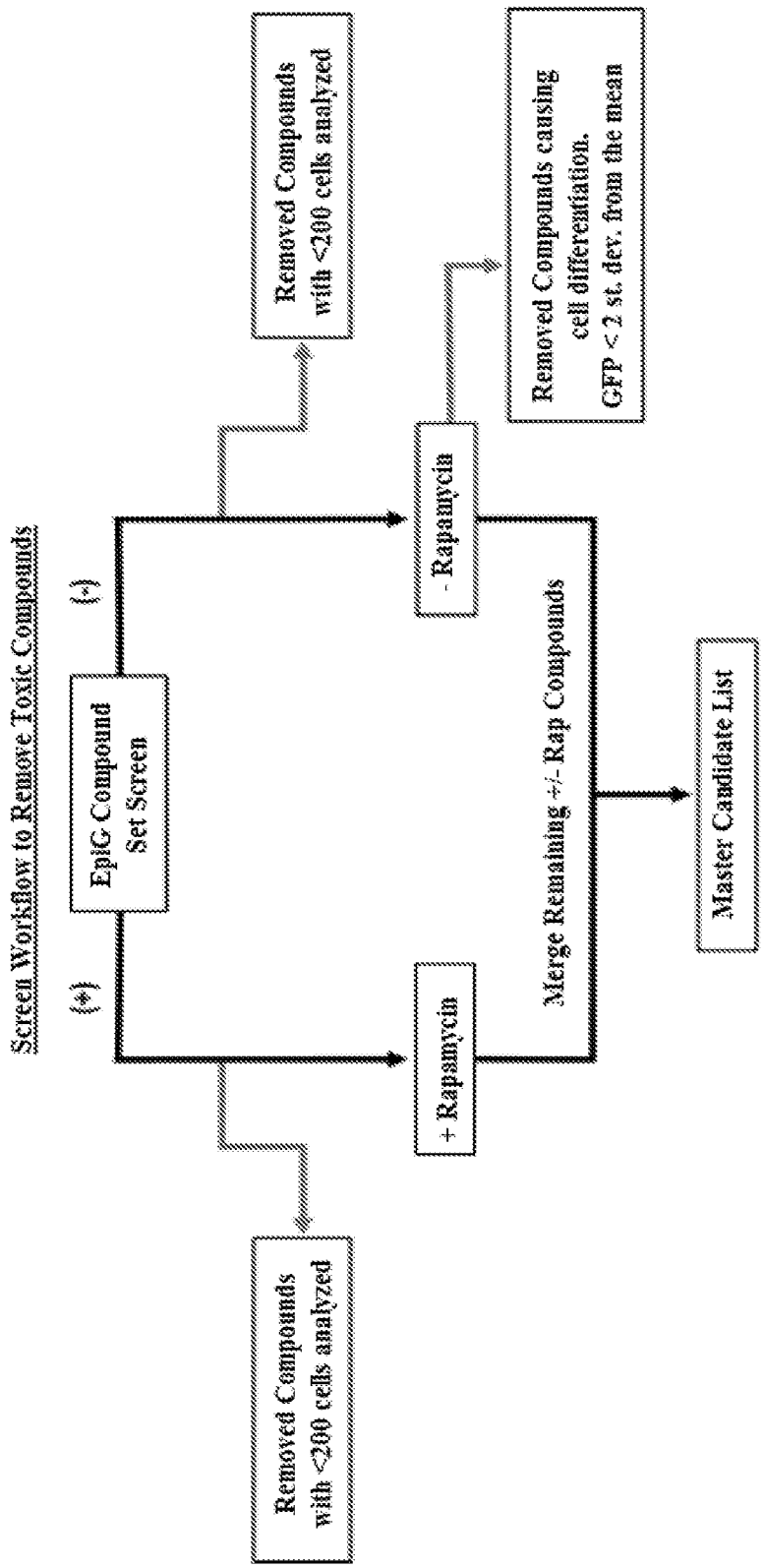
Figure 5E:
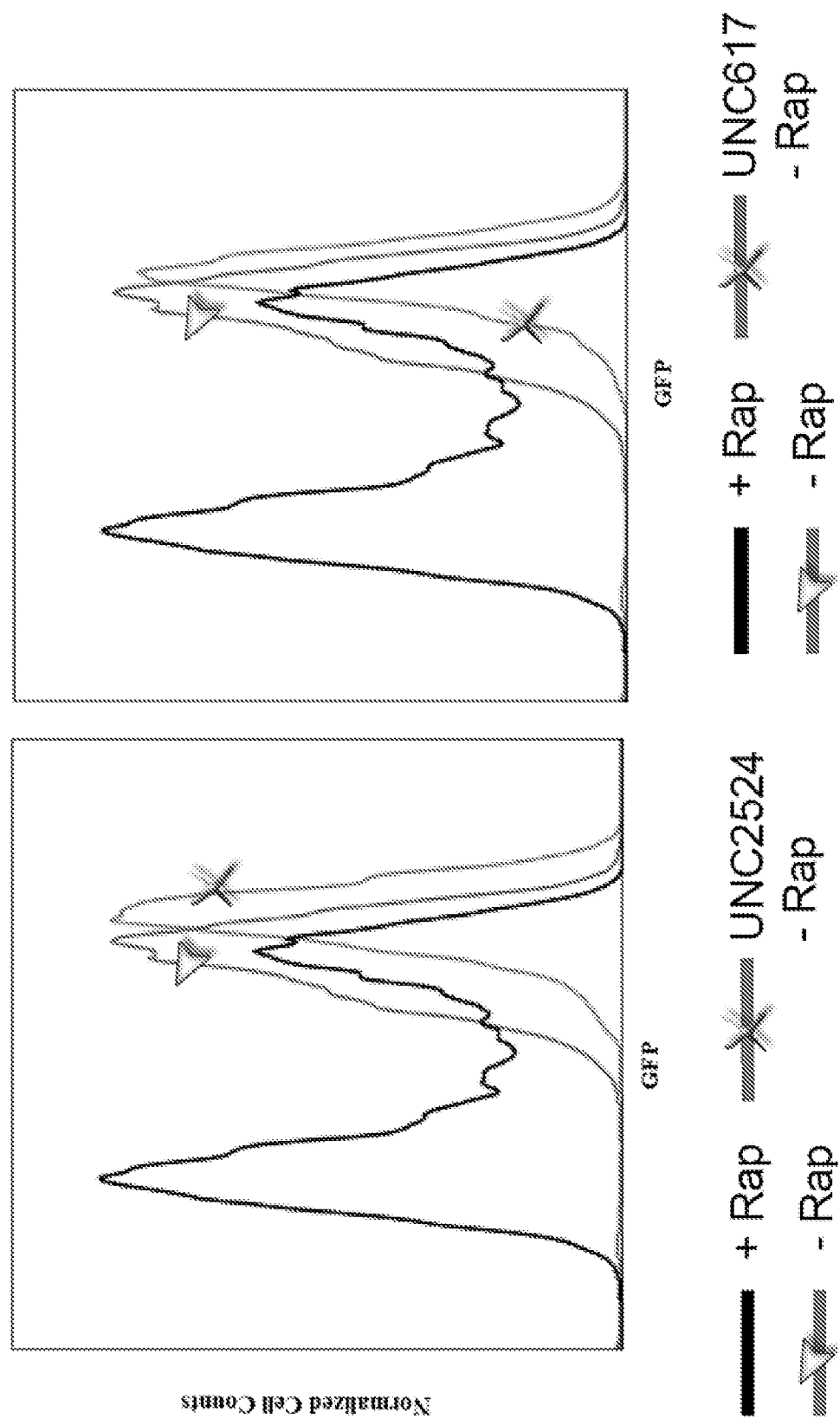

Next, compounds were identified that caused differentiation of ES cells by analyzing the % GFP (+) positive population in the minus rapamycin counterscreen. Compounds which resulted in a greater than 10% reduction in GFP positive cell populations compared to the mean were removed from the data set moving forward as Oct4 repression is a sign of cellular differentiation (FIG. 5C). Lead inhibitors of HP1-mediated heterochromatin formation, UNC2524 and UNC617, did not decrease GFP positive population levels, but demonstrated increased expression of GFP compared to controls, indicating greater gene activation (FIG. 5E). Only compounds which did not cause CiA:Oct4 repression independent of csHP1α recruitment or result in cell toxicity in either the plus or minus rapamycin screens were used to generate the final dataset for the screen (FIG. 5D).

Referring to FIG. 4A-D, a representative high-throughput flow cytometry screen for modulators of HP1-mediated heterochromatin formation is shown. Specifically, FIG. 4A shows a representative diagram outlining the primary screening strategy workflow over a 3 day experimental time course. FIG. 4B shows a representative cartoon of the CiA:Oct4 system utilizing chemical induced proximity (CIP) to recruit csHP1α. Addition of rapamycin facilitated the bridging of the Gal4-FKBP and FRB-csHP1α fusion resulting in heterochromatin formation and gene repression. FIG. 4C shows a representative histogram of GFP fluorescence intensity for top inhibitors of HP1-mediated repression (UNC2524 and UNC617) at 10 µM compared to +/−6 nM rapamycin controls. FIG. 4D shows representative results of a EpiG small molecule screen showing % GFP (+) populations plus 6 nM rapamycin. Inset boxes contain inhibitors or enhancers of HP1-mediated gene repression as indicated by altered level of GFP expression.

Referring to FIG. 5A and FIG. 5B, CiA:Oct4 N118/N163 cells were treated with (FIG. 5B) and without (FIG. 5A) 6 nM rapamycin for 48 hrs and analyzed by flow cytometry. The top panel shows a representative histogram of GFP fluorescence intensity including all single, non-autofluorescent cells. Gate indicates +/−GFP populations. Cell population was gated using forward scatter area by side scatter area (bottom, left). Single cells were enriched from cell population by gating forward scatter area by forward scatter height (bottom, middle). Non-autofluorescent cells were enriched from the singlet population by gating 488 nm excitation in BL1 channel (GFP) by 561 nm excitation YL4 channel (PE-Cy7) (bottom, right). Referring to FIG. 5C, representative results of EpiG small molecule counter screen showing % GFP (+) populations with no rapamycin are shown. Internal box contains compounds that resulted in decreased GFP fluorescence levels due to compound toxicity or cell differentiation. Referring to FIG. 5D, a representative cartoon depicts workflow used to exclude compounds from the EpiG screen results. All compounds in both the +/−rapamycin primary and counter screens that caused fewer than 200 cells to be analyzed were excluded due to a lack of statistical confidence in flow cytometry data. Compounds in the counterscreen that have GFP expression levels greater than 10% below the mean were excluded. Compounds decreasing GFP expression without rapamycin present indicates the compounds cause cell differentiation and are not representative of healthy mouse ES cells. Referring to FIG. 5E, representative histograms of lead inhibitors UNC2524 and UNC617 without HP1 recruitment (grey with "X") compared to +rapamycin (black) and −rapamycin (grey with arrow) controls.

4. Functional Analysis of Lead Screen Compounds

To characterize the lead compounds and elucidate their biological functions, a dose response curve was performed at 10, 5, 2.5, 1.25, and 0 µM of compound with and without rapamycin. This allowed the maximum biological activity of the compounds to be determined without compromising cell viability. Similar to the screening approach, CiA:Oct4 N118/N163 cells were seeded in 96 well plate format and grown with and without rapamycin-mediated HP1 recruitment. Compound and media were added daily and samples were assayed by flow cytometry at 48-hours to determine the effect of inhibiting the HP1 pathway on GFP expression.

% GFP (+) positive values were converted to % inhibition by normalizing the values 0-100 based on control samples. Without wishing to be bound by theory, the response curves demonstrate dose-dependent activity in the biological assay relating increasing compound concentration with increased inhibition of the HP1 pathway. UNC617, believed to be a G9a/GLP inhibitor, demonstrated the most potent response in this assay ($IC_{50}$ 1.0 µM), followed by UNC2524, UNC00000557, and UNC1875 with $IC_{50}$ values of 1.8, 2.4, 3.1, and 3.4 µM respectively (FIG. 6A) (Kim et al., 2016). Expanded dose response curves for 12 of the top inhibitors can be found in FIG. 7A with rapamycin treatment and FIG. 7B without rapamycin treatment. Data points missing are due to compound toxicity leading to cell differentiation and decreased GFP expression. Without wishing to be bound by theory, these data indicate that a 5-10 µM dose maximized compound assay activity and cell viability for the top screen hits.

To exclude the possibility that the lead compounds were inhibiting rapamycin's ability to recruit csHP1α to the CiA:Oct4 locus, the function of the lead compounds in was examined in an orthogonal recruitment system. HP1 was fused to the tetracycline repressor (TetR) and stably expressed in a mouse ES cell line expressing a blue fluorescent protein (BFP) reporter gene upstream of the tetracycline response element (TRE). Like rapamycin addition, absence of doxycycline causes TetR-HP1 to be recruited to the TRE resulting in HP1-heterochromatin formation. Addition of doxycycline inhibits TetR from binding to TRE leading to gene activation (FIG. 6C). Compounds UNC00000557, UNC617, UNC2524, and UNC1875 were tested at 5 µM for 48 hrs with and without TetR-HP1 recruitment. All compounds tested were shown to significantly inhibit HP1-mediated heterochromatin formation with UNC617 and UNC2524 remaining the most potent inhibitors (FIG. 6D). Further, only UNC1875 demonstrated a minimal decrease in median BFP expression independent of TetR-HP1 recruitment while all other compounds resulted in either no change or increased BFP expression compared to controls, indicating an activation of gene expression (FIG. 6E). These data corroborated the primary screen results and demonstrated, using an orthogonal recruitment method, that lead inhibitor compounds block HP1 repression at a different gene locus.

Figure 8:
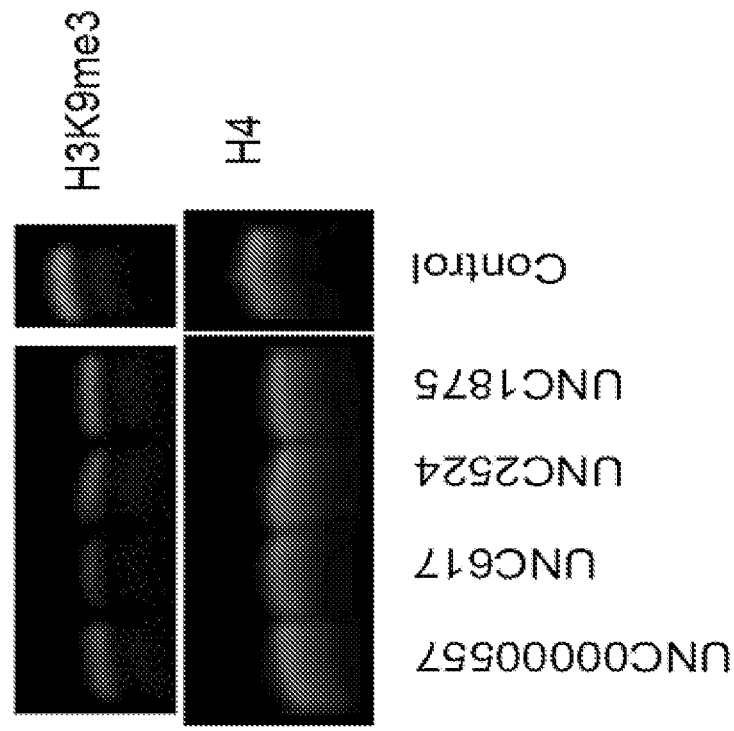
FIG. 8 shows representative data indicating that lead screen compounds decrease global H3K9me2/3.
Figure 8:
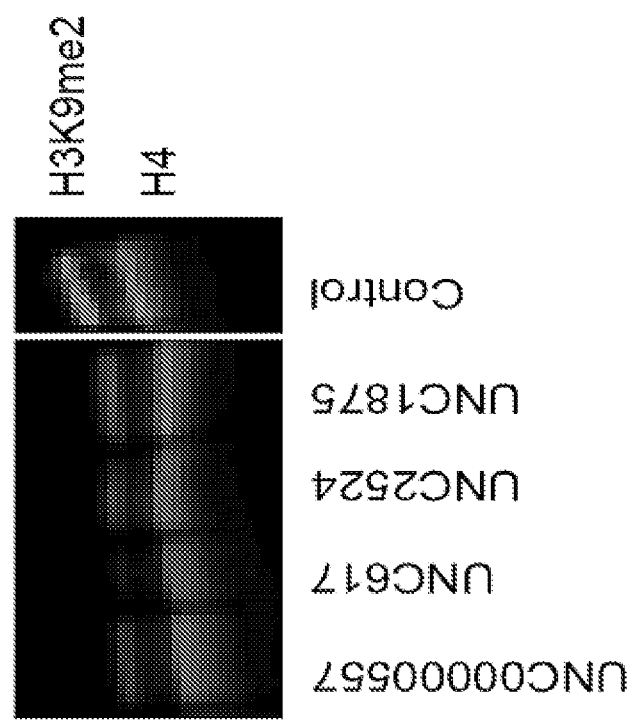

HP1 gene repression and silencing is mediated by H3K9me3 deposition. To determine if the lead compounds were effecting global H3K9me levels, CiA:Oct4 N118/N163 cells were grown in 6 well plate format with the addition of 10 µM compound for 48 hours. After 48-hours of compound treatment, nuclei were isolated and total histones were extracted using 0.2 N HCl. Total extracted histone proteins were quantified by Bradford Coomassie and equal total protein was loaded per sample for gel electrophoresis and subsequent western blot analysis. Total H3K9me2 and H3K9me3 levels were assayed and normalized to histone H4 (FIG. 8). Quantification of H3K9me2 and H3K9me3 western blots demonstrated that all lead compounds tested resulted in decreased global H3K9me2/3. UNC617 treatment resulted in near total loss of H3K9me2/3 while UNC2524 and UNC00000557 had roughly equivalent decreases in H3K9 methylation. UNC1875 also decreased H3K9me2/3, but not to the extent of the other compounds.

Figure 9A:
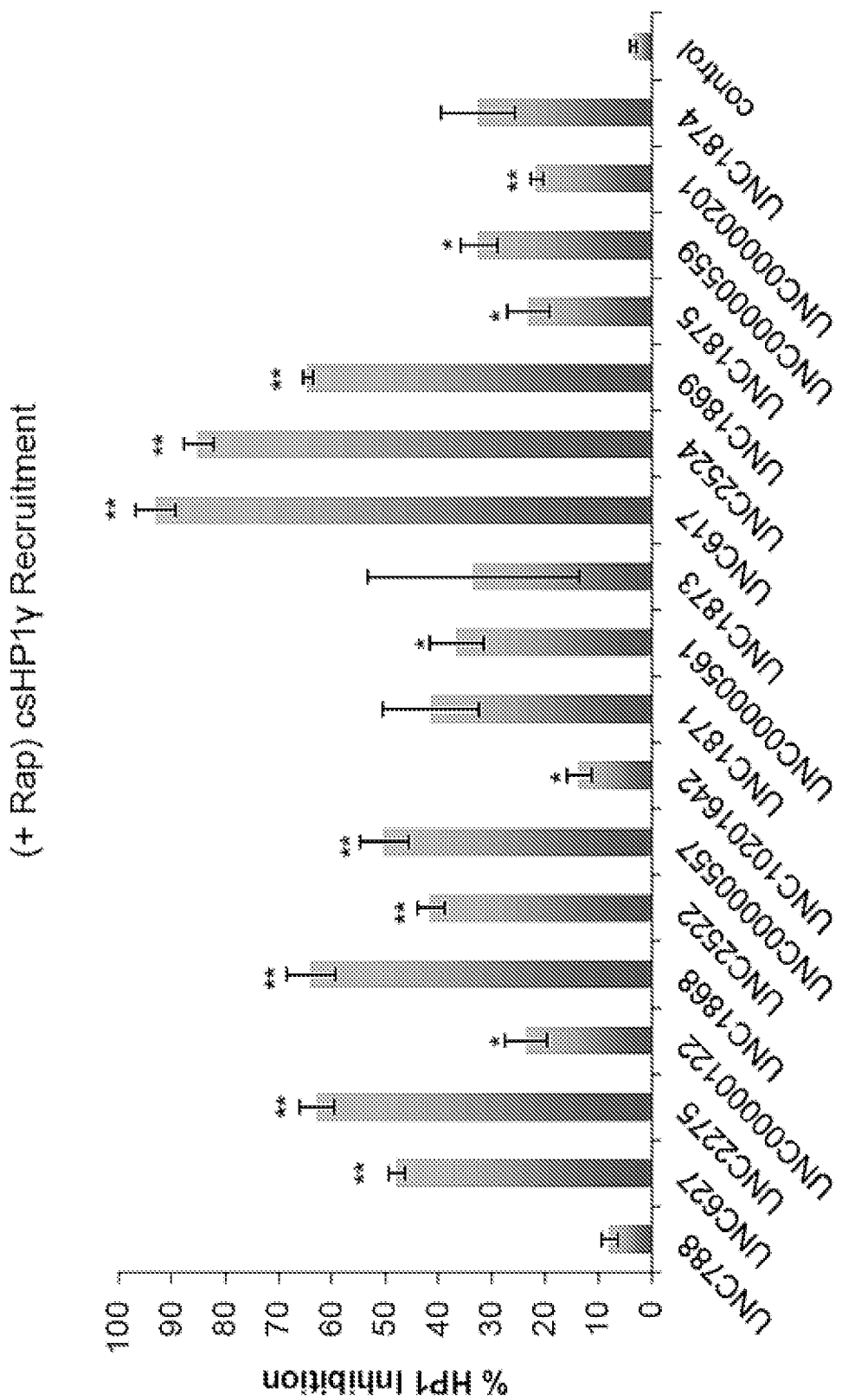
FIG. 9 show representative data indicating that lead screen compounds inhibit csHP1γ-mediated gene repression.
Figure 9B:
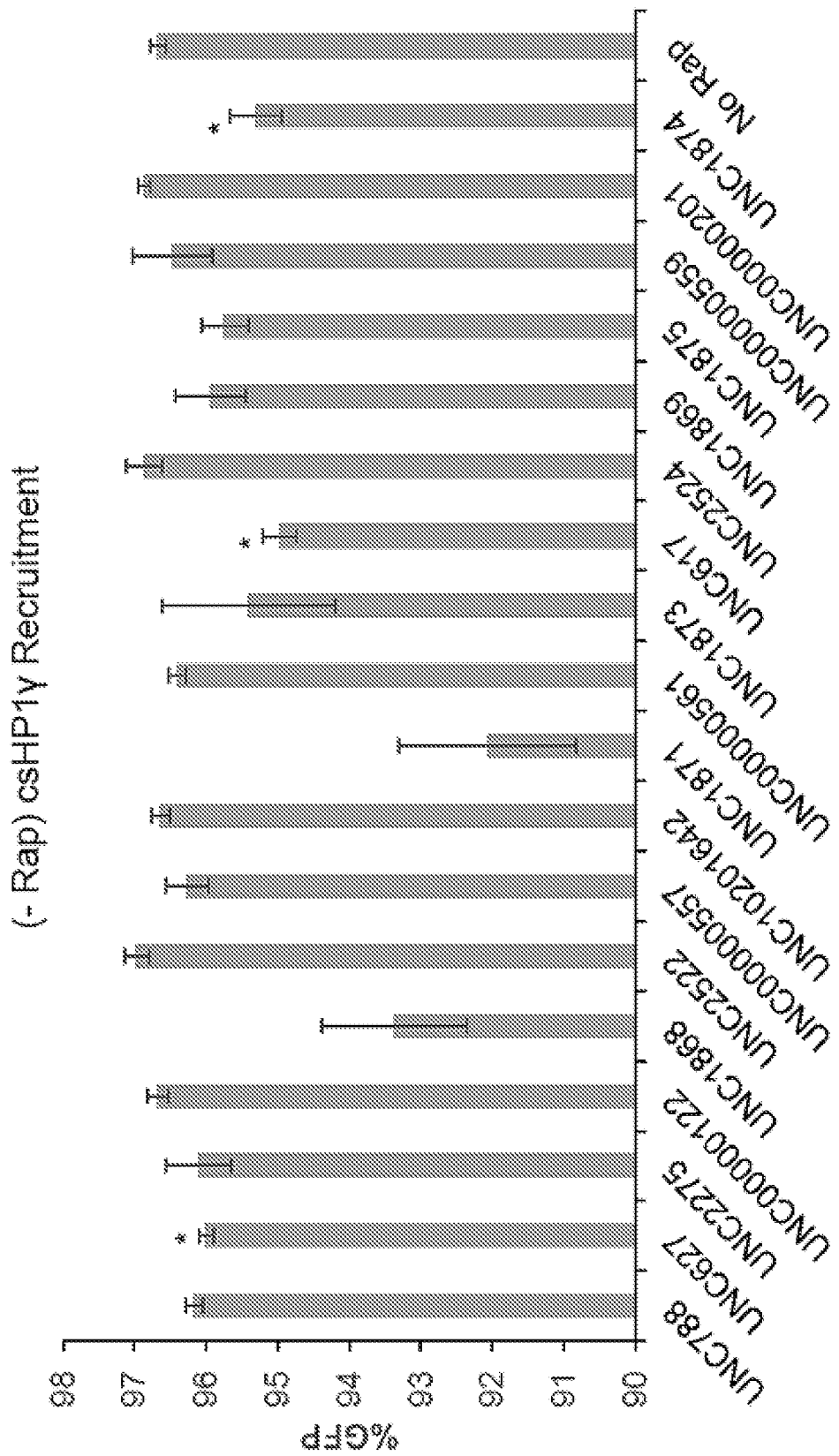

HP1 has three isoforms, HP1α HP1β and HP1γ. HP1α and HP1γ were previously identified to function similarly upon recruitment to the CiA:Oct4 locus whereas HP1β was not able to appreciably repress the reporter allele (unpublished observations). In order to determine compound activity upon recruitment of csHP1γ, CiA:Oct4 ES cells containing the N118 (Gal4-FKBP) plasmid were infected with the N192 (FRB-csHP1γ) vector using lentivirus to yield a stable CiA:Oct4 N118/N192 cell line. After 48-hrs of 5 µM compound treatment with and without rapamycin, the % GFP (+) populations were determined by flow cytometry analysis. Without wishing to be bound by theory, the results demonstrated that UNC617 and UNC2524 were the most potent inhibitors of csHP1γ. Nearly all lead compounds demonstrated significant inhibition of csHP1γ's ability to repress the CiA:Oct4 locus (FIG. 9A). Additionally, very low compound toxicity and independent repression of the CiA:Oct4 allele was observed with the greatest reductions being ~3 and 4% for UNC1868 and UNC1871 (FIG. 9B). Without wishing to be bound by theory, the reproducible inhibition of functionally similar HP1 isoforms demonstrates the robustness of the assay and provides greater evidence that the top screen compounds represent novel inhibitors of the HP1-pathway.

Figure 6A:
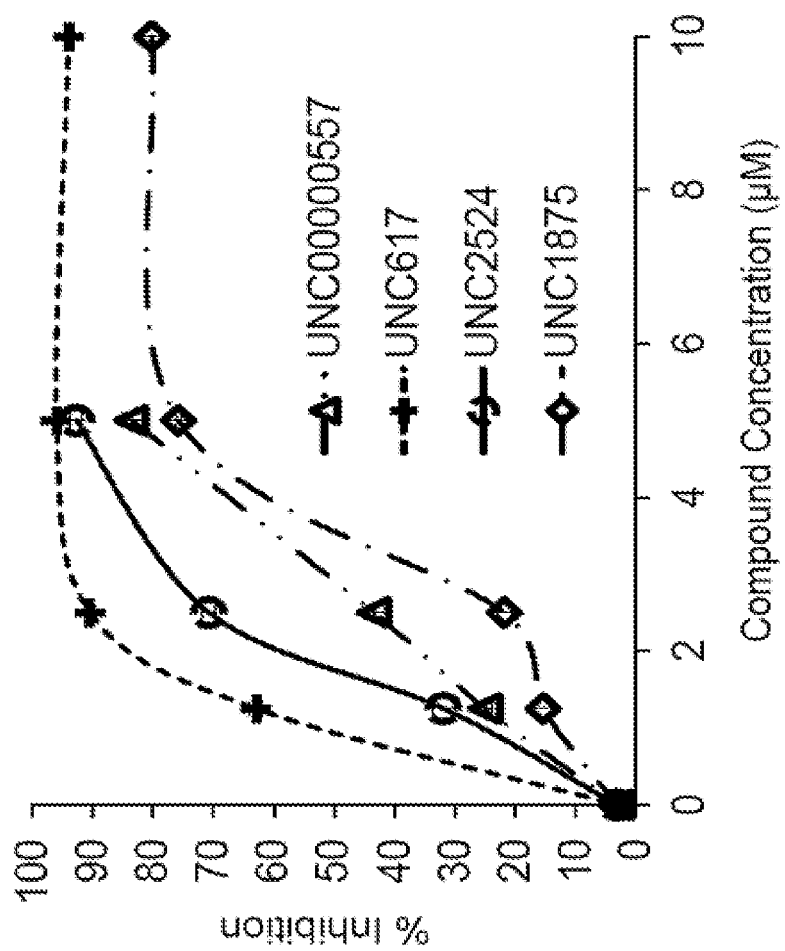
FIG. 6A-E show representative data indicating that lead screen compounds demonstrate dose-dependent response and decreased global H3K9me2/3, and are validated by an orthogonal TetR-HP1 recruitment system.
Figure 6B:
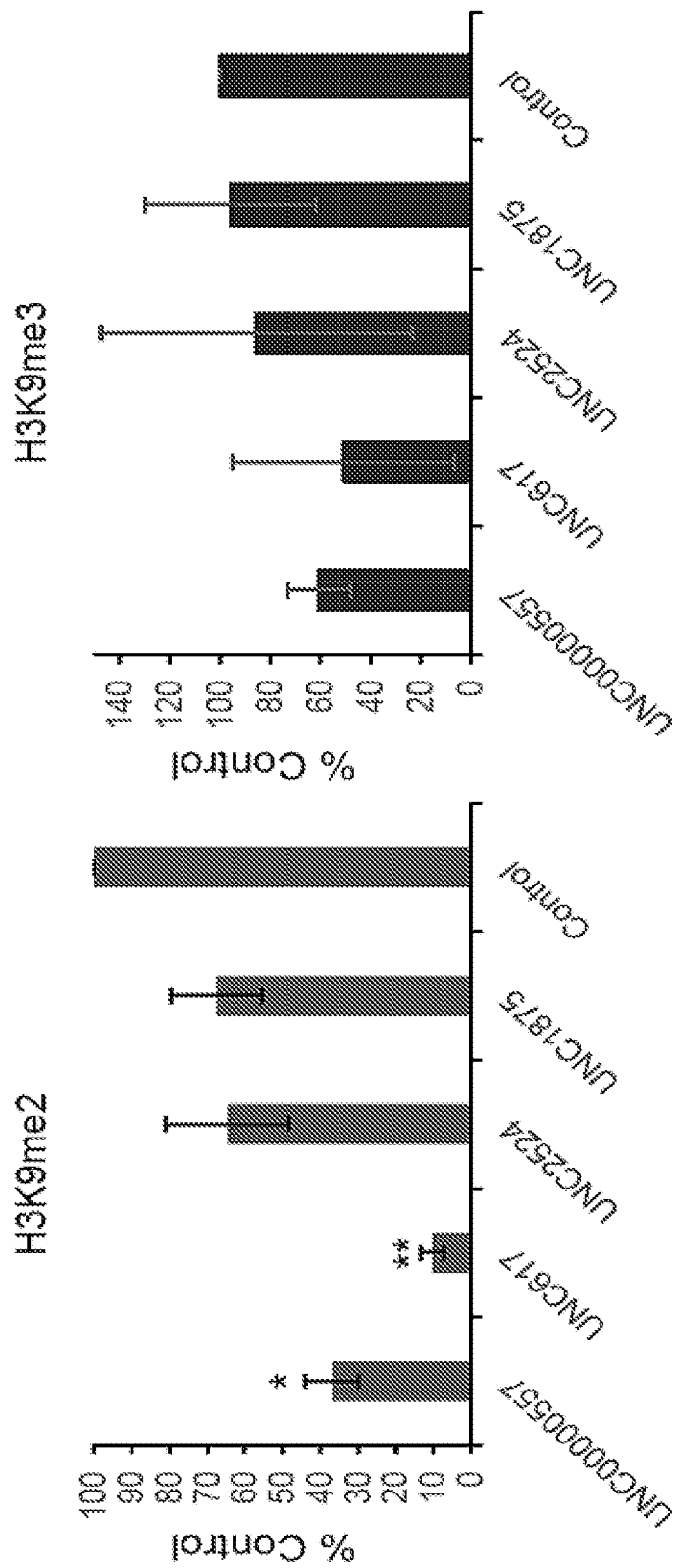
Figure 6C:
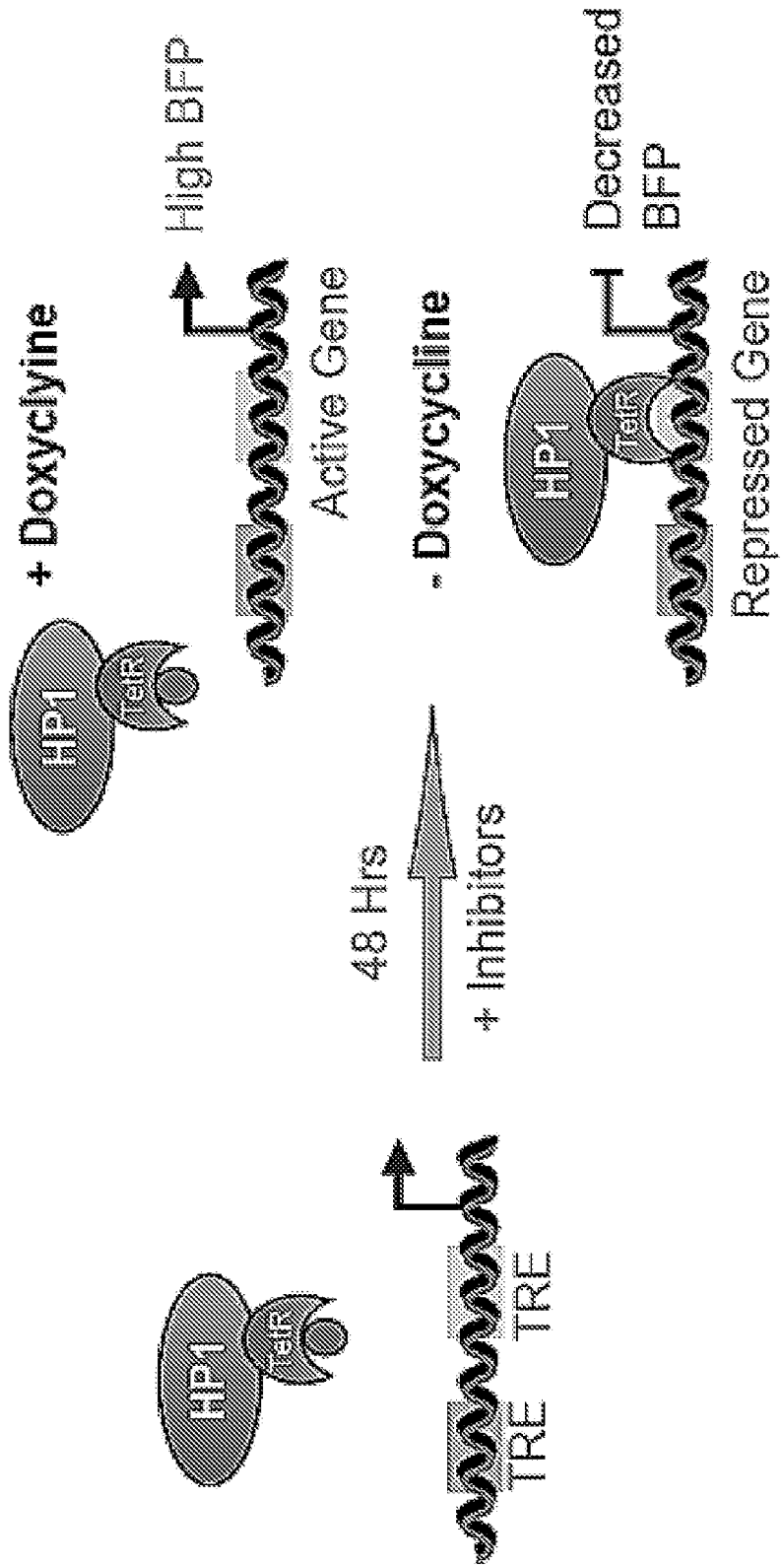
Figure 6D:
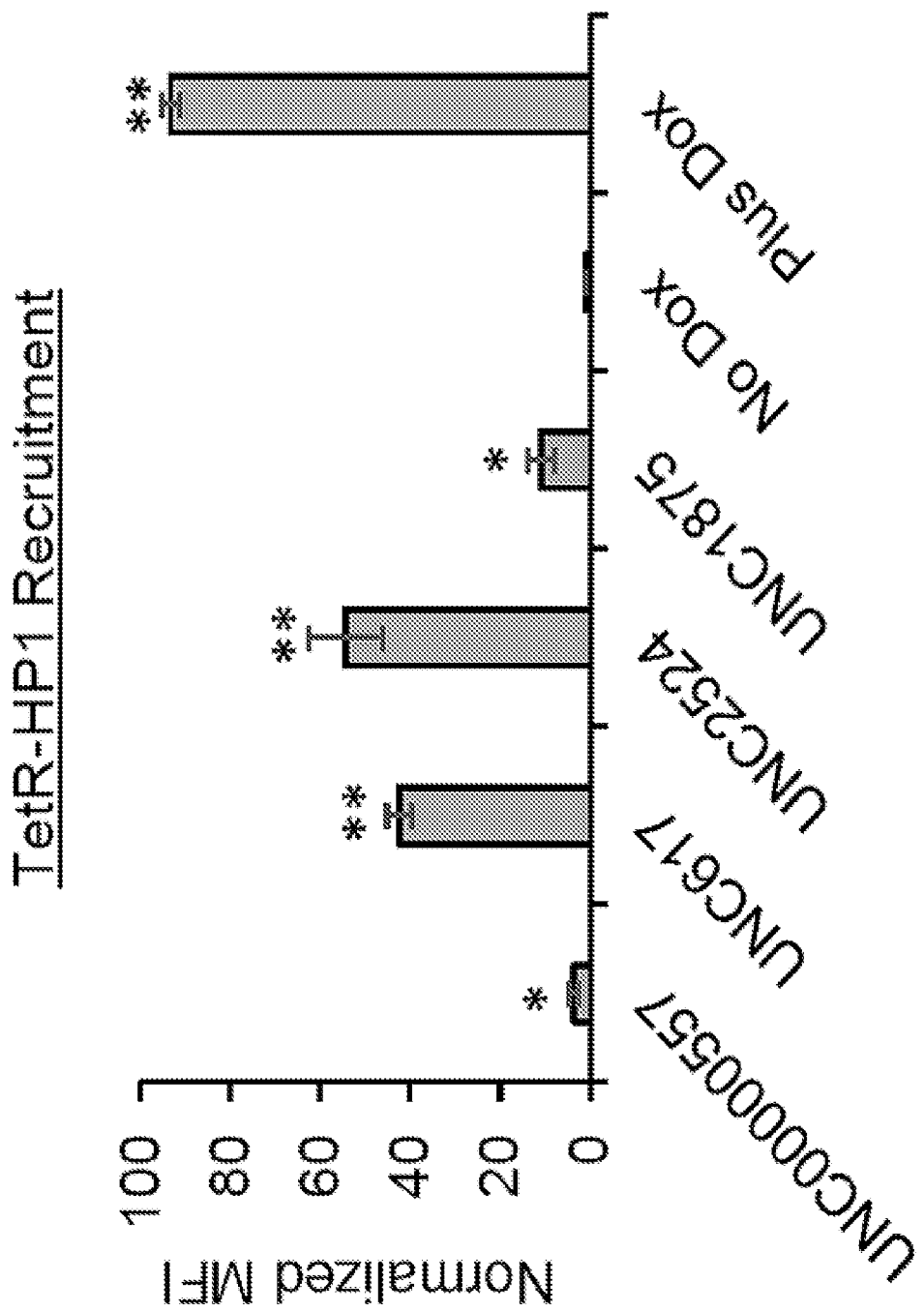
Figure 6E:
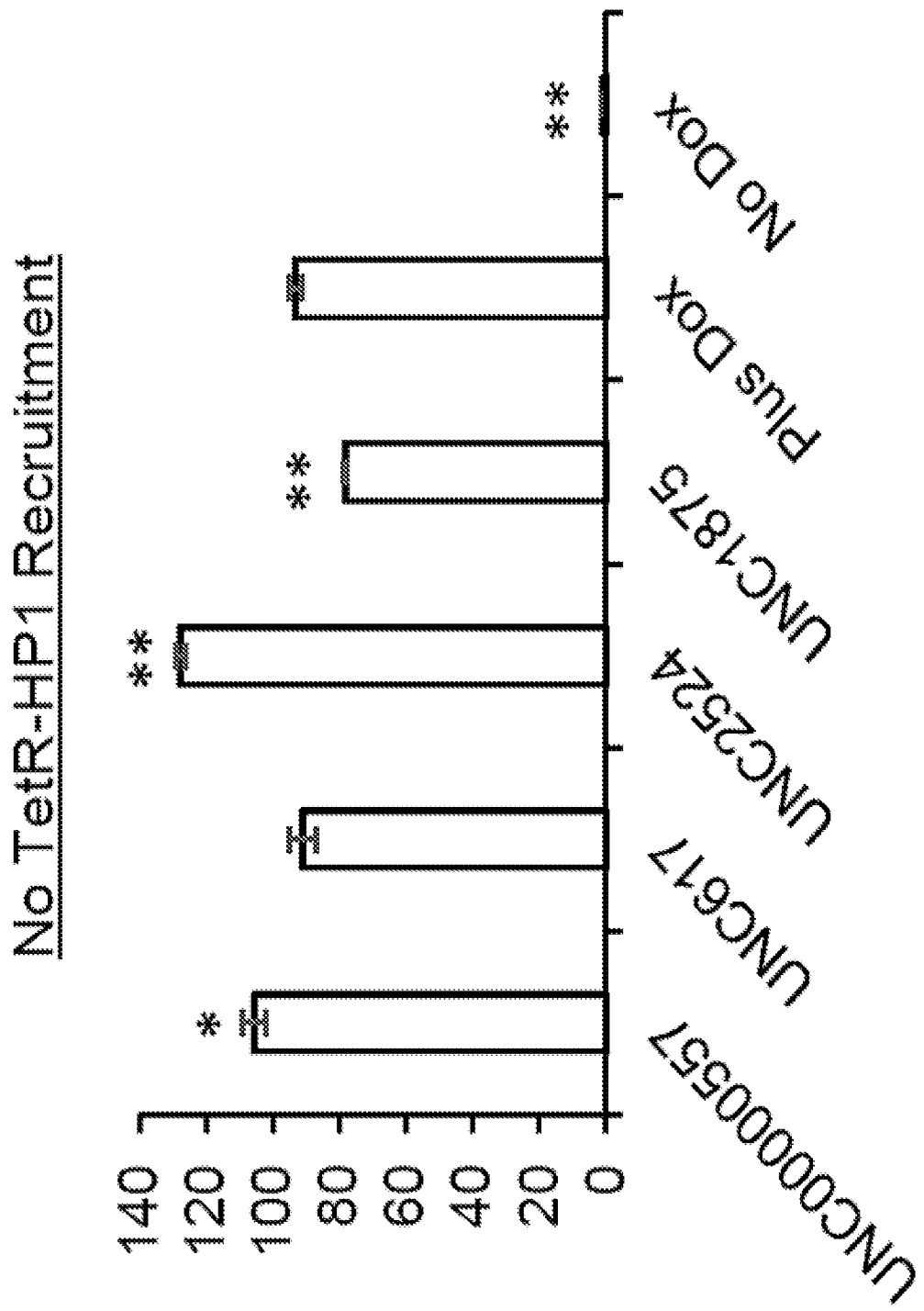

Referring to FIG. 6A, dose response curves were conducted for 4 lead compounds (UNC00000557, UNC617, UNC2524, and UNC1875). CiA:Oct4 N118/N163 cells were treated with compound at 10, 5, 2.5, 1.25, and 0 µM doses over 48 hrs+/−6 nM rapamycin. Flow cytometry analysis was used to determine the % GFP (+) population, and those values were converted to % inhibition. $IC_{50}$ values are displayed in the associated chart. Experiment was performed in biological triplicate. Referring to FIG. 6B, Western blot of acid extracted histones showing H3K9me2 and H3K9me3 levels in CiA:Oct4 N118/N163 cells following treatment with UNC00000557, UNC617, UNC2524, and UNC1875+/−6 nM rapamycin for 48 hours normalized to histone H4 are shown. Referring to FIG. 6C, a cartoon depicting the TetR-HP1 orthogonal recruitment system and the outcome of BFP expression after 48 hrs of inhibitors +/−1 µg/ml doxycycline is shown. Referring to FIG. 6D and FIG. 6E, normalized levels of median BFP expression after 48 hrs of 5 µM compound treatment with (FIG. 6D) and without (FIG. 6E) HP1 recruitment are shown. n≥3. (p≤0.05*, 0.01**).

Figure 7A:
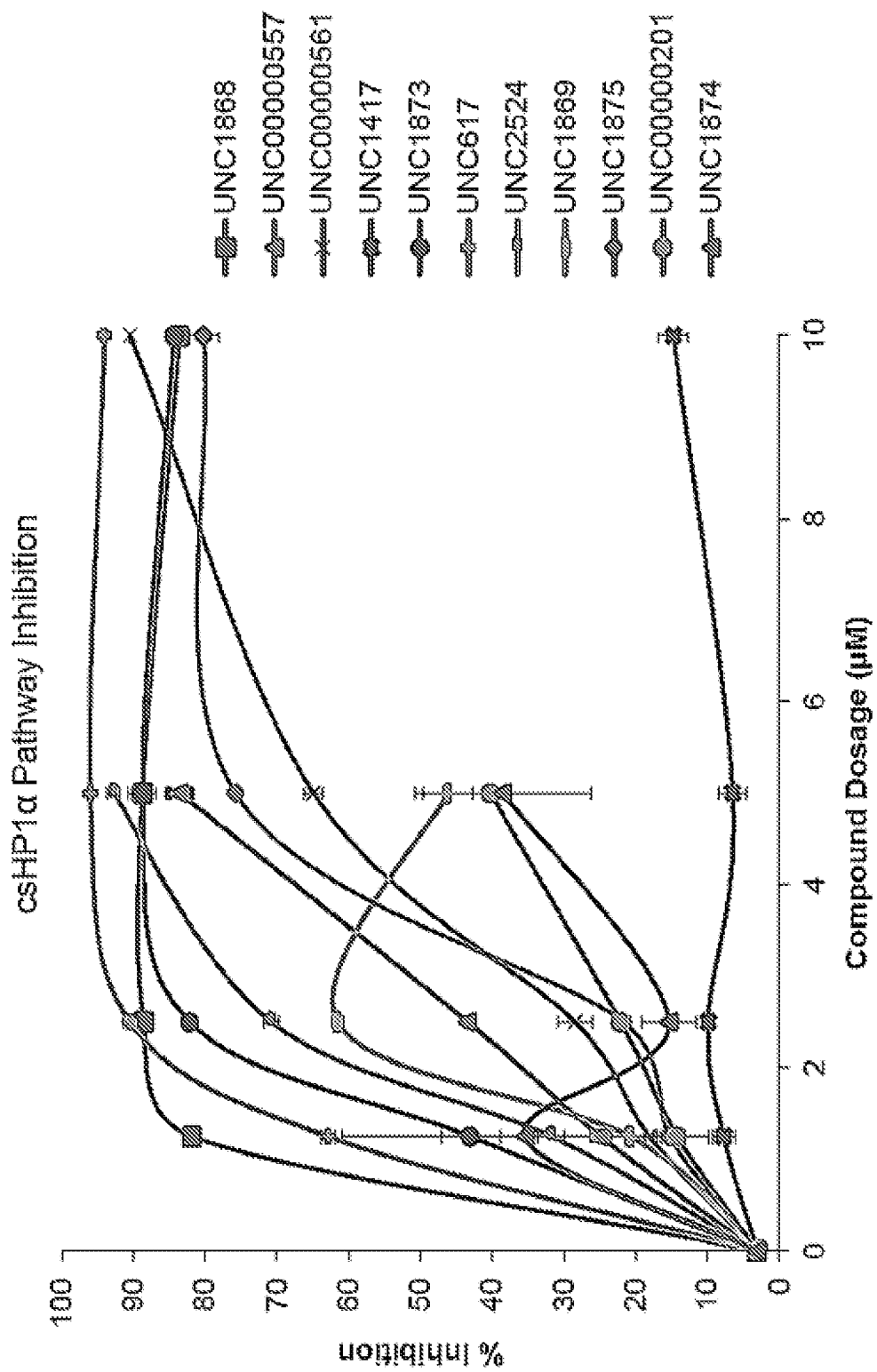
FIG. 7A and FIG. 7B show representative dose response curves for lead screen compounds+/−Rapamycin.
Figure 7B:
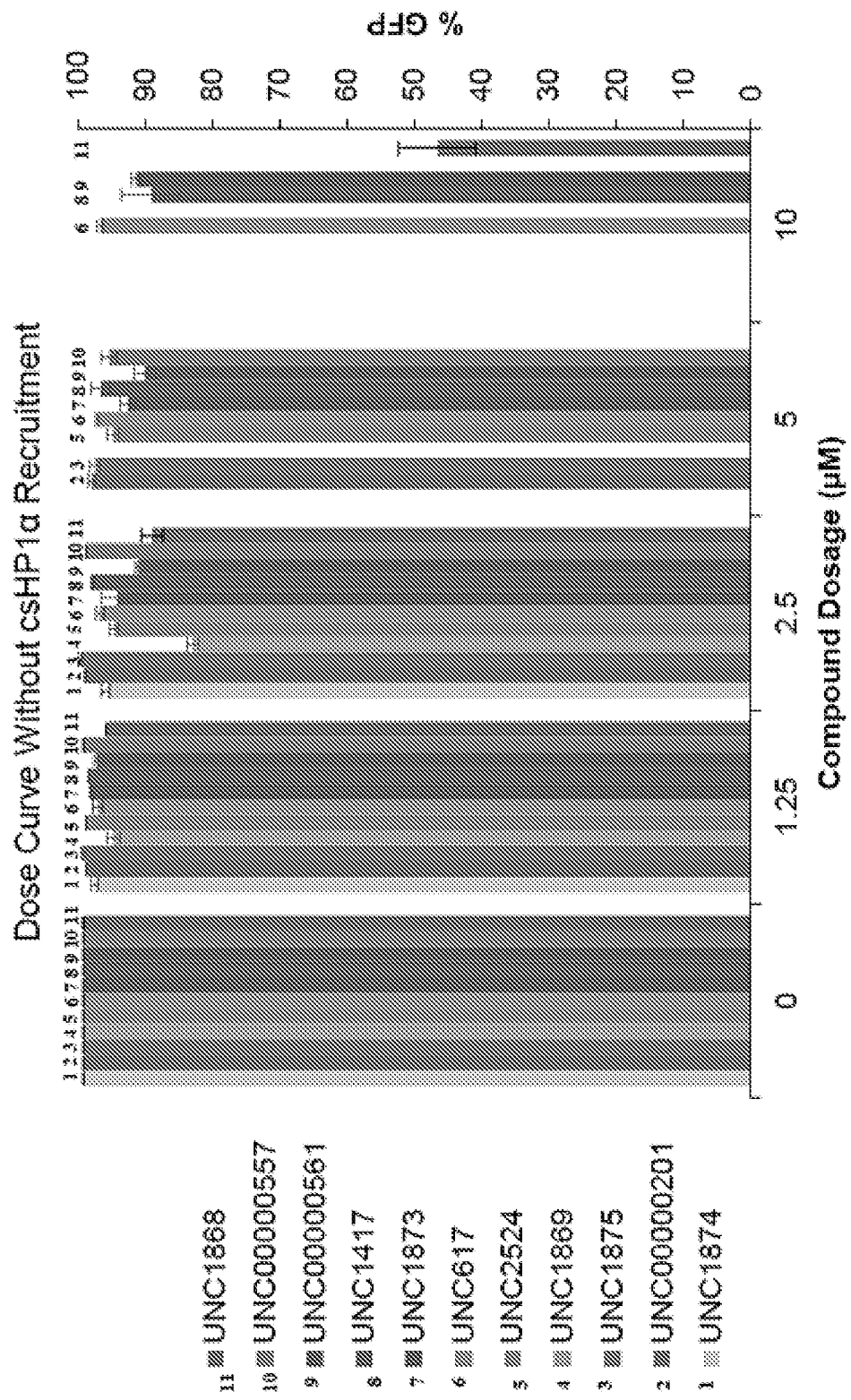

Referring to FIG. 7A, dose response curves were conducted for lead compounds identified in the primary screen. CiA:Oct4 N118/N163 cells were treated with compound at 10, 5, 2.5, 1.25, and 0 µM doses over 48 hrs+6 nM rapamycin. Flow cytometry analysis was used to determine the % GFP (+) population, and those values were converted to % inhibition. Referring to FIG. 7B, similar dose response curves were performed as outlined above, but without rapamycin. Data shows % GFP (+) population. Missing data points were not determined due to lack of cell viability. Experiment was performed in biological triplicate. Error bars represent standard error. (n≥3).

Referring to FIG. 8, CiA:Oct4 N118/N163 cells were treated with 10 µM of lead compounds for 48 hours. Nuclei were purified and histones were further extracted by acid. 1-2.5 µg of total protein, as determined by standard Coomassie Bradford assay, was loaded into 4-20% Bis-tris gels and transferred to PVDF according to standard procedures. Global H3K9me2/3 levels were determined by western blot analysis using a Licor Odyssey imager using rabbit anti-H3K9me2 and anti-H3K9me3 antibodies (top). Mouse anti-H4 was the loading control (bottom).

Referring to FIG. 9A and FIG. 9B, CiA:Oct4 N118/N192 cells were treated with top lead compounds at 5 µM for 48 hrs with (FIG. 9A) and without (FIG. 9B) 6 nM rapamycin. Flow cytometry analysis was used to determine the % GFP (+) population. Data was converted to % inhibition for the +rapamycin samples. Experiments were performed in biological triplicate. (n≥3) (p≤0.05*, 0.01**).

5. Structure-Activity Relationship of UNC2524

Despite elucidating the general phenotypes of the new HP1 pathway inhibitors with respect to chromatin state, the mechanism by which the compounds were inhibiting HP1-mediated gene repression remained unclear. To this end, UNC2524 was chosen for further investigation due to its potent inhibitory phenotype in the assays in addition to having no known targets or function. Structure-activity relationship was performed with UNC2524 as the parent compound to accomplish two goals: (1) to optimize compound activity in the CiA:Oct4 assay; and (2) to determine if the compound was tolerant to side-chain modification for subsequent experimentation and chemical modification.

Figure 10A:
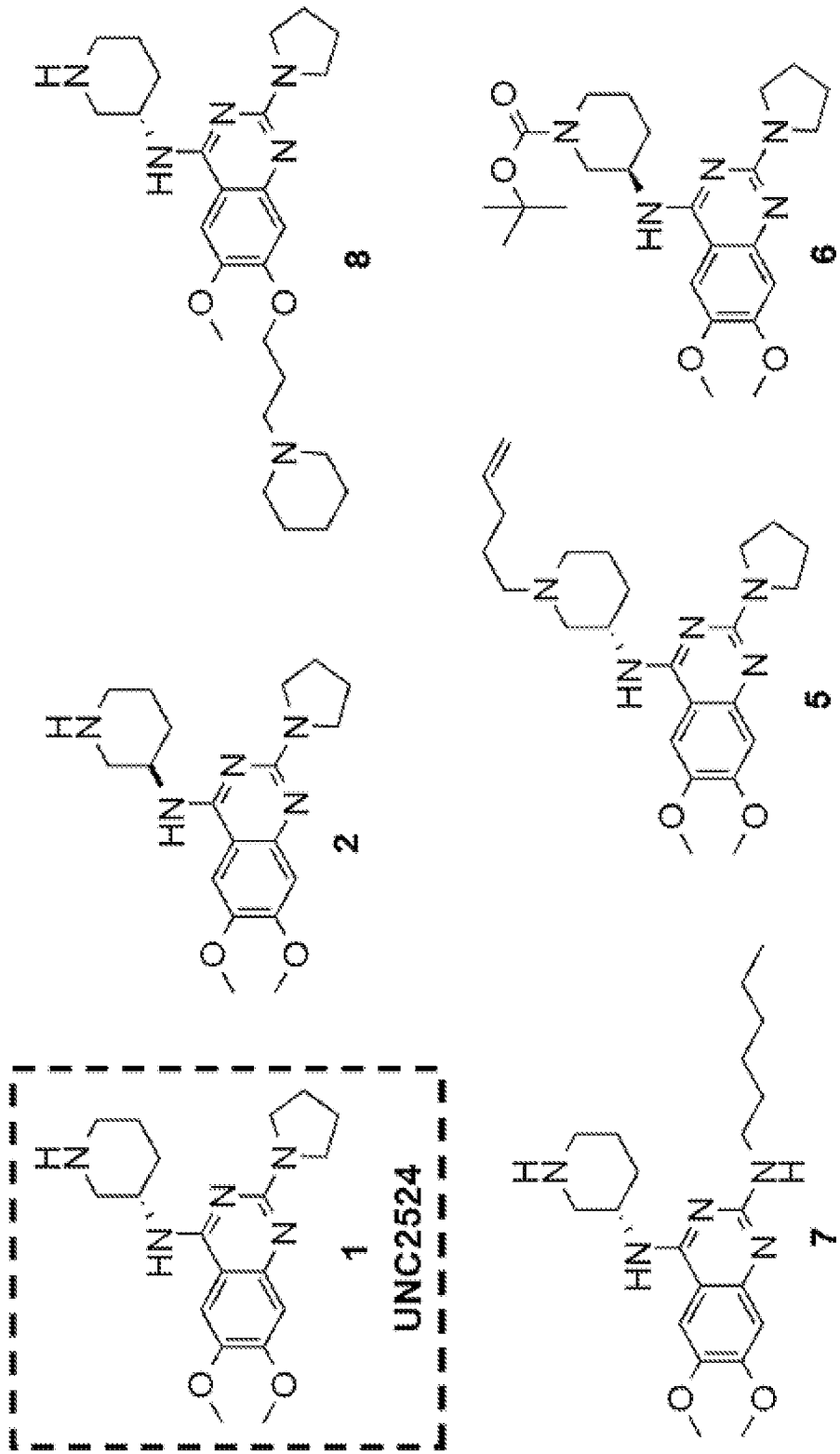
FIG. 10A and FIG. 10B shows representative data pertaining to a structure-activity relationship (SAR) study of compound 1 (UNC2524).

Compounds 2-8 were chemically synthesized from UNC2524 (compound 1) (FIG. 10A). To ascertain the biological activity of these chemical derivatives, CiA:Oct4 N118/N163 cells were used. Cells were treated with rapamycin plus compounds 2 and 5-8 for 48-hours prior to analysis by flow cytometry. Compound activity was confirmed by an increase in % inhibition compared to control samples. Compounds 5 and 6 added a pentenal chain and BOC group to the piperidine ring while compound 7 substituted a hexyl chain for the pyrrolidine. These additions resulted in a decrease in inhibition (FIG. 10B), so these regions of the parent molecule, 1, were not suitable places to attach an affinity handle. Further, it was identified that the 7-methoxy side chain was amenable to modification with a benzene ring in compound 8, while preserving most of the biological activity (~51%). Finally, an increase in activity over the parent was observed in compound 2 by changing the stereochemistry of the piperidine ring. Combining these data, compound 2 was selected as a base for incorporating a biotin tag onto the 7-methoxy sidechain of the compound, hereafter referred to as compound 3.

Figure 10B:
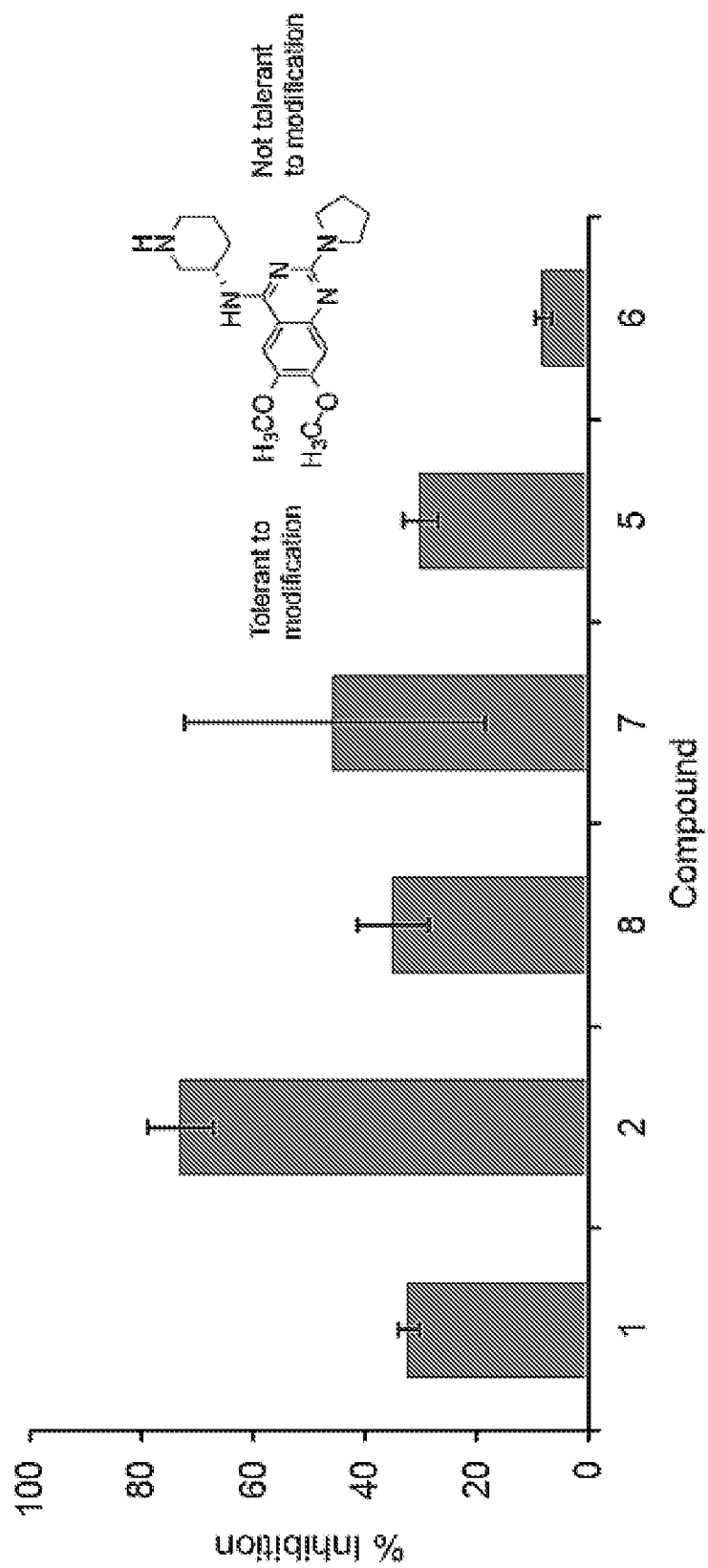

Referring to FIG. 10A, a series of compounds derived from compound 1 (UNC2524) were designed to optimize compound activity and determine amenability of compounds for affinity purification methods. Referring to FIG. 10B, CiA:Oct4 N118/N163 cells were treated with SAR compounds at 10 μM for 48 hrs+/−6 nM rapamycin. Flow cytometry analysis was used to determine the % GFP (+) population. Compound 7 treatment resulted in toxicity and low cell counts. These data were normalized to % inhibition compared to untreated controls. n≥3. (p≤0.05*, 0.01**).

6. Compound 2 Inhibits HP1-Mediated Gene Repression

Figure 11A:
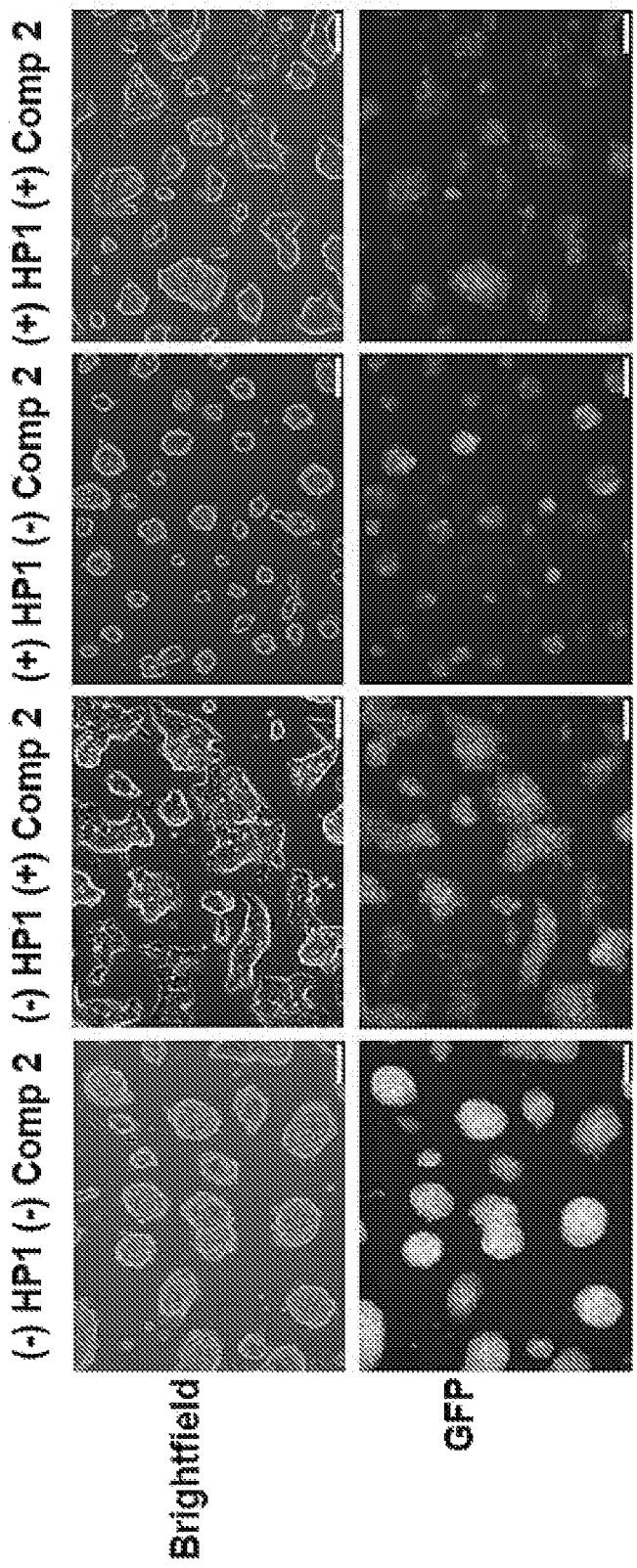
FIG. 11A-G show representative data demonstrating the compound 2 inhibits HP1-mediated gene repression and decreased H3K9me3.
Figure 11B:
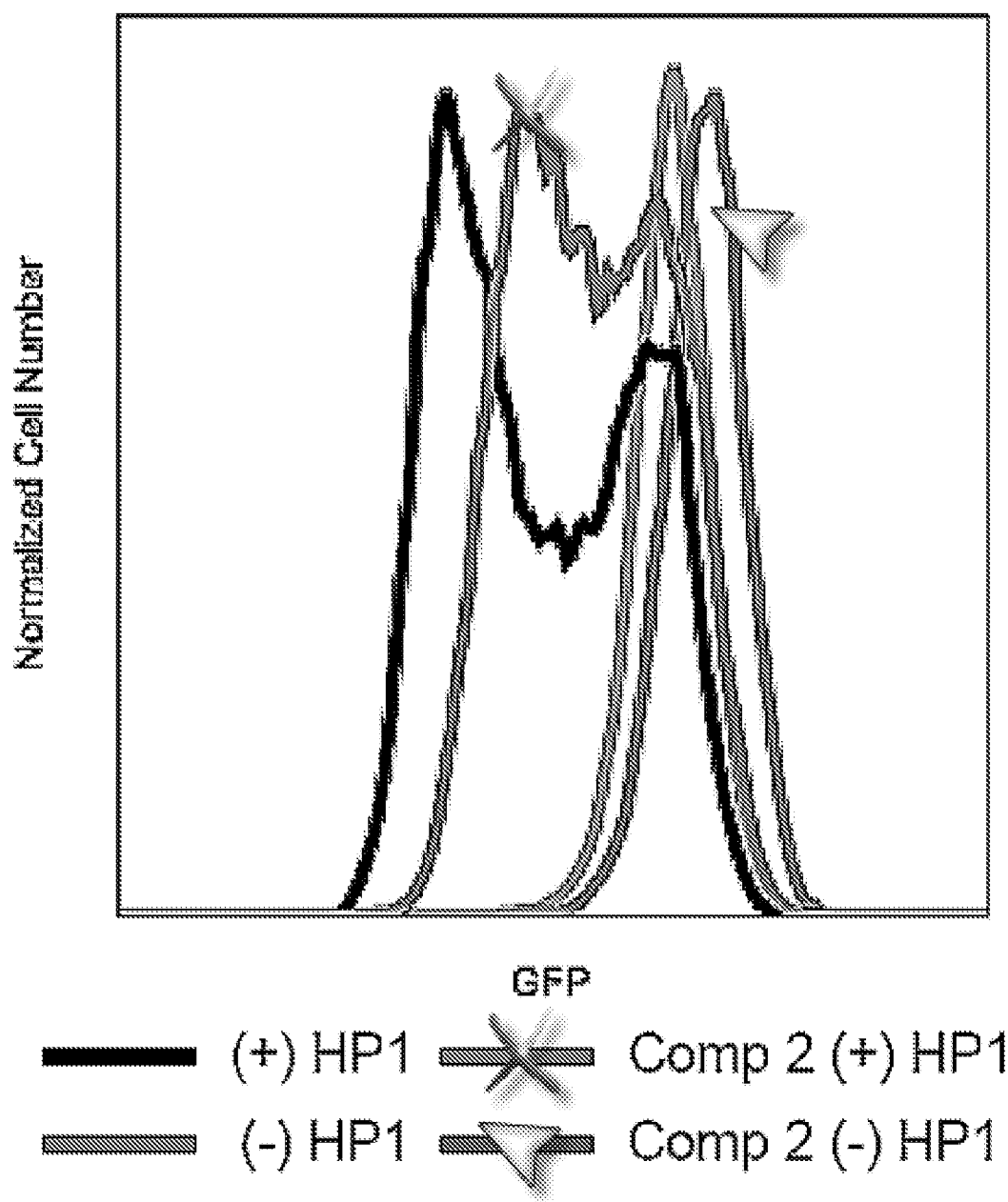
Figure 11C:
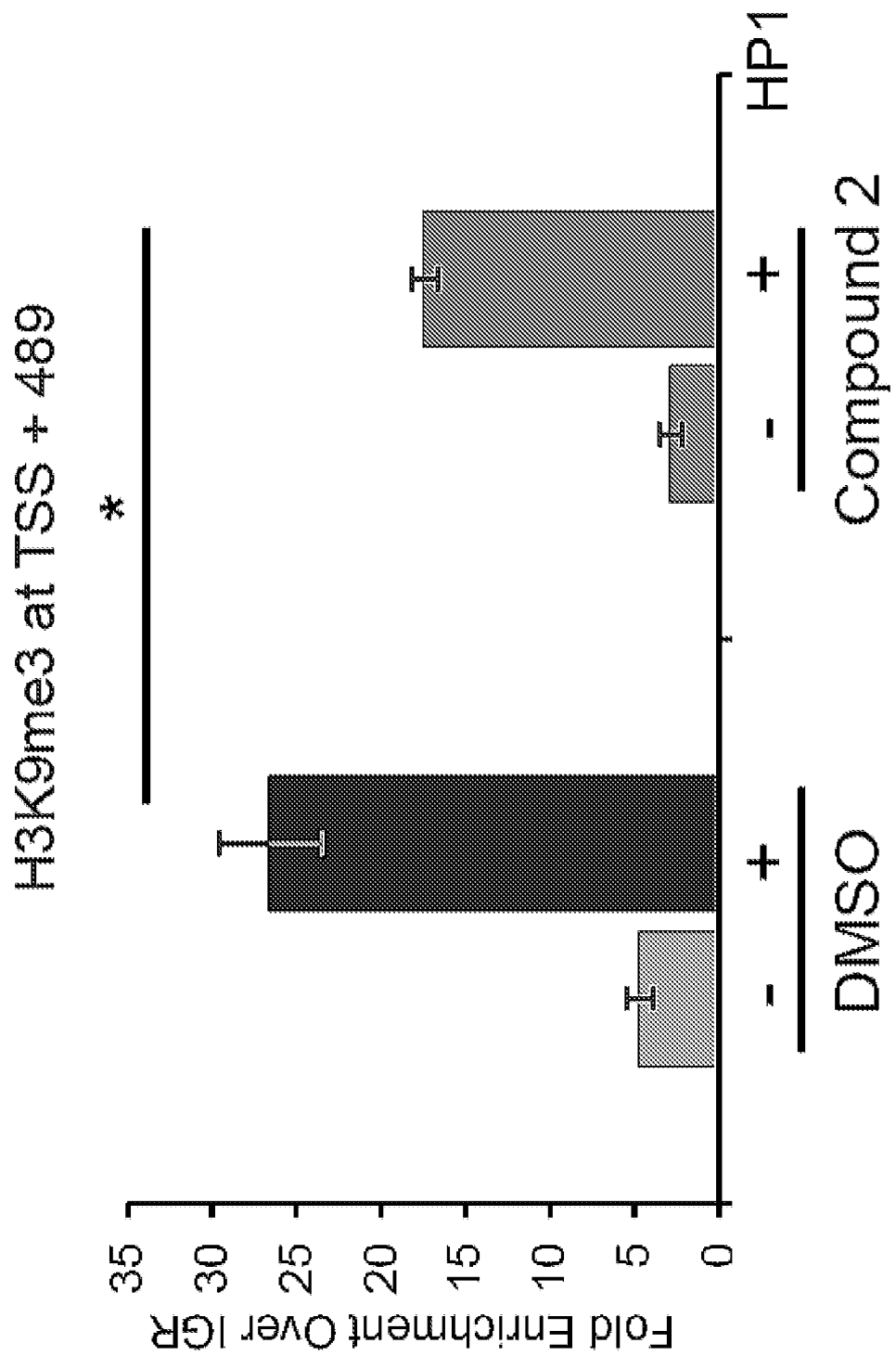
Figure 11D:
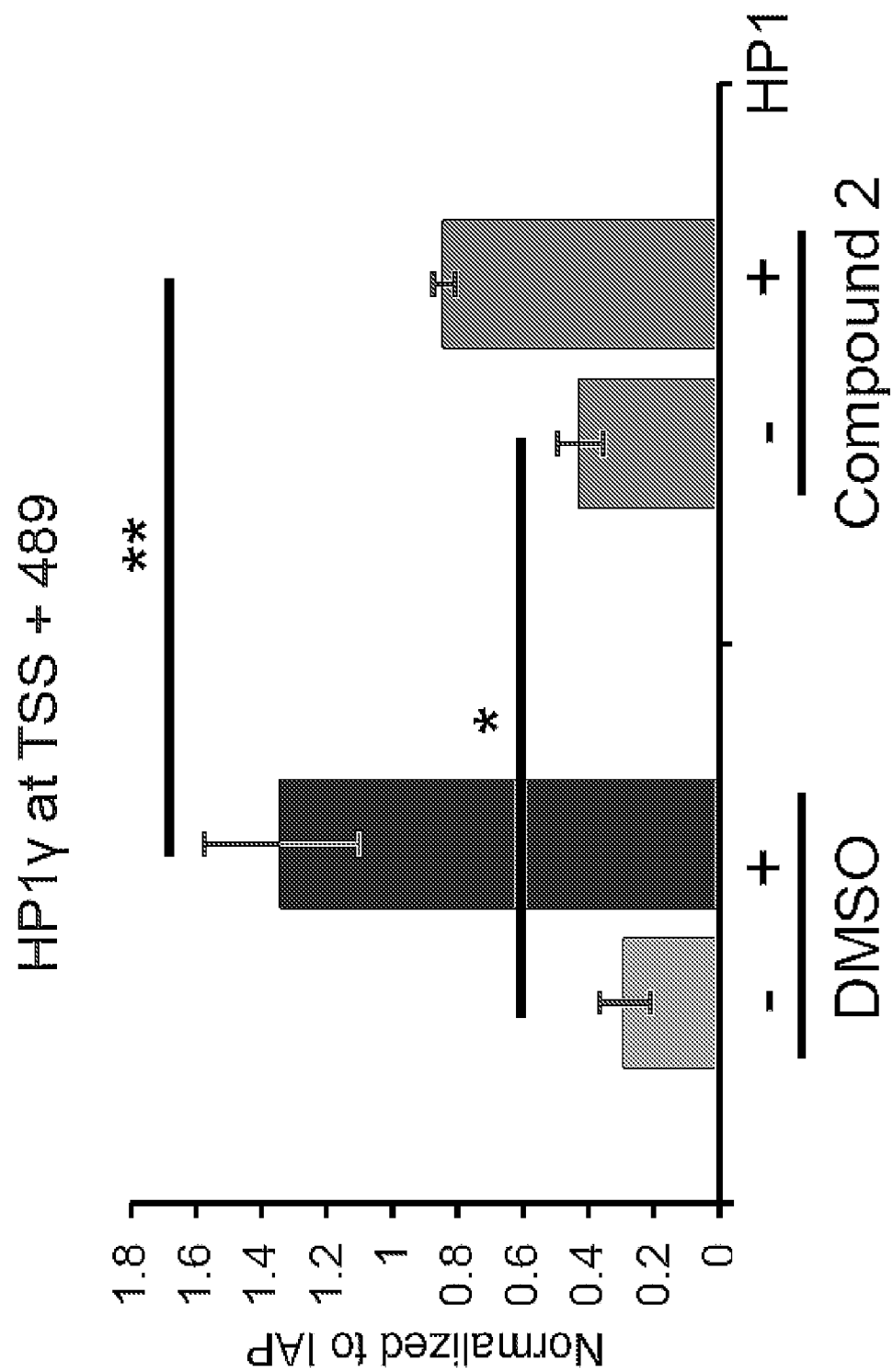
Figure 11E:
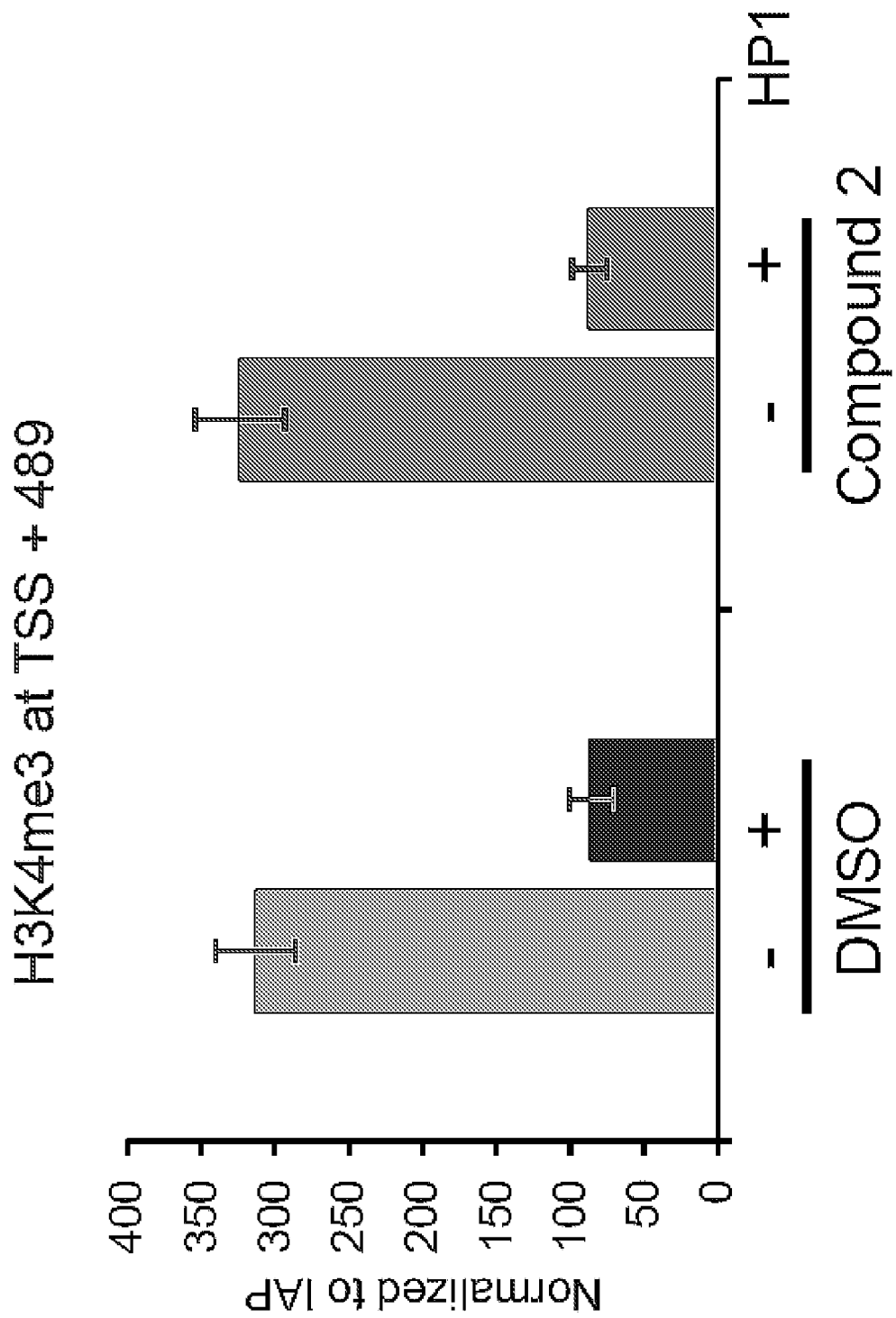
Figure 11F:
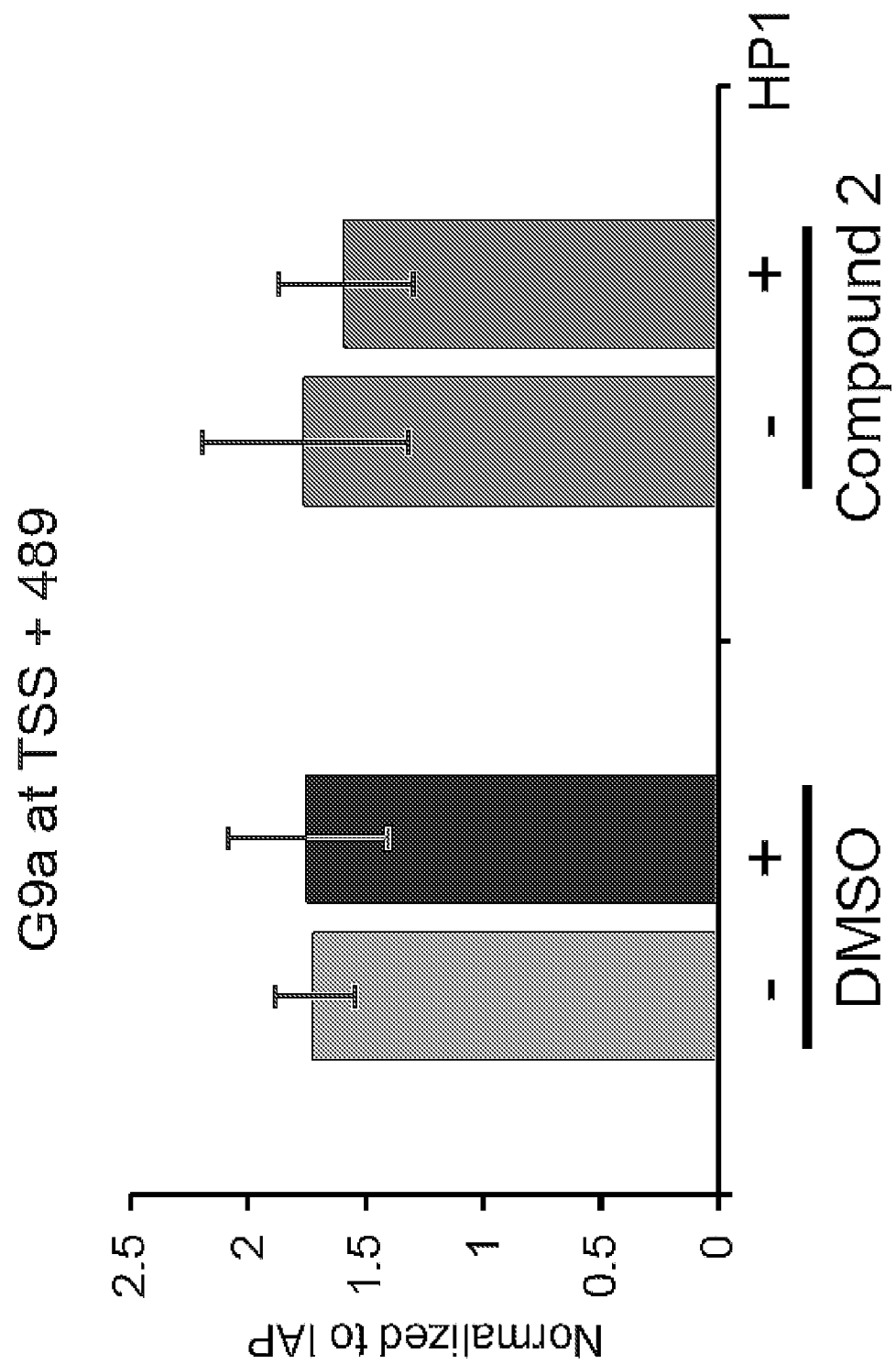
Figure 11G:
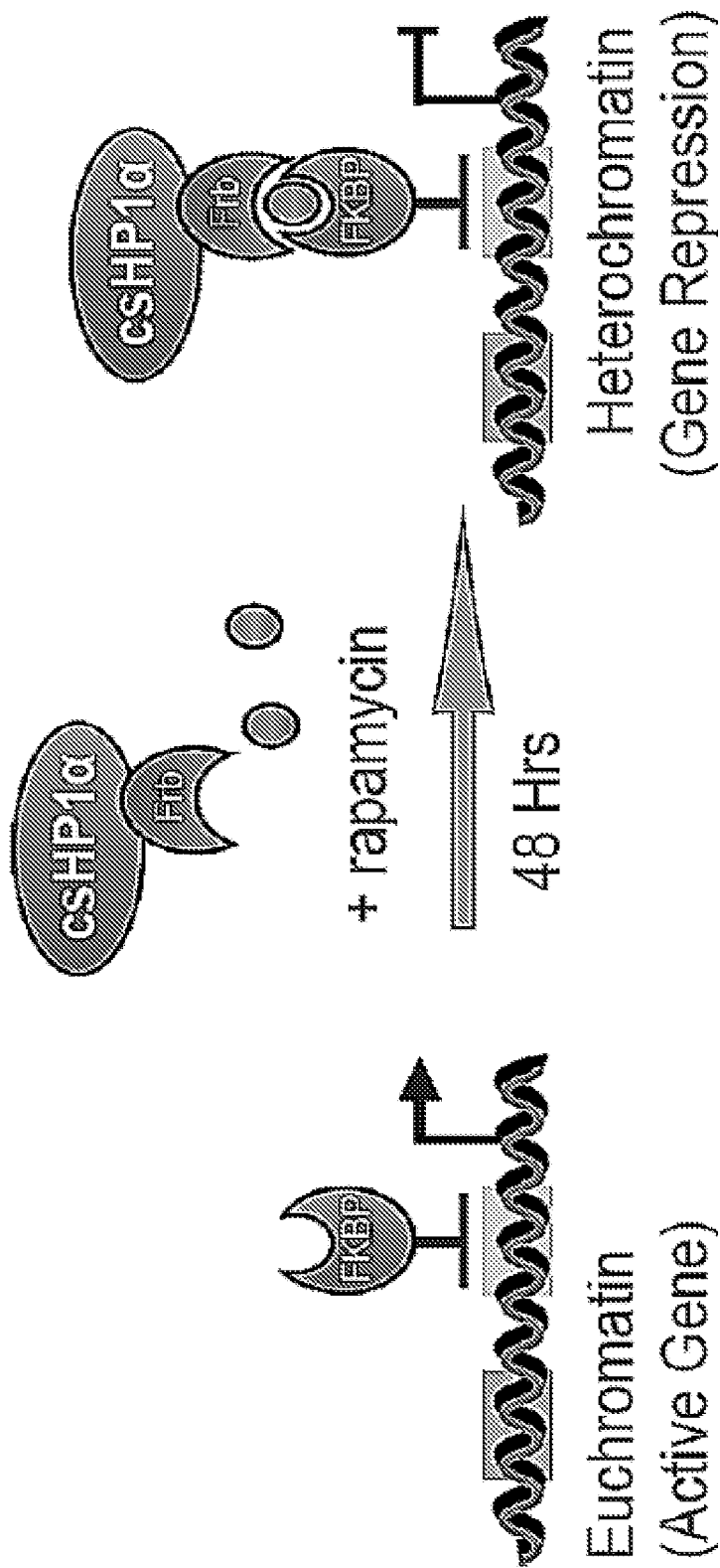

In order to confirm that compound 2 was inhibiting H3K9me3 deposition, CiA:Oct4 N118/N163 cells were grown for 48-hours with rapamycin mediating HP1 recruitment, +/−compound 2 (FIG. 11G). Representative brightfield and fluorescence images were taken for the four sample types ((−) rapamycin/(−) compound 2, (−) rapamycin/(+) compound 2, (+) rapamycin/(−) compound 2, (+) rapamycin/(+) compound 2). ES cell colony morphology was good in all samples, though rapamycin did result in a slightly decreased colony size. Compound 2 did not result in gross cell differentiation or effect colony morphology compared to controls (FIG. 11A). Subsequently, all samples were analyzed by flow cytometry to confirm the inhibitory effects of compound 2 on HP1-mediated gene repression. FIG. 11B is a representative histogram confirming that compound 2 results in increased GFP expression with (grey with "X") and without (grey with arrow) rapamycin compared to untreated controls.

Chromatin immunoprecipitation (ChIP) was used to determine the levels of H3K9me3 at the Oct4 locus upon treatment with compound 2. It was previously demonstrated that enrichment of the H3K9me3 was greatest between 400-700 base pairs (bp) downstream of the transcriptional start site (TSS) (Hathaway et al., 2012). For this reason, the levels of H3K9me3 were analyzed at 489 bp downstream of the TSS in all four sample conditions. qPCR was used to amplify this region in addition to an intergenic control region. The ΔΔCt method was used to determine relative fold enrichment of H3K9me3 normalized to the intergenic control region. Samples lacking rapamycin did not show enrichment in H3K9m3 due to no csHP1α recruitment. Conversely, H3K9me3 increased ~26 fold when treated with rapamycin leading to csHP1α recruitment. Addition of compound 2 decreased the enrichment of H3K9me3 by ~9 fold compared to the plus rapamycin control samples (FIG. 11C).

To further characterize the effects of compound 2 on the HP1-heterochromatin pathway, perturbations in the levels of HP1γ, H3K4me3, and G9a at the CiA:Oct4 locus were assayed for using ChIP followed by RT-qPCR analysis. Enrichment levels were determined at 489 bp downstream of the TSS and normalized to a house-keeping gene, intracisternal A-type particles (IAP). As shown previously, HP1γ functions similarly to HP1α in our inhibition assay. Because csHP1α is being actively recruited to the CiA:Oct4 locus, it was decided to measure HP1γ levels to determine if HP1 recruitment was inhibited by compound 2. Interestingly, HP1γ levels increased upon treatment with compound 2 alone by 46% compared to controls. Despite a small increase in HP1γ caused by compound 2 alone, HP1γ levels were shown to significantly decrease 37% upon HP1-mediated gene repression in the presence of compound 2 compared to control samples with HP1 recruitment alone (FIG. 11D). The histone mark H3K4me3 is associated with active gene transcription and was previously reported to decrease upon HP1-mediated gene repression (Hathaway et al. (2012) Cell 149(7): 1447-1460). H3K4me3 levels were enriched ~3.7-fold in samples lacking HP1 recruitment as expected. No change in H3K4me3 levels were detected upon compound 2 treatment despite the decrease in H3K9me3 (FIG. 11E). Finally, the histone lysine methyltransferase enzyme G9a was demonstrated to be required for silencing of Oct4 during cell differentiation and development (Feldman et al. (2006) Nature Cell Biology 8(2): 188-194). G9a levels were assayed to determine if G9a is contributing to HP1-mediated gene repression in the inhibition assay. No significant changes in G9a levels were observed across the four treatment conditions indicating that G9a is either not being recruited to the CiA:Oct4 locus under the assay conditions or it is possible that it is simply not detected by the assay (FIG. 11F). Without wishing to be bound by theory, these data corroborate the microscopy images and histograms demonstrating that compound 2 increased GFP expression due to a loss of repressive H3K9me3 mark.

Referring to FIG. 11A, CiA:Oct4 csHP1α recruiting cells were incubated with 7.5 μM compound 2+/−6 nM rapamycin for 48 hrs and representative brightfield and GFP fluorescence images were acquired at 20×. Referring to FIG. 11B, CiA:Oct4 csHP1α recruiting cells were incubated with 7.5 μM compound 2+/−6 nM rapamycin for 48 hrs. GFP expression was analyzed by flow cytometry. Referring to FIG. 11C-F, following 48 hr treatment with compound 2+/−6 nM rapamycin, chromatin was isolated to determine enrichment levels of H3K9me3 (FIG. 11C), HP1γ (FIG. 11D), H3K4me3 (FIG. 11E), and G9a (FIG. 11F) at the transcriptional start site (TSS)+489 position. Graph shows fold change decrease in H3K9me3, HP1γ, H3K4me3, and G9a, respectively, in the presence of compound 2 compared to control samples. n≥3 (p≤0.05*, 0.01**). Referring to FIG. 11G, a cartoon of the CiA:Oct4 system utilizing chemical induced proximity (CIP) to recruit csHP1α is shown. Addition of rapamycin facilitated the bridging of the Gal4-FKBP and FRB-csHP1α fusion resulting in HP1-heterochromatin formation and gene repression.

7. Novel Components of HP1 Pathway Identified by Chemical Proteomics

Figure 12A:
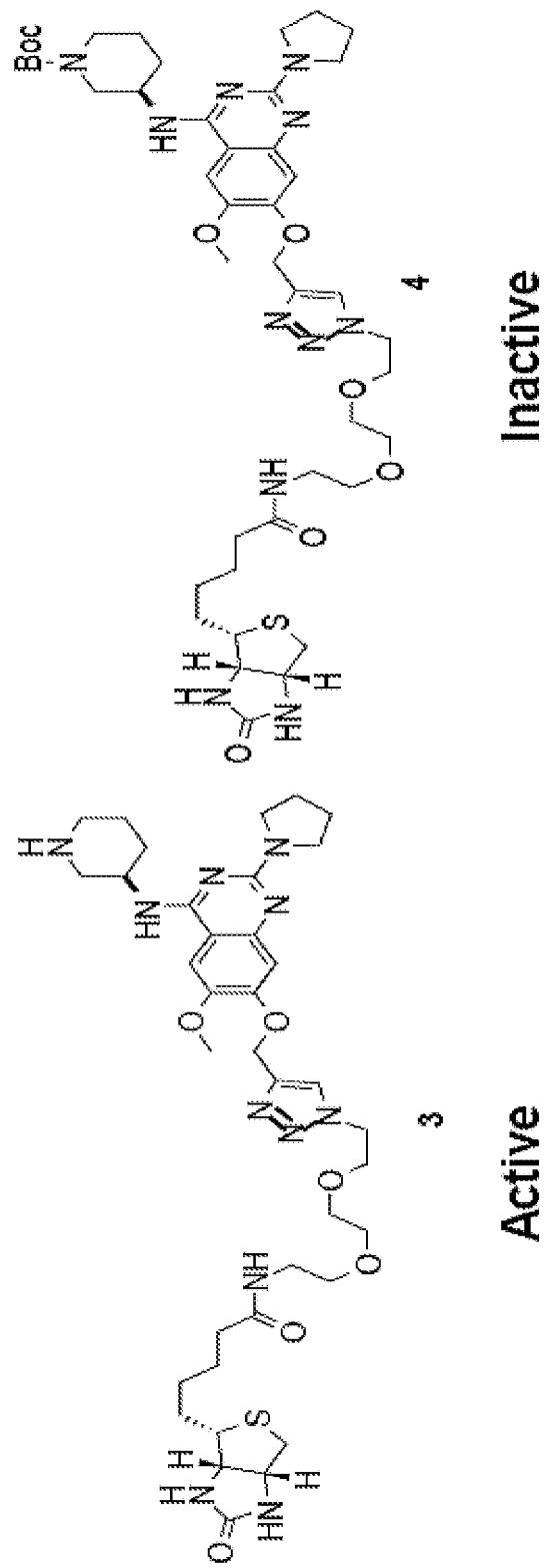
FIG. 12A and FIG. 12B show representative data demonstrating that chemical proteomics identify putative HP1 pathway components.

Compound 2 is a novel small molecule that functions by inhibiting the HP1 pathway for gene repression. To identify cellular targets of compound 2, chemical affinity purification and quantitative mass spectrometry approaches were combined. Biotin tagged compound 3 was the active affinity reagent. Biotin tagged compound 4 contained an inactivating BOC group to function as a negative control affinity reagent (FIG. 12A).

Figure 12B:
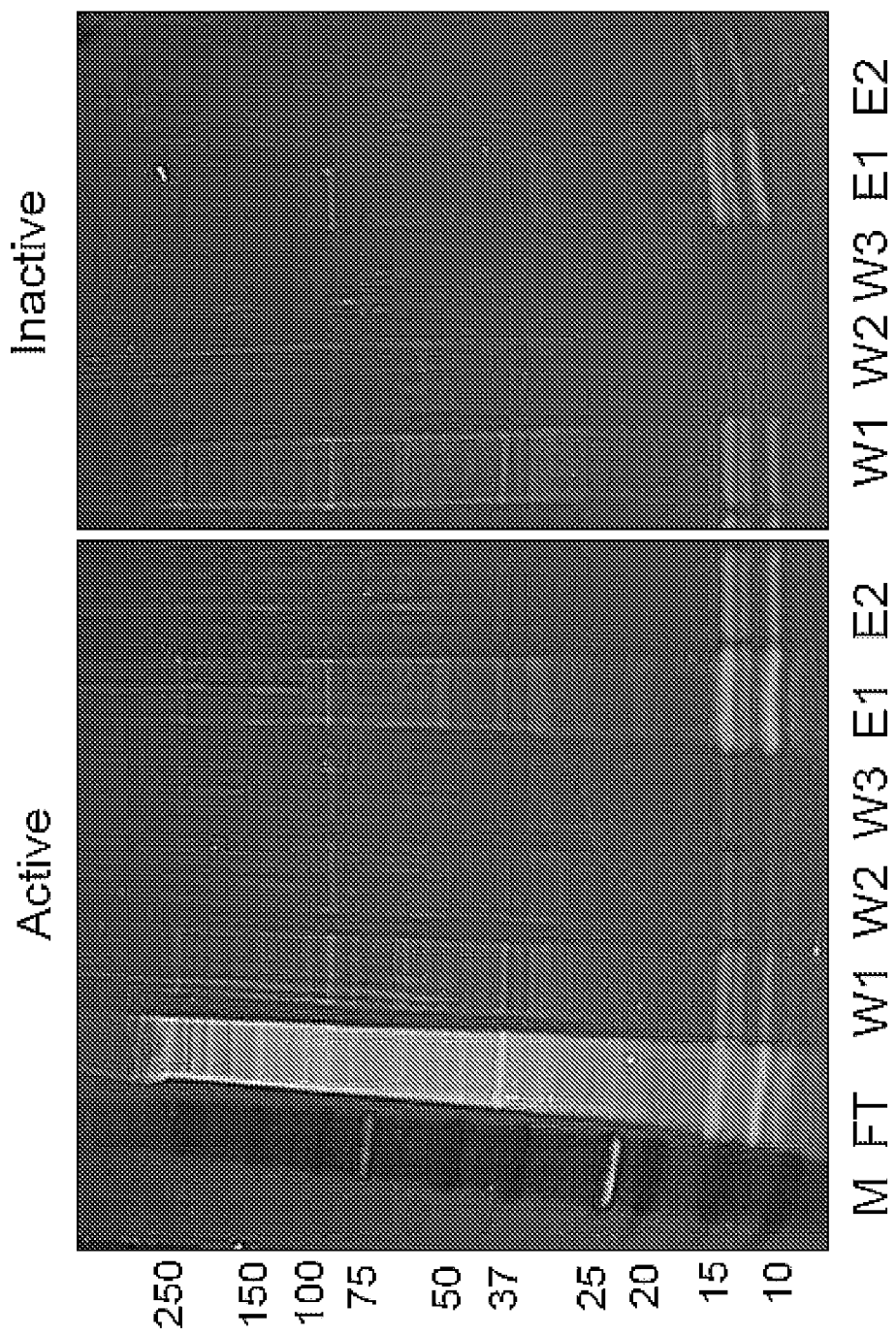

CiA:Oct4 N118/N163 cells were grown to confluency and nuclei were harvested. Nuclei were lysed and the genomic DNA sheared by probe sonication to decrease sample viscosity and aid in protein purification. The nuclear lysates were incubated with active (compound 3) and inactive (compound 4) biotin tagged compounds. Additional negative control samples included beads alone, and preincubating the nuclear lysates with excess compound 2 prior to pulldown with the active biotin tagged compound 3. Magnetic streptavidin beads were used to pulldown bound proteins. Samples were washed and eluted with excess compound 2 (E1) and finally with 3 mM D-biotin (E2). Pulldown fractions from compound 3 and 4 were run on bis-tris glycine gels and stained with Sypro Ruby stain for visualization (FIG. 12B).

Elution fractions were precipitated and samples were prepared for quantitative LC-MS/MS analysis using isobaric tags for relative and absolute quantitation (iTRAQ). Quantitative analysis identified proteins enriched in the active affinity purification sample compared to the various negative controls (Table 2). Proteins that had greater than two unique peptides and a sample-to-control ratio of 1.4 or greater were considered for further analysis. Several proteins that bound to the active compound are known to play a role in chromatin biology (Table 3). These include novel contributors to the HP1 pathway, (Supt6H, Hmgn2, Taf10, Hdgfrp2, Nasp, Hmgn1, Eny2, Tmpo, and Kmt2B/Mll4), as well as Mphosph8 or Mpp8, a known member of the HUSH complex which contributes to heterochromatin (Tchasovnikarova et al. (2015) *Science* 348(6242)).

TABLE 2

| Category | Parameter | Description |
| --- | --- | --- |
| Assay | Type of assay | Cell-based. Mouse embryonic CiA:Oct4 stem cells |
|  | Target | HP1 heterochromatin pathway |
|  | Primary measurement | Detection of GFP fluorescence intensity |
|  | Key reagents | CiA:Oct4 cell line. Rapamycin |
|  | Assay protocol | Can be found in methods section "small molecule high-throughput screen" |
|  | Additional comments | Assay reported by Hathaway et al. 201212 |
| Library | Library size | ~960 compounds |
|  | Library composition | Verified and unknown epigenetic pathway targeting compounds |
|  | Source | The Eshelman School of Pharmacy, Division of Chemical Biology and Medicinal Chemistry, Center for Integrative Chemical Biology and Drug Discovery, The University of North Carolina at Chapel Hill, Chapel Hill, NC 27599 |
|  | Additional comments | Compounds are resuspended in DMSO and stored at −20° C. |
| Screen | Format | 96 well plates |
|  | Concentration(s) tested | 10 μM in 0.1% DMSO |
|  | Plate controls | 0.1% DMSO |
|  | Reagent/compound dispensing system | TECAN Freedom Evo liquid handling robot or multichannel repeat pipet |
|  | Detection instrument and software | iQue high-throughput flow cytometer by IntelliCyt |
|  | Assay validation/QC | Inhibitors were two standard deviations above the mean |
|  | Additional comments | % GFP (+) populations were determined by gating cells based on untreated controls |
| Post-HTS analysis | Hit criteria | Two standard deviations above or below the mean |
|  | Hit rate | 3.5% |
|  | Additional assay(s) | Compounds were counter screened without rapamycin present to eliminate compounds that caused differentiation of ES cells. Activity was confirmed by dose-response |
|  | Confirmation of hit purity and structure | Lead compound was resynthesized for structure activity relationship studies |
|  | Additional comments | Compounds that yielded fewer than 200 events by flow cytometry were removed due to toxicity |

TABLE 3

| Gene | UniProt Descriptions |
|---|---|
| Supt6H | Transcription elongation factor SPT6. Associated with SETD2, SETD1a, KDM6a |
| Hmgn2 | Non-histone chromosomal protein HMG-17. Interacts with histone octamer |
| Taf10 | Transcription initiation factor TFIID subunit 10. Component of PCAF histone acetylase complex |
| Hdgfrp2 | Hepatoma-derived growth factor-related protein 2. Binds condensed chromatin and histone methyl-lysines |
| Nasp | Nuclear autoantigenic sperm protein. Histone H1 binding |
| Hmgn1 | Non-histone chromosomal protein HMG-14. Interacts with histone octamer |
| Mphosph8 | M-phase phosphoprotein. HUSH complex H3K9 methylation |
| Eny2 | Transcription and mRNA export factor ENY2. Associated with HAT complex, SAGA |
| Tmpo | Lamina-associated polypeptide 2 |
| Kmt2b/Mll4 | Histone-lysine-methyltransferase |

Referring to FIG. 12A, the active compound 3 and inactive control compound 4 were used for chemical affinity purification to identify binding targets of compound 2 from CiA:Oct4 N118/N163 sonicated nuclear lysates. Referring to FIG. 12B, a representative SDS-PAGE gel of the affinity pulldown experiment stained with Sypro Ruby stain is shown. M-marker, FT-flow through, W1-wash 1, W2-wash 2, W3-wash 3, E1-elution 1, E2-elution 2.

Referring to Table 3, iTRAQ LC-MS/MS was used to quantitate the differences in protein enrichment in the active compound 3 sample compared to the controls. Table lists enriched protein targets pulled down by active compound 3 with a summary of their UniProt descriptions.

8. Kmt2B/Mll4 and Hdgfrp2 are Novel Contributors to the HP1-Mediated Gene Repression Pathway To determine if the identified targets function in HP1-mediated gene repression, shRNA knock-downs directed against Kmt2B/Mll4, Hdgfrp2, Supt6H, and Tmpo were used. In theory, if compound 2 is inhibiting any of these putative binding partners leading to inhibition of the HP1 pathway, then knock-down of the proteins should recapitulate the compound phenotype.

Figure 13:
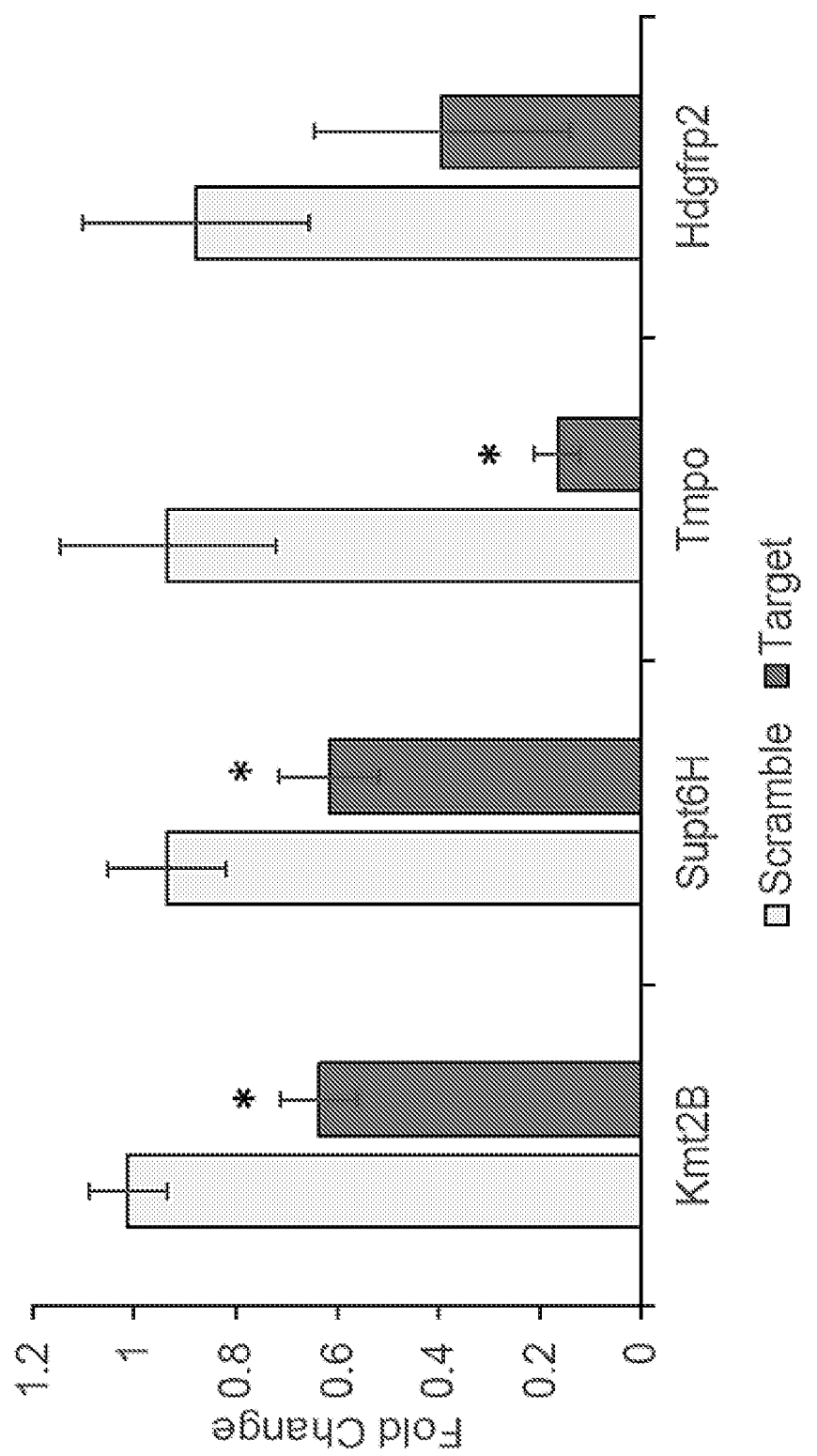
FIG. 13 shows representative qRT-PCR data demonstrating knock-down of shRNA targeted genes.

Lentiviral infection with the pTRIPZ vector allowed for stable integration of the shRNA construct under a doxycycline inducible promoter. CiA:Oct4 N205 (ZFHD1-FKBP T2A cleavage site FRB-csHP1α) cells were used for this study to allow for selection of the shRNA while maintaining the capacity to recruit csHP1α to the Oct4 locus. CiA:Oct4 N205 cells expressing the shRNA constructs were grown with rapamycin in the presence of 1 μg/ml doxyclycine for 48 hours. Samples without rapamycin or without doxycycline induction did not alter GFP levels as expected (data not shown). Knock-down of target mRNA levels were confirmed by qRT-PCR and normalized to β-actin. Kmt2B/Mll4 and Supt6H were suppressed ~40%, while Tmpo and Hdgfrp2 were knocked-down by 70-80% (FIG. 13). Like compound treatment, cells were analyzed by flow cytometry to determine if the shRNA knock-downs could recapitulate the inhibition of GFP repression demonstrated by compound 2 and normalized to a nonsense shRNA control. Supt6H and Tmpo showed little to no inhibitory effects demonstrating no direct role in the HP1 gene silencing pathway. Kmt2B/Mll4 and Hdgfrp2 significantly inhibited the ability of the HP1 pathway to repress the Oct4 locus. Without wishing to be bound by theory, these data indicate that Kmt2B/Mll4 and Hdgfrp2 represent novel HP1 pathway members that contribute to gene repression.

Referring to FIG. 13, CiA:Oct4 N205 cells containing inducible shRNA constructs targeted against Kmt2B/Mll4, Hdgfrp2, Supt6H, and Tmpo were induced with 1 μg/mL doxycycline for 48 hrs+/−6 nM rapamycin. Knock-down was confirmed by extracting total RNA for RT-qPCR. Samples were normalized against β-actin to determine fold change using comparative ΔΔCt method. (n≥3) (p≤0.05*).

Figure 14:
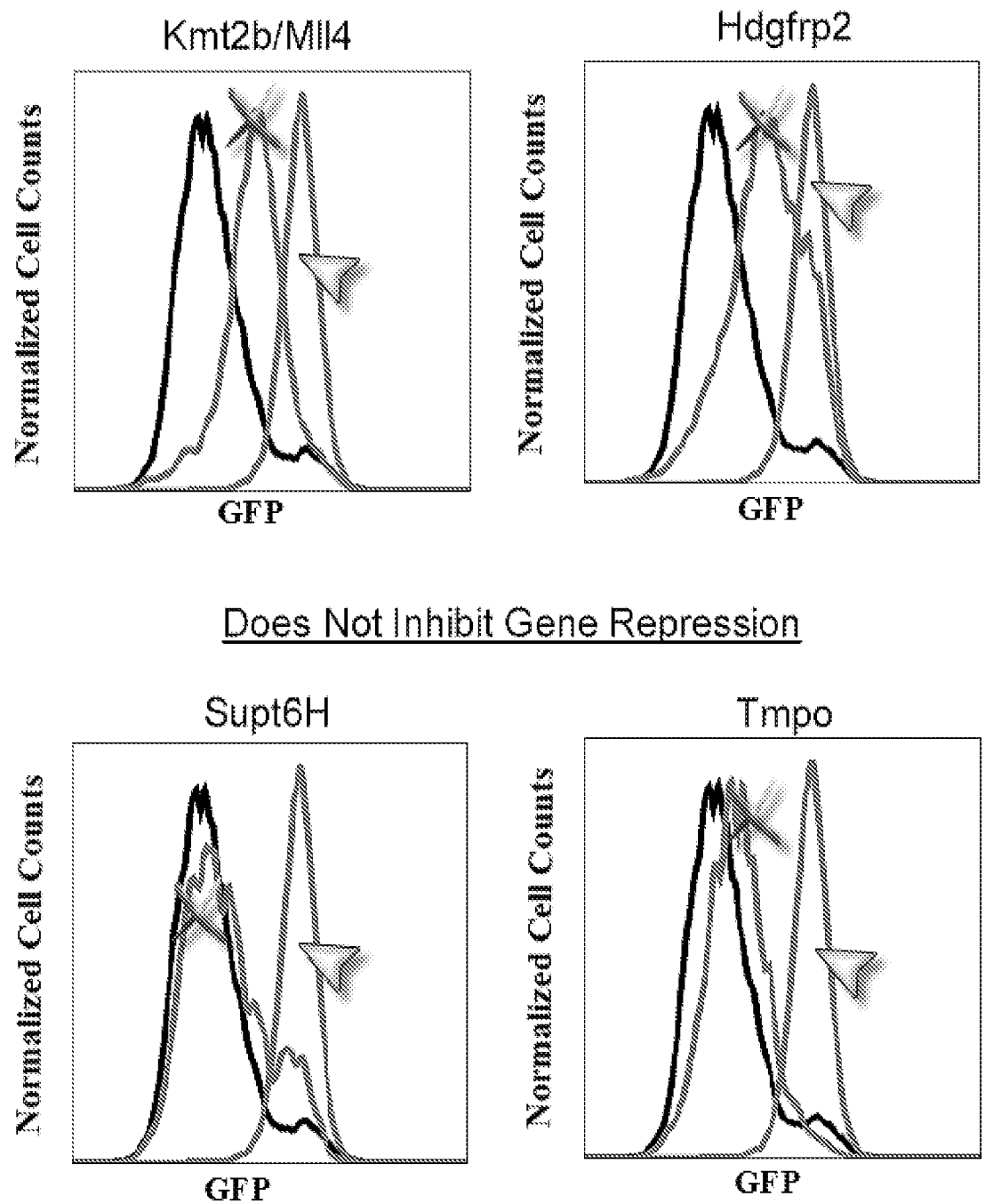
FIG. 14 shows representative data demonstrating that shRNA knock-down of target genes inhibits HP1-mediated heterochromatin.

Referring to FIG. 14, CiA:Oct4 N205 cells containing inducible shRNA constructs targeted against Kmt2B/Mll4, Hdgfrp2, Supt6H, and Tmpo were induced with 1 μg/mL doxycycline for 48 hrs+/−6 nM rapamycin. Flow cytometry analysis was used to determine the % GFP (+) population as compared to nonsense shRNA control. Results were classified into those that inhibited (top), or did not inhibit (bottom) HP1 pathway gene repression.

TABLE 4

| shRNA Target | Median GFP | Fold Change (Compared to Scramble + Rap) |
|---|---|---|
| Scramble + Rap | 7477.75 ± 66 | Reference |
| Scramble − Rap | 49330± 1383 | 6.6 ± 0.37 |
| Kmt2B/Mll4 | 18190.25 ± 217 | 2.43 ± 0.06 |
| Hdgfrp2 | 25669.25 ± 553 | 3.43 ± 0.14 |
| Supt6H | 11045 ± 112 | 1.48 ± 0.03 |
| Tmpo | 9023 ± 31 | 1.2 ± 0.01 |

9. Small Molecule Modulators of the HP1 Pathway

Heterochromatin gene repression is a key developmental epigenetic pathway, responsible for silencing genes critical for the proper timing of mammalian development (Bilodeau, Kagey, Frampton, Rahl, & Young, 2009). After development, disruption of epigenetic pathways has been demonstrated to drive diverse classes of human cancer. Components of the HP1 heterochromatin pathway have been identified as dysregulated in breast, uterine, prostate, and pancreatic carcinomas (De Koning et al., 2009). Overexpression of pathway components is correlated with poor outcomes for patients with breast and liver cancer (De Koning et al., 2009; Wong et al., 2016). Even though inhibition of heterochromatin is an attractive target class, there are currently no FDA approved therapeutics targeting the HP1 heterochromatin pathway.

Here, a novel small molecule high-throughput screening approach was used to identify modulators of HP1-mediated heterochromatin formation. Primary and secondary screens with and without rapamycin respectively, allowed for internal control and elimination of compounds that were toxic to cells or caused cellular differentiation and GFP reduction independent of HP1 recruitment. 34 inhibitors were identified that decreased HP1-mediated gene repression leading to an increase in cellular GFP expression. Top inhibitor compounds included UNC00000557, UNC617, UNC1875, and UNC2524. This screen also resulted in one enhancer of the HP1 pathway, UNC00000202. UNC617 was reported as an inhibitor of the histone methyltransferase G9a which functions by adding the H3K9me2 mark (Kim et al., 2016). Inhibition of the H3K9me2 mark would result in decreased ability to form the H3K9me3 necessary for heterochromatin formation. Identifying relevant inhibitors like UNC617 validates this approach for identifying modulators of the HP1 pathway.

Leading compounds were characterized with an inhibitory phenotype by demonstrating their dose-dependent response in this cellular assay. Each of the leading compounds possessed $IC_{50}$'s of 1-5 µM while UNC617 and UNC2524 possessed the greatest potency in the real time HP1-mediated assay. Lead screen compounds further demonstrated inhibition of the csHP1γ isoform in a similar manner to csHP1α. UNC617 and UNC2524 remained the most effective inhibitors of the 20 top compounds screened against csHP1γ recruitment. These results add a robustness and confidence to this screen data because functionally similar isoforms of HP1 are similarly inhibited. Finally, it was determined that the top inhibitory compounds decreased whole cell H3K9me2 and H3K9me3. As methylation of H3K9 is indicative of heterochromatin domain formation and these compounds inhibit that formation, it is expected that these compounds decrease H3K9me2/3 marks at the Oct4 locus. Without wishing to be bound by theory, the reduction in global levels indicates that the compounds are functioning not only at the Oct4 locus, but are whole cell inhibitors of the HP1 pathway for gene repression.

Top screen compounds were further shown to inhibit the csHP1γ isoform in a similar manner to csHP1α. UNC617 and UNC2524 remained the most effective inhibitors of the 20 top compounds screened against csHP1γ recruitment. Without wishing to be bound by theory, these results further increased the robustness and confidence in the primary screen data, because functionally similar isoforms of HP1 were similarly inhibited. Finally, it was determined that the top inhibitory compounds trended towards decreased whole cell H3K9me2 and H3K9me3 levels, but significant reductions were not reproducibly observed for all compounds. It was found that measuring the steady-state kinetics of histone marks was confounded due to balancing compound activity with compound toxicity. As methylation of H3K9 indicates HP1-heterochromatin domain formation and the compounds inhibited that formation, it was expected that the compounds would decrease H3K9me2/3 marks at the Oct4 locus. The trend towards a reduction in global levels indicated that the compounds were functioning not only at the Oct4 locus but are whole cell inhibitors of the HP1 pathway for gene repression.

Structure-activity relationship optimization studies identified compound 2 as the most potent inhibitor of HP1-mediated gene repression. Using ChIP analysis, the CiA:Oct4 allele was characterized to determine the effect of compound 2 treatment on HP1-heterochromatin pathway function. Compound 2 similarly inhibited H3K9me3 deposition and HP1γ localization. By inhibiting HP1 recruitment during HP1-mediated gene repression, H3K9me2/3 levels were expected to decrease due to a lack of recruitment scaffold for the histone lysine methyltransferase enzymes. H3K4me3 was previously shown to exist in an inverse relationship to H3K9me3. Surprisingly, an increase in H3K4me3 as H3K9me3 decreased was not observed with compound 2 treatment. Without wishing to be bound by theory, compound 2 treatment allowed for the separation of two previously linked epigenetic marks and may represent a means to study this interaction in the future.

Lysine-methyltransferase 2B (Kmt2B) and hepatoma-derived growth factor-related protein 2 (Hdgfrp2) demonstrated a significant inhibitory phenotype upon recruitment of csHP1α to the Oct4 locus. Interestingly, Kmt2B has primarily been reported as a histone methyltransferase that adds methyl marks on H3K4, not repressive H3K9me3. H3K4 methylation is typically associated with active euchromatin. Kmt2B was also reported to be required for marking H3K4me1 marks on certain enhancer and promoter regions which had a repressive phenotype (Hu et al., 2013). It was reported that loss of Kmt2B caused a decrease in H3K4me1 and led to an increase in gene expression (Cheng et al., 2014). Without wishing to be bound by theory, compound treatment may be inhibiting the maintenance of the H3K4me1 repressive mark leading to increased gene expression.

Hdgfrp2 is closely related to the lens epithelium-derived growth factor/transcriptional co-activator p75 (LEDGF/p75) which is known to bind the integrase enzyme of HIV leading to incorporation into active regions of chromatin (Baude et al., 2016). Hdgfrp2 contributed to the efficiency and specificity of HIV integration, but prefers binding repressed chromatin marks (Wang et al., 2012). In addition to viral integration, Hdgfrp2 was reported to interact with HP1β (CBX1) during DNA repair of silenced genes (Baude et al., 2016). HP1 has a growing role in DNA damage responses that is yet to be fully elucidated (Dinant & Luijsterburg, 2009). Hdgfrp2, like Supt6H, also interacts with IWS1 which contributes to hepatocellular carcinoma (HCC) development and may also contribute to H3K9me3 as Hdgfrp2 is overexpress in these cancer cells (Gao et al., 2015). Finally, HP1 pathway components such as SETDB1 are also upregulated in HCC (Wong et al., 2016). Combining these intersecting roles of Hdgfrp2 and HP1, it is logical that inhibition of these processes would decrease HP1s ability to form heterochromatin.

Heterochromatin protein 1 (HP1) is critical to the formation and maintenance of heterochromatin domains. HP1 facilitates the recruitment of histone lysine methyltransferase enzymes leading to the spread of H3K9me3 marks to neighboring histones resulting in gene silencing. Epigenetic regulation of gene silencing is critical for proper cell differentiation during mammalian development. Multiple HP1 pathway components are upregulated in human cancers, making this pathway an untapped therapeutic target. Despite its importance as a major mammalian regulatory pathway for gene expression, there are few known chemical modulators of the HP1 pathway.

Here, a biased small molecule library composed of epigenetic targeting compounds was used to identify inhibitors of the HP1 pathway, using a high-throughput flow cytometry screening platform. The CiA:Oct4 screening platform allowed for modular recruitment of specific protein activities to an endogenous locus in a temporally controlled manner, and yielded GFP expression data with single cell resolution. Using this approach, a series of potent inhibitors with dose-dependent responses was identified that were validated in an orthogonal recruitment system. These inhibitors represent a new class of chemotherapeutics targeting cancers with amplified HP1 pathway activity. Through a combination of medicinal chemistry optimization and affinity purification proteomics, novel components of the HP1-mediated gene repression pathway were identified. It was confirmed that Kmt2B/Mll4 and Hdgfrp2 shRNA knock-downs inhibit HP1-mediated gene repression. Without wishing to be bound by theory, these findings expand understandings of the HP1 pathway and demonstrate, despite extensive traditional genetic studies, that there may yet be unexplored protein components to be characterized in HP1-mediated gene repression pathway.

10. Chemical Structures of Inhibitors of HP1-Mediated Gene Repression

Figure 15:
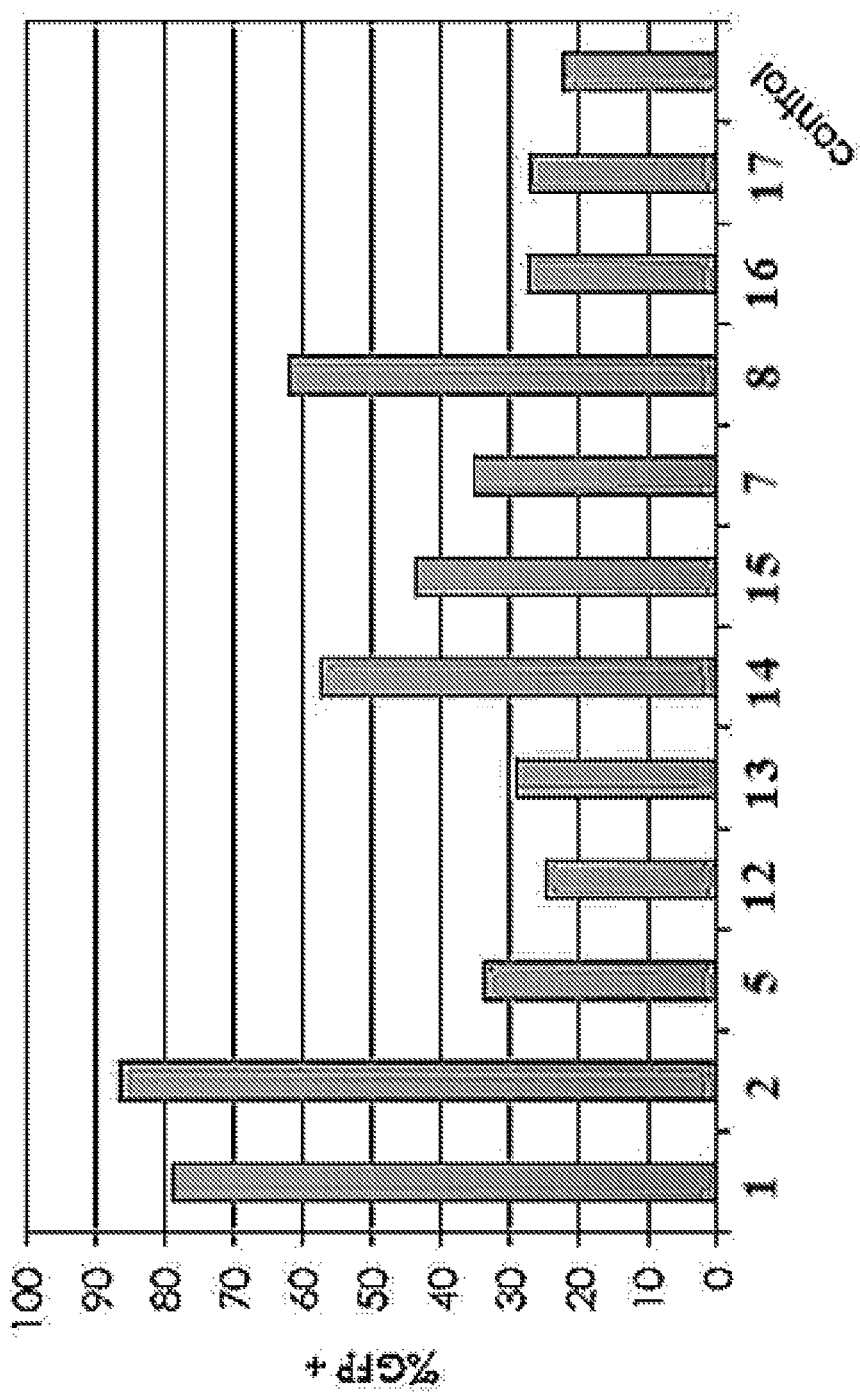
FIG. 15 shows representative data pertaining to the activity of UNC2524 (compound 1) and structurally similar analogs.

A summary of the structures of small molecules evaluated for their ability to inhibit HP1-mediated gene repression are illustrated in Table 4 below. The activity of the compounds is illustrated in FIG. 15.

TABLE 4
| No. | Structure |
|---|---|
| 1 | 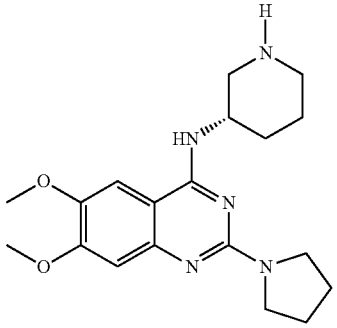 [SMILES: COc1cc2nc(N3CCCC3)nc(N[C@H]3CCCNC3)c2cc1OC] |
| 2 | 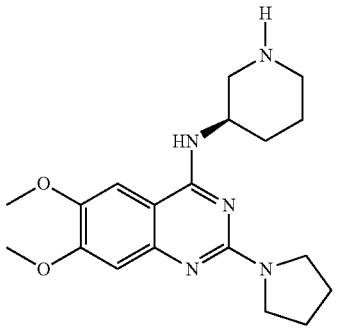 [SMILES: COc1cc2nc(N3CCCC3)nc(N[C@@H]3CCCNC3)c2cc1OC] |
| 3 | 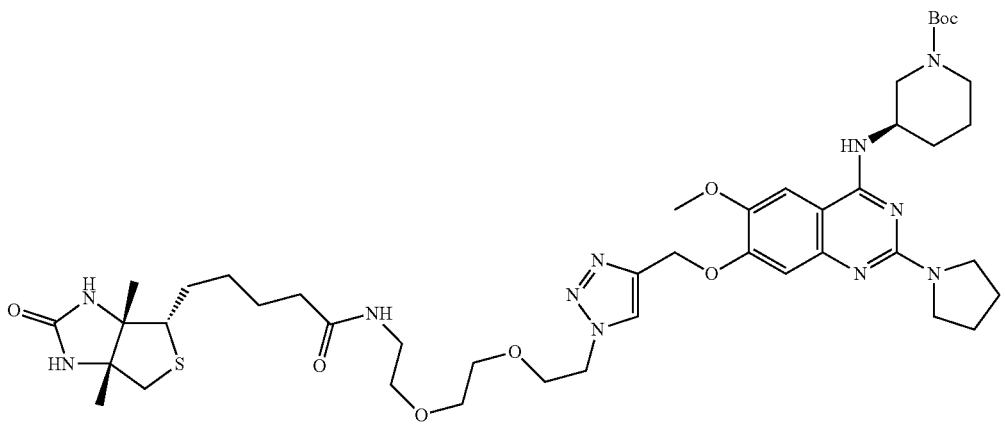 [SMILES: COc1cc2c(N[C@@H]3CCCN(C(=O)OC(C)(C)C)C3)nc(N3CCCC3)nc2cc1OCc1cn(CCOCCOCCNC(=O)CCCC[C@@H]2SC[C@]3(C)NC(=O)N[C@]23C)nn1] |
| 4 | 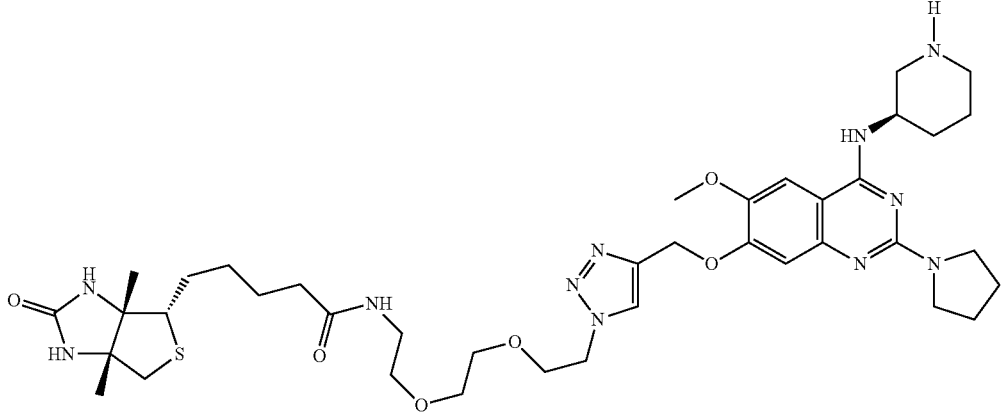 [SMILES: COc1cc2c(N[C@@H]3CCCNC3)nc(N3CCCC3)nc2cc1OCc1cn(CCOCCOCCNC(=O)CCCC[C@@H]2SC[C@]3(C)NC(=O)N[C@]23C)nn1] |

TABLE 4-continued

| No. | Structure |
|---|---|
| 5 | 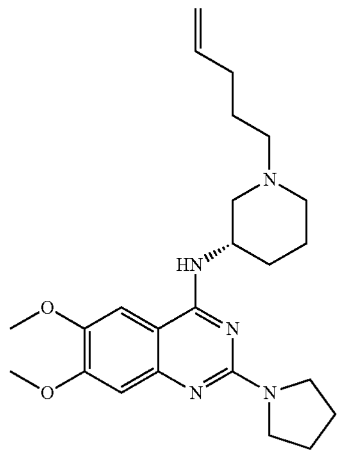 [SMILES: C=CCCCN1CCC[C@H](Nc2nc(N3CCCC3)nc3cc(OC)c(OC)cc23)C1] |
| 6 | 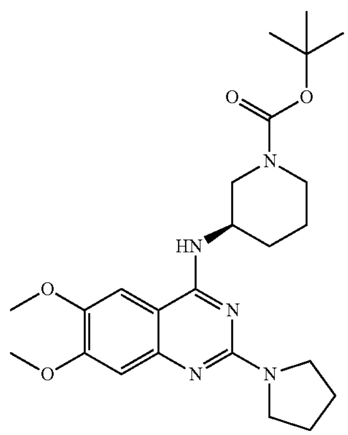 [SMILES: COc1cc2nc(N3CCCC3)nc(N[C@@H]3CCCN(C(=O)OC(C)(C)C)C3)c2cc1OC] |
| 7 | 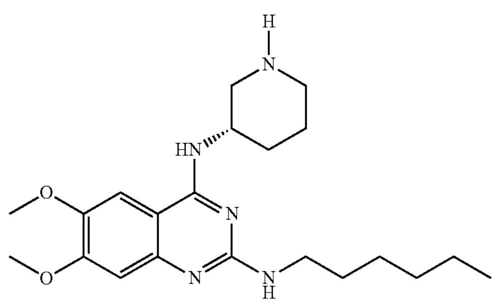 [SMILES: CCCCCCNc1nc(N[C@H]2CCCNC2)c2cc(OC)c(OC)cc2n1] |
| 8 | 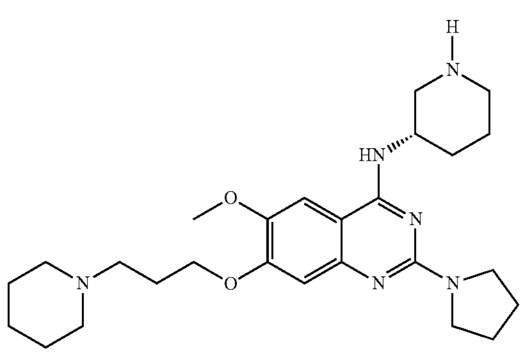 [SMILES: COc1cc2c(N[C@H]3CCCNC3)nc(N3CCCC3)nc2cc1OCCCN1CCCCC1] |

TABLE 4-continued

| No. | Structure |
|---|---|
| 10 | 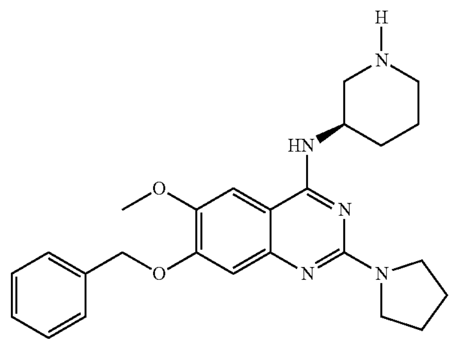 [SMILES: COc1cc2c(N[C@@H]3CCCNC3)nc(N3CCCC3)nc2cc1OCc1ccccc1] |
| 11 | 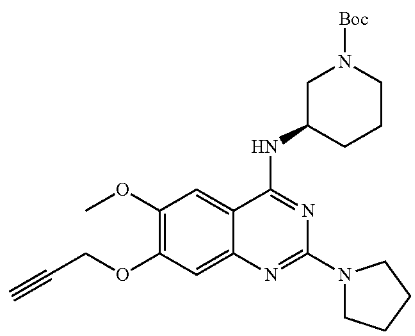 [SMILES: C#CCOc1cc2nc(N3CCCC3)nc(N[C@@H]3CCCN(C(=O)OC(C)(C)C)C3)c2cc1OC] |
| 12 | 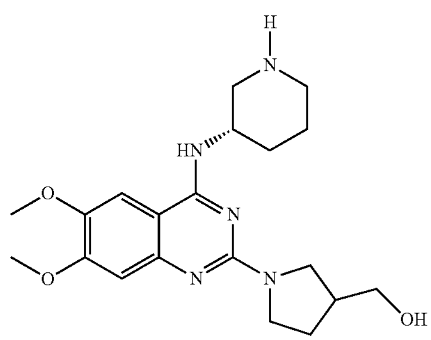 [SMILES: COc1cc2nc(N3CCC(CO)C3)nc(N[C@H]3CCCNC3)c2cc1OC] |
| 13 | 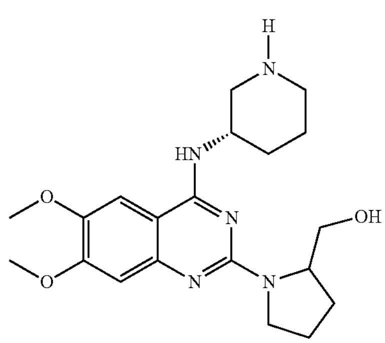 [SMILES: COc1cc2nc(N3CCCC3CO)nc(N[C@H]3CCCNC3)c2cc1OC] |

TABLE 4-continued

| No. | Structure |
|---|---|
| 14 | 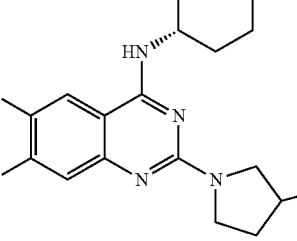 |
| 15 | 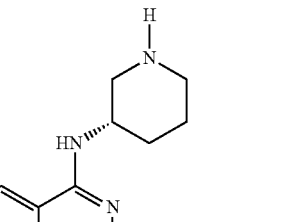 |
| 16 | 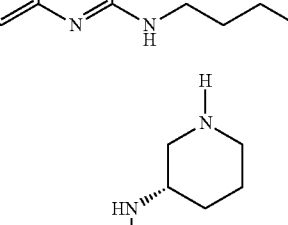 |
| 17 | 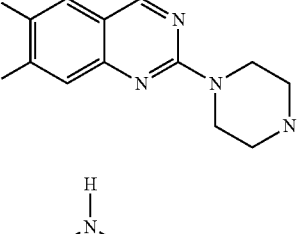 |

J. PROPHETIC EXAMPLES

CiA was previously used to study the molecular events following HP1-mediated heterochromatin assembly. However, understanding both the order and contribution of each event to heterochromatin gene repression requires the ability to intervene on each step. Because the induction and maintenance of gene repression involves many distinct enzymes, chemical inhibition is used to separate the individual actions of enzymes and to establish the order-of-events in heterochromatin assembly. Unfortunately, to date few such molecules are available (Rodrfguez-Paredes and Esteller (2011) Nat. Med. 17: 330-9; Finley and Copeland (2014) Chem. Biol. 21: 1196-1210). As detailed above, the disclosed CiA system was used to conduct a high throughput screen for modulators of heterochromatin repression (see also FIG. 16A and FIG. 16B). A library of ~1,200 compounds with known activity was screened against epigenetic targets and a series of lead compounds identified. Here, these compounds will be used to order the enzymatic stages of heterochromatin assembly.

Figure 16A:
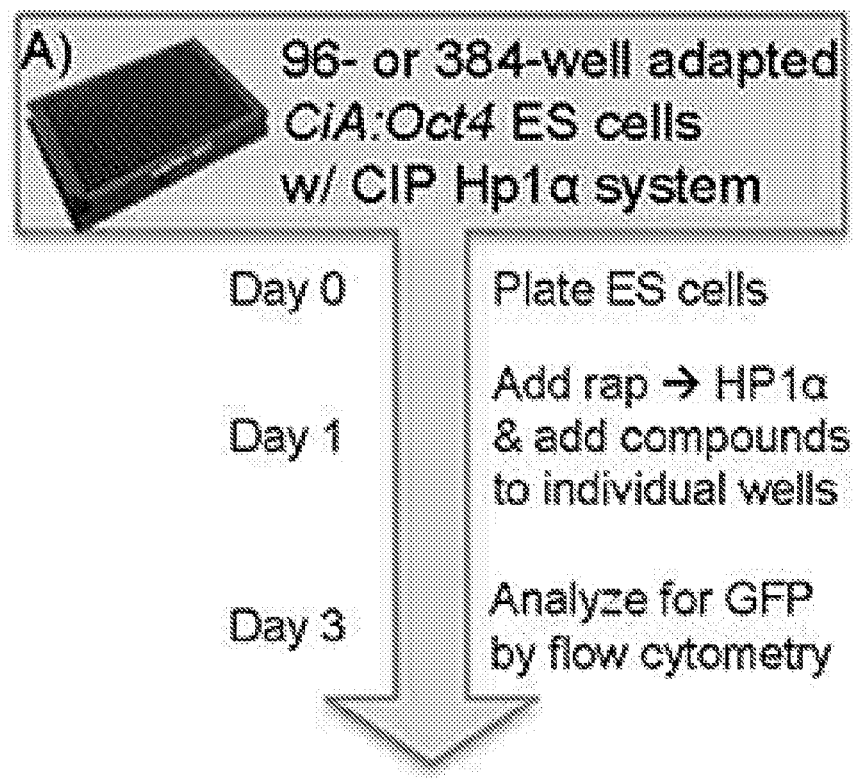
FIG. 16A and FIG. 16B show representative data pertaining to a small molecule screen of ~1,200 compounds for inhibitors or enhancers of HP1-mediated gene repression.

Referring to FIG. 16A, a screen design is shown.

Figure 16B:
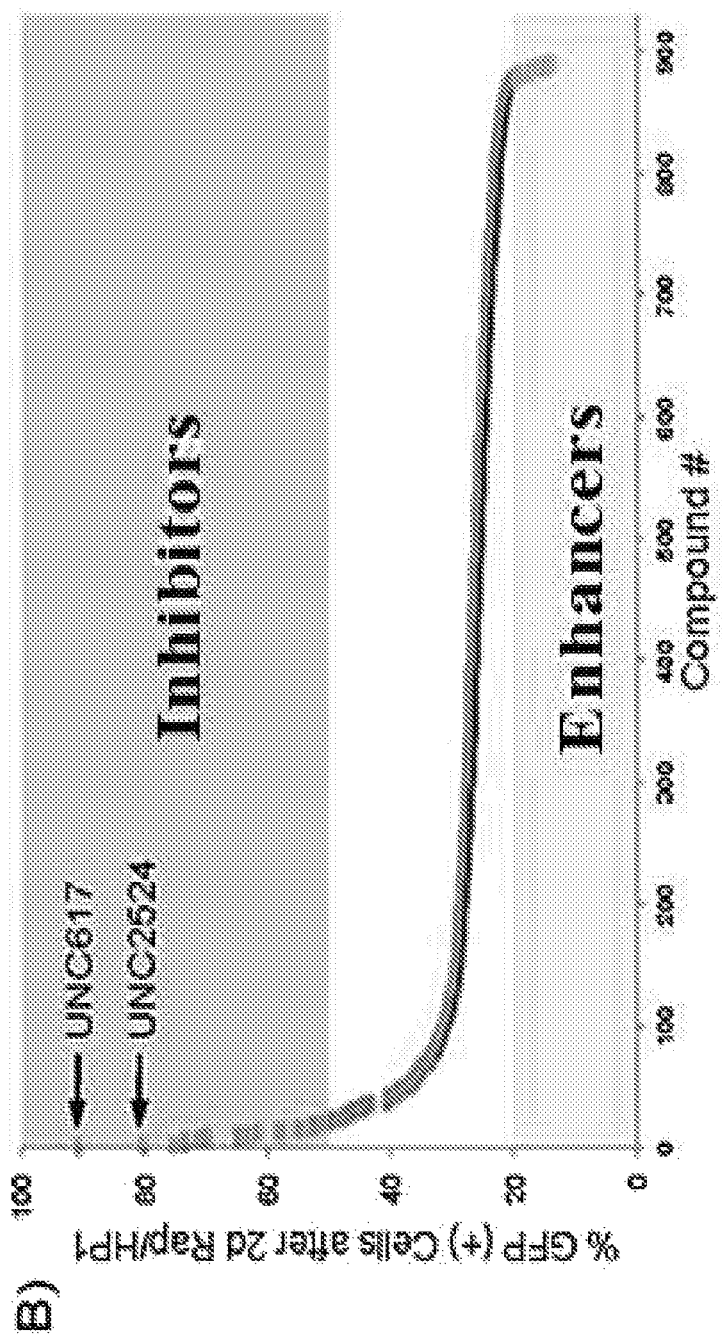

Referring to FIG. 16B, the percent GFP (+) cells after 2 days of rapamycin-mediated HP1 recruitment. Control cells without compound added were 24% GFP (+). Wells with greater than 55% cells GFP (+) scored as an inhibitor and wells less than 20% cells GFP (+) scored as enhancers. Top scoring inhibitor compounds, UNC617 and UNC2524 are indicated.

1. Identify and Order the Key Molecular Events of HP1-Stimulated Gene Repression UNC617 and UNC2524 share structural similarities to reported inhibitors of GLP/G9a (Kubicek et al. (2007) *Mol. Cell* 25: 473-481; Vedadi et al. (2011) *Nat. Chem. Biol.* 7: 566-74; Liu et al. (2013) *J. Med. Chem.* 56: 8931-8942). UNC617 is potent and selective for GLP and G9a in vitro, while UNC2524 has no detectable activity against GLP/G9a (data not shown). Here, the activities of these two compounds on HP1 heterochromatin formation will be characterized and the key molecular step at which they interfere identified.

a. Determine the Stages of HP1-Mediated Heterochromatin Generation Inhibited by UNC617 and UNC2524

Figure 17A:
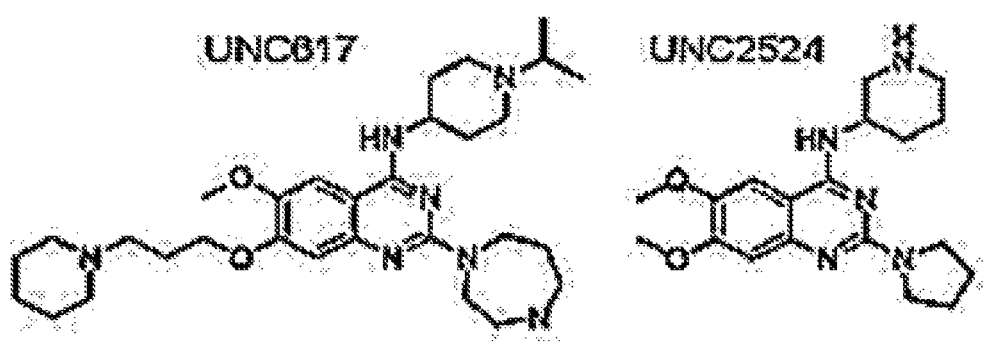
FIG. 17A and FIG. 17B shows representative data pertaining to inhibition of HP1-mediated gene repression by UNC617 and UNC2524.
Figure 17B:
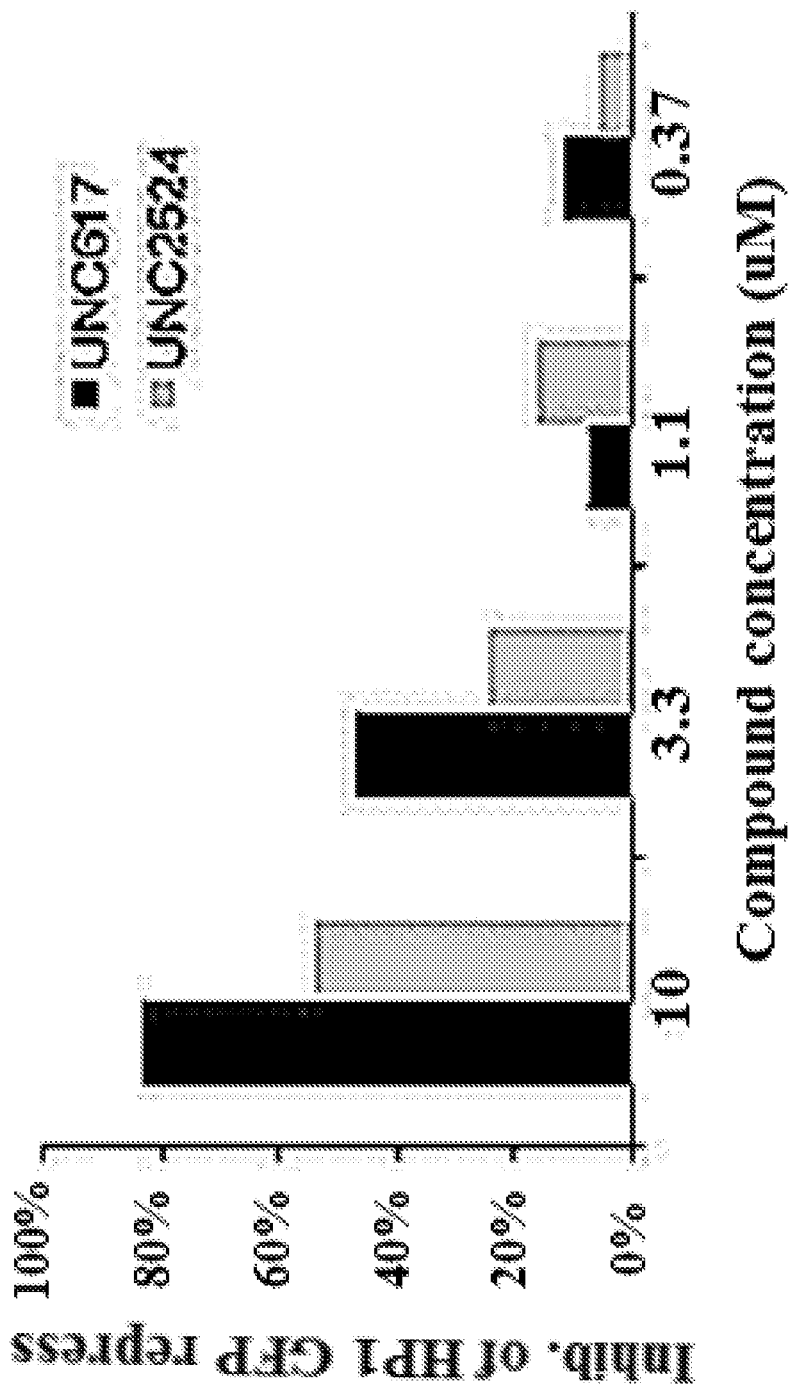

CiA:Oct4 ES cells will be treated with a concentration range of UNC617 or UNC2524 (100 nM-10 µM) during induction of HP1-mediated gene repression where they exhibited activity in our primary assay (FIG. 17A and FIG. 17B). Many enzymatic events follow rapamycin-mediated recruitment of HP1α to the CiA locus including: removal of active chromatin marks, deposition of repressive marks including H3K9me3, gene repression, and DNA methylation. ChIP will be performed over a time course quantify heterochromatin associated histone modifications (H3K9me1/2 and H3K9me3), and also the potential enrichment of endogenous HP1. To examine if compounds inhibit accumulation of DNA methylation, samples will be tested with bisulfite analysis. Compound activity will also be tested on HP1β and -γ.

Referring to FIG. 17A, the structures of UNC617 and UNC2524 are shown.

Referring to FIG. 17B, GFP repression after 2 days rapamycin mediated HP1 recruitment to CiA:Oct4 with compound as indicated. Inhibitory activity scored compared to DMSO only control samples.

b. Determine Whether UNC617 and UNC2524 Inhibit HP1 Heterochromatin Formation at LOCI Other than Oct4

Next, the activity of these compounds on CiA:β EF-1α (strong promoter) will be evaluated. Repression will be initiated at CiA:β EF-1α with CIP of HP1(-α, -β, or -γ) and add UNC617 or UNC2524 (100 nM-10 µM) and measure GFP gene activity by flow cytometry, H3K9me3 enrichment by ChIP, and DNA methylation by bisulfite analysis. This will test if compounds act on HP1 assembly at an independent loci or only at Oct4.

Without wishing to be bound by theory, it is anticipated that UNC617 and UNC2524 will inhibit methylation of H3K9 in vivo at the CiA promoter in response to HP1 recruitment. If this is not observed, however, ChIP will be used to examine other chromatin modifications known to correlate with heterochromatin, e.g., H3K4me3 loss, histone acetylation loss, or recruitment of endogenous HP1 activity. Without wishing to be bound by theory, it is anticipated that these compounds will allow ordering of events required to assemble heterochromatin. In vitro binding of compounds will be tested by isothermal titration calorimetry (ITC) with purified proteins known to be involved in HP1 heterochromatin, such as: HP1-α, -β, and -γ, GLP, G9a, Suv39H1, SETDB1, UHRF1, DNMT3a, and nuclear lamina proteins (Leavitt and Freire (2001) *Curr. Opin. Struct. Biol.* 11: 560-566; Ladbury et al. (2010) *Nat. Rev. Drug Discov.* 9: 23-7). Targets will be verified in vivo by using pTRIPZ inducible shRNA lentivirus to knock down the target and mimic inhibitor results.

2. Define the Mechanism-of-Action by which the Disclosed Compounds Inhibit HP1 Mediated Repression and Test in a Physiologic Heterochromatin Model.

To learn more about the core molecular mechanism of HP1 gene repression, the molecular target of UNC2524 (UNC617's target is G9a) can be isolated, verified, and characterized. It will also be verified that both UNC617 and UNC2524 function to antagonize HP1 activity in an orthogonal and physiologically relevant mammalian development model using RA-induced heterochromatin.

a. Identify the Target of UNC2524

Over a dozen chemical analogues of UNC2524 were previously prepared to examine the structure activity relationship (SAR) (Park and Park (2012) *Angew. Chem. Int. Ed. Engl.* 51: 5447-51; Schenone et al. (2013) *Nat. Chem. Biol.* 9: 232-40; Ziegler et al. (2013) *Angew. Chem. Int. Ed. Engl.* 52: 2744-92). An affinity reagent analogue of UNC2524 and a UNC2524-inactive derivative (with a bulky chemical group at a key position), both coupled to a biotin tag, has also been prepared. Any stable binding protein partners will be isolated by applying ES cell lysates over a column containing UNC2524-biotin or UNC2524-inactive-biotin tethered to a streptavidin resin. Preliminary (non-quantitative) mass spectrometry work demonstrate the feasibility of this technique: 2 potential interacting proteins have been isolated (see FIG. 18). One is Lamin B1, a nuclear periphery protein that aids chromatin attachment to the inner nuclear membrane and is important for proper heterochromatin assembly (Gonzalez-Sandoval et al. (2015) *Cell* 163: 1333-1347; Mattout et al. (2015) *Genome Biol.* 16: 174). Immunoblot for Lamin B1 verified that Lamin B1 interacts with biotin-UNC2524 using (FIG. 19). To confirm Lamin B1 and look for additional targets of UNC2524, this purification strategy will be used together with quantitative isobaric mass spec identification. Any resulting interacting proteins (including Lamin B1) will be verified in vitro and in vivo, by ITC and shRNA knockdown, respectively.

Figure 18:
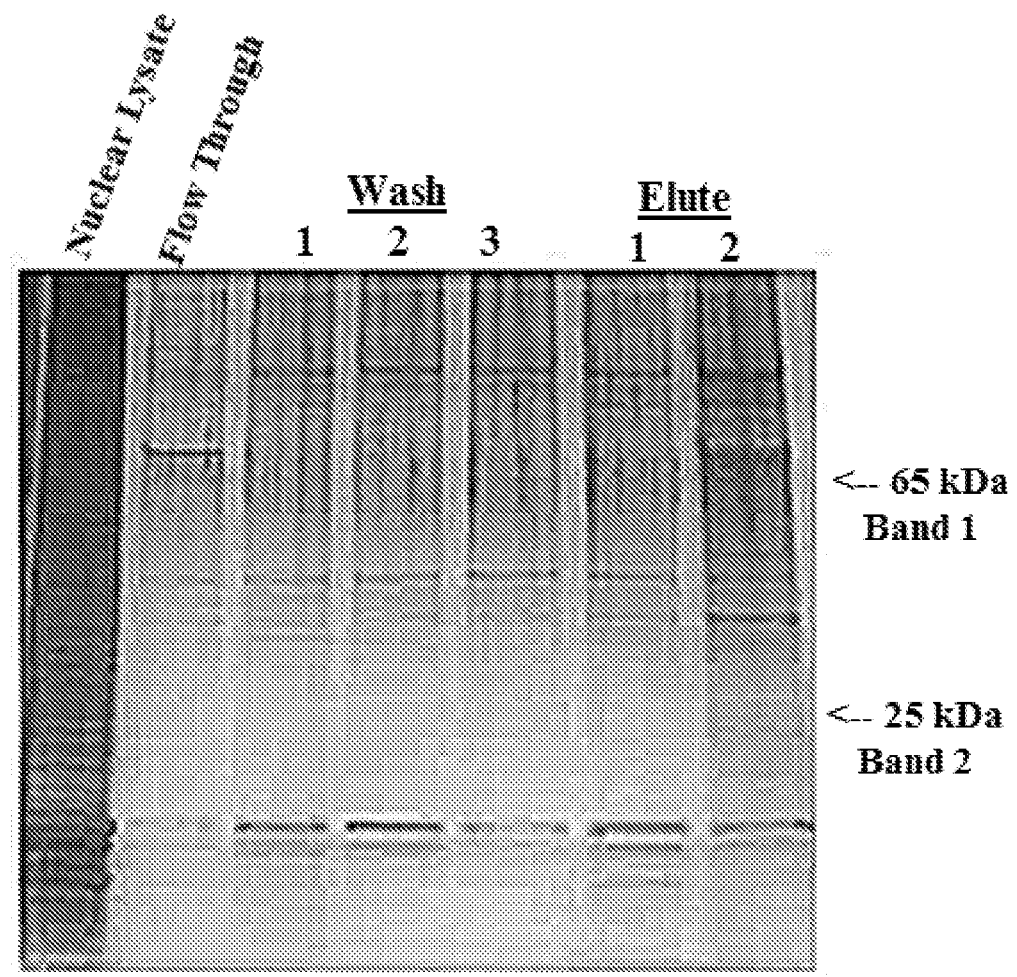
FIG. 18 shows representative data pertaining to the affinity purification of biotin-UNC2524 interacting proteins.
Figure 19:
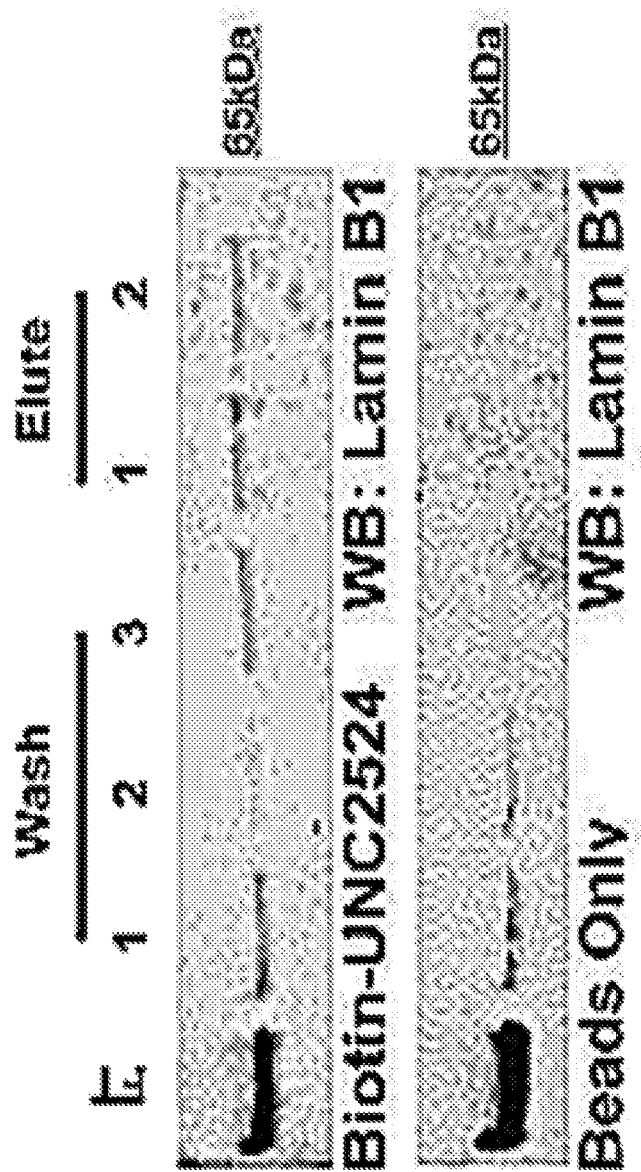
FIG. 19 shows representative data pertaining to Lamin B1 Western blot of biotin-UNC2524 purification.

Referring to FIG. 18, nuclear lysates were incubated with biotin-UNC2524 and bound to a streptavidin resin. Samples were washed 3× with 150 mM NaCl. Proteins were eluted with excess UNC2524 (E1) and free biotin (E2). Indicated bands were cut and sent for mass spectrometry analysis. Band 1 was identified as Lamin B1.

Referring to FIG. 19, the experiment was run as described for FIG. 18. The samples were visualized by Western blot as indicated.

b. Test Effects of UNC617 and UNC2524 on Physiologic RA Induced Heterochromatin.

Figure 20:
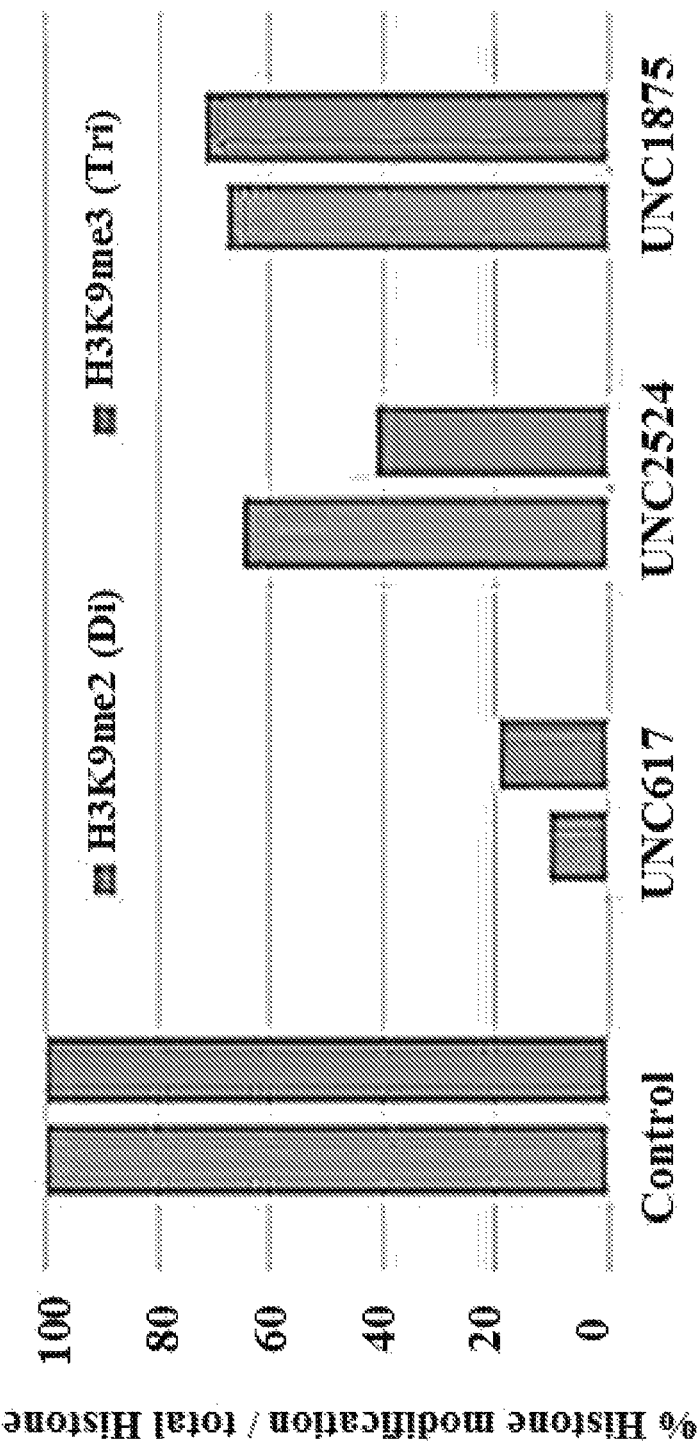
FIG. 20 shows representative data pertaining to whole cell Histone modification levels.
Figure 21:
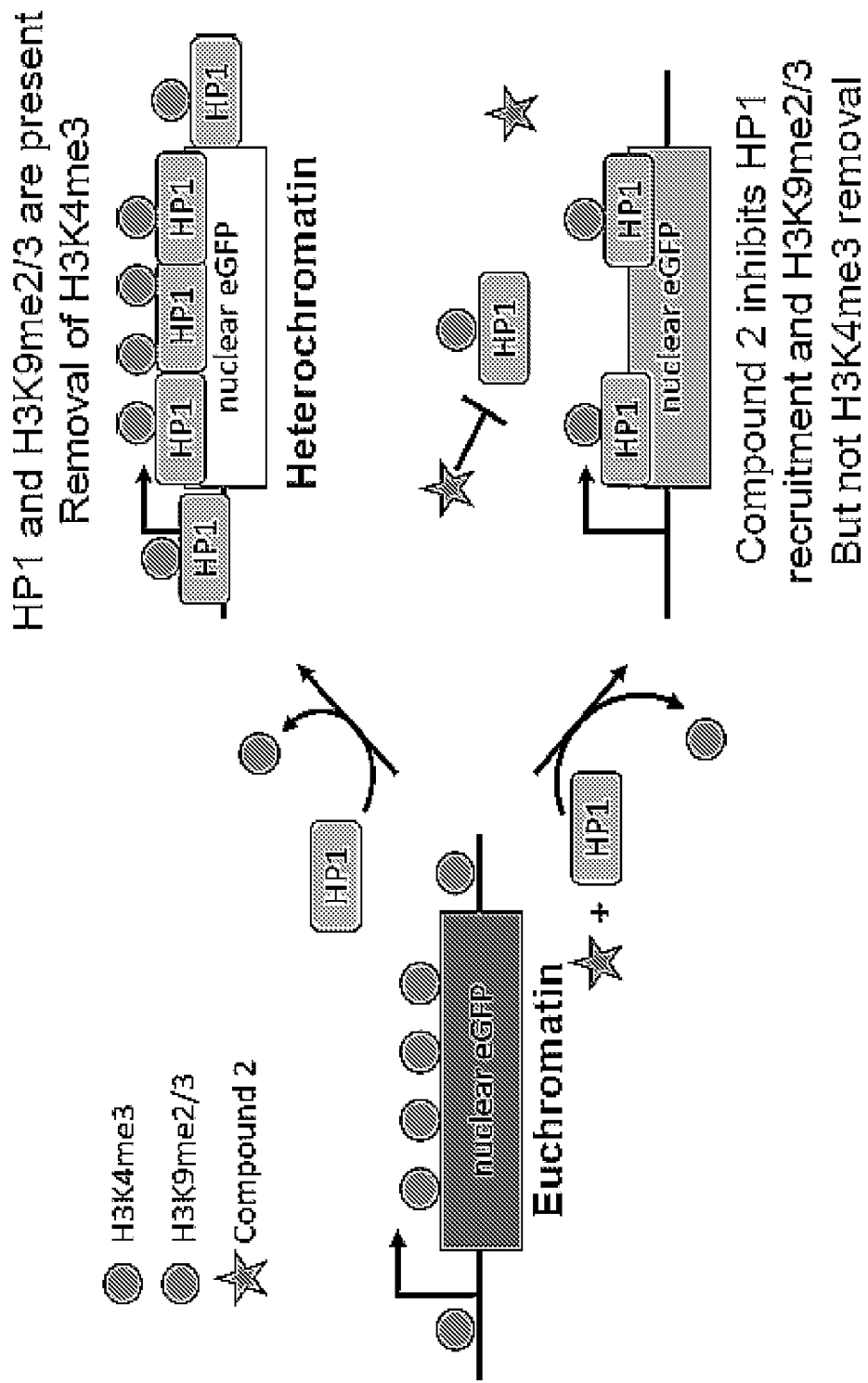
FIG. 21 shows a representative schematic illustrating inhibition of HP1 recruitment and H3K9me2/3 by compound 2.

The ability to reduce global H3K9-me2 and -me3 levels with the novel HP1 inhibitors was previously examined (see FIG. 20). UNC617 and UNC2524 were both found to significantly block bulk di- and tri-H3K9 methylation in ES cells. To examine if this reduction in HMT activity leads to reduced naturally stimulated heterochromatin signaling at Oct4 (as in SAID), UNC617 or UNC2524 (100 nM-10 µM) will be added simultaneously with 5 µM RA addition. Oct4-GFP will be measured by flow cytometry, H3K9me3 enrichment by ChIP, and DNA methylation levels by bisulfite sequencing at 2, 4, and 6 days post RA addition output measurements. Expression and chromatin modifications will also be examined at other RA regulated genes such as Sox2INanoa and use using GAPDH as a control.

Referring to FIG. 20, TC1 ES cells were incubated 48 hrs with compound. Histones marks were measured by Western blot densitometry with the indicated antibody. The results were normalized over the total Histone H4 as a percentage of untreated controls.

Without wishing to be bound by theory, it is anticipated that the molecular target of UNC2524 will be verified and both novel small molecule inhibitors will be used to isolate the role of individual enzymatic activities in heterochromatin assembly. In an alternative strategy to isolate weaker interacting proteins, a photoactivatable analogue of UNC2524 was prepared that employs a benzophenone based photocross-linking moiety that is activated with application of 355 nm UV light and isolated via click chemistry to a resin of choice (Schenone et al. (2013) *Nat. Chem. Biol.* 9: 232-40; Mackinnon and Taunton (2009) *Curr. Protoc. Chem. Biol.* 1: 55-73). As with the biotin affinity reagent, there are non-active control analogues for UNC2524. Candidate proteins will be verified in vivo and in vitro with shRNA knockdown and ITC, respectively. Without wishing to be bound by theory, it is anticipated that the disclosed HP1 pathway inhibitors will slow RA driven ES cell differentiation, mimicking what was observed with HP1 recruitment to CiA:Oct4. If, however, this is not seen, differences between RA induced heterochromatin and CIP HP1-α or-γ induced heterochromatin will be investigated.

K. REFERENCES

Allfrey, V. G., Faulkner, R., & Mirsky, A. E. (1964). Acetylation and Methylation of Histones and Their Possible Role in the Regulation of Rna Synthesis. Proceedings of the National Academy of Sciences of the United States of America, 51(1938), 786-94. http://doi.org/10.1073/pnas.51.5.786

Arrowsmith, C. H., Bountra, C., Fish, P. V., Lee, K., & Schapira, M. (2012). Epigenetic protein families: a new frontier for drug discovery. Nature Reviews Drug Discovery, 11(5), 384-400. http://doi.org/10.1038/nrd3674

Baude, A., Aaes, T. L., Zhai, B., Al-Nakouzi, N., Oo, H. Z., Daugaard, M., Jäättelä, M. (2016). Hepatoma-derived growth factor-related protein 2 promotes DNA repair by homologous recombination. Nucleic Acids Research, 44(5), 2214-26. http://doi.org/10.1093/nar/gkv1526

Bilodeau, S., Kagey, M. H., Frampton, G. M., Rahl, P. B., & Young, R. A. (2009). SetDB1 contributes to repression of genes encoding developmental regulators and maintenance of ES cell state. Genes & Development, 23(21), 2484-9. http://doi.org/10.1101/gad.1837309

Black, J. C., Van Rechem, C., & Whetstine, J. R. (2012). Histone Lysine Methylation Dynamics: Establishment, Regulation, and Biological Impact. Molecular Cell, 48(4), 491-507. http://doi.org/10.1016/j.molcel.2012.11.006

Canzio, D., Chang, E. Y., Shankar, S., Kuchenbecker, K. M., Simon, M. D., Madhani, H. D., Al-Sady, B. (2011). Chromodomain-Mediated Oligomerization of HP1 Suggests a Nucleosome-Bridging Mechanism for Heterochromatin Assembly. Molecular Cell, 41(1), 67-81. http://doi.org/10.1016/j.molcel.2010.12.016

Ceol, C. J., Houvras, Y., Jane-Valbuena, J., Bilodeau, S., Orlando, D. A., Battisti, V., Zon, L. I. (2011). The histone methyltransferase SETDB1 is recurrently amplified in melanoma and accelerates its onset. Nature, 471. http://doi.org/10.1038/nature09806

Cheng, J., Blum, R., Bowman, C., Hu, D., Shilatifard, A., Shen, S., & Dynlacht, B. D. (2014). A Role for H3K4 Monomethylation in Gene Repression and Partitioning of Chromatin Readers. Molecular Cell, 53(6), 979-992. http://doi.org/10.1016/j.molcel.2014.02.032

Chiba, T., Saito, T., Yuki, K., Zen, Y., Koide, S., Kanogawa, N., Yokosuka, O. (2015). Histone lysine methyltransferase SUV39H1 is a potent target for epigenetic therapy of hepatocellular carcinoma. International Journal of Cancer, 136(2), 289-298. http://doi.org/10.1002/ijc.28985

Dawson, M. a, & Kouzarides, T. (2012). Cancer epigenetics: from mechanism to therapy. Cell, 150(1), 12-27. http://doi.org/10.1016/j.cell.2012.06.013

De Koning, L., Savignoni, A., Boumendil, C., Rehman, H., Asselain, B., Sastre-Garau, X., & Almouzni, G. (2009). Heterochromatin protein 1alpha: a hallmark of cell proliferation relevant to clinical oncology. EMBO Molecular Medicine, 1(3), 178-191. http://doi.org/10.1002/emmm.200900022

Dinant, C., & Luijsterburg, M. S. (2009). The emerging role of HP1 in the DNA damage response. Molecular and Cellular Biology, 29(24), 6335-40. http://doi.org/10.1128/MCB.01048-09

Fritsch, L., Robin, P., Mathieu, J. R. R., Souidi, M., Hinaux, H., Rougeulle, C., Ait-Si-Ali, S. (2010). A Subset of the Histone H3 Lysine 9 Methyltransferases Suv39h1, G9a, GLP, and SETDB1 Participate in a Multimeric Complex. Molecular Cell, 37(1), 46-56. http://doi.org/10.1016/j.molcel.2009.12.017

Gao, K., Xu, C., Jin, X., Wumaier, R., Ma, J., Peng, J., Zhang, P. (2015). HDGF-related protein-2 (HRP-2) acts as an oncogene to promote cell growth in hepatocellular carcinoma. Biochemical and Biophysical Research Communications, 458(4), 849-855. http://doi.org/10.1016/j.bbrc.2015.02.042

Greer, E. L., & Shi, Y. (2012). Histone methylation: a dynamic mark in health, disease and inheritance. Nature Reviews Genetics, 13(5), 343-357. http://doi.org/10.1038/nrg3173

Hathaway, N. A., Bell, O., Hodges, C., Miller, E. L., Neel, D. S., & Crabtree, G. R. (2012). Dynamics and Memory of Heterochromatin in Living Cells. Cell, 149(7), 1447-1460. http://doi.org/10.1016/j.cell.2012.03.052

Hu, D., Gao, X., Morgan, M. A., Herz, H.-M., Smith, E. R., & Shilatifard, A. (2013). The MLL3/MLL4 branches of the COMPASS family function as major histone H3K4 monomethylases at enhancers. Molecular and Cellular Biology, 33(23), 4745-54. http://doi.org/10.1128/MCB.01181-13

Kim, Y., Lee, H.-M., Xiong, Y., Sciaky, N., Hulbert, S. W., Cao, X., . . . Jiang, Y. (2016). Targeting the histone methyltransferase G9a activates imprinted genes and improves survival of a mouse model of Prader-Willi syndrome. Nature Medicine, 23(2), 213-222. http://doi.org/10.1038/nm.4257

Livak, K. J., & Schmittgen, T. D. (2001). Analysis of Relative Gene Expression Data Using Real-Time Quantitative PCR and the 2-ΔΔCT Method. Methods, 25(4), 402-408. http://doi.org/10.1006/meth.2001.1262

MacDonald, I. A., & Hathaway, N. A. (2015). Epigenetic roots of immunologic disease and new methods for examining chromatin regulatory pathways. Immunology and Cell Biology, 93(3), 261-70. http://doi.org/10.1038/icb.2014.105

Moazed, D. (2001). Common themes in mechanisms of gene silencing. Molecular Cell, 8(3), 489-98. Retrieved from http://www.ncbi.nlm.nih.gov/pubmed/11583612

Pattenden, S. G., Simon, J. M., Wali, A., Jayakody, C. N., Troutman, J., McFadden, A. W., Davis, I. J. (2016). High-throughput small molecule screen identifies inhibitors of aberrant chromatin accessibility. *Proceedings of* the *National Academy of Sciences of the United States of America*, 113(11), 3018-23. http://doi.org/10.1073/pnas.1521827113

Tchasovnikarova, I. A., Timms, R. T., Matheson, N. J., Wals, K., Antrobus, R., Göttgens, B., Lehner, P. J. (2015). Epigenetic silencing by the HUSH complex mediates position-effect variegation in human cells. *Science*, 348 (6242). Retrieved from http://science.sciencemag.org/content/348/6242/1481

Tiscornia, G., Singer, O., & Verma, I. M. (2006). Production and purification of lentiviral vectors. *Nature Protocols*, 1(1), 241-245. http://doi.org/10.1038/nprot.2006.37

Wallrath, L. L., Vitalini, M. W., & Elgin, S. C. R. (2014). Heterochromatin: A Critical Part of the Genome. In J. L. Workman & S. M. Abmayr (Eds.), *Fundamentals of Chromatin* (pp. 529-552). New York, N.Y.: Springer New York.

Wang, H., Jurado, K. A., Wu, X., Shun, M.-C., Li, X., Ferris, A. L., . . . Engelman, A. (2012). HRP2 determines the efficiency and specificity of HIV-1 integration in LEDGF/p75 knockout cells but does not contribute to the antiviral activity of a potent LEDGF/p75-binding site integrase inhibitor. *Nucleic Acids Research*, 40(22), 11518-11530. http://doi.org/10.1093/nar/gks913

Wong, C.-M., Wei, L., Law, C.-T., Ho, D. W.-H., Tsang, F. H.-C., Au, S. L.-K., Ng, I. O.-L. (2016). Up-regulation of histone methyltransferase SETDB1 by multiple mechanisms in hepatocellular carcinoma promotes cancer metastasis. *Hepatology*, 63(2), 474-487. http://doi.org/10.1002/hep.28304

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

SEQUENCE LISTING

```
<160> NUMBER OF SEQ ID NOS: 22

<210> SEQ ID NO 1
<211> LENGTH: 134
<212> TYPE: PRT
<213> ORGANISM: artificial sequence
<220> FEATURE:
<223> OTHER INFORMATION: synthetic construct

<400> SEQUENCE: 1

Cys Ala Ala Cys Ala Gly Ala Ala Gly Gly Cys Thr Cys Gly Ala Gly
1               5                   10                  15

Ala Ala Gly Gly Thr Ala Thr Ala Thr Thr Gly Cys Thr Gly Thr Thr
            20                  25                  30

Gly Ala Cys Ala Gly Thr Gly Ala Gly Cys Gly Gly Gly Ala Gly Ala
        35                  40                  45

Ala Cys Thr Cys Thr Gly Ala Thr Thr Gly Ala Gly Ala Ala Ala Gly
    50                  55                  60

Thr Ala Gly Thr Gly Ala Ala Gly Cys Cys Ala Cys Ala Gly Ala Thr
65                  70                  75                  80

Gly Thr Ala Cys Thr Thr Thr Cys Thr Cys Ala Ala Thr Cys Ala Gly
                85                  90                  95

Ala Gly Thr Thr Cys Thr Cys Cys Thr Gly Cys Cys Thr Ala Cys Thr
                100                 105                 110

Gly Cys Cys Thr Cys Gly Gly Ala Ala Thr Thr Cys Ala Ala Gly Gly
        115                 120                 125

Gly Gly Cys Thr Ala Cys
        130

<210> SEQ ID NO 2
<211> LENGTH: 134
<212> TYPE: PRT
<213> ORGANISM: artificial sequence
<220> FEATURE:
<223> OTHER INFORMATION: synthetic construct

<400> SEQUENCE: 2

Gly Thr Ala Gly Cys Cys Cys Thr Thr Gly Ala Ala Thr Thr Cys
1               5                   10                  15

Cys Gly Ala Gly Gly Cys Ala Gly Thr Ala Gly Gly Cys Ala Gly Gly
```

```
                20                  25                  30

Ala Gly Ala Ala Cys Thr Cys Thr Gly Ala Thr Gly Ala Gly Ala
            35                  40                  45

Ala Ala Gly Thr Ala Cys Ala Thr Cys Thr Gly Thr Gly Gly Cys Thr
        50                  55                  60

Thr Cys Ala Cys Thr Ala Cys Thr Thr Thr Cys Thr Cys Ala Ala Thr
65                  70                  75                  80

Cys Ala Gly Ala Gly Thr Thr Cys Thr Cys Cys Gly Cys Thr Cys
                85                  90                  95

Ala Cys Thr Gly Thr Cys Ala Ala Cys Ala Gly Cys Ala Ala Thr Ala
            100                 105                 110

Thr Ala Cys Cys Thr Ala Cys Thr Cys Gly Ala Gly Cys Cys Thr Thr
        115                 120                 125

Cys Thr Gly Thr Thr Gly
    130

<210> SEQ ID NO 3
<211> LENGTH: 150
<212> TYPE: PRT
<213> ORGANISM: artificial sequence
<220> FEATURE:
<223> OTHER INFORMATION: synthetic construct

<400> SEQUENCE: 3

Cys Ala Ala Cys Ala Gly Ala Ala Gly Gly Cys Thr Cys Gly Ala Gly
1               5                   10                  15

Ala Ala Gly Gly Thr Ala Thr Ala Thr Thr Gly Cys Thr Gly Thr Thr
            20                  25                  30

Gly Ala Cys Ala Gly Thr Gly Ala Gly Cys Gly Cys Ala Gly Cys Ala
        35                  40                  45

Cys Thr Gly Ala Cys Thr Cys Ala Thr Ala Cys Ala Thr Thr Gly Ala
    50                  55                  60

Ala Gly Thr Thr Cys Thr Thr Gly Thr Gly Thr Gly Ala Ala Gly
65                  70                  75                  80

Cys Cys Ala Cys Ala Gly Ala Thr Gly Thr Ala Cys Ala Ala Gly Ala
                85                  90                  95

Ala Cys Thr Thr Cys Ala Ala Thr Gly Thr Ala Thr Gly Ala Gly Thr
            100                 105                 110

Cys Ala Gly Thr Gly Cys Thr Gly Thr Gly Cys Cys Thr Ala Cys Thr
        115                 120                 125

Gly Cys Cys Thr Cys Gly Gly Ala Ala Thr Thr Cys Ala Ala Gly Gly
    130                 135                 140

Gly Gly Cys Thr Ala Cys
145                 150

<210> SEQ ID NO 4
<211> LENGTH: 150
<212> TYPE: PRT
<213> ORGANISM: artificial sequence
<220> FEATURE:
<223> OTHER INFORMATION: synthetic construct

<400> SEQUENCE: 4

Gly Thr Ala Gly Cys Cys Cys Thr Thr Gly Ala Ala Thr Thr Cys
1               5                   10                  15

Cys Gly Ala Gly Gly Cys Ala Gly Thr Ala Gly Gly Cys Ala Cys Ala
            20                  25                  30
```

```
Gly Cys Ala Cys Thr Gly Ala Cys Thr Ala Cys Ala Thr
            35                  40                  45

Thr Gly Ala Ala Gly Thr Thr Cys Thr Thr Gly Thr Ala Cys Ala Thr
 50                  55                  60

Cys Thr Gly Thr Gly Gly Cys Thr Thr Cys Ala Cys Thr Ala Cys Ala
 65                  70                  75                  80

Ala Gly Ala Ala Cys Thr Thr Cys Ala Ala Thr Gly Thr Ala Thr Gly
                85                  90                  95

Ala Gly Thr Cys Ala Gly Thr Gly Cys Th

```
Thr Thr Cys Gly Gly Thr Cys Cys Thr Gly Ala Cys Ala Ala Ala
        35                  40                  45

Gly Ala Cys Ala Ala Gly Thr Thr Gly Ala Ala Thr Ala Cys Ala Thr
        50                  55                  60

Cys Thr Gly Thr Gly Gly Cys Thr Thr Cys Ala Cys Thr Ala Thr Thr
65                  70                  75                  80

Cys Ala Ala Cys Thr Thr Gly Thr Cys Thr Thr Thr Gly Gly Thr Cys
                85                  90                  95

Ala Gly Gly Ala Cys Cys Gly Ala Ala Gly Gly Cys Gly Cys Thr Cys
                100                 105                 110

Ala Cys Thr Gly Thr Cys Ala Ala Cys Ala Gly Cys Ala Ala Thr Ala
                115                 120                 125

Thr Ala Cys Cys Thr Thr Cys Thr Cys Gly Ala Gly Cys Cys Thr Thr
        130                 135                 140

Cys Thr Gly Thr Thr Gly
145                 150

<210> SEQ ID NO 7
<211> LENGTH: 150
<212> TYPE: PRT
<213> ORGANISM: artificial sequence
<220> FEATURE:
<223> OTHER INFORMATION: synthetic construct

<400> SEQUENCE: 7

Cys Ala Ala Cys Ala Gly Ala Ala Gly Gly Cys Thr Cys Gly Ala Gly
1               5                   10                  15

Ala Ala Gly Gly Thr Ala Thr Ala Thr Thr Gly Cys Thr Gly Thr Thr
                20                  25                  30

Gly Ala Cys Ala Gly Thr Gly Ala Gly Cys Gly Ala Ala Gly Thr Ala
        35                  40                  45

Gly Ala Cys Cys Gly Cys Ala Thr Cys Ala Gly Thr Gly Ala Ala Thr
        50                  55                  60

Gly Gly Ala Ala Gly Ala Gly Ala Thr Gly Thr Gly Ala Ala Gly
65                  70                  75                  80

Cys Cys Ala Cys Ala Gly Ala Thr Gly Thr Ala Cys Thr Cys Thr Thr
                85                  90                  95

Thr Cys Cys Ala Thr Thr Cys Ala Cys Thr Gly Ala Thr Gly Cys Gly
                100                 105                 110

Gly Thr Cys Thr Ala Cys Thr Thr Thr Gly Cys Cys Thr Ala Cys Thr
                115                 120                 125

Gly Cys Cys Thr Cys Gly Gly Ala Ala Thr Thr Cys Ala Ala Gly Gly
        130                 135                 140

Gly Gly Cys Thr Ala Cys
145             150

<210> SEQ ID NO 8
<211> LENGTH: 150
<212> TYPE: PRT
<213> ORGANISM: artificial sequence
<220> FEATURE:
<223> OTHER INFORMATION: synthetic construct

<400> SEQUENCE: 8

Gly Thr Ala Gly Cys Cys Cys Cys Thr Thr Gly Ala Ala Thr Thr Cys
1               5                   10                  15

Cys Gly Ala Gly Gly Cys Ala Gly Thr Ala Gly Gly Cys Ala Ala Ala
```

```
            20                  25                  30
Gly Thr Ala Gly Ala Cys Cys Gly Cys Ala Thr Cys Ala Gly Thr Gly
            35                  40                  45

Ala Ala Thr Gly Gly Ala Ala Gly Ala Gly Thr Ala Cys Ala Thr
        50                  55                  60

Cys Thr Gly Thr Gly Gly Cys Thr Thr Cys Ala Cys Thr Ala Thr Cys
65                  70                  75                  80

Thr Cys Thr Thr Cys Cys Ala Thr Cys Ala Cys Thr Gly Ala Thr
                85                  90                  95

Gly Cys Gly Gly Thr Cys Thr Ala Cys Thr Thr Cys Gly Cys Thr Cys
            100                 105                 110

Ala Cys Thr Gly Thr Cys Ala Ala Cys Ala Gly Cys Ala Ala Thr Ala
            115                 120                 125

Thr Ala Cys Cys Thr Thr Cys Thr Cys Gly Ala Gly Thr Cys Thr Thr
        130                 135                 140

Cys Thr Gly Thr Thr Gly
145             150
```

<210> SEQ ID NO 9
<211> LENGTH: 19
<212> TYPE: PRT
<213> ORGANISM: artificial sequence
<220> FEATURE:
<223> OTHER INFORMATION: synthetic construct

<400> SEQUENCE: 9

```
Cys Thr Cys Thr Ala Thr Gly Thr Gly Gly Thr Gly Ala Cys
1               5                   10                  15

Gly Ala Gly
```

<210> SEQ ID NO 10
<211> LENGTH: 20
<212> TYPE: PRT
<213> ORGANISM: artificial sequence
<220> FEATURE:
<223> OTHER INFORMATION: synthetic construct

<400> SEQUENCE: 10

```
Thr Cys Thr Cys Ala Ala Ala Cys Ala Thr Gly Ala Thr Cys Thr Gly
1               5                   10                  15

Gly Gly Thr Cys
        20
```

<210> SEQ ID NO 11
<211> LENGTH: 22
<212> TYPE: PRT
<213> ORGANISM: artificial sequence
<220> FEATURE:
<223> OTHER INFORMATION: synthetic construct

<400> SEQUENCE: 11

```
Cys Ala Ala Gly Cys Thr Gly Gly Ala Gly Thr Ala Cys Ala Ala Cys
1               5                   10                  15

Thr Ala Cys Ala Ala Cys
            20
```

<210> SEQ ID NO 12
<211> LENGTH: 20
<212> TYPE: PRT
<213> ORGANISM: artificial sequence
<220> FEATURE:

```
<223> OTHER INFORMATION: synthetic construct

<400> SEQUENCE: 12

Ala Gly Thr Thr Cys Ala Cys Cys Thr Thr Gly Ala Thr Gly Cys Cys
1               5                   10                  15

Gly Thr Thr Cys
        20

<210> SEQ ID NO 13
<211> LENGTH: 20
<212> TYPE: PRT
<213> ORGANISM: artificial sequence
<220> FEATURE:
<223> OTHER INFORMATION: synthetic construct

<400> SEQUENCE: 13

Ala Thr Gly Cys Cys Cys Cys Thr Cys Ala Gly Cys Thr Ala Thr Cys
1               5                   10                  15

Ala Cys Ala Cys
        20

<210> SEQ ID NO 14
<211> LENGTH: 21
<212> TYPE: PRT
<213> ORGANISM: artificial sequence
<220> FEATURE:
<223> OTHER INFORMATION: synthetic construct

<400> SEQUENCE: 14

Thr Thr Gly Thr Cys Cys Ala Thr Thr Cys Thr Cys Thr Cys Cys Thr
1               5                   10                  15

Thr Thr Thr Cys Cys
        20

<210> SEQ ID NO 15
<211> LENGTH: 19
<212> TYPE: PRT
<213> ORGANISM: artificial sequence
<220> FEATURE:
<223> OTHER INFORMATION: synthetic construct

<400> SEQUENCE: 15

Cys Cys Ala Thr Thr Gly Thr Gly Gly Gly Ala Ala Cys Ala Ala Cys
1               5                   10                  15

Cys Ala Gly

<210> SEQ ID NO 16
<211> LENGTH: 22
<212> TYPE: PRT
<213> ORGANISM: artificial sequence
<220> FEATURE:
<223> OTHER INFORMATION: synthetic construct

<400> SEQUENCE: 16

Thr Ala Gly Ala Gly Gly Ala Thr Cys Thr Cys Gly Ala Thr Thr Cys
1               5                   10                  15

Ala Gly Thr Thr Cys Cys
        20

<210> SEQ ID NO 17
<211> LENGTH: 21
<212> TYPE: PRT
<213> ORGANISM: artificial sequence
<220> FEATURE:
```

<223> OTHER INFORMATION: synthetic construct

<400> SEQUENCE: 17

Gly Gly Ala Cys Cys Gly Ala Ala Ala Gly Ala Ala Ala Thr Thr Ala
1               5                   10                  15

Gly Ala Gly Gly Ala
            20

<210> SEQ ID NO 18
<211> LENGTH: 20
<212> TYPE: PRT
<213> ORGANISM: artificial sequence
<220> FEATURE:
<223> OTHER INFORMATION: synthetic construct

<400> SEQUENCE: 18

Cys Ala Gly Gly Cys Ala Cys Ala Gly Ala Thr Gly Ala Ala Gly Thr
1               5                   10                  15

Ala Ala Gly Gly
            20

<210> SEQ ID NO 19
<211> LENGTH: 19
<212> TYPE: PRT
<213> ORGANISM: artificial sequence
<220> FEATURE:
<223> OTHER INFORMATION: synthetic construct

<400> SEQUENCE: 19

Cys Cys Cys Ala Ala Cys Thr Ala Cys Thr Cys Ala Cys Cys Gly Thr
1               5                   10                  15

Cys Thr Cys

<210> SEQ ID NO 20
<211> LENGTH: 20
<212> TYPE: PRT
<213> ORGANISM: artificial sequence
<220> FEATURE:
<223> OTHER INFORMATION: synthetic construct

<400> SEQUENCE: 20

Cys Ala Gly Gly Gly Ala Ala Gly Ala Thr Gly Gly Ala Cys Thr Thr
1               5                   10                  15

Cys Cys Thr Gly
            20

<210> SEQ ID NO 21
<211> LENGTH: 20
<212> TYPE: PRT
<213> ORGANISM: artificial sequence
<220> FEATURE:
<223> OTHER INFORMATION: synthetic construct

<400> SEQUENCE: 21

Ala Gly Ala Gly Cys Gly Ala Thr Thr Cys Thr Gly Ala Cys Thr Cys
1               5                   10                  15

Thr Gly Ala Cys
            20

<210> SEQ ID NO 22
<211> LENGTH: 22
<212> TYPE: PRT
<213> ORGANISM: Artificial sequence
<220> FEATURE:

```
<223> OTHER INFORMATION: synthetic construct

<400> SEQUENCE: 22

Thr Ala Gly Ala Gly Ala Cys Thr Gly Ala Cys Ala Cys Cys Thr Thr
1               5                   10                  15

Cys Ala Ala Gly Ala Cys
            20
```

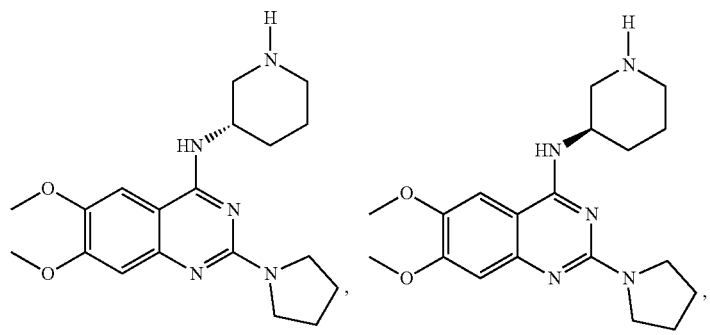

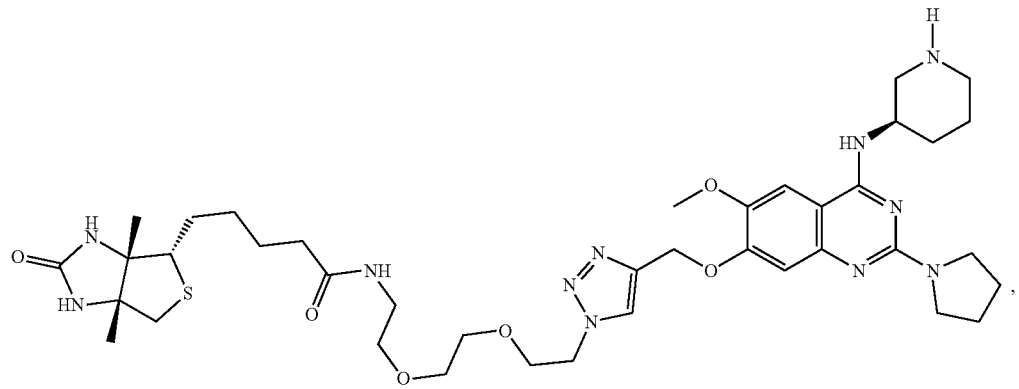

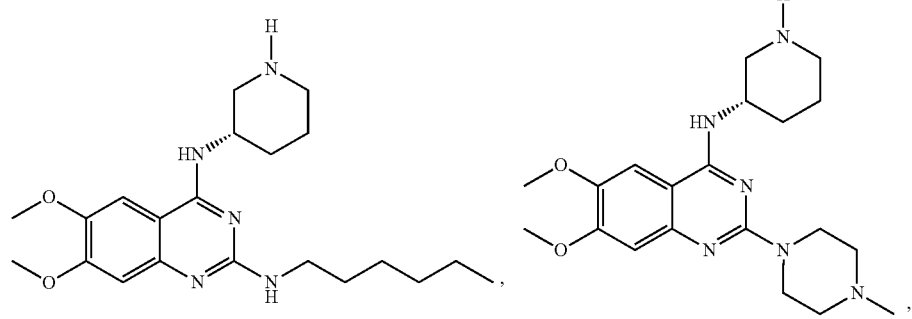
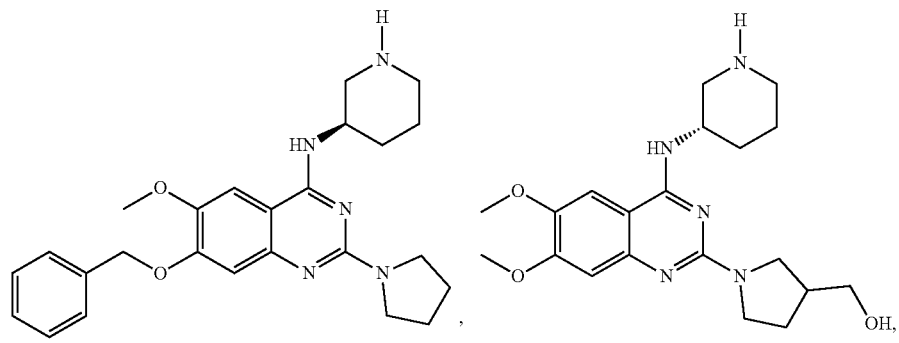
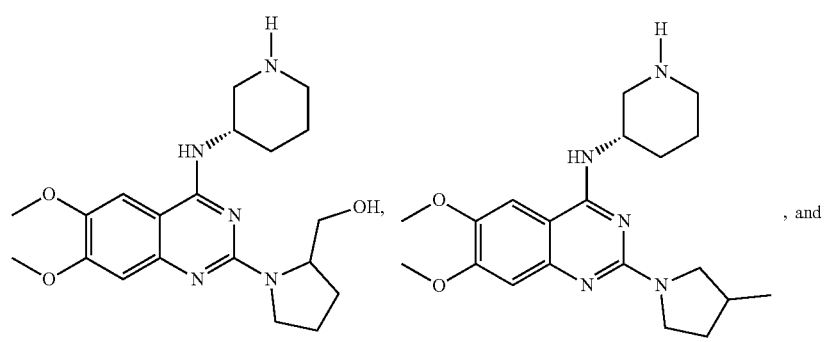, and
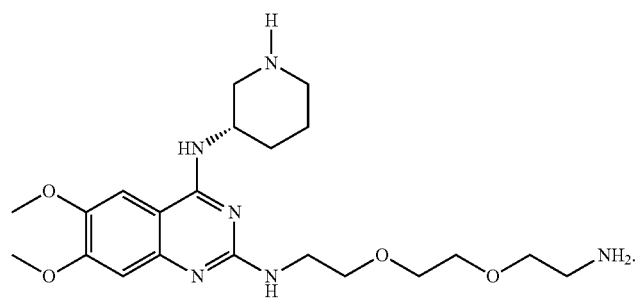 [SMILES: COc1cc2nc(NCCOCCOCCN)nc(N[C@H]3CCCNC3)c2cc1OC]

14. The compound of claim 1, wherein the compound is:
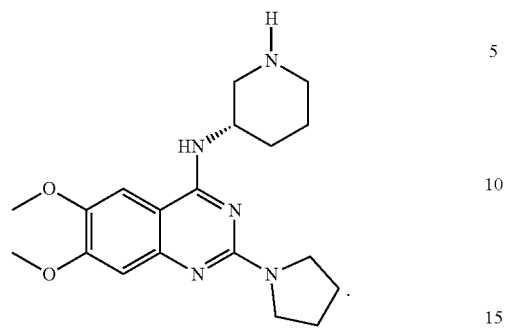

What is claimed is:

1. A compound having a structure represented by a formula:

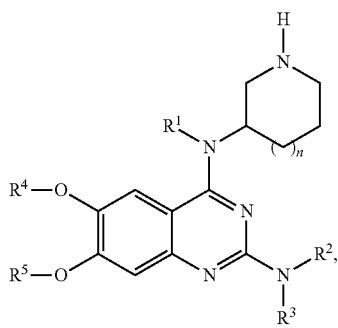

wherein n is selected from 0 and 1;

wherein $R^1$ is H or C1-C4 alkyl;

wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4; or wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$;

wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

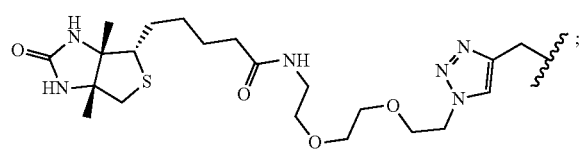 [SMILES: *Cc1cn(CCOCCOCCNC(=O)CCCC[C@@H]2SC[C@]3(C)NC(=O)N[C@]23C)nn1]

or wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$;

or a pharmaceutically acceptable salt thereof.

2. The compound of claim 1, wherein n is 1.

3. The compound of claim 1, wherein each of $R^2$ and $R^3$ is independently selected from H, C1-C8 alkyl, —$CH_2CH_2NH_2$, —$(CH_2CH_2O)_m$—H, and —$(CH_2CH_2O)_m$—$CH_2CH_2NH_2$, wherein m is 1, 2, 3, or 4.

4. The compound of claim 1, wherein $R^2$ and $R^3$, together with the intervening N, form a five-membered non-aromatic heterocycle, a five-membered aromatic heterocycle, a six-membered non-aromatic heterocycle, or a six-membered aromatic heterocycle, wherein the heterocycle contains 0, 1, or 2 further heteroatoms selected from O, N, and S, and wherein the heterocycle is substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$.

5. The compound of claim 1, wherein $R^2$ and $R^3$, together with the intervening N, form a five-membered non-aromatic heterocycle substituted with 0, 1, 2, or 3 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$.

6. The compound of claim 1, wherein each of $R^4$ and $R^5$ is independently selected from H, C1-C8 alkyl, benzyl, —$(CH_2CH_2O)_m$—H wherein m is 1, 2, 3, or 4, —$(CH_2CH_2O)_p$—$CH_2CH_2NH_2$ wherein p is 0, 1, 2, 3, or 4, —$CH_2CCH$, and a moiety having the structure:

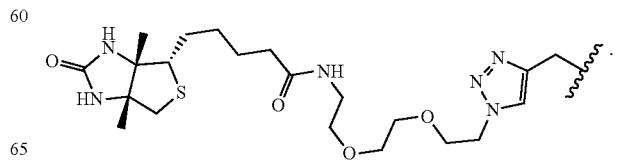

7. The compound of claim 1, wherein each of $R^4$ and $R^5$ is methyl.

8. The compound of claim 1, wherein $R^4$ and $R^5$, together with the intervening atoms, form a five-membered heterocycle or a six-membered heterocycle, wherein the heterocycle is substituted with 0, 1, 2, 3, or 4 groups independently selected from methyl, ethyl, n-propyl, isopropyl, hydroxyl, fluoro, chloro, bromo, iodo, —$NH_2$, —$NHCH_3$, —$N(CH_3)_2$, —$CH_2OH$, and —$CH_2CH_2OH$.

9. The compound of claim 1, wherein $R^4$ and $R^5$ are together isopropylidene.

10. The compound of claim 1, wherein the compound has the structure:

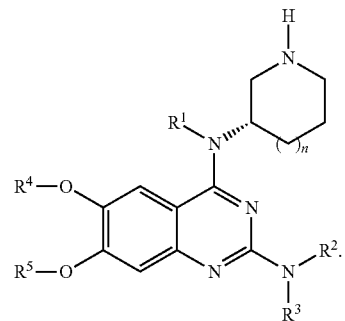

11. The compound of claim 1, wherein the compound has the structure:

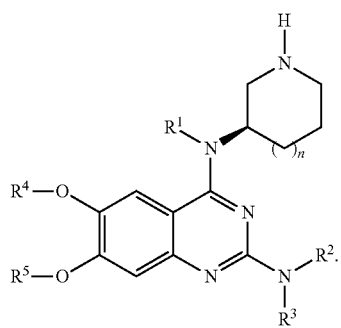

12. The compound of claim 1, wherein the compound has a structure represented by a formula:

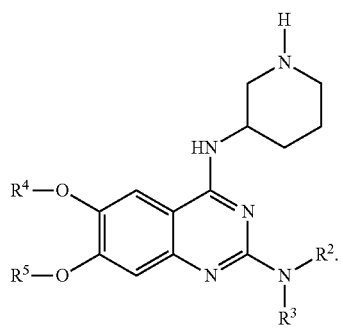

13. The compound of claim 1, wherein the compound is selected from: